(12) United States Patent
Chang et al.

(10) Patent No.: US 8,435,961 B2
(45) Date of Patent: May 7, 2013

(54) METHODS AND COMPOSITIONS FOR INCREASING THE ACTIVITY OF INHIBITORY RNA

(75) Inventors: Paul Chang, Cambridge, MA (US); Anthony Leung, Somerville, MA (US); Phillip A. Sharp, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/821,967

(22) Filed: Jun. 23, 2010

(65) Prior Publication Data

US 2011/0097328 A1 Apr. 28, 2011

Related U.S. Application Data

(60) Provisional application No. 61/269,626, filed on Jun. 26, 2009.

(51) Int. Cl.
*A61K 31/70* (2006.01)
*A61K 31/00* (2006.01)
*A61K 39/395* (2006.01)

(52) U.S. Cl.
USPC .............................. 514/44; 514/2; 424/130.1

(58) Field of Classification Search .................. None
See application file for complete search history.

(56) References Cited

U.S. PATENT DOCUMENTS

| | | | |
|---|---|---|---|
| 4,704,692 A | 11/1987 | Ladner | |
| 4,816,397 A | 3/1989 | Boss et al. | |
| 4,816,567 A | 3/1989 | Cabilly et al. | |
| 4,873,316 A | 10/1989 | Meade et al. | |
| 4,946,778 A | 8/1990 | Ladner et al. | |
| 5,484,596 A | 1/1996 | Hanna et al. | |
| 6,277,613 B1 | 8/2001 | De Lange et al. | |
| 6,599,728 B2 | 7/2003 | Morin et al. | |
| 6,713,059 B2 | 3/2004 | Kende et al. | |
| 2002/0142334 A1 | 10/2002 | Brown et al. | |
| 2003/0170859 A1 | 9/2003 | Christenson et al. | |
| 2004/0115710 A1 | 6/2004 | Li et al. | |
| 2004/0203145 A1 | 10/2004 | Zamore et al. | |
| 2005/0037988 A1 | 2/2005 | Zamore et al. | |
| 2005/0058982 A1 | 3/2005 | Han et al. | |
| 2005/0153918 A1 | 7/2005 | Chabot et al. | |
| 2005/0227919 A1* | 10/2005 | Ashworth et al. | 514/12 |
| 2006/0058255 A1 | 3/2006 | Chen et al. | |
| 2006/0127891 A1* | 6/2006 | McSwiggen et al. | 435/6 |
| 2006/0134787 A1 | 6/2006 | Zamore et al. | |
| 2006/0167225 A1 | 7/2006 | Gurskaya | |
| 2006/0204981 A1 | 9/2006 | Li et al. | |
| 2007/0105114 A1 | 5/2007 | Li et al. | |
| 2007/0161003 A1 | 7/2007 | Morris et al. | |
| 2007/0179160 A1 | 8/2007 | Helleday | |
| 2007/0264654 A1 | 11/2007 | Wiley et al. | |
| 2008/0015144 A1 | 1/2008 | Brownlee | |
| 2008/0076156 A1 | 3/2008 | Inouye et al. | |
| 2008/0207555 A1 | 8/2008 | Moss et al. | |
| 2008/0262062 A1 | 10/2008 | Ossovskaya et al. | |
| 2009/0028861 A1 | 1/2009 | Takagi et al. | |
| 2011/0151538 A1 | 6/2011 | Bayer et al. | |

FOREIGN PATENT DOCUMENTS

| | | |
|---|---|---|
| WO | WO 99/64606 | 12/1999 |
| WO | WO 01/75164 | 10/2001 |
| WO | WO 02/068579 | 9/2002 |
| WO | WO 2006/66048 | 6/2006 |
| WO | WO 2008/016356 | 2/2008 |
| WO | WO 2009/027650 | 3/2009 |
| WO | WO 2009/59994 | 5/2009 |

OTHER PUBLICATIONS

Cullen et al. Immunology and Cell Biology 2005, vol. 83, pp. 217-223.*
Zhang et al. Journal of Virology 2007, vol. 81, pp. 11246-11255.*
Zhu et al. RNA Biology 2008, vol. 5, pp. 65-67.*
Ame et al., "The PARP superfamily," *Bioessays* 26: 882-893 (2004).
Aravin et al., "A novel class of small RNAs bind to MILI protein in mouse testes," *Nature* 442: 203-207 (2006).
Candé et al., "Regulation of cytoplasmic stress granules by apoptosis-inducing factor," *J. Cell Sci.* 117: 4461-4468 (2004).
Chang et al., "Tankyrase-1 polymerization of poly(ADP-ribose) is required for spindle structure and function," *Nat. Cell Biol.* 7: 1133-1139 (2005).
Cohen-Armon et al., "DNA-independent PARP-1 activation by phosphorylated ERK2 increases Elk1 activity: a link to histone acetylation," *Mol. Cell* 25: 297-308 (2007).
Elbashir et al., "RNA interference is mediated by 21- and 22-nucleotide RNAs," *Genes Dev.* 15: 188-200 (2001).
Girard et al., "A germline-specific class of small RNAs binds mammalian Piwi proteins," *Nature* 442: 199-202 (2006).
Graille et al., "Crystal structure of a *Staphylococcus aureus* protein a domain complexed with the Fab fragment of a human IgM antibody: structural basis for recognition of B-cell receptors and superantigen activity," *Proc. Acad. Sci. U.S.A.* 97: 5399-5404 (2000).
Grivna et al., "A novel class of small RNAs in mouse spermatogenic cells," *Genes Dev.* 20: 1709-1714 (2006).
Haince et al., "PARP1-dependent kinetics of recruitment of MRE11 and NBS1 proteins to multiple DNA damage sites," *J. Biol. Chem.* 283: 1197-1208 (2008).
Hatakeyama et al., "Purification and characterization of poly(ADP-ribose) glycohydrolase. Different modes of action on large and small poly(ADP-ribose)," *J. Biol. Chem.* 261: 14902-14911 (1986).
Jones et al., "A novel peptide tag for detection and purification of recombinant expressed proteins," *Protein Expr. Purif.* 53: 404-410 (2007).
Kedersha et al., "Dynamic shuttling of TIA-1 accompanies the recruitment of mRNA to mammalian stress granules," *J. Cell Biol.* 151: 1257-1268 (2000).
Köhler et al., "Continuous cultures of fused cells secreting antibody of predefined specificity," *Nature* 256: 495 (1975).

(Continued)

*Primary Examiner* — Tracy Vivlemore
(74) *Attorney, Agent, or Firm* — Clark & Elbing LLP; Kristina Bieker-Brady

(57) ABSTRACT

The invention provides methods for increasing the activity of an inhibitory RNA (RNAi) in a subject requiring administering one or more poly-ADP-ribose polymerase (PARP) inhibitors and/or one or more PARG activators to the subject. The invention also provides methods for increasing the activity of an inhibitory RNA in a cell or cell population requiring contacting a cell or cell population with one or more PARP inhibitors and/or one or more PARG activators. The invention further provides compositions and kits containing one or more PARP inhibitors and/or one or more PARG activators.

12 Claims, 36 Drawing Sheets

OTHER PUBLICATIONS

Köhler et al., "Derivation of specific antibody-producing tissue culture and tumor lines by cell fusion," *Eur. J. Immunol.* 6: 511-519 (1976).

Köhler et al., "Fusion between immunoglobulin-secreting and nonsecreting myeloma cell lines," *Eur. J. Immunol.* 6: 292-295 (1976).

Lau et al., "Characterization of the piRNA complex from rat testes," *Science* 313: 363-367 (2006).

Lichty et al., "Comparison of affinity tags for protein purification," *Protein Expr. Purif.* 41:98-105 (2005).

McCafferty et al., "Phage antibodies: filamentous phage displaying antibody variable domains," *Nature* 348: 552-554 (1990).

McCaffrey et al., "RNA interference in adult mice," *Nature* 418: 38-39 (2002).

Meyer-Ficca et al., "Human poly(ADP-ribose) glycohydrolase is expressed in alternative splice variants yielding isoforms that localize to different cell compartments," *Exp. Cell. Res.* 297: 521-532 (2004).

Mocikat, "Improving the expression of chimeric antibodies following homologous recombination in hybridoma cells," *J. Immunol. Methods* 225: 185-189 (1999).

Nottbahn et al., "A colorimetric substrate for poly(ADP-ribose) polymerase-1, VPARP, and tankyrase-1," *Agnew. Chem. Int. Ed. Engl.* 46: 2066-2069 (2007).

Paddison et al., "Short hairpin RNAs (shRNAs) induce sequence-spcific silencing in mammalian cells," *Genes Dev.* 16: 948-958 (2002).

Putt et al., "An enzymatic assay for poly(ADP-ribose) polymerase-1 (PARP-1) via the chemical quantitation of NAD(+): application to the high-throughput screening of small molecules as potential inhibitors," *Anal. Biochem.* 326: 78-86 (2004).

Roben et al., "VH3 family antibodies bind domain D of staphylococcal protein A," *J. Immunol.* 154: 6437-6445 (1995).

Schagat et al., "Micro RNA biosensors: application for the psiCHECK vector," *Promega Notes* 99: 16-18 (2008).

Srikumaran et al., "Bovine x mouse hybridomas that secrete bovine immunoglobulin G1," *Science* 220: 522-523 (1983).

Tourrière et al., "The RasGAP-associated endoribonuclease G3BP assembles stress granules," *J. Cell Biol.* 160: 823-831 (2003).

Tuesday Session, The Authors Journal Compilation. International Society for Neurochemistry. *J. Neurochem.* 102: 76-147 (2007).

Turner et al., "A synthetic lethal siRNA screen identifying genes mediating sensitivity to a PARP inhibitor," *EMBO J.* 27: 1368-1377 (2008).

Ward et al., "Binding activities of a repertoire of single immunoglobulin variable domains secreted from *Escherichia coli*," *Nature* 341: 544-546 (1989).

Yu et al., "RNA interference by expression of short-interfering RNAs and hairpin RNAs in mammalian cells," *Proc. Natl. Acad. Sci. U.S.A.* 99: 6047-6052 (2002).

International Search Report from PCT Application WO2010/151773, dated Dec. 20, 2010.

International Search Report from PCT Application WO2010/151664, dated Feb. 9, 2011.

International Search Report from PCT Application WO2010/151656, dated Jan. 12, 2011.

Ashmun et al., "Deletion of the zinc-binding motif of CD13/aminopeptidase N molecules results in loss of epitopes that mediate binding of inhibitory antibodies," *Blood* 79: 3344-3349, 1992.

Bowie et al., "Deciphering the message in protein sequences: tolerance to amino acid substitutions," *Science* 247: 1306-1310, 1990.

Bryant et al., "Poly(ADP-ribose) polymerase inhibitors as potential chemotherapeutic agents," *Biochem. Soc. Trans.* 32: 959-961, 2004.

Erlenbach et al., "Single amino acid substitutions and deletions that alter the G protein coupling properties of the V2 vasopressin receptor identified in yeast by receptor random mutagenesis," *J. Biol. Chem.* 276: 29382-29392, 2001.

Green et al., "Loss of the circadian clock-associated protein 1 in *Arabidopsis* results in altered clock-regulated gene expression," *Proc. Natl. Acad. Sci. U.S.A.* 96: 4176-4179, 1999.

Kuno et al., "Structure and function of the intracellular portion of the mouse interleukin 1 receptor (type I). Determining the essential region for transducing signals to activate the interleukin 8 gene," *J. Biol. Chem.* 268: 13510-13518, 1993.

MacKay et al., "An In vivo analysis of the vestigial gene in *Drosophilia melanogaster* defines the domains required for Vg function," *Genetics* 163: 1365-1373, 2003.

Noutoshi et al., "A single amino acid insertion in the WRKY domain of the *Arabidopsis* TIR-NBS-LRR-WRKY-type disease resistance protein SLH1 (sensitive to low humidity 1) causes activation of defense responses and hypersensitive cell death," *Plant J.* 43: 873-888, 2005.

Ratnam et al., "Current development of clinical inhibitors of poly(ADP-ribose) polymerase in oncology," *Clin. Cancer Res.* 13: 1383-1388, 2007.

Shih et al., "Self-cleavage of fusion protein in vivo using TEV protease to yield native protein," *Protein Sci.* 14: 936-941, 2005.

Wang et al., "Strategies for short hairpin RNA delivery in cancer gene therapy," *Expert Opin. Biol. Ther.* 9: 1357-1368, 2009.

Watson et al., *Molecular Biology of the Gene*, 4th edition, Jane Reece Gillen (ed.), Menlo Park, CA: The Benjamin/Cummings Publishing Company, Inc., pp. 342-343, 442, 445, 1987.

\* cited by examiner

Polylinker Sequence (SEQ ID NO: 29):

```
CTGTACAAGTCCGGACTCAGATCTCGAGCTCAAGCTTCGAATTCTGCAGTCGAC   1374
      BspE I      Bgl II Xho I Sac I  Hind III   EcoRI   Pst I  Sal I/Acc I GGTACCGCGGCCCGGGATCCACCGGATCTAGATAACTGATCATAATCAGCCAT   1426
 Kpn I Sac II Apa I  BamH I      Xba I      Bcl I
        Xma I/Sma I
```

HeLa
hTERT-RPE hTERT-RPE

G3BP Structure

METHODS AND COMPOSITIONS FOR INCREASING THE ACTIVITY OF INHIBITORY RNA

CROSS-REFERENCE TO RELATED APPLICATIONS

This application claims the benefit of the filing date of U.S. Provisional Application No. 61/269,626, filed Jun. 26, 2009, herein incorporated by reference in its entirety.

STATEMENT AS TO FEDERALLY FUNDED RESEARCH

This invention was made with government support under Grant Nos. CA042063 and CA133404, awarded by the National Institutes of Health. The government has certain rights in this invention.

FIELD OF THE INVENTION

The present invention relates to the field of molecular biology and molecular medicine.

BACKGROUND OF THE INVENTION

Poly-adenosine diphosphate (ADP)-ribose (PAR) polymers are the product of post-translational modifications carried out by PAR polymerases (PARPs). PAR is polymerized by PARPs onto acceptor proteins using nicotinamide adenine dinucleotide ($NAD^+$) as substrate (FIG. 1). PAR polymers are localized to distinct cellular structures in different phases of the cell cycle and localize to the mitotic spindle during mitosis (FIG. 2). There are at least 18 PARPs in the human genome: the domain structure for several PARPs is depicted in FIG. 3. However, the specific biological function and protein substrates of these PARPs are not fully characterized (Ame et al., *Bioessays* 26:882-893, 2004). The identification of the function and the substrates of each member of this family of proteins has been difficult to date.

PAR polymers are required for normal cell division and PARP knockouts in *Drosophila melanogaster* are embryonic lethal (Tulin et al., *Genes Dev.* 16:2108-2119, 2002). The concentration, length, and extent of PAR branching are regulated by a balance of activities of the PARPs and PAR glycohydrolase (PARG), a highly specific, processive endo- and exo-glycosidase (Hatakeyama et al., *J. Biol. Chem.* 261: 14902-14911, 1986). Poly-ADP-ribose polymers have generally been implicated for a role in several different human diseases including cancer, ischemic injury, inflammatory diseases, cardiovascular diseases, and neurodegenerative disorders.

We have discovered that PARP13 and PARG modulate the activity of inhibitory RNAs (RNAi molecules) in the cell. Inhibitory RNA molecules may be used in the laboratory to knockdown the expression of a specific gene and its corresponding encoded protein in a cell. Inhibitory RNA technology is presently being used to develop molecular therapies for several diseases. Methods and compositions to increase the effectiveness of inhibitory RNA activity in vitro and in vivo (e.g., in a subject receiving molecular therapy) are presently desired.

SUMMARY OF THE INVENTION

The present invention provides methods for increasing (e.g., at least 10%, 20%, 30%, 40%, 50%, 60%, 70%, 80%, 90%, 95%, or 100%) the activity of one or more (e.g., at least 1, 2, 3, 4, or 5) RNAi molecules in a subject requiring administering to the subject a therapeutically effective amount of one or more (1, 2, 3, 4, or 5) PARP inhibitors (e.g., PARP13.1 inhibitors) and/or one or more (e.g., 1, 2, 3, 4, or 5) PARG activators (e.g., PARG activators and/or ARH activators). The invention further provides methods for increasing (e.g., at least 10%, 20%, 30%, 40%, 50%, 60%, 70%, 80%, 90%, or 100%) the activity of one or more (e.g., at least 1, 2, 3, 4, or 5) RNAi molecules in a cell or cell population requiring contacting the cell or cell population with one or more (e.g., 1, 2, 3, 4, or 5) PARP inhibitors (e.g., PARP13.1 inhibitors) and/or PARG activators (e.g., PARG activators and/or ARH3 activators). In each of the above methods, the one or more PARP inhibitors and/or one or more PARG activators may be administered to the subject or added to the culture medium in combination with one or more additional RNAi molecules or recombinant viruses containing a sequence encoding one or more RNAi molecules (e.g., therapeutic RNAi molecules).

In each of the above embodiments, the PARP inhibitors may be a PARP13.1 inhibitor, such as an antibody or antibody fragment that binds to a PARP13.1 protein or PARP13.1 fusion protein, an RNAi molecule (e.g., a RNAi molecule that includes a sequence that is complementary or is identical to one of SEQ ID NOS: 40 or 106-112), and/or a small molecule. In each of the above embodiments, the PARG activators may be one or more nucleic acid containing a sequence at least 80% identical (e.g., at least 85%, 90%, 95%, 99%, or even 100% identical) to PARG (SEQ ID NO: 42) or ARH3 (SEQ ID NO: 41), or one or more proteins encoded by one or more of these nucleic acids.

The invention further provides pharmaceutical compositions and kits containing one or more PARP inhibitors (e.g., PARP13.1 inhibitors) and/or one or more PARG activators (e.g., PARG activators and/or ARH3 activators).

The above methods provide a increase in the ability of an RNAi molecule to decrease the expression of a target gene in a cell (e.g., decrease the levels of a mRNA of a gene or decrease the levels of a protein encoded by the target gene in the cell).

By the term "activities of PARP13.1" is meant one or more (e.g., 1, 2, 3, 4, or 5) biological activities of a polypeptide encoded by one or more nucleic acid(s) containing a sequence that is at least 80% identical (e.g., at least 85%, 90%, 95%, 96%, 97%, 98%, 99%, or even 100% identical to PARP13.1 (SEQ ID NO: 19). For example, one biological activity of PARP13.1 is the addition of an ADP-ribose molecule to a substrate (e.g., a protein, a RNA molecule, a DNA molecule, a lipid, or a small molecule), the addition of ADP-ribose molecule to a pre-existing ADP-ribose or poly-ADP-ribose molecule attached to a substrate (e.g., a protein, a RNA molecule, a DNA molecule, a lipid, or a small molecule), the addition of ADP-ribose molecule to generate a branched poly-ADP-ribose molecule attached to a substrate (e.g., a protein, a RNA molecule, a DNA molecule, a lipid, or a small molecule). Another example of a PARP13.1 activity is the regulation or modulation (e.g., decrease or inhibition) of RNAi activity in the cell (e.g., decreasing the level of one or more target mRNA molecules in a cell). PARP13.1 may regulate or modulate the activity of RNAi in a cell by adding an ADP-ribose molecule to a substrate protein (e.g., a protein involved in the regulation or processing of an RNAi molecule in a cell). An example of a substrate of PARP13.1 is Argonaut 2. Additional substrates of PARP13.1 may be identified using the methods described herein.

By the term "ARH3" or "poly-ADP-ribose glycohydrolase ARH3" is meant a nucleic acid having containing a sequence that is at least 80% identical (e.g., at least 85%, 90%, 95%, 96%, 97%, 98%, 99%, or even 100% identical) to the sequence of SEQ ID NO: 41, or one or more polypeptides encoded by these nucleic acids.

By the term "ARH3 fusion protein" or "poly-ADP-ribose glycohydrolase ARH3 fusion protein" is meant a polypeptide containing a polypeptide tag and a sequence having at least 80% identity (e.g., at least 85%, 90%, 95%, 96%, 97%, 98%, 99%, or even 100% identity) to a protein encoded by ARH3 (SEQ ID NO: 41). The polypeptide tag of an ARH3 fusion protein may be located at the N- and/or C-terminus of the protein. The polypeptide tag may contain one or more of a fluorescent protein (e.g., a green fluorescence protein), a peptide epitope recognized by specific antibodies, a protein that is bound by a partner binding protein with high affinity (e.g., biotin and streptavidin), a His$_6$-tag, or one or more (e.g., 1, 2, 3, 4, 5, 6, or 7) protease recognition sequence(s) (e.g., one or more of a TEV protease or Factor Xa protease recognition sequence). ARH3 fusion proteins may be purified using antibodies specific for the polypeptide tag. For example, antibodies specific for the polypeptide tag or proteins that bind specifically to the protein sequence in the polypeptide tag may bound to a bead (e.g., a magnetic bead) or polymer surface in order to allow for the purification of the ARH3 fusion protein. An ARH3 fusion protein may also be purified and subsequently treated with one or more (e.g., 1, 2, or 3) protease(s) to remove the polypeptide tag from the ARH3 fusion protein. An ARH3 fusion protein preferably has the same cellular localization and biological activity as the wild-type ARH3 protein. Methods for the generation and purification of ARH3 fusion proteins are described herein.

By the term "biotinylated" is meant the covalent attachment of a biotin molecule to a small molecule, surface, or protein. A biotin molecule may be attached to a small molecule, surface, or protein using methods known in the art including, but not limited to, attachment to primary amines (e.g., epsilon-amines and N-terminal α-amines of a protein), as well as attachment at a sulfhydryl group, and a carboxyl group. Small molecules (e.g., NAD$^+$) and proteins (e.g., one or more of the PARP fusion proteins described herein) may be biotinylated. Biotinylated NAD$^+$ is available from a number of commercial sources including R & D Systems, Gentaur, and Trevigen (e.g., 6-biotin-17-NAD). Biotinylated small molecules and substrates may be specifically bound and/or purified using streptavidin, a protein that has a high affinity for biotin (Ka~$10^{13}$ M$^{-1}$), or surfaces covalently attached to streptavidin (e.g., streptavidin-coated beads).

By the term "cell lysate" is meant the contents of the cell once the plasma membrane has been disrupted or permeabilized. Cell lysate also includes the contents of the intracellular organelles (e.g., endoplasmic reticulum, nucleus, mitochondria, chloroplasts, Golgi apparatus, and lysosome) upon disruption of their respective membranes. Cell lysate contains an unpurified mixture of proteins, small molecule metabolites, and nucleic acids (e.g., DNA and RNA). Cell lysate may be prepared from any type of cell, e.g., a mammalian cell (e.g. human, mouse, rat, and monkey cell), a bacterial cell, fungal cell, and a yeast cell. Cell lysate may be obtained by any methods known in the art including physical disruption (e.g., sonication, homogenization, or freeze/thaw procedures) or chemical disruption (e.g., treatment with a detergent (e.g., Triton-X-100 and NP-40)). Cell lysate may be prepared from a cell expressing one or more of the nucleic acid(s) that encode one or more PARP, PARG, and/or ARH3 proteins and/or one or more PARP, PARG, and/or ARH3 fusion protein(s). Cell lysate may also be prepared from a cell arrested in a specific stage of the cell cycle (e.g., mitosis or S-phase) or may be prepared from asynchronous cells.

By the term "constitutive promoter" is meant a promoter that is placed 5' relative to a nucleic acid sequence encoding a protein, wherein the promoter regulates the consistent expression of a nucleic acid encoding a protein. The sequence of the constitutive promoter may be directly (no extraneous nucleotides) 5' to the first nucleotide of the sequence encoding the protein (e.g., a PARP, PARG, and/or ARH3 protein and/or a PARP, PARG, and/or ARH3 fusion protein as described herein) or may be between 1-20 nucleotides, 1-100 nucleotides, 10-260 nucleotides, 100-700 nucleotides, or 100 to 2,000 nucleotides from the first nucleotide of the sequence encoding the protein. Examples of constitute promoters include, but are not limited to, bacterial promoters (e.g., E. coli $\sigma^{70}$, $\sigma^s$, $\sigma^{32}$, or $\sigma^{54}$ promoters; B. subtilis $\sigma^A$ or $\sigma^B$ promoters; T7 RNA polymerase-based promoters; and bacteriophage SP6 promoter), yeast promoters (e.g., pCyc, pAdh, pSte5, ADH1, cyc100, cyc70, cyc43, cyc28, cyc16, pPGK1, pCYC, GPD (TDH3), and CLB1 promoters), and mammalian promoters (e.g., cytomegalovirus immediate early gene-based promoters, SV40 early promoter, and Rous sarcoma virus promoter). A constitutive promoter may be used to mediate the expression of a nucleic acid (e.g., one or more nucleic acids encoding a PARP, PARG, and/or ARH3 protein, and/or a PARP, PARG, and/or ARH3 fusion protein as described herein) in a transgenic mammalian, bacterial, or yeast cell.

By the term "decrease in the level of target mRNA" is meant a reduction (e.g., at least 5%, 10%, 15%, 20%, 25%, 30%, 35%, 40%, 45%, 50%, 55%, 60%, 65%, 70%, 75%, 80%, 85%, 90%, 95%, 99%, or even 100%) in the level of one or more (e.g., 1, 2, 3, 4, 5, 6, 7, 8, 9, or 10) mRNA molecules that contains a sequence that is complementary or identical to a sequence contained within one or more inhibitory RNA molecule(s). For example, contacting a cell or administering to a subject one or more (e.g., 1, 2, 3, 4, or 5) inhibitory RNA molecules may result in a reduction (e.g., at least 5%, 10%, 15%, 20%, 30%, 40%, 50%, 60%, 70%, 80%, 90%, 95%, 99%, or even 100%) in the level of several (e.g., 1, 2, 3, 4, or 5) different mRNAs that share homology (e.g., at least 50%, 60%, 70%, 80%, 90%, or 95% homology at the nucleic acid level) or are different splice variants of the same gene (e.g., different splice variants of mRNAs transcribed from the same gene or different alleles of the same gene). The level of decrease of a target mRNA in a cell can be measured using a variety of methods known in the art, including, but not limited to, reverse-transcriptase polymerase chain reaction (RT-PCR) and real-time quantitative RT-PCR.

By the term "effective amount" or "therapeutically effective amount" is meant the amount of the agent administered to a subject, to a cell, or to a cell population that elicits a specific desirable effect. For example, the amount of an agent (e.g., one or more PARP inhibitor(s) and/or one or more PARG activator(s)) that increases (e.g., by at least 5%, 10%, 15%, 20%, 30%, 40%, 50%, 60%, 70%, 80%, 90%, 95%, or 100%) the activity of one or more (e.g., 1, 2, 3, 4, or 5) RNAi molecules in a cell or reduces the amount of one or more RNAi molecules needed to achieve a reduction in the expression of one or more target genes (e.g., a reduction in the levels of one or more target mRNAs and/or a reduction in the levels of one or more proteins encoded by one or more target mRNAs). The effective amount or therapeutically effective amount of a PARP inhibitor and/or PARG activator may determined by a skilled artisan using methods known in the art and the methods described herein.

By "labeled nicotinamide adenine dinucleotide" or "labeled NAD+" is meant a molecule of nicotinamide adenine dinucleotide (NAD+) that is covalently labeled with a fluorescent molecule, a colorimetric molecule, or a molecule that is recognized by a specific partner protein (e.g., biotinylation), or labeled with a radioisotope. One example of a labeled NAD+ is biotinylated NAD+ (e.g., 6-biotin-14-NAD). Examples of radiolabeled NAD+ include, but are not limited to, $^{14}$C-adenine-NAD+, $^{32}$P-NAD+, and $^{3}$H-NAD+. Additional examples of labeled NAD+ are known in the art.

By the term "short RNA or DNA aptamer" is meant a short sequence of DNA or RNA nucleotides that binds to a specific target molecule (e.g., a protein or a target RNA or DNA molecule). A DNA or RNA aptamer that specifically binds to its target molecule (e.g., one or more (e.g., 1, 2, 3, 4, or 5) of the nucleic acids encoding a PARP, PARG, and/or ARH3 protein, and/or a PARP, PARG, and/or ARH3 fusion protein (as described herein) may decrease (e.g., by at least 10%, 20%, 30%, 40%, 50%, 60%, 70%, 80%, 90%, or 100%) or increase (e.g., by at least 10%, 20%, 30%, 40%, 50%, 60%, 70%, 80%, 90%, or 100%) one or more (e.g., 1, 2, 3, 4, or 5) activities or expression (e.g., mRNA or protein level) of the respective target molecule. For example, a specific DNA or RNA aptamer may bind to one or more of the above-described PARP proteins or PARP fusion proteins and increase or decrease the poly-ADP ribosylation activity of the protein, the amount of poly-ADP ribose attached to the protein, or the levels of one or more (e.g., 1, 2, 3, 4, 5, 6, 7, 8, 9, or 10) PARP proteins or PARP fusion proteins. The specific DNA or RNA aptamer may also bind to one or more nucleic acids (e.g., DNA or RNA) that encode a specific PARP, PARG, and/or ARH3 protein (e.g., a nucleic acid that encodes a protein having at least 80% sequence identity (e.g., at least 85%, 90%, 95%, 96%, 97%, 98%, 99%, or even 100%) to PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), PARP16 (SEQ ID NO: 24), PARG (SEQ ID NO: 42), and ARH3 (SEQ ID NO: 41)), and mediate an increase or decrease in the expression (e.g., protein and/or mRNA level) of the PARP, PARG, or ARH3. A specific example of an RNA aptamer is an inhibitory RNA (RNAi) molecule. Methods for the design of RNAi molecules are known in the art. Examples of specific RNAi molecules that may be used to decrease the expression of a PARP, PARG, and/or ARH3 protein, and/or PARP, PARG, and/or ARH3 fusion protein are described herein. An RNA or DNA aptamer may also be designed to decrease the expression of any target gene expressed in a cell (e.g., a decrease in the expression of an mRNA transcribed from a target gene and/or a decrease in the level of a protein translated from a mRNA targeted by a RNA or DNA aptamer).

By the term "fluorescent protein" is meant a protein that absorbs light of a specific wavelength (e.g., absorption wavelength) and emits light with a longer wavelength (e.g., emission wavelength). The term fluorescent protein encompasses natural fluorescent proteins (i.e., the natural form of the fluorescent protein without any genetic manipulations) and genetically mutated fluorescent proteins (e.g., fluorescent proteins engineered to change the identity of one or more amino acid residues). Several different examples of fluorescent proteins are known in the art, including, but not limited to, green fluorescent proteins (e.g., GFP, Emerald, Superfolder GFP, Azami Green, mWasabi, TagGFP, TurboGFP, AcGFP, ZsGreen, T-Sapphire, and T-Sapphire), blue fluorescent proteins (e.g., EBFP, EBFP2, Azurite, mTagBFP), cyan fluorescent proteins (e.g., ECFP, mECFP, Cerulean, CyPet, AmCyan1, Midori-Ishi Cyan, TagCFP, mTFP1 (Teal)), yellow fluorescent proteins (e.g., EYFP, Topaz, Venus, mCitrine, YPet, TanYFP, PhiYFP, ZsYellow1, and mBanana), orange fluorescent proteins (e.g., Kurabira Orange, Kurabira Orange2, mOrange, mOrange2, dTomato, dTomato-Tandem, TagRFP, TagRFP-T, DsRed, DsRed2, DsRed-Express (T1), DsRed-Monomer, and mTangerine), and red fluorescent proteins (e.g., mRuby, mApple, mStrawberry, AsRed2, mRFP1, JRed, mCherry, HcRed1, mRaspberry, dKeima-Tandem, HcRed-Tandem, mPlum, and AQ143). Fluorescent proteins may be attached to the N- and/or C-terminus of a target protein (e.g., one or more of the PARP, PARG, and/or ARH3 fusion proteins described herein). Fusion proteins tagged with a fluorescent protein (e.g., one or more of the PARP, PARG, and/or ARH3 fusion proteins described herein) may be analyzed using fluorescence-based techniques known in the art (e.g., fluorescence microscopy, fluorescence plate readers, fluorescence-assisted cell sorting, and use of a second antibody specific for the fluorescent protein).

By the term "inducible promoter" is meant a promoter that is placed 5' relative to a nucleic acid sequence encoding a protein, wherein the promoter induces (or represses) the expression of a nucleic acid upon addition (or removal) of a specific molecule or protein. The sequence of the inducible promoter may be directly (no extraneous nucleotides) 5' to the first nucleotide of the sequence encoding the protein (e.g., a PARP fusion protein as described herein) or may be between 1-20 nucleotides, 1-100 nucleotides, 10-260 nucleotides, 100-700 nucleotides, or 100 to 2,000 nucleotides from the first nucleotide of the sequence encoding the protein. Examples of inducible promoters include, but are not limited to alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. An inducible promoter may be used to regulate the expression of a nucleic acid (e.g., one or more nucleic acids encoding a PARP, PARG, and/or ARH3 protein and/or PARP, PARG, and/or ARH3 fusion protein as described herein) in a transgenic mammalian, bacterial, or yeast cell.

By the term "nuclear lysate" is meant the contents of a nucleus upon disruption of the nuclear membrane. Nuclear lysate contains an unpurified mixture of proteins, small molecule metabolites, and nucleic acids (e.g., DNA and RNA). Nuclear lysate may be prepared from any type of nucleated cell, e.g., a mammalian cell (e.g. human, mouse, rat, and monkey cell), a fungal cell, a yeast cell, or a plant cell. Nuclear lysate may be obtained by any methods known in the art including stepped lysis using two different concentrations of detergents (e.g., NP-40) or a combination of physical treatment to rupture the plasma membrane and chemical treatment to rupture the nuclear membrane. Nuclear lysate may be prepared from a cell expressing one or more of the nucleic acid(s) of the invention that encode a one or more PARP, PARG, or ARH3 proteins or PARP, PARG, or ARH3 fusion protein(s).

By "PAR" or "poly-ADP ribose" is meant a chain of two or more ADP-ribose molecules. The two or more molecules of ADP-ribose making up PAR may occur in a single linear chain or as a branched chain with one or more branches (e.g., at least 1, 2, 3, 4, 5, 6, 7, 8, 9, or 10 branches). Poly-ADP ribose may be attached to a specific substrate (e.g., protein, lipid, DNA, RNA, or small molecule) by the activity of one or more PARP proteins or PARP fusion proteins (e.g., one or more (e.g., 1, 2, 3, 4, 5, 6, 7, 8, 9, 10, 11, 12, 13, 14, 15, 16, 17, 18, 19, 20, 21, or 22) of PARP1, PARP2, PARP3, PARP3.2, PARP3.3, PARP4, PARP5A, PARP5B, PARP6, PARP7, PARP8, PARP9, PARP10, PARP11, PARP12, PARP13.1, PARP13.2, PARP14, PARP15.1, PARP15.2, and PARP16, or one or more of their respective fusion proteins) or removed by the activity of one or more PARG protein, PARG fusion protein, ARH3 protein, or ARH3 fusion protein (e.g., PARG protein or ARH3). Attachment of poly-ADP-ribose to a substrate protein may affect the biological activity of the substrate protein, localization of the protein, or the identity and number of proteins that bind to the target substrate (e.g., protein). PARP proteins may also be modified by the covalent attachment of poly-ADP-ribose. The addition of poly-ADP ribose to a PARP protein may occur by "auto-modification" or "auto-modulation" (i.e., a specific PARP catalyzes the attachment of poly-ADP ribose to itself) or may occur by the activity of one or more (e.g., 1, 2, 3, 4, 5, 6, 7, 8, 9, or 10) other PARP proteins.

By the term "poly-ADP-ribose glycolase" or "PARG" is meant any enzyme that has the ability to remove an ADP-ribose attached to a substrate (e.g., a protein, RNA molecule, DNA molecule, or lipid) or to remove one or more ADP-ribose molecules from a pre-existing poly-ADP-ribose molecule covalently attached to a substrate (e.g., a protein, RNA molecule, DNA molecule, or lipid). For example, a PARG may be one or more nucleic acids containing a sequence having at least 80% identity (e.g., at least 85%, 90%, 95%, 96%, 97%, 98%, 99%, or even 100%) to PARG (SEQ ID NO: 42) or ARH3 (SEQ ID NO: 41), or one or more polypeptides encoded by these nucleic acids. A PARG may have additional biological activities, such as decreasing (e.g., by at least 10%, 20%, 30%, 40%, 50%, 60%, 70%, 80%, 90%, 95%, or even 100%) the formation or rate of formation of a stress granule in a cell or increasing the rate of disassembly of a stress granule. The term PARG also includes the isoforms of PARG proteins described in Meyer-Ficca et al., *Exp. Cell. Res.* 297(2):521-532, 2004.

By the term "PARG protein" or "poly-ADP-ribose glycolase protein" is meant is meant a polypeptide encoded by a nucleic acid containing a sequence having at least 80% sequence identity (e.g., at least 85%, 90%, 95%, 96%, 97%, 98%, 99%, or even 100% identical) to the sequence of SEQ ID NO: 42.

By the term "PARG fusion protein" or "poly-ADP-ribose glycolase fusion protein" is meant a polypeptide containing a polypeptide tag and a sequence encoded by a nucleic acid containing a sequence having at least 80% sequence identity (e.g., at least 85%, 90%, 95%, 96%, 97%, 98%, 99%, or even 100% identity) to PARG (SEQ ID NO: 42). The polypeptide tag of a PARG fusion protein may be located at the N- and/or C-terminus of the protein. The polypeptide tag may contain one or more of a fluorescent protein (e.g., a green fluorescence protein), a peptide epitope recognized by specific antibodies, a protein that is bound by a partner binding protein with high affinity (e.g., biotin and streptavidin), a $His_6$-tag, or one or more (e.g., 1, 2, 3, 4, 5, 6, or 7) protease recognition sequence(s) (e.g., one or more of a TEV protease or Factor Xa protease recognition sequence). PARG fusion proteins may be purified using antibodies specific for the polypeptide tag. For example, antibodies specific for the polypeptide tag or proteins that bind specifically to the protein sequence in the polypeptide tag may bound to a bead (e.g., a magnetic bead) or polymer surface in order to allow for the purification of the PARG fusion protein. A PARG fusion protein may also be purified and subsequently treated with one or more (e.g., 1, 2, or 3) protease(s) to remove the polypeptide tag from the PARG fusion protein. A PARG fusion protein preferably has the same cellular localization and biological activity as the wild-type PARG protein. Methods for the generation and purification of PARG fusion proteins are described herein.

By the term "poly-ADP-ribose glycolase activator" or "PARG activator" is meant an agent that increases (e.g., at least 10%, 20%, 30%, 40%, 50%, 60%, 70%, 80%, 90%, or even 100%) the expression (e.g., protein and/or mRNA level) or one or more (e.g., 1, 2, 3, 4, or 5) biological activities of one or more (e.g., 1, 2, 3, 4, 5, 6, 7, 8, 9, or 10) PARG proteins. For example, a PARG activator may increase the levels of one or more (e.g., 1, 2, 3, 4, 5, 6, 7, 8, 9, or 10) nucleic acids containing a nucleic acid sequence having at least 80% sequence identity (e.g., at least 85%, 90%, 95%, 96%, 97%, 98%, 99%, or even 100%) to PARG (SEQ ID NO: 42) or ARH3 (SEQ ID NO: 41), or increase the level of one or more (e.g., 1, 2, 3, 4, 5, 6, 7, 8, 9, or 10) polypeptides encoded by these nucleic acids. A PARG activator may increase one or more of the biological activities of a PARG including the ability to remove a ADP-ribose attached to a substrate (e.g., a protein, RNA molecule, DNA molecule, lipid, or small molecule), the ability to remove one or more ADP-ribose molecules from a pre-existing poly-ADP-ribose molecule covalently attached to one or more substrate(s) (e.g., a protein, RNA molecule, DNA molecule, lipid, or small molecule), the ability to decrease or prevent the formation or the rate of formation of a stress granule in a cell, or the ability to increase the rate of disassembly of a stress granule. Non-limiting examples of PARG activators include one or more nucleic acids containing a nucleic acid having at least 80% sequence identity (e.g., at least 85%, 90%, 95%, 96%, 97%, 98%, 99%, or even 100%) to PARG (SEQ ID NO: 42) or ARH3 (SEQ ID NO: 41).

By the term "poly-ADP-ribose glycolase inhibitor" or "PARG inhibitor" is meant an agent that decreases (e.g., at least 10%, 20%, 30%, 40%, 50%, 60%, 70%, 80%, 90%, or even 100%) the expression (e.g., protein and/or mRNA level) or one or more (e.g., 1, 2, 3, 4, or 5) biological activities of one or more (e.g., 1, 2, 3, 4, 5, 6, 7, 8, 9, or 10) PARGs. For example, a PARG inhibitor may decrease the levels of one or more (e.g., 1, 2, 3, 4, 5, 6, 7, 8, 9, or 10) nucleic acids containing a nucleic acid sequence having at least 80% sequence identity (e.g., at least 85%, 90%, 95%, 96%, 97%, 98%, 99%, or even 100%) to PARG (SEQ ID NO: 42) or ARH3 (SEQ ID NO: 41), or decrease the level of one or more (e.g., 1, 2, 3, 4, 5, 6, 7, 8, 9, or 10) polypeptides encoded by these nucleic acids. A PARG inhibitor may decrease one or more (e.g., 1, 2, 3, 4, or 5) of the biological activities of a PARG including, but not limited to, the ability to remove a ADP-ribose attached to one or more substrate(s) (e.g., a protein, RNA molecule, DNA molecule, lipid, or small molecule), the ability to remove one or more ADP-ribose molecules from a pre-existing poly-ADP-ribose molecule covalently attached to a substrate (e.g., a protein, RNA molecule, DNA molecule, lipid, or small molecule), the ability to decrease or prevent the formation or the rate of formation of a stress granule in a cell, or the ability to increase the rate of disassembly of a stress granule. Non-limiting examples of PARG inhibitors include antibodies or antibody fragments that specifically bind to PARG protein, ARH3 protein, PARG fusion protein, or ARH3 fusion protein; RNAi molecules (e.g., a nucleic acid sequence that contains the sequence of one of SEQ ID NOS: 34-37), or small molecules.

By the term "peptide fragment" is meant a protein having at least 2 amino acids (e.g., at least 5, 10, 15, 20, 25, 30, 35, 40, 45, 50, 55, 60, 65, 70, 75, 80, 85, 90, 95, or 100 amino acids), but having fewer amino acids than the wild-type protein. Non-limiting examples of peptide fragments have between 2 to 250 amino acids, 5 to 200 amino acids, between 5 to 150 amino acids, or between 5 to 100 amino acids. A peptide fragment may also represent a protein that has been processed to remove one or more (e.g., 1, 2, or 3) post-translational targeting sequences (e.g., nuclear localization sequence, ER signal peptide, mitochondrial targeting signal, nuclear export sequence, or N-terminal secretion sequence).

By "poly-ADP ribose polymerase nucleic acid" or "PARP nucleic acid" is meant any nucleic acid containing a sequence that has at least 80% sequence identity (e.g., at least 85%, 90%, 95%, 96%, 97%, 98%, 99%, or even 100% sequence identity) to one or more of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). A PARP nucleic acid encodes a protein that has a catalytic activity of attaching an ADP-ribose to a substrate (e.g., protein, DNA, RNA, lipid, or small molecule) or attaching one or more ADP-ribose molecules to an ADP-ribose molecule already attached to the substrate (e.g., protein, DNA, RNA, lipid, or small molecule) to create poly-ADP ribose. A PARP nucleic acid may encode a protein having additional activities to those described above (e.g., mediates increased stress granule formation, role in progression through mitosis or cytokinesis, and modulation (e.g., increase or decrease) of RNAi function).

By "poly-ADP ribose polymerase protein" or "PARP protein" is meant polypeptide containing a sequence having at least 80% identity (e.g., at least 85%, 90%, 95%, 96%, 97%, 98%, 99%, or even 100% identity) to a protein encoded by a nucleic acid sequence containing the sequence of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). A PARP protein may contain one or more (e.g., 1, 2, 3, 4, 5, 6, 7, 8, 9, or 10) post-translational modifications, e.g., phosphorylation and ADP-ribosylation (e.g., at least 1, 2, 3, 4, 5, 6, 7, 8, 9, or 10 ADP-ribose molecules) on one or more amino acid residues. Post-translation modification of a PARP protein may occur within a cell (e.g., a transgenic cell described above) or in vitro using purified enzymes. PARP protein activity assays may be performed as described herein.

By "poly-ADP ribose polymerase fusion protein" or "PARP fusion protein" is meant a polypeptide containing a polypeptide tag and a sequence having at least 80% identity (e.g., at least 85%, 90%, 95%, 96%, 97%, 98%, 99%, or even 100% identity) to a protein encoded by one or more of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). The polypeptide tag of a PARP fusion protein may be located at the N- and/or C-terminus of the protein. The polypeptide tag may contain one or more of a fluorescent protein (e.g., a green fluorescence protein), a peptide epitope recognized by specific antibodies, a protein that is bound by a partner binding protein with high affinity (e.g., biotin and streptavidin), a $His_6$-tag, or one or more (e.g., 1, 2, 3, 4, 5, 6, or 7) protease recognition sequence(s) (e.g., one or more of a TEV protease or Factor Xa protease recognition sequence). The PARP fusion proteins of the invention may be purified using antibodies specific for the polypeptide tag. For example, antibodies specific for the polypeptide tag or proteins that bind specifically to the protein sequence in the polypeptide tag may be bound to a bead (e.g., a magnetic bead) or polymer surface in order to allow for the purification of the PARP fusion protein. A PARP fusion protein may also be purified and subsequently treated with one or more (e.g., 1, 2, or 3) protease(s) to remove the polypeptide tag from the PARP fusion protein. A PARP fusion protein preferably has the same cellular localization and biological activity as the wild-type PARP protein. Methods for the generation and purification of PARP fusion proteins are described herein.

By "PARP13.1" is meant one or more nucleic acid(s) containing a sequence having at least 80% identity (e.g., at least 85%, 90%, 95%, 96%, 97%, 98%, 99%, or even 100%) to PARP13.1 (SEQ ID NO: 19), or one or more polypeptides encoded by one or more of these nucleic acids.

By "PARP activator" or "poly-ADP-ribose polymerase activator" is meant an agent that increases the expression (e.g., mRNA and/or protein level) and/or one or more (e.g., 1, 2, 3, 4, 5, 6, 7, 8, 9, or 10) biological activities of one or more PARPs. For example, a PARP activator may increase the level of one or more (e.g., 1, 2, 3, 4, 5, 6, 7, 8, 9, 10, 11, 12, 13, 14, 15, 16, 17, 18, 19, or 20) PARP nucleic acids or PARP proteins (described above). A PARP activator may increase one or more biological activities of a PARP protein including, but not limited to, the ability to attach a poly-ADP-ribose molecule to one or more substrate(s) (e.g., a protein, DNA molecule, RNA molecule, lipid, or small molecule), the ability to promote formation of a stress granule, the ability to nucleate the formation of a stress granule, the ability to disassemble a stress granule, the ability to decrease stress granule assembly, the ability to localize to a stress granule, the ability of a PARP protein to bind to one or more of its substrates, the ability of a PARP protein to localize to the nucleus or the mitotic spindle, the ability to promote cell proliferation, the ability to promote progression through cytokinesis, and the ability to inhibit the activity of an RNAi in a cell. Specific PARP activators include nucleic acids encoding one or more (e.g., 1, 2, 3, 4, 5, 6, 7, 8, 9, 10, 11, 12, 13, 14, 15, 16, 17, 18, 19, or 20) PARPs or the catalytic domains of one or more PARPs. For example, a PARP activator may be a nucleic acid containing a nucleic acid sequence having at least 80% sequence identity (e.g., at least 85%, 90%, 95%, 96%, 97%, 98%, 99%, or even 100%) to PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6

(SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), and PARP16 (SEQ ID NO: 24). Specific PARP activators may increase the expression and/or one or more (e.g., 1, 2, 3, 4, or 5) biological activities of a specific PARP or a specific subset of PARPs (e.g., one or more of PARP5A, PARP12, PARP13.1, PARP13.2, and PARP15; PARP11; and one or more of PARP1, PARP2, PARP5A, PARP5B, PARP7, PARP8, PARP14, and PARP16).

By "PARP inhibitor" or "poly-ADP-ribose polymerase inhibitor" is meant an agent that decreases the expression (e.g., mRNA or protein level) and/or one or more (e.g., 1, 2, 3, 4, 5, 6, 7, 8, 9, or 10) biological activities of one or more PARPs. For example, a PARP inhibitor may decrease the level of one or more (e.g., 1, 2, 3, 4, 5, 6, 7, 8, 9, 10, 11, 12, 13, 14, 15, 16, 17, 18, 19, or 20) PARP nucleic acids or PARP proteins (described above). A PARP inhibitor may decrease one or more (e.g., 1, 2, 3, 4, or 5) biological activities of a PARP protein including, but not limited to, the ability to attach a poly-ADP-ribose molecule to a substrate (e.g., a protein, DNA molecule, RNA molecule, lipid, or small molecule), the ability to promote formation of a stress granule, the ability to nucleate the formation of a stress granule, the ability to disassemble a stress granule, the ability to decrease stress granule assembly, the ability to localize to a stress granule, the ability of a PARP protein to bind to one or more of its substrates, the ability of a PARP protein to localize to the nucleus or the mitotic spindle, the ability to promote cell proliferation, the ability to promote progression through cytokinesis, and the ability to inhibit the activity of an RNAi in a cell. Specific PARP inhibitors include antibody or antibody fragments that specifically bind one or more PARP proteins (e.g., an antibody or antibody fragment that binds to PARP13.1), one or more RNA aptamers (e.g., RNAi molecules; e.g., SEQ ID NOS: 40 and 43-136), and one or more small molecules. Specific PARP inhibitors may decrease the expression and/or one or more biological activities (e.g., 1, 2, 3, 4, or 5) of a specific PARP or a specific subset of PARPs (e.g., one or more (e.g., 1, 2, 3, 4, or 5) of PARP5A, PARP12, PARP13.1, PARP13.2, and PARP15; PARP 11; PARP13.1; and one or more (e.g., 1, 2, 3, 4, 5, 6, 7, or 8) of PARP 1, PARP2, PARP5A, PARP5B, PARP7, PARP8, PARP14, and PARP16).

By "PARP biological activity" is meant one or more (e.g., 1, 2, 3, 4, or 5) of the ability of a PARP protein or PARP fusion protein to catalyze the attachment of a single ADP-ribose to a target substrate (e.g., a protein, DNA, RNA, lipid, or small molecule), the ability to attach one or more ADP-ribose molecules to a ADP-ribose molecule already attached to a substrate, the ability to add a branched ADP-ribose molecule to a pre-existing poly-ADP-ribose, the ability to localize to the cell nucleus, the ability to localize to stress granules, the ability to catalyze the formation or nucleate stress granules, the ability to catalyze the disassembly of stress granules, the ability to promote cell division or progression through mitosis, and the ability to activate or inhibit RNAi activity in the cell. Specific PARP proteins have a different subset of biological activities. For example, PARP1, PARP2, PARP5A, PARP5B, PARP7, PARP8, PARP14, and PARP16 have the ability to localize to the nucleus and play a role in mitosis and cell division. PARP 5A, PARP12, PARP13.1, PARP13.2, and PARP15 have the ability to localize to stress granules and play a role in the formation or nucleation of stress granules. PARP11 has the ability to localize to stress granules and plays a role in inhibiting stress granule formation or increasing the disassembly of stress granules. PARP13 inhibits the activity of RNAi in the cell. An additional PARP activity is "auto-modification" or "auto-modulation," that is, attachment of one or more ADP-ribose molecules to itself. Such auto-modulation of a PARP protein may result in an increase or decrease in any of the above-listed PARP activities. Assays for the measurement of the activity of each specific PARP are described herein.

By "polypeptide tag" is meant a protein sequence that is located at the 5' and/or 3' end of a polypeptide sequence of an expressed protein (e.g., one or more PARP proteins as described herein). A polypeptide tag may include one or more of a protease recognition sequence (e.g., 1, 2, 3, 4, 5, or 6 of the same or different protease recognition sequences), a epitope tag (e.g., 1, 2, 3, 4, or 5 epitope tags), a peptide that has a high affinity binding partner (e.g., biotin and streptavidin), or one or more (e.g., 1, 2, 3, or 4) tag(s) which aids in protein purification (e.g., a $His_6$ tag). The polypeptide tag may later be cleaved from the purified fusion protein by incubation with one or more (e.g., 1, 2, 3, or 4) protease(s) which cleaves the fusion protein at one or more protease recognition sequence(s) (e.g., 1, 2, 3, 4, 5, 6, or 7) within the sequence of the polypeptide tag. Examples of polypeptide tags are described herein.

By "positioned 3" is meant a second nucleic acid sequence that is located after the 3' terminus of a first nucleic acid sequence (the second nucleotide sequence starts at the nucleotide following the 3' terminus of the first sequence) or the second nucleic acid sequence begins at a nucleotide that follows the 3' terminus of the first nucleic acid (e.g., the second nucleotide sequence starts at least 1, 2, 3, 4, 5, 6, 7, 8, 9, 10, 15, 20, 25, 30, 35, 40, 45, 50, 60, 70, 80, 90, 100, 200, 300, or 400 nucleotides following the 3' terminus of the first nucleic acid).

By "positioned 5" is meant a second nucleic acid sequence that is located before the 5' terminus of a first nucleic acid sequence (the second nucleotide sequence ends at the nucleotide preceding the 5' terminus of the first sequence) or the second nucleic acid sequence ends at a nucleotide that precedes the 5' terminus of the first nucleic acid (e.g., the second nucleotide sequence ends at least 1, 2, 3, 4, 5, 6, 7, 8, 9, 10, 15, 20, 25, 30, 35, 40, 45, 50, 60, 70, 80, 90, 100, 200, 300, or 400 nucleotides before the 5' terminus of the first nucleic acid).

By the term "propensity to develop disease" is meant the calculated probability of a subject (e.g., a human) to develop a disease (e.g., a stress granule-related disorder or cancer). The probability of developing a disease may be calculated based on a number of factors including a variety of health indicators (e.g., blood pressure, cholesterol, and levels of pro-inflammatory cytokines), biological factors (e.g., weight, age, and sex), and genetic susceptibility to disease (e.g., expression of a heritable mutation in a gene, expression of a polymorphic sequence associated with a disease, and expression of an allele associated with a disease). The propensity to develop disease in a specific patient population may be compared to a different patient population (e.g., a patient population not receiving a therapy).

By the term "protease recognition sequence" is meant a short peptide sequence that is recognized as a substrate and cleaved by one or more (e.g., 1, 2, 3, 4, or 5) proteases. Protease target sequences are often 3-20 amino acids in length and often require certain amino acids to be located at specific positions within the target sequence, while any amino acid may be placed at other positions within the target sequence. For example, the protease recognition sequence for TEV protease is Glu-X-X-Tyr-X-Gln-Ser (SEQ ID NO: 26), where X represents a position that may be filled by any amino acid. Additional examples of protease recognition sequences are known in the art and include, without limitation, factor Xa (Ile-Glu/Asp-Gly-Arg), Ala-64 subtilisin (Gly-Ala-His-Arg), clostripain (Arg and Lys-Arg), collagenase (Pro-Val-Gly-Pro), enterokinase (Asp-Asp-Asp-Asp-Lys), renin (Pro-Phe-His-Leu-Leu), and α-thrombin (Leu-Val-Pro-Arg-Gly-Ser). One or more of the same or different protease recognition sequence(s) may be included in the polypeptide tag of any of the PARP, PARG, or ARH3 fusion proteins described herein. A protease recognition sequence may be placed 5' or 3' to an amino acid sequence to be removed from the protein. The polypeptide sequence of the protease recognition sequence may directly abut the sequence encoding a PARP or may be separated from the remaining coding sequence by one or more amino acids (e.g., 1, 2, 3, 4, 5, 6, 7, 8, 9, 10, 11, 12, 13, 14, 15, 16, 17, 18, 19, 20, 25, 30, 40, or 50 amino acids). An amino acid sequence that may be removed from the protein may include one or more antigenic sequence(s), a $His_6$-tag, a fluorescent protein, a peptide sequence that has high affinity to a second protein that was used to purify the protein (e.g., $His_6$ tag or hemagglutinin tag), or a peptide sequence that was used to stabilize the protein during purification (e.g., albumin).

By the term "purified" is meant purified from other common components normally present within the cell. For example, a purified protein is purified away from the other cellular proteins, nucleic acids, and small metabolites present within the cell. A purified protein is at least 85% pure by weight (e.g., at least 90%, 95%, 96%, 97%, 98%, 99%, or even 100% pure) from other proteins, nucleic acids, or small metabolites present in the cell. A purified nucleic acid is at least 85% free of other contaminating nucleic acid molecules or adjoining sequences found in the cell.

By the term "inhibitory RNA" or "RNAi" is meant a short double-stranded RNA molecule that mediates the down-regulation of a target mRNA in a cell. An RNAi molecule is typically 15 to 32 nucleotides in length. RNAi molecules are also known as siRNAs, small RNAs, or microRNAs. The design and therapeutic effectiveness of RNAi molecules is described in McCaffrey et al. (Nature 418:38-39, 2002). The RNAi molecules are at least 15 nucleotides, preferably, 17, 18, 19, 20, 21, 22, 23, 24, 25, 26, 27, 28, 29, 30, 31, 32, 33, 34, or nucleotides in length and even up to 50 or 100 nucleotides in length (inclusive of all integers in between). Non-limiting examples of RNAi molecules are at least 80% identical (e.g., at least 85%, 90%, 95%, 96%, 97%, 98%, 99%, or even 100% identical) to or complementary to the translational start sequence or the nucleic acid sequence encoding the first 10, 20, 30, 40, 50, 60, 70, 80, 90, or 100 amino acids of a PARP, PARG, or ARH3 selected from a nucleic acid sequence containing a sequence at least 80% identical to one of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), PARP16 (SEQ ID NO: 24), PARG (SEQ ID NO: 42), or ARH3 (SEQ ID NO: 41). An RNAi molecule may target any part of the sequence encoding the target protein (e.g., any part of an mRNA encoding one of the above listed PARP, PARG, or ARH3 proteins). Additional examples of RNAi molecules are described herein (e.g., RNAi molecules that reduce the expression of PARP13.1; SEQ ID NOS: 40 and 106-112).

The specific requirements and modifications of small RNA are known in the art and are described, for example in PCT Publication No. WO01/75164, and U.S. Application Publication Nos. 20060134787, 20050153918, 20050058982, 20050037988, and 20040203145, the relevant portions of which are herein incorporated by reference. siRNAs can also be synthesized or generated by processing longer double-stranded RNAs, for example, in the presence of the enzyme dicer under conditions in which the dsRNA is processed to RNA molecules of about 17 to about 26 nucleotides. siRNAs can also be generated by expression of the corresponding DNA fragment (e.g., a hairpin DNA construct). Generally, the siRNA has a characteristic 2- to 3-nucleotide 3' overhanging ends, preferably these are (2'-deoxy) thymidine or uracil. The siRNAs typically comprise a 3' hydroxyl group. Single-stranded siRNAs or blunt-ended dsRNA may also be used. In order to further enhance the stability of the RNA, the 3' overhangs may be stabilized against degradation. For example, the RNA may be stabilized by including purine nucleotides, such as adenosine or guanosine. Alternatively, substitution of pyrimidine nucleotides by modified analogs, e.g., substitution of uridine 2-nucleotide overhangs by (2'-deoxy)thymidine is tolerated and does not affect the efficiency of RNAi. The absence of a 2' hydroxyl group significantly enhances the nuclease resistance of the overhang in tissue culture medium.

siRNA molecules can also be obtained through a variety of protocols including chemical synthesis or recombinant production using a Drosophila in vitro system. They can be commercially obtained from companies such as Dharmacon Research Inc. or Xeragon Inc., or they can be synthesized using commercially available kits such as the Silencer™ siRNA Construction Kit from Ambion (catalog number 1620) or HiScribe™ RNAi Transcription Kit from New England BioLabs (catalog number E2000S).

Alternatively siRNA can be prepared using standard procedures for in vitro transcription of RNA and dsRNA annealing procedures such as those described in Elbashir et al. (Genes & Dev., 15:188-200, 2001), Girard et al. (Nature 442:199-202, 2006), Aravin et al. (Nature 442:203-207, 2006), Grivna et al. (Genes Dev. 20:1709-1714, 2006), and Lau et al. (Science 313:305-306, 2006). siRNAs may also be obtained by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the small RNAs.

Short hairpin RNAs (shRNAs), as described in Yu et al. (Proc. Natl. Acad. Sci. U.S.A. 99:6047-6052, 2002) or Paddison et al. (Genes & Dev. 16:948-958, 2002), incorporated herein by reference, may also be used. shRNAs are designed such that both the sense and antisense strands are included within a single RNA molecule and connected by a loop of nucleotides (3 or more). shRNAs can be synthesized and purified using standard in vitro T7 transcription synthesis as described above and in Yu et al. (supra). shRNAs can also be subcloned into an expression vector that has the mouse U6 promoter sequences which can then be transfected into cells and used for in vivo expression of the shRNA.

A variety of methods and reagents are available for transfection, or introduction, of dsRNA into mammalian cells including but not limited to: TranIT-TKO™ (Mirus, Cat. # MIR 2150), Transmessenger™ (Qiagen, Cat. # 301525), Oligofectamine™ and Lipofectamine™ (Invitrogen, Cat. # MIR 12252-011 and Cat. #13778-075), siPORT™ (Ambion, Cat. #1631), and DharmaFECT™ (Fisher Scientific, Cat. # T-2001-01). Agents are also commercially available for electroporation-based methods for transfection of siRNA, such as siPORTer™ (Ambion Inc. Cat. # 1629). Microinjection techniques can also be used. The small RNA can also be transcribed from an expression construct introduced into the cells, where the expression construct includes a coding sequence for transcribing the small RNA operably-linked to one or more transcriptional regulatory sequences. Where desired, plasmids, vectors, or viral vectors can also be used for the delivery of dsRNA or siRNA and such vectors are known in the art. Protocols for each transfection reagent are available from the manufacturer. Additional methods are known in the art and are described, for example in U.S. Patent Application Publication No. 20060058255.

By the term "RNAi activity" is meant the ability of an inhibitory RNAi molecule, containing a sequence that is complementary or identical to a sequence present in one or more target mRNA molecules, to degrade, reduce the level, or catalyze the hydrolysis or cleavage of the one or more target mRNA molecules.

By the term "specifically binds" is meant a protein, nucleic acid (e.g., DNA or RNA), or molecule that binds one or more target molecules (e.g., polypeptides, DNA molecules, or RNA molecules) present in a cell, while not binding the majority of other proteins, DNA molecules, RNA molecules, or small molecules present within a cell, cell lysate, extracellular medium, or biological sample. For example, an antibody provided by the invention may bind to a single PARP (e.g., PARP13.1), PARG, or ARH protein, a PARP, PARG, or ARH3 fusion protein, or may bind more than one (e.g., 2, 3, 4, 5, 6, 7, 8, 9, 10, 11, 12, 13, 14, 15, 16, 17, 18, 19, or 20 or more) PARP, PARG, or ARH3 proteins and/or PARP, PARG, or ARH3 fusion proteins in a cell, cell lysate, extracellular medium, or biological sample.

By "substrate" or "solid surface" is meant a surface on which a moiety or protein is covalently attached which allows for the binding and/or purification of a PARP, PARG, and/or ARH3 fusion protein. The PARP, PARG, and/or ARH3 fusion protein will bind to the substrate or solid surface through its polypeptide tag. Moieties or peptides covalently attached to the substrate or solid surface include, but are not limited to, monoclonal or polyclonal antibodies specific for an antigenic peptide in the polypeptide tag (e.g., anti-GFP antibody binding to GFP in the polypeptide tag), specific metal complexes bound by a peptide located in the polypeptide tag (e.g., $Ni^+$ binding to a $His_6$ polypeptide tag), or a specific binding protein for a peptide located in the polypeptide tag (e.g., IgG binding to a ZZ-domain in the polypeptide tag). Examples of a substrate or solid surface include, but are not limited to, a bead (e.g., a magnetic bead), a surface in a multi-well plate, and beads in column (e.g., column chromatography). One or more PARP, PARG, and/or ARH3 protein(s) and/or PARP, PARG, and/or ARH3 fusion protein(s) may be bound to a substrate or solid surface and eluted from the substrate or solid surface by contacting the substrate or solid surface with an elution buffer (e.g., a high salt elution buffer), a ligand that competes for binding to the substrate or solid surface, or competes for binding to the polypeptide tag (e.g., a non-bound antibody that specifically binds to the protein in the polypeptide tag), or by treating the bound fusion protein with a protease that recognizes the one or more (e.g., 1, 2, 3, 4, 5, 6, or 7) specific cleavage recognition sequence(s) found in the polypeptide tag.

By the term "target protein" or "substrate protein" is meant a protein that is bound by one or more (e.g., 1, 2, 3, 4, or 5) PARP protein(s), PARG protein(s), ARH3 protein(s), PARP fusion protein(s), PARG fusion protein(s), and/or ARH3 fusion protein(s); covalently modified by attachment of a ADP-ribose molecule by the activity of one or more (e.g., 1, 2, 3, 4, or 5) PARP protein(s) or PARP fusion protein(s); or contains a poly-ADP-ribosyl group that is hydrolyzed by the activity of one or more (e.g., 1, 2, 3, 4, or 5) PARG proteins, PARG fusion proteins, ARH3 proteins, or ARH3 fusion proteins. A target or substrate protein may be co-localized in the nucleus or in a stress granule, and/or may localize to the mitotic spindle during cytokinesis. A target protein or substrate protein may localize to different structures or organelles within a cell during different stages of the cell cycle (e.g., interphase, S-phase, prophase, metaphase, telephase, and anaphase) and may have an activity in the formation, nucleation, or disassembly of stress granules, an activity in cell proliferation or progression through cytokinesis, an activity in the regulation of RNAi activity, or an activity in the processing of an RNAi in a cell. A target or substrate protein may be a PARP, PARG, or ARH3 protein (described herein) or may be any other substrate protein (e.g., a protein implicated for a role in a disease or any other protein targeted to knockdown).

Specific examples of PARP substrates include proteins involved in the activity or processing of RNAi molecules in a cell. For example, one substrate of PARP13.1 is Argonaut 2, a protein involved in the processing of RNAi molecules in mammalian cells. Additional examples of PARP substrate proteins may be involved in the formation of protein/RNA complexes involved in the processing of RNAi molecules, the degradation of target mRNA molecules, the regulation in the formation of protein/RNA complexes involved in the processing of RNAi molecules, or the regulation of the processing of RNAi molecules within cells.

By the term "transgenic cell" is a meant a cell expressing one or more nucleic acids introduced by recombinant DNA technology. For example, a transgenic cell may express a nucleic acid encoding one or more (e.g., 1, 2, 3, 4, 5, 6, 7, 8, 9, 10, 11, 12, 13, 14, 15, 16, 17, or 18) of the presently described PARP, PARG, and/or ARH3 proteins and/or one or more of the PARP, PARG, and/or ARH3 fusion proteins. A transgenic cell may be a mammalian cell (e.g., a mouse, rat, monkey, or human cell), a bacterial cell, a fungal cell, a yeast cell, or a plant cell. The transgenic cell may express the introduced nucleic acids from an inducible promoter or a constitutive promoter. The transgenic cell may also be located within a transgenic animal or may be cultured in tissue culture. The introduced one or more nucleic acid(s) may be integrated in the chromosome of a cell or may be expressed from a plasmid.

By "ZZ-domain" is meant a polypeptide sequence encoded by a nucleic acid having at least 80% identity (e.g., at least 85%, 90%, 95%, 96%, 97%, 98%, 99%, or even 100% identity) to the *Staphylcoccus aureus* protein A domain encoded by SEQ ID NO: 27. The ZZ domain has the ability to bind to Fcγ (the constant region of IgG involved in effector functions) and Fab (the Ig fragment responsible for antigen recognition). The specific structure and binding properties of the ZZ-domain are described in Graille et al. (*Proc. Natl. Acad. Sci. U.S.A.* 97:5399-5404, 2000) and Roben et al. (*J. Immunol.*

154:6437-6445, 1995). Expression of the ZZ-domain in the polypeptide tag allows for the purification of a fusion protein (e.g., one or more PARP fusion proteins as described herein) by the use of an Fc-containing protein (e.g., IgG).

Other features and advantages of the invention will be apparent from the following description of the preferred embodiments thereof, and from the claims.

BRIEF DESCRIPTION OF THE DRAWINGS

The application file contains drawings executed in color (FIGS. 2, 5, 9-11, 16-18, and 20-22). Copies of this patent or patent application with color drawings will be provided by the Office upon request and payment of the necessary fee.

FIG. 26A is picture of an immunoblot of a 4-12% SDS-PAGE gel containing proteins immunoprecipitated with an anti-GFP antibody from lysate from HeLa S3 cells transfected with a pEGFP-C1 plasmid expressing TIA1-GFP, PABP-GFP, G3BP-GFP, or Ago2-GFP following treatment with 0 or 20 nM pateamine A for 30 minutes. The immunoblot was developed using a polyclonal anti-poly-ADP-ribose antibody.

FIG. 26B is a picture of an immunoblot of an SDS-PAGE gel containing proteins immunoprecipitated from lysate from untransfected HeLa S3 cells using anti-G3BP and anti-Ago2 antibodies following treatment with 0 or 250 µM sodium arsenite for 60 minutes. The immunoblot was developed using a polyclonal anti-poly-ADP-ribose antibody.

FIG. 26C is a picture of an immunoblot of an SDS-PAGE gel containing proteins immunoprecipitated from lysate from HeLa S3 cells transfected with a pEGFP-C1 plasmid expressing G3BP1-GFP (full-length), G3BP1-A-GFP (domain A), G3BP1-ABC-GFP (domains A, B, and C), G3BP1-BC-GFP (domains B and C), G3BP1-BCD-GFP (domains B, C, and D), and G3BP1-D-GFP (domain D) following treatment with 0 or 250 µM sodium arsenite for 60 minutes. The immunoblot was developed using a polyclonal anti-poly-ADP-ribose antibody.

FIG. 26D is a picture of an immunoblot of an SDS-PAGE gel containing proteins immunoprecipitated from lysate from HeLa S3 cells transfected with a pEGFP-C 1 plasmid expressing TIA1-GFP (full-length) or TIA1ΔRRM (mutant lacking RRM domain) following treatment with 0 or 250 µM sodium arsenite for 60 minutes. The immunoblot was developed using a polyclonal anti-poly-ADP-ribose antibody.

DETAILED DESCRIPTION

Figure 1:
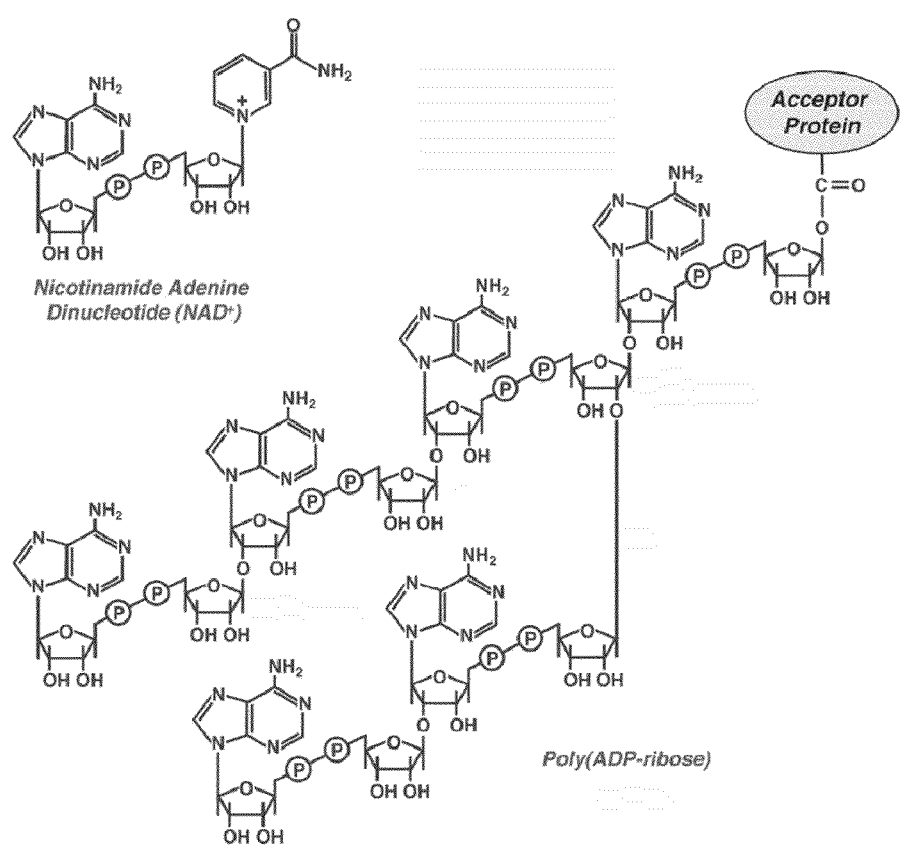
FIG. 1 is a picture of the chemical structure of nicotinamide adenine dinucleotide (NAD$^+$) and poly-ADP ribose.
Figure 2:
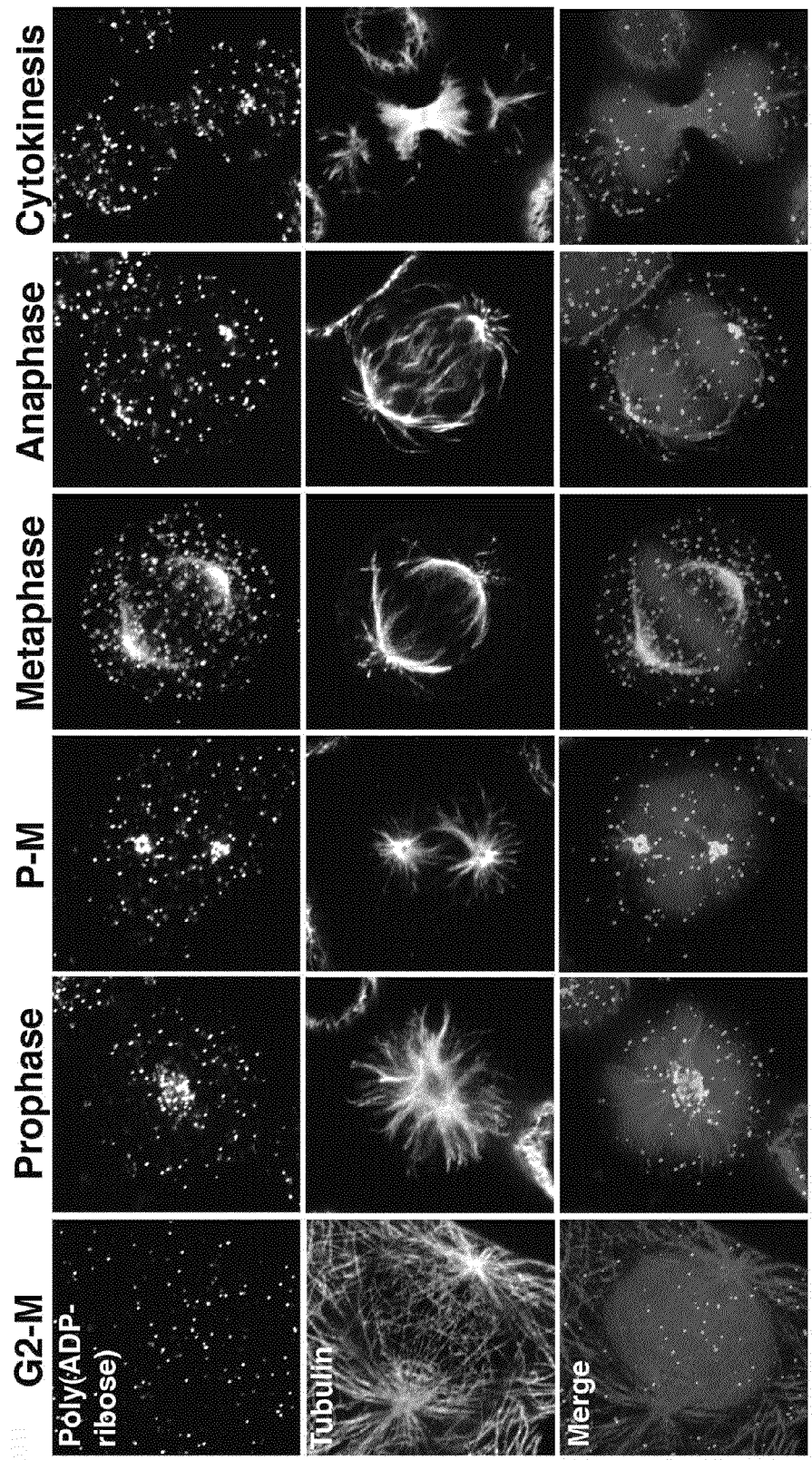
FIG. 2 is a set of micrographs showing the mitotic localization of poly-ADP ribose in HeLa cells during G2-M, prophase, prometaphase (P-M), metaphase, anaphase, and cytokinesis stages of the cell cycle using fluorescence microscopy following staining with rabbit anti-PAR antibodies labeled with Alexa 488 and X-rhodamine NHS esters.

We have discovered that specific PARP proteins (e.g., PARP13.1) and PARG have an effect on inhibitory RNA (RNAi) activity in a cell. The invention therefore provides methods, compositions, and kits for the modulating (e.g., increasing or decreasing) the activity of inhibitory RNA (RNAi) in a cell.

Methods for Increasing Inhibitory RNA Activity in a Subject, Cell, or Cell Population The inventions provides methods for increasing the RNAi activity in a subject requiring administering to the subject one or more (e.g., 1, 2, 3, 4, 5, 6, 7, 8, 9, or 10) PARP inhibitors (e.g., PARP13.1 inhibitors) and/or one or more (e.g., 1, 2, 3, 4, 5, 6, 7, 8, 9, or 10) PARG activators (e.g., PARG activators and/or ARH3 activators). In these methods, the one or more PARP inhibitor(s) desirably decreases (e.g., by at least 5%, 10%, 20%, 30%, 40%, 50%, 60%, 70%, 80%, 90%, 95%, 99%, or even 100%) the expression (e.g., protein and/or mRNA level) and/or one or more (e.g., 1, 2, 3, 4, or 5) activities of PARP13.1. For example, the one or more PARP inhibitor(s) may decrease the level of one or more (e.g., 1, 2, 3, 4, or 5) nucleic acid(s) comprising a nucleic acid sequence having at least 80% sequence identity (e.g., at least 85%, 90%, 95%, 99%, or even 100% identity) to PARP13.1 (SEQ ID NO: 19), or decrease the level of one or more polypeptides (e.g., 1, 2, 3, 4, or 5) encoded by one or more of these nucleic acid sequences. In additional examples of these methods, the one or more PARP13.1 activities is the poly-ADP-ribosylation of one or more (e.g., 1, 2, 3, 4, or 5) target proteins (e.g., a protein that regulates the activity or processing of RNAi in a cell, e.g., Argonaut 2).

Non-limiting examples of PARP13.1 inhibitors include antibodies and antibody fragments that selectively bind to PARP13.1 and/or PARP13.1 fusion proteins; one or more RNAi molecules containing a sequence complimentary to or identical to a sequence contained in SEQ ID NO: 19 (e.g., RNAi molecules containing the sequence of one of SEQ ID NOS: 40 and 106-112); or a small molecule identified using the screening assays described herein.

In different embodiments of this method, the one or more PARG activators selectively increase (e.g., by at least 5%, 10%, 20%, 30%, 40%, 50%, 60%, 70%, 80%, 90%, 95%, or 100%) the expression (e.g., protein and/or mRNA level) and/or one or more (e.g., 1, 2, 3, 4, or 5) activities of PARG and/or ARH3. In additional embodiments of this method, the increase (e.g., at least 5%, 10%, 20%, 30%, 40%, 50%, 60%, 70%, 80%, 90%, or 100%) in expression of PARG and/or ARH3 is an increase in the level of one or more (e.g., 1, 2, 3, 4, or 5) nucleic acid(s) comprising a sequence having at least 80% sequence identity (e.g., at least 85%, 90%, 95%, 99%, or even 100% identity) to PARG (SEQ ID NO: 42) or ARH3 (SEQ ID NO: 41), and/or an increase in the level of one or more (e.g., 1, 2, 3, 4, or 5) polypeptides encoded by one or more of these nucleic acids. In different examples of these methods, the one or more activities of PARG or ARH3 is the hydrolysis of poly-ADP-ribose (e.g., a poly-ADP-ribose molecule that is covalently attached to a substrate protein, e.g., a protein that regulates the activity or processing of RNAi in a cell (e.g., Argonaut 2)). Non-limiting examples of PARG activators include one or more nucleic acids containing a sequence that is at least 80% identical (e.g., at least 85%, 90%, 95%, 99%, or even 100% identical) to SEQ ID NO: 42 or SEQ ID NO: 41, or one or more polypeptides encoded by one or more of these nucleic acids.

In desirable embodiments of these methods, the administration of one or more (e.g., 1, 2, 3, 4, or 5) PARP inhibitors and/or one or more (e.g., 1, 2, 3, 4, or 5) PARG activators results in at least a 5% increase (e.g., at least 10%, 15%, 20%, 30%, 40%, 50%, 60%, 70%, 80%, 90%, 95%, or 100%) increase in the activity of a RNAi in a subject compared to a subject or a population of subjects not administered a PARP inhibitor and/or PARG activator.

The activity of an RNAi in a cell may be measured using methods known in the art and described herein. For example, the activity of a RNAi in a cell may be measured using the commercially available vectors: psiCHECK™-1, psiCHECK™-2, and pGL4.72[hRlucCP]™ vectors (Promega). The levels of an mRNA targeted by an RNAi in a cell may be measured using any method known in the art including, but not limited to, reverse-transcriptase PCR(RT-PCR) and real time quantitative RT-PCR. The level of RNAi activity in a cell may also be determined by measuring the levels of one or more proteins encoded by the mRNA targeted by a specific RNAi molecule. Methods for measuring the level of a specific protein are known in the art and include, but are not limited to, antibody-based techniques, such as immunoblotting, enzyme-linked immunoadsorbent assay (ELISA), and fluorescence-assisted cell sorting (FACS).

The methods of the invention may be used to decrease the amount of a therapeutic RNAi molecule administered to a subject (e.g., decrease the amount of one or more therapeutic RNAi molecules administered to achieve a therapeutic effect or increase the effectiveness of one or more therapeutic RNAi molecules administered to a subject). For example, one or more PARP inhibitors may be administered in combination (e.g., at the same time, during overlapping time periods, or non-overlapping time periods) with one or more therapeutic RNAi molecules to a subject. The one or more therapeutic RNA molecules may be administered to a subject using any method known in the art including non-infectious recombinant viral vectors (e.g., recombinant non-infectious retroviral or lentiviral vectors).

In one example, the one or more PARP inhibitors and/or one or more PARG activators may be administered together in a single dose or may be administered separately in one or more separate doses (e.g., 1, 2, 3, 4, 5, 6, 7, 8, 9, or 10 doses). The amount of one or more PARP inhibitors and/or one or more PARG activators that may be administered to a subject per dose may be between 10 ng and 1 mg, 100 ng and 1 mg, 500 ng and 1 mg, 1 µg and 1 mg, 10 µg and 1 mg, 100 µg and 1 mg, 500 µg and 1 mg, 500 µg and 5 mg, 0.1 mg and 1 g, 0.1 mg and 750 mg, 0.1 mg and 600 mg, 0.1 mg and 500 mg, 10 mg and 450 mg, 10 mg and 400 mg, 10 mg and 350 mg, 10 mg and 350 mg, and 10 mg and 250 mg. Various combinations of the one or more PARP inhibitors and/or one or more PARG activators are contemplated herein, for example, administration of one or more (e.g., 1, 2, 3, 4, 5, 6, 7, 8, 9, or 10) PARP inhibitors alone, administration of one or more (e.g., 1, 2, 3, 4, 5, 6, 7, 8, 9, or 10) PARG activators alone, and administration of one or more (e.g., 1, 2, 3, 4, or 5) PARP inhibitors and one or more (e.g., 1, 2, 3, 4, or 5) PARG activators together.

The one or more PARP inhibitors and/or one or more PARG activators may be administered to the subjects once a day, twice a day, three times a day, once a week, twice a week, three times a week, four times a week, five times a week, six times a week, seven times a week, bi-weekly, tri-weekly, or monthly. The one or more PARP inhibitors and/or one or more PARG activators may be administered via the same route of administration or via different routes of administration. For example, the one or more PARP inhibitors may be administered orally and the one or more PARG activators may be administered parenterally (e.g., subcutaneously). The one or more PARP inhibitors and/or one or more PARG activators may be formulated for any known route of administration, including oral, intravenous, intraarterial, intraocular, intranasal, intramuscular, and subcutaneous administration. The one or more PARP inhibitors and/or one or more PARG activators may also be formulated for administration in a sustained-release form. The therapeutically effective dose of the one or more PARP inhibitors and/or one or more PARG activators may be determined by a skilled physician using methods known in the art, in addition to the in vitro assays described herein.

The invention similarly provides methods of increasing (e.g., at least 5%, 10%, 15%, 20%, 30%, 40%, 50%, 60%, 70%, 80%, 90%, or 100%) the activity of an RNAi in a cell or a cell population by contacting the cell or cell population with an effective amount of one or more (e.g., 1, 2, 3, 4, or 5) PARP inhibitors and/or one or more (e.g., 1, 2, 3, 4, or 5) PARG activators (as described for the treatment of subjects above). In these methods, the one or more PARP inhibitors and/or one or more PARG activators are added to the tissue culture medium to increase (e.g., at least 10%, 20%, 30%, 40%, 50%, 60%, 70%, 80%, 90%, 95%, or 100%) the activity of one or more RNAi molecules in a cell or a cell population. Cells that may be treated using these methods include a mammalian cell (e.g., a human, mouse, rat, monkey, or rabbit cell) or a plant cell. Preferred mammalian cells that may be used in these methods include, without limitation, a fibroblast, endothelial cell, myocyte, neuron, hepatocyte, lymphocyte, myeloid cell, thyroid cell, osteocyte, adipocyte, tenocyte, chondrocyte, kidney cell, spermatocyte, oocyte, or sperm. The concentration of the one or more PARP inhibitors and/or the one or more PARG activators to be added to the culture medium may be determined using the methods described herein (e.g., methods for the measurement of RNAi activity).

Combination Therapy

As described above, a number of RNAi-based molecular therapies are presently being developed for humans. The one or more PARP inhibitors and/or one or more PARG activators may be administered to a subject with one or more additional RNAi-based molecular therapies (e.g., one or more RNAi molecules or recombinant viruses containing a sequence that encodes one or more RNAi molecules). The methods provided by the invention provide a means to increase the effectiveness of RNAi-based therapeutics administered or delivered to a subject and/or provide a means to decrease the amount of an RNAi-based therapeutic required to achieve a therapeutic result (e.g., a beneficial therapeutic effect) in a subject.

Pharmaceutical Compositions

The invention further provides pharmaceutical compositions for increasing (e.g., at least 5%, 10%, 15%, 20%, 30%, 40%, 50%, 60%, 70%, 80%, 90%, or 100%) the activity of one or more (e.g., 1, 2, 3, 4, or 5) RNAi molecules in a cell. For example, the compositions of the invention may include one or more (e.g., 1, 2, 3, 4, or 5) PARP inhibitors (e.g., PARP13.1 inhibitors) and/or one or more (e.g., 1, 2, 3, 4, or 5) PARG activators (e.g., PARG protein and ARH3 activators). The one or more PARP inhibitors and/or one or more PARG activators that may be used as pharmaceutical compositions for increasing the activity of one or more RNAi molecules may also be identified using the screening assays provided herein.

Examples of pharmaceutical compositions for increasing the activity of one or more RNAi molecules in a cell include one or more of an antibody or antibody fragment that specifically binds to PARP13.1; an RNAi molecule that decreases (e.g., at least 5%, 10%, 20%, 30%, 40%, 50%, 60%, 70%, 80%, 90%, 95%, or even 100%) the expression of PARP13.1 (e.g., an RNA molecule that includes one of the sequences of SEQ ID NOS: 40 and 106-112); one or more nucleic acids containing a sequence having at least 80% sequence identity (e.g., at least 85%, 90%, 95%, 96%, 97%, 98%, 99%, or even 100%) to PARG (SEQ ID NO: 42) or ARH3 (SEQ ID NO: 41); and one or more small molecules or metabolites identified in the screening assays provided herein. Specific PARP inhibitors that are RNAi molecules are shown in Table 1 below.

TABLE 1

| Specific PARP RNAi molecules | | |
|---|---|---|
| PARP1 | AAGCCUCCGCUCCUGAACAAU | SEQ ID NO: 43 |
| PARP2A | AAUCAGUGUAAUGAACUACUA | SEQ ID NO: 44 |
| PARP2B | AAUGAUUCAGCUAUUAGAAGA | SEQ ID NO: 45 |
| PARP3 | GGACCCAGGUGUAUGAGGACUACAA | SEQ ID NO: 46 |
| PARP4 | AAACAAGGAUUUCUACUAAGA | SEQ ID NO: 47 |
| PARP5A | AACAAUUCACCGUCGUCCUCU | SEQ ID NO: 48 |
| PARP5B | AAGCUUCAGAAUGGUGCAAAU | SEQ ID NO: 49 |
| PARP6 | CCCAACAAUGGAAACAUCUGAGCAA | SEQ ID NO: 50 |
| PARP6 | UUGCUCAGAUGUUUCCAUUGUUGGG | SEQ ID NO: 51 |
| PARP6 | GGUUCAAGGCAAGUGGUACCAUCAA | SEQ ID NO: 52 |
| PARP6 | UUGAUGGUACCACUUGCCUUGAACC | SEQ ID NO: 53 |
| PARP6 | CAAAGUGGAAGUGUUUGGCUACCCU | SEQ ID NO: 54 |
| PARP6 | AGGGUAGCCAAACACUUCCACUUUG | SEQ ID NO: 55 |
| PARP6 | CAGAACAGAGGAUUCCAACAUUGAA | SEQ ID NO: 56 |
| PARP6 | UUCAAUGUUGGAAUCCUCUGUUCUG | SEQ ID NO: 57 |
| PARP7 | UGAGGUCUUUGAGGCCAAUAUUAAA | SEQ ID NO: 58 |
| PARP7 | UUUAAUAUUGGCCUCAAAGACCUCA | SEQ ID NO: 59 |
| PARP7 | GACUUUCUGCAAGGCACUUGUAUUU | SEQ ID NO: 60 |
| PARP7 | AAAUACAAGUGCCUUGCAGAAAGUC | SEQ ID NO: 61 |
| PARP7 | UCCUCCACCUCUUGAAGCAACUUCA | SEQ ID NO: 62 |
| PARP7 | UGAAGUUGCUUCAAGAGGUGGAGGA | SEQ ID NO: 63 |
| PARP7 | AAUGAUGACCAGAGUUACCCUUAUU | SEQ ID NO: 64 |
| PARP7 | AAUAAGGGUAACUCUGGUCAUCAUU | SEQ ID NO: 65 |
| PARP8 | GGAAGAUUCUGAAGGUGACAAUGAU | SEQ ID NO: 66 |
| PARP8 | AUCAUUGUCACCUUCAGAAUCUUCC | SEQ ID NO: 67 |
| PARP8 | CCCACAACUGGAAGCUGAUUUGUCA | SEQ ID NO: 68 |
| PARP8 | UGACAAAUCAGCUUCCAGUUGUGGG | SEQ ID NO: 69 |
| PARP8 | GAAGUGGAAUCUAUCUUAGUCCAAU | SEQ ID NO: 70 |
| PARP8 | AUUGGACUAAGAUAGAUUCCACUUC | SEQ ID NO: 71 |
| PARP8 | GCCUUAUGUGAAGUGAUCACCUCAU | SEQ ID NO: 72 |

TABLE 1-continued

Specific PARP RNAi molecules

| | | |
|---|---|---|
| PARP8 | AUGAGGUGAUCACUUCACAUAAGGC | SEQ ID NO: 73 |
| PARP9 | GCCGGAGCAGCAGCUUACAAUGAAA | SEQ ID NO: 74 |
| PARP9 | UUUCAUUGUAAGCUGCUGCUCCGGC | SEQ ID NO: 75 |
| PARP9 | CCCUCUGAAUUUGUGUACAAAGACU | SEQ ID NO: 76 |
| PARP9 | AGUCUUUGUACACAAAUUCAGAGGG | SEQ ID NO: 77 |
| PARP9 | GGACCCUACUGUUGCUGCCUUUAAA | SEQ ID NO: 78 |
| PARP9 | UUUAAAGGCAGCAACAGUAGGGUCC | SEQ ID NO: 79 |
| PARP9 | UGGCAGACGGCAGAUGUAAUUGUUA | SEQ ID NO: 80 |
| PARP9 | UAACAAUUACAUCUGCCGUCUGCCA | SEQ ID NO: 81 |
| PARP10 | CAUGGUGCAGGGUAGAGGGAUUAUG | SEQ ID NO: 82 |
| PARP10 | CAUAAUCCCUCUACCCUGCACCAUG | SEQ ID NO: 83 |
| PARP10 | GCCUGGUGGAGAUGGUGCUAUUGAU | SEQ ID NO: 84 |
| PARP10 | AUCAAUAGCACCAUCUCCACCAGGC | SEQ ID NO: 85 |
| PARP10 | AGACGUCGCUCUCUUGCCACUUGAA | SEQ ID NO: 86 |
| PARP10 | UUCAAGUGGCAAGAGAGCGACGUCU | SEQ ID NO: 87 |
| PARP10 | UGGGCAGCAUUAGCUGCCAUGUGUU | SEQ ID NO: 88 |
| PARP10 | AACACAUGGCAGCUAAUGCUGCCCA | SEQ ID NO: 89 |
| PARP11 | CAACAAACAAUGAAGUGGAUGACAU | SEQ ID NO: 90 |
| PARP11 | AUGUCAUCCACUUCAUUGUUUGUUG | SEQ ID NO: 91 |
| PARP11 | CAGCCGGAUACCAACAGUCAGUGUU | SEQ ID NO: 92 |
| PARP11 | AACACUGACUGUUGGUAUCCGGCUG | SEQ ID NO: 93 |
| PARP11 | CAAACCCUUGUGGCUCCAUUUCUUU | SEQ ID NO: 94 |
| PARP11 | AAAGAAAUGGAGCCACAAGGGUUUG | SEQ ID NO: 95 |
| PARP11 | UGCCACCACACUGGGAGAAUGUGAA | SEQ ID NO: 96 |
| PARP11 | UUCACAUUCUCCCAGUGUGGUGGCA | SEQ ID NO: 97 |
| PARP12 | UCCACCUCUGCAGGUUCAUGGUCUA | SEQ ID NO: 98 |
| PARP12 | UAGACCAUGAACCUGCAGAGGUGGA | SEQ ID NO: 99 |
| PARP12 | UGCCAGAAAUUUGCCAACAUUACAA | SEQ ID NO: 100 |
| PARP12 | UUGUAAUGUUGGCAAAUUUCUGGCA | SEQ ID NO: 101 |
| PARP12 | GGUGAGCAGGCUGCCUACCAUUUAU | SEQ ID NO: 102 |
| PARP12 | AUAAAUGGUAGGCAGCCUGCUCACC | SEQ ID NO: 103 |
| PARP12 | AGGAUUUGGACAACAUGGAACUUAU | SEQ ID NO: 104 |
| PARP12 | AUAAGUUCCAUGUUGUCCAAAUCCU | SEQ ID NO: 105 |
| PARP13 | GCUGACCCAAGAGUAGCACUUGUUA | SEQ ID NO: 106 |
| PARP13 | UAACAAGUGCUACUCUUGGGUCAGC | SEQ ID NO: 107 |
| PARP13 | CCGGUGGCAGAUGCUUAUUGGUAAA | SEQ ID NO: 108 |
| PARP13 | UUUACCAAUAAGCAUCUGCCACCGG | SEQ ID NO: 109 |
| PARP13 | GCUCACGGAACUAUGAGCUGAGUUU | SEQ ID NO: 40 |
| PARP13 | AAACUCAGCUCAUAGUUCCGUGAGC | SEQ ID NO: 110 |
| PARP13 | UGCCUCAGUGGUAUGUGCAGCAGAU | SEQ ID NO: 111 |
| PARP13 | AUCUGCUGCACAUACCACUGAGGCA | SEQ ID NO: 112 |
| PARP14 | UGGCCUGUCUAAUGAUGACUUUCAA | SEQ ID NO: 113 |
| PARP14 | UUGAAAGUCAUCAUUAGACAGGCCA | SEQ ID NO: 114 |
| PARP14 | CCUGGUGCUGAUGACUACAGUUUAA | SEQ ID NO: 115 |
| PARP14 | UUAAACUGUAGUCAUCAGCACCAGG | SEQ ID NO: 116 |
| PARP14 | GCCACUUUCUGUGUUCCCAUACUAU | SEQ ID NO: 117 |
| PARP14 | AUAGUAUGGGAACACAGAAAGUGGC | SEQ ID NO: 118 |
| PARP14 | GAAGAGUCACUAGAUCUUCCCUUAU | SEQ ID NO: 119 |
| PARP14 | AUAAGGGAAGAUCUAGUGACUCUUC | SEQ ID NO: 120 |
| PARP15 | GAUGAAUUCACUAACUGGUCAAGAA | SEQ ID NO: 121 |
| PARP15 | UUCUUGACCAGUUAGUGAAUUCAUC | SEQ ID NO: 122 |
| PARP15 | CCUAUCACAGUUGCUGAUAACAUAA | SEQ ID NO: 123 |
| PARP15 | UUAUGUUAUCAGCAACUGUGAUAGG | SEQ ID NO: 124 |
| PARP15 | GGACUGACAUGAAUCAUCAGCUGUU | SEQ ID NO: 125 |
| PARP15 | AACAGCUGAUGAUUCAUGUCAGUCC | SEQ ID NO: 126 |
| PARP15 | CGAGUACUUACUGGAGUCUUCACAA | SEQ ID NO: 127 |
| PARP15 | UUGUGAAGACUCCAGUAAGUACUCG | SEQ ID NO: 128 |
| PARP16 | CAGUGCAGGGAAGGCAGAGUUUGAA | SEQ ID NO: 129 |
| PARP16 | UUCAAACUCUGCCUUCCCUGCACUG | SEQ ID NO: 130 |
| PARP16 | GAGACCAAAGGAGAACGAGACCUAA | SEQ ID NO: 131 |
| PARP16 | UUAGGUCUCGUUCUCCUUUGGUCUC | SEQ ID NO: 132 |
| PARP16 | GACUUGAGCCUGGCCCUCAUAUACA | SEQ ID NO: 133 |
| PARP16 | UGUAUAUGAGGGCCAGGCUCAAGUC | SEQ ID NO: 134 |
| PARP16 | CCCAAGUACUUCGUGGUCACCAAUA | SEQ ID NO: 135 |
| PARP16 | UAUUGGUGACCACGAAGUACUUGGG | SEQ ID NO: 136 |

The pharmaceutical compositions provided by the invention may further include one or more (e.g., 1, 2, 3, 4, 5, 6, 7, 8, 9, or 10) secondary agents. Non-limiting examples of secondary agents that may be included in the compositions of the invention are one or more chemotherapeutic agent(s), one or more non-steroidal anti-inflammatory drug(s), one or more immunosuppressive agent(s), one or more calcineurin inhibitor(s), or one or more analgesic(s). Examples of these classes of therapeutic agents are known in the art.

The dose of one or more secondary agents that may be included in the compositions of the invention may be between 0.1 mg and 2 g, 0.1 mg and 1.5 mg, 0.1 mg and 1 g, 0.1 mg and 750 mg, 1 mg and 650 mg, 1 mg and 550 mg, 1 mg and 500 mg, 10 mg and 450 mg, 10 mg and 400 mg, 10 mg and 350 mg, 10 mg and 350 mg, and 10 mg and 250 mg.

The compositions may be formulated using any known method including formulation as a pill, an injectible fluid (e.g., in PBS), or in a sustained-release form. The compositions may be formulated for any specific route of administration including oral, intramuscular, intraocular, intranasal, subcutaneous, intraarterial, and intravenous administration. In one embodiment, a sequence encoding a PARP13.1 inhibitor (e.g., a sequence encoding an RNAi sequence targeting PARP13.1 (e.g., one of SEQ ID NOS: 40 and 106-112)) and a sequence encoding one or more (e.g., 1, 2, 3, 4, or 5) therapeutic RNAi molecules may be contained in a single viral vector (e.g., a non-infectious recombinant retroviral or lentiviral vector).

Kits

The invention further provides kits containing one or more (e.g., 1, 2, 3, 4, 5, 6, 7, 8, 9, or 10) of the pharmaceutical compositions described herein. The kits may further contain materials to aid in the administration of the pharmaceutical agents (e.g., a syringe). The kits may contain one or more doses of a pharmaceutical agent provided by the invention. The kits may further contain instructions for administering the pharmaceutical compositions to a subject and/or one or more specific therapeutic RNAi molecules or one or more recombinant viruses encoding one or more therapeutic RNAi molecules. In one example, the kit includes a viral vector (e.g., a recombinant non-infectious retroviral or lentiviral vector) containing a sequence encoding a PARP13.1 inhibitor (e.g., a sequence encoding an RNAi sequence targeting PARP13.1 (e.g., one of SEQ ID NOS: 40 and 106-112)) and a sequence encoding one or more (e.g., 1, 2, 3, 4, or 5) therapeutic RNAi molecules.

PARP, PARG, and ARH3 Fusion Proteins

General Design

The invention provides fusion proteins for each PARP, PARG, and ARH3. The fusion proteins may be used to identify unique biological activities for each PARP, PARG, and ARH3 protein and to identify specific inhibitors and activators for each PARP, PARG, or ARH3, or specific subsets of these proteins. The invention provides nucleic acid sequences encoding these PARP, PARG, and ARH3 fusion proteins. The nucleic acids contain a sequence that is at least 80% identical (e.g., at least 85%, 90%, 95%, 96%, 97%, 98%, 99%, or even 100% identical) to the full-length sequence of PARP1 (SEQ ID NO: 1 or 2), PARP2 (SEQ ID NO: 3), PARP3 (SEQ ID NO: 4), PARP3.2 (SEQ ID NO: 5), PARP3.3 (SEQ ID NO: 6), PARP4 (SEQ ID NO: 7), PARP5A (SEQ ID NO: 8 or 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NO: 15), PARP10.2 (SEQ ID NO: 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15.1 (SEQ ID NO: 22), PARP15.2 (SEQ ID NO: 23), PARP16 (SEQ ID NO: 24), PARG (SEQ ID NO: 42), or ARH3 (SEQ ID NO: 41).

The nucleic acids of the invention further contain nucleic acid sequences encoding one or two polypeptide tags. The nucleic acids encoding a polypeptide tag may be placed at a position 5' or a position 3' to the sequence encoding a PARP, PARG, or ARH3 protein. For example, the 3' end of a nucleic acid sequence encoding a polypeptide tag may directly abut (i.e., no intervening nucleotides) the 5' end of a nucleic acid sequence encoding a PARP, PARG, or ARH3 protein. In another example, the 5' end of a nucleic acid sequence encoding a polypeptide tag may directly abut (i.e., no intervening nucleotides) the 3' end of nucleic acid sequence encoding a PARP, PARG, or ARH3 protein. In another example, one or more nucleotides (e.g., at least 2, 3, 4, 5, 10, 15, 20, 25, 30, 35, 40, 45, 50, 60, 70, 80, 90, 100, 200, 300, or 400 nucleotides) separate the 5' end of the sequence encoding the polypeptide tag from the 3' end of the sequence encoding a PARP protein, or separate the 3' end of the sequence encoding the polypeptide tag from the 5' end of the sequence encoding the PARP protein. Sequences encoding the polypeptide tags are described in further detail below.

Polypeptide Tags

Polypeptide tags may be attached to a native protein sequence in order to aid in the purification of the protein, to label the protein for visualization in the cell, and/or to increase the thermodynamic stability and/or half-life of a protein. Nucleic acids encoding a polypeptide tag(s) may include one or more of the following sequences: a sequence encoding an epitope which may be recognized by a specific antibody recognizing the epitope (e.g., 1, 2, 3, 4 or 5 antigenic peptide sequences); a sequence encoding a protein that is bound with high affinity by a specific binding partner; one or more (e.g., 1, 2, 3, 4, or 5) sequence(s) encoding a peptide sequence that aids in purification (e.g., a $His_6$ tag); one or more (e.g., 1, 2, 3, 4, 5, 6, or 7) sequence(s) encoding a protease recognition sequence; and one or more (e.g., 1, 2, 3, or 4) sequences encoding a protein or a domain of a protein which increases the thermodynamic stability or half-life of the protein. The size of the nucleic acid sequence encoding the polypeptide tag may be between 1-50 nucleotides, 1-100 nucleotides, 1-200 nucleotides, 1-300 nucleotides, 1-400 nucleotides, 1-500 nucleotides, 200-500 nucleotides, 1-1,000 nucleotides, 1-5,000 nucleotides, 1-8,000 nucleotides, 1-10,000 nucleotides, or 1-20,000 nucleotides. Several polypeptide tags and sequences encoding polypeptide tags are known in the art. Non-limiting examples of sequences that may be incorporated in polypeptide tags are described below.

The nucleic acids encoding a polypeptide tag may contain sequences for one or more (e.g., 1, 2, 3, 4, or 5) epitopes or antigenic peptide sequences. Epitopes incorporated into polypeptide tags may be used to aid in the purification of a fusion protein, for e.g., by use of an antibody that specifically binds to the epitope. Examples of epitope sequences include, but are not limited to, a FLAG peptide (DYKDDDDK; SEQ ID NO: 30); a glutathione-S-transferase (GST) peptide; a KT3 peptide (KPPTPPPEPET; SEQ ID NO: 31); a hemagglutinin peptide (YPYDVPDYA; SEQ ID NO: 32), a calmodulin-binding peptide (*Methods in Molecular Biology: E. coli Gene Expression Protocols*, volume 205, Humana Press, 2003, pp. 79-97), a R-tag peptide (Jones et al., *Protein Expr. Purif.* 53:404-410, 2007), a V5 peptide, a c-myc peptide, and peptides derived from chitin-binding protein (CBP), CYD, Strep II, HPC, and maltose binding protein (MBP), as described in Lichty et al. (*Protein Expr. Purif.* 41:98-105, 2005).

Nucleic acids encoding a polypeptide tag may contain sequences for one or more (e.g., 1, 2, 3, 4, or 5) proteins with specific binding partners. Desirably, the specific binding partner has a high affinity (e.g., $K_D$<150 nM or $K_D$<250 nM) to the peptide sequence in the polypeptide tag. Non-limiting examples of sequences that encode a protein with a high-affinity binding partner is biotin and the ZZ-domain of *S. aureus* protein A (e.g., a nucleic acid sequence with at least 80% identity to SEQ ID NO: 27). Additionally, the polypeptide tag may contain one or more peptide sequences that aid in the purification of the protein. Non-limiting examples of peptide sequences that aid in the purification of a protein include a $His_6$ tag, chitin-binding protein (CBP), maltose-binding protein (MBP), and glutathione-S-transferase (GST). For example, a protein containing a polypeptide tag containing a $His_6$ tag may be purified by passing a crude cellular lysate over a metal matrix (e.g., a $Ni^+$-Sepharose resin).

A polypeptide tag may also contain a sequence encoding a protein that increases the thermodynamic stability, half-life, and/or solubility of a protein. Non-limiting examples of peptides that increase the solubility of a protein include thioredoxin and poly(NANP). Additional non-limiting examples of proteins that increase the thermodynamic stability or half-life of a protein include the Fc domain of an antibody and albumin. A polypeptide tag may also contain one or more (e.g., 1, 2, 3, or 4) sequences encoding a protein that allows for the visualization of the fusion protein in the cell (e.g., a polypeptide tag containing a sequence encoding a fluorescent protein, such as green fluorescence protein).

A polypeptide tag may also contain one or more (e.g., 1, 2, 3, 4, 5, 6, or 7) protease recognition sequences. A fusion protein may be treated with one or more (e.g., 1, 2, 3, or 4) specific proteases that cleave the fusion protein at the one or more specific protease recognition sequences at any step in the purification process (e.g., after being bound to a resin or solid surface) to remove the polypeptide tag(s) from the remainder of the fusion protein. Non-limiting examples of protease recognition sequences include TEV protease (Glu-X-X-Tyr-X-Gln-Ser; SEQ ID NO: 26), factor Xa (Ile-Glu/Asp-Gly-Arg), Ala-64 subtilisin (Gly-Ala-His-Arg), clostripain (Arg and Lys-Arg), collagenase (Pro-Val-Gly-Pro), enterokinase (Asp-Asp-Asp-Asp-Lys), renin (Pro-Phe-His-Leu-Leu), and α-thrombin (Leu-Val-Pro-Arg-Gly-Ser). When a polypeptide tag is present at the N-terminus of a fusion protein, a protease recognition sequence is preferably located at a position 3' to a peptide sequence encoding an epitope, a sequence encoding a protein that is bound with high affinity by a specific binding partner, or a sequence encoding a peptide sequence that aids in purification. When a polypeptide tag is present at the C-terminus of a fusion protein, a protease recognition sequence is preferably located at a position 5' to a peptide sequence encoding an epitope, a sequence encoding a protein that is bound with high affinity by a specific binding partner, and/or a sequence encoding a peptide sequence that aids in purification. A polypeptide tag may contain one or more (e.g., 1, 2, 3, 4, 5, 6, or 7) of the same or different protease recognition sequences in tandem (i.e., without intervening amino acids) or with one or more (e.g., 1, 2, 3, 4, 5, 6, 7, 8, 9, or 10) intervening amino acids between each protease recognition sequence. Methods for the treatment of a fusion protein containing a protease recognition sequence in the polypeptide tag with one or more protease(s) are known in the art.

Expression Vectors

A number of expression vectors for the expression of a nucleic acid encoding one or more nucleic acids encoding a PARP, PARG, and/or ARH3 fusion protein of the invention are known in the art. Different examples of expression vectors are available for expression of the PARP, PARG, and/or ARH3 fusion proteins in mammalian cells, insect cells, yeast cells, and bacterial cells. For example, the pEGFP-C1 mammalian vector (Invitrogen) contains a CMV promoter sequence, a nucleic acid sequence encoding green fluorescence protein, a multiple cloning site for insertion of nucleic acid sequence encoding a PARP, PARG, or ARH3 nucleic acid (e.g., a sequence with 80% to one of SEQ ID NOS: 1-24, 41, and 42). Additional non-limiting examples of publicly-available mammalian expression vectors include constitutive expression vectors Gateway® pDEST™26, pDEST™27, pDEST™40, and pDEST™47 (Invitrogen); adenoviral expression vectors (e.g., pAd/CM/V5-Dest Gateway® Vector Kit (Invitrogen); episomal expression vectors pCEP4 and pEBNA DEST (Invitrogen); lentiviral expression vectors (e.g., ViraPower™ Bsd; Invitrogen); and regulated expression vectors Gateway® pT-Rex™-DEST 30 and pT-Rex™-DEST 31 (Invitrogen). Non-limiting examples of bacterial expression vectors include Gateway®pDEST™14; Gateway®pDEST™15; Gateway®pDEST™17; Gateway®pDEST™24; Gateway® pET-DEST42; pEM7/Bsd; pEM7/Zeo; pRSET A, B, & C; pRSET-BFP; pRSET-CFP; pRSET-EmGFP; pTrcHIs A, B, & C; and pTrcHIs2 A, B, & C vectors (Invitrogen). Non-limiting examples yeast expression vectors include pAO815; pGAPZ A, B, & C; pPIC3.5K; pPIC9K; pTEF1/Bsd; pTEF1/Zeo; pYC2/CT; pYES2; pYES2/CT; and pYES3/CT (Invitrogen). Non-limiting examples of insect and baculovirus expression vectors include Gateway® pDEST™10; Gateway® pDEST™20; Gateway® pDEST™8; Gateway® pMT-DEST™48; pAC5.1/V5-His A, B, & C; pFastBac Dual; and pIB/V5-His-DEST (Invitrogen).

The expression vectors used to express a fusion protein may include one or more (e.g., 1, 2, 3, 4, or 5) constitutive promoter sequences and/or one or more (e.g., 1, 2, 3, 4, or 5) inducible promoter sequences. Non-limiting examples of constitutive promoter sequences include bacterial promoters (e.g., $E.$ $coli$ $\sigma^{70}$, $\sigma^s$, $\sigma^{32}$, or $\sigma^{54}$ promoters; $B.$ $subtilis$ $\sigma^A$ or $\sigma^B$ promoters; T7 RNA polymerase-based promoters; and a bacteriophage SP6 promoter), yeast promoters (e.g., pCyc, pAdh, pSte5, ADH1, cyc100, cyc70, cyc43, cyc28, cyc16, pPGK1, pCYC, GPD (TDH3), and CLB1 promoters), and mammalian promoters (e.g., cytomegalovirus immediate early gene-based promoters, SV40 early promoter, and Rous sarcoma virus promoter). Non-limiting examples of inducible promoter sequences include alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. Several different mammalian expression vectors available that allow for the inducible expression of a nucleic acid sequence (e.g., a PARP fusion protein) are publicly available including pTet-On-Advanced (Clontech), pERV3 (Stratagene), pNEBR-R1 (New England BioLabs), and pCMV5-CymR (Qbiogene).

PARP, PARG, and ARH3 Proteins

The above-described methods for the generation of PARP, PARG, or ARH3 fusion proteins may be modified to generate PARP, PARG, or ARH3 proteins. In these methods, the expression vectors that contain a nucleic acid sequence encoding a PARP, PARG, or ARH3 fusion protein may be modified to remove the nucleic acid sequences encoding the polypeptide tag. The modified vector may then be introduced into a cell to generate a transgenic cell for the expression of the full-length or wild-type PARP, PARG, or ARH3 protein. The produced PARP, PARG, or ARH3 protein may contain one or more post-translational modifications, including phosphorylation and poly-ADP-riboyslation. The post-translational modifications may be introduced using recombinant enzymes in vitro or may be the result of processing within the transgenic cell.

Methods for the expression and purification of one or more PARP, PARG, and ARH3 proteins are the same as those employed for the corresponding PARP, PARG, and ARH3 fusion proteins, with the exception that affinity purification using antibodies and molecules that specifically recognize the polypeptide tag will not be employed.

Transgenic Cells and Mammals

One or more nucleic acids encoding a PARP, PARG, and/or ARH3 protein, and/or PARP, PARG, and/or ARH3 fusion protein may be introduced into a transgenic cell using methods known in the art, including, but not limited to electroporation, microinjection, lipid-mediated transfection (e.g., liposomal delivery systems), calcium phosphate-mediated transfection, DEAE dextran-mediated transfection, DNA transfection by biolistics, DNA transfection mediated by polybrene, and virus-mediated transduction.

The one or more nucleic acids encoding a PARP, PARG, and/or ARH3 protein, and/or PARP, PARG, and/or ARH3 fusion protein may be introduced into any type of cell, including, but not limited to, a mammalian cell (e.g., a human, mouse, rat, monkey, or rabbit cell), a yeast cell, a bacterial cell, or an insect cell. A mammalian cell that expresses one or more nucleic acids encoding a PARP, PARG, and/or ARH3 protein, and/or PARP, PARG, and/or ARH3 fusion protein may include a fibroblast, an epithelial cell, an endothelial cell, a smooth muscle cell, a hepatocyte, a kidney cell, and a lymphocyte. Additional examples of suitable mammalian cell lines include COS-7 monkey kidney cells, CV-1, L cells, C127 cells, 3T3 cells, Chinese hamster ovary (CHO) cells, human embryonic kidney (HEK) cells, HeLa cells (e.g., HeLa S3 or HeLa Kyoto cells), 293 cells, 293T cells, and BHK cell lines. One or more nucleic acids may also be expressed in a cell (e.g., a mammalian cell, a bacterial cell, or a yeast cell) that has been engineered to express one or more (e.g., 1, 2, 3, or 4) chaperone proteins, one or more (e.g., 1, 2, 3, or 4) enzymes that promote the post-translational modification of proteins, and/or contain one or more (e.g., 1, 2, 3, or 4) mutations in the nucleic acids encoding one or more (e.g., 1, 2, 3, or 4) proteins that have a negative effect on the expression of a transgenic protein (e.g., a PARP fusion protein), such as a specific RNAse or protease. An example of a bacterial cell that has been engineered to contain a mutation in a RNAse is BL21 Star™ (Invitrogen). A variety of cells are commercially available for the expression of one or more recombinant proteins (e.g., one or more PARP, PARG, and/or ARH3 fusion proteins), including, but not limited to, bacterial competent cells (e.g., BL21-AI™ One Shot®, One Shot®-BL21(DE3), and One Shot®-BL21(DE3) pLysE, One Shot® BL21(DE3) pLysS (Invitrogen); and mammalian competent cells (e.g., Espresso Competent Hela S3 Cells, Espresso Competent CHO-K1 cells, and Espresso Competent HEK 293 cells (Neuromics), MaxPAK Competent HeLa S3 cells, MaxPAK Competent CHO-K1 cells, and MaxPAK Competent HEK 293 cells (Genlantis)).

A transgenic cell that contains one or more nucleic acids encoding a PARP, PARG, and/or ARH3 protein, and/or PARP, PARG, and/or ARH3 fusion protein may a stable cell line (e.g., a cell that has integrated the one or more nucleic acids encoding a PARP fusion protein into one or more of its chromosomes). Alternatively, a transgenic cell may contain the one or more nucleic acids encoding a PARP, PARG, and/or ARH3 protein, and/or PARP, PARG, and/or ARH3 fusion protein in a plasmid or on an artificial chromosome, which replicates independently of the chromosomes of the cell.

A transgenic mammal may also be produced from a transgenic cell containing one or more nucleic acids encoding a PARP, PARG, and/or ARH3 protein, and/or a PARP, PARG, and/or ARH3 fusion protein. A transgenic animal may be a mouse, a rat, a bovine, an ovine, a caprine, a porcine, a horse, a rabbit, or a monkey. The nucleic acid encoding one or more PARP, PARG, and/or ARH3 proteins, and/or PARP, PARG, and/or ARH3 fusion proteins may contain a tissue-specific promoter that allows the expression of one or more transgenic proteins into a biological fluid of the mammal (e.g., into the milk or serum of the transgenic mammal). For example, a protein may be engineered for expression in the milk of a mammal by placing the sequence encoding the protein downstream of the casein promoter (U.S. Pat. No. 4,873,316). A PARP, PARG, and/or ARH3 protein, and/or PARP, PARG, and/or ARH3 fusion protein produced in a biological fluid of a transgenic mammal may be purified as described below.

Methods for the production of a transgenic mammal from a transgenic cell are known in the art and include, without limitation, methods that require the transfer of a nucleus from a transgenic cell to an enucleated oocyte and/or the microinjection of one or more nucleic acids (e.g., a plasmid or an artificial chromosome) encoding one or more PARP, PARG, and/or ARH3 proteins, and/or PARP, PARG, and/or ARH3 fusion proteins into an oocyte. Such genetically manipulated oocytes may then be transferred into a recipient female host to produce a transgenic mammal.

Cell Lysates

Cell lysates may be prepared from the transgenic cells containing a nucleic acid encoding one or more PARP, PARG, and/or ARH3 proteins, and/or PARP, PARG, and/or ARH3 fusion proteins of the invention. Cell lysates may be prepared by any methods known in the art, including both physical disruption methods and chemical disruption methods. Physical disruption methods include, but are not limited to sonication, homogenization, and rapid freeze/thaw lysis. Chemical disruption methods include, but are not limited to, the use of lysis buffers (e.g., buffers containing a detergent such as Triton-X-100 and NP-40). Following lysis of the cell membrane using chemical and/or physical disruption methods, the lysate may optionally be centrifuged to remove cellular debris and/or partially purified by one or more (e.g., 1, 2, 3, 4, 5, 6, or 7) of the following steps: salt gradient precipitation (e.g., ammonium sulfate precipitation), size exclusion chromatography or dialysis, and column chromatography (e.g., affinity chromatography, size exclusion chromatography, anion exchange chromatography, and cation exchange chromatography). The cell lysate may also be treated with one or more (e.g., 1, 2, or 3) of a DNAse, RNAse, or lipase prior to further use. One or more (e.g., 1, 2, 3, 4, or 5) protease inhibitors may also be added to the cell lysate prior to use.

PARP, PARG, and ARH Protein and Fusion Protein Purification

One or more PARP, PARG, and/or ARH3 proteins, and/or PARP, PARG, and/or ARH3 fusion proteins may be fully or partially purified (e.g., at least 60%, 70%, 80%, 85%, 90%, 95%, and 99% pure from other proteins in the cell) from cell lysates, a biological medium (e.g., cell culture medium from a transgenic cell), or a biological fluid (e.g., blood, serum, or milk) from transgenic mammal expressing one or more (e.g., 1, 2, 3, 4, 5, 6, 7, 8, 9, 10, 11, 12, 13, 14, 15, 16, 17, 18, 19, or 20 or more) nucleic acids encoding a PARP, PARG, and/or ARH3 protein, and/or a PARP, PARG, and/or ARH3 fusion protein of the invention. Alternatively, one or more (e.g., 1, 2, 3, 4, 5, 6, 7, 8, 9, 10, 11, 12, 13, 14, 15, 16, 17, 18, 19, or 20 or more) PARP, PARG, and/or ARH3 proteins, and/or PARP, PARG, and/or ARH3 fusion proteins may be fully or partially purified from the extracellular medium of a transgenic cell expressing one or more nucleic acids encoding a PARP, PARG, and/or ARH3 protein, and/or a PARP, PARG, and/or ARH3 fusion protein of the invention. In each example, a cell lysate, biological fluid (e.g., milk or serum), or extracellular medium containing one or more PARP, PARG, and/or ARH3 proteins, and/or PARP, PARG, and/or ARH3 fusion proteins is collected.

Methods for the purification of a recombinant protein from a cell lysate, biological fluid, or extracellular medium are known in the art. For example, in instances where the PARP, PARG, and/or ARH3 fusion protein contains an epitope, an antibody specific for the epitope (e.g., anti-GFP antibodies, anti-FLAG antibodies, anti-GST antibodies, anti-hemagglutinin antibodies, anti-c-myc antibodies, and anti-V5 antibodies) may be used to purify one or more PARP, PARG, and/or ARH3 fusion protein(s). In another example, a PARP, PARG, and/or ARH3 fusion protein may contain a polypeptide tag containing a sequence that aids in affinity purification of the protein (e.g., a $His_6$ tag, a calmodulin-binding protein tag, a glutathione S-transferase protein tag, a strep II tag, a HPC tag, a maltose-binding protein tag). In each example, a solid surface, resin, or bead (e.g., magnetic bead) may be covalently attached to a protein or molecule specifically bound by the protein sequence located in the polypeptide tag. In such instances, contacting the one or more PARP, PARG, and/or ARH3 fusion protein(s) with the solid surface, resin, or bead will cause the selective binding of the one or more PARP, PARG, and/or ARH3 fusion protein(s) with the solid surface, resin, or bead. The remaining non-bound proteins will not bind and may be washed away using an appropriate buffer. Specific methods for the affinity purification of proteins are known in the art.

One or more PARP, PARG, and/or ARH3 fusion proteins may also be purified from a cell lysate, biological sample, or a extracellular medium by a purification protocol including, but limited to: salt precipitation (e.g., ammonium sulfate precipitation), pH precipitation, precipitation using organic solvents, high performance liquid chromatography (HPLC), column chromatography, ion exchange chromatography (e.g., cation exchange chromatography and anion exchange chromatography), immobilized metal affinity chromatography, gel filtration, or size exclusion chromatography or dialysis. One or more (e.g., 1, 2, 3, 4, 5, 6, or 7) of these steps may also be used in combination with an affinity purification step as described above.

The one or more purified PARP, PARG, and/or ARH3 proteins, and/or PARP, PARG, and/or ARH3 fusion proteins may be dialyzed to exchange the buffer or concentrated prior to use in one or more of the assays described herein (e.g., PARP, PARG, and/or ARH3 activity assays or assays for the identification of a specific PARP activator or inhibitor). The one or more purified PARP, PARG, and/or ARH3 proteins, and/or PARP, PARG, and/or ARH3 fusion proteins may be stored at −70° C. in the presence or absence of one or more (e.g., 1, 2, 3, 4, or 5) stabilizing proteins including, but not limited to, albumin.

PARP Protein and PARP Fusion Protein Assays

The biological activity of the one or more PARP proteins and PARP fusion proteins of the invention include, but are not limited to, one or more (e.g., 1, 2, 3, 4, or 5) of the ability to covalently attach an ADP-ribose molecule to one or more (e.g., 1, 2, 3, 4, or 5) substrate(s) (e.g., a protein, a RNA molecule, a DNA molecule, or a lipid), the ability to covalently attach an ADP-ribose molecule to a ADP-ribose residue covalently attached to a substrate, the ability to add a branched ADP-ribose molecule to a pre-existing poly-ADP-ribose, the ability to localize to the cell nucleus, the ability to localize to stress granules, the ability to catalyze the formation or nucleation of stress granules, the ability to catalyze the disassembly of stress granules, the ability to promote cell division and mitosis, or the ability to inhibit RNAi activity in the cell. Specific PARP proteins have a different subset of biological activities: PARP1, PARP2, PARP5A, PARP5B, PARP7, PARP8, PARP14, and PARP16 have the ability to localize to the nucleus and/or the ability to promote cell division and mitosis; PARP5A, PARP12, PARP13.1, PARP13.2, and PARP15 have the ability to localize to stress granules and the ability to promote or nucleate stress granule formation; PARP11 has the ability to localize to stress granules and the ability to promote disassembly of stress granules or prevent the formation of stress granules; and PARP13.1 has the ability to decrease the activity of RNAi (e.g., the ability of an RNAi molecule to decrease the level of a targeted mRNA and the level of one or more proteins encoded by the targeted mRNA) and the ability to add one or more ADP-ribose molecules to Argonaut.

Assays to measure the ability of one or more PARP proteins and PARP fusion protein(s) to covalently attach an ADP-ribose to one or more (e.g., 1, 2, 3, 4, or 5) substrate(s) (e.g., a protein, a RNA, a DNA, or a lipid) involve the incubation of one or more PARP fusion protein(s) with the one or more substrate(s) in the presence of a labeled $NAD^+$ molecule (e.g., radiolabeled, fluorescently-labeled, and colorimetrically-labeled $NAD^+$). A radiolabeled $NAD^+$ substrate may contain one or more radioisotopes including, but not limited to, $^{14}C$ (e.g., $^{14}C$-adenine), $^{32}P$, and $^3H$. Additional $NAD^+$ substrates include fluorescently-labeled $NAD^+$ (Putt et al., *Anal. Biochem.* 78:326, 2004), colorimetrically-labeled $NAD^+$ (Nottbohn et al., *Agnew. Chem. Int. Ed.* 46:2066-2069, 2007), and biotinylated $NAD^+$ (6-biotin-17-NAD; R & D Systems). Following incubation of the one or more (e.g., 1, 2, 3, 4, 5, 6, 7, 8, 9, 10, 11, 12, 13, 14, 15, 16, 17, 18, 19, or 20 or more) PARP proteins and/or the one or more PARP fusion proteins with the labeled $NAD^+$ and one or more (e.g., 1, 2, 3, 4, or 5) substrate molecules, the specific labeling of the substrate(s) with one or more labeled ADP-ribose molecules is determined by measuring the amount of the label associated with the $NAD^+$ that is covalently bound to the one or more substrate molecules. An increase (e.g., at least 5%, 10%, 15%, 20%, 30%, 40%, 50%, 60%, 70%, 80%, 90%, or 100%) in the amount of the label associated with the $NAD^+$ that is covalently bound to the one or more substrate(s) indicates PARP protein or PARP fusion protein activity.

In another example of a PARP assay, the auto-modification of one or more (e.g., 1, 2, 3, 4, 5, 6, 7, 8, 9, 10, 11, 12, 13, 14, 15, 16, 17, 18, 19, or 20 or more) PARP proteins or PARP fusion protein(s) is measured by incubating the one or more PARP proteins and/or PARP fusion proteins of the invention with a labeled $NAD^+$ substrate and subsequently, measuring the amount of the label associated with the $NAD^+$ covalently bound to the one or more PARP fusion proteins. An increase in the amount of the label associated with the $NAD^+$ covalently bound to the one or more PARP fusion proteins indicates PARP fusion protein auto-modification.

In an alternative assay, one or more (e.g., 1, 2, 3, 4, 5, 6, 7, 8, 9, 10, 11, 12, 13, 14, 15, 16, 17, 18, 19, or 20 or more) PARP proteins and/or PARP fusion proteins may be incubated with one or more (e.g., 1, 2, 3, 4, or 5) substrates and a non-labeled $NAD^+$. The poly-ADP-ribosylation of the one or more substrates may be measured by contacting the one or more substrates with a poly-ADP-ribose antibody. For example, a sample of substrate proteins may be electrophoresed and immunoblotted with an anti-poly-ADP-ribose antibody. An increased number of proteins or an increased level of detection using an anti-poly-ADP ribose antibody indicates an increase in the activity of the one or more PARP fusion proteins.

Assays to measure the ability of a PARP protein and/or PARP fusion protein to localize to a specific cellular structure or organelle using immunofluorescence microscopy are known in the art. For example, antibodies specific for one or more PARP proteins and/or fusion proteins, and antibodies specific for one or more proteins or molecules specific to a cellular structure or organelle (e.g., cytoskeleton, mitochondria, trans-Golgi network, endoplasmic reticulum, early endosome, centrosome, GW bodies, nuclear envelope, lysosome, peroxisomes, histones, Cajal bodies, nucleus, and mitochondria) may be used to perform immunofluorescent microscopy. Localization of one or more PARP proteins and/or PARP fusion proteins may be measured in high-throughput experiments by co-localization of one or more PARP proteins and/or fusion proteins with one or more proteins specific for a cellular structure or organelle (e.g., proteins listed in FIG. 10). Localization of one or more PARP proteins and/or PARP fusion proteins in the nucleus may also be demonstrated by co-localization of a dye that stains DNA and an antibody that specifically binds the one or more PARP proteins and/or PARP fusion proteins (e.g., co-localization of an antibody specific for one or more PARP proteins and/or PARP fusion proteins, and 4',6-diamindino-2-phenylindole (DAPI)).

Localization of one or more PARP proteins and/or PARP fusion proteins to a specific cell structure or organelle may occur only during one or more (e.g., 1, 2, 3, 4, 5, or 6) specific stages of the cell cycle, including, but not limited to, G2-M, prophase, prometaphase (P-M), metaphase, anaphase, cytokinesis, $G_0$, and $G_1$ stages. For the purposes described herein, a PARP protein and/or PARP fusion protein is deemed to have the ability to localize to a specific cellular structure or organelle if it localizes to the specific cellular structure or organelle in at least one stage (e.g., mitosis or cytokinesis) of the cell cycle.

The ability of a PARP protein and/or fusion protein to promote stress granule assembly or to inhibit stress granule assembly may be measured using fluorescence microscopy. In such a method, cells are treated with one or more PARP inhibitors, one or more PARP activators, or a nucleic acid encoding one or more PARP proteins and/or PARP fusion proteins, and are subsequently fixed and immunostained with antibodies specific for one or more stress granule protein (e.g., one or more of eIF3, eIF1A, eIF2α, eIF3η, eIF4A1, eIF4e, and G3BP). An increase in the number of foci containing one or more stress granule proteins (e.g., intense immunostaining in distinct cellular structures) indicates an increase in the formation of stress granules. A decrease in the number of foci containing one or more stress granule proteins, likewise, indicates a decrease in the formation of stress granules. In such assays, stress granule formation may be induced by exposure to stress conditions, for example, by treatment with sodium arsenite and pateamine A.

The ability of one of more PARP proteins and/or PARP fusion proteins to promote cell division and mitosis may be measured using any method known in the art. For example, cell proliferation assays including, but not limited to, standard cell counting assays, BrdU labeling, and quantitative assays for DNA synthesis such as $^3$H-thymidine incorporation may be used to measure the ability of one or more PARP proteins and/or PARP fusion proteins to promote cell division and mitosis. Likewise, inhibition of one or more PARP proteins and/or PARP fusion proteins with the ability to promote cell division and mitosis may result in cell death. Several assays to measure cell death are known in the art, including, but not limited to Hoechst 33342 staining of chromatin, propidium iodide staining, annexin V staining of phosphoserine, and 3-(4,5-dimethylthiazol-2-yl)-2,5-diphenyl tetrazolium bromide (MTT) staining.

Assays for measuring RNAi activity in a cell are available in the art. For example, psiCHECK™-1, psiCHECK™-2, and pGL4.72[hRlucCP]™ vector assay systems provide methods for the measurement of RNAi activity in a cell. In these assays systems, luciferase is used a primary reporter gene and a target sequence (i.e., the target of one or more RNAi molecules) is cloned a multiple cloning region located downstream of the luciferase translational stop codon. Initiation of the RNAi process towards the target gene results in the cleavage and subsequent degradation of the fusion mRNA encoded by the vectors (i.e., upon treatment of the transfected cell with a vector-target RNAi molecule). Measurement of decreased luciferase activity in the transfected cells following treatment with the vector-target RNAi indicates the activity of RNAi in the cell. For example, in experiments using the psiCHECK assay system, a cell transfected with the psiCHECK vector is treated with the vector-target RNAi and with an activator or inhibitor of one or more (e.g., 1, 2, 3, 4, 5, 6, 7, 8, 9, or 10) PARP proteins and/or PARP fusion proteins (e.g., 1, 2, 3, 4, or 5 RNAi molecules targeting a specific PARP), or PARG activator or PARG inhibitor (e.g., one or more RNAi molecules targeting PARG or ARH3). Transfected cells treated with the vector-target RNAi and with a PARP inhibitor or activator that demonstrate increased luciferase activity relative to a transfected cell treated with the vector-target RNAi alone indicate that the specific targeted PARP activates or inhibits RNAi activity in the cell, respectively. Cells treated with a PARP inhibitor or activator that demonstrate decreased luciferase activity relative to a cell treated with vector-target RNAi alone indicate that the specific targeted PARP inhibits or activates RNAi activity in the cell, respectively. Correspondingly, transfected cells treated with the vector-target RNAi and with a PARG inhibitor or activator that demonstrate increased luciferase activity relative to a transfected cell treated with the vector-target RNAi alone indicate that the specific targeted PARG (e.g., PARG or ARH3) activates or inhibits RNAi activity in the cell, respectively. Cells treated with a PARG inhibitor or activator that demonstrate decreased luciferase activity relative to a cell treated with vector-target RNAi alone indicate that the specific targeted PARG (e.g., PARG or ARH3) inhibits or activates RNAi activity in the cell, respectively.

Figure 3:
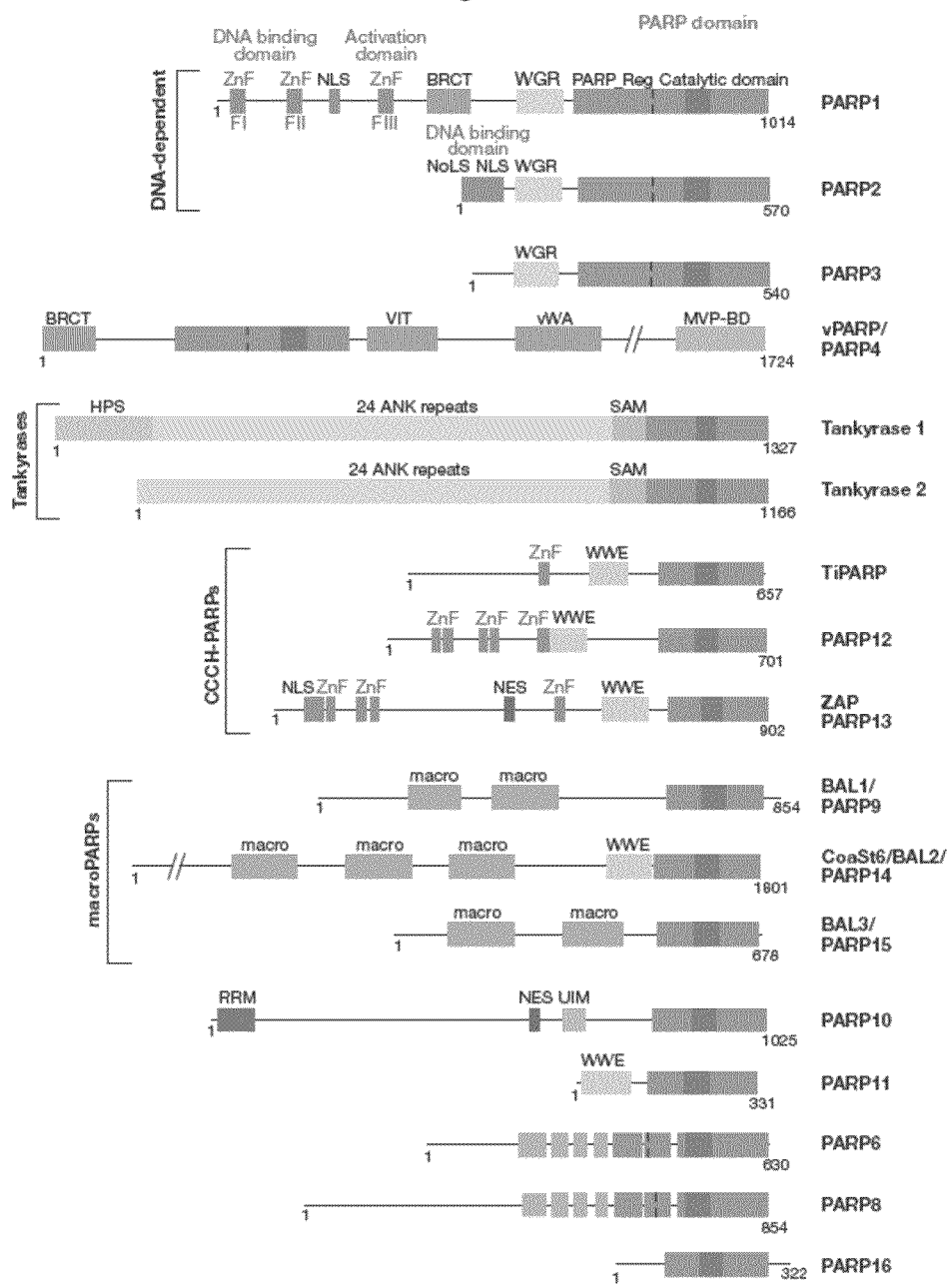
FIG. 3 is a set of schematic diagrams showing the domain organization of PARP1, PARP2, PARP3, PARP4, tankyrase 1 (PARP5A), tankyrase 2 (PARP5B), TiPARP (PARP7), PARP12, PARP13, PARP9, PARP14, PARP15, PARP10, PARP11, PARP6, PARP8, and PARP16.

Any of the above-referenced PARP protein and/or PARP fusion protein activity assays may be performed to determine the activity of PARP protein or PARP fusion protein sequence encoded by a nucleic acid having at least 80% sequence identity to one of SEQ ID NOS: 1-24. The domain structure of several PARP proteins are shown in FIG. 3. Preferred mutations in the wild-type sequences of PARP proteins (e.g., SEQ ID NOS: 1-24) do not introduce amino acid changes in the catalytic domain in FIG. 3. In addition, the biological activity of a PARP protein and/or PARP fusion protein containing a sequence having at least 80% sequence identity to one of SEQ ID NOS: 1-24 may be assessed using any of the above-described cellular or in vitro assays.

PARG and ARH3 Protein and Fusion Protein Assays

The activity of one or more PARG protein, ARH3 protein, PARG fusion protein, and/or ARH3 fusion protein may be determined using assays known in the art. PARG and ARH3 proteins herein have been demonstrated to decrease or prevent the formation of stress granules. Assays for the measurement of stress granule formation and disassembly are described herein.

Additional assays for PARG and ARH3 proteins (and fusion proteins) include the hydrolysis of poly-ADP-ribose. Labeled poly-ADP-ribose (e.g., $^{32}$P, $^{14}$C, or biotinylated ADP) may be used as a substrate for the measurement of the hydrolysis and release of ADP-ribose from a labeled and/or attached poly-ADP-ribose polymer.

Additional assays for PARG and ARH3 proteins involve the use of antibodies specific for poly-ADP-ribose. For example, cells may be transfected with a nucleic acid that overexpresses a PARG protein, ARH3 protein, PARG fusion protein, and/or ARH3 fusion protein and cells untreated or treated with a stress condition (e.g., sodium arsenite). Cells that contain an active form of a PARG protein, ARH3 protein, PARG fusion protein, and/or ARH3 fusion protein show decreased staining for poly-ADP-ribose than cells transfected with a control form or inactive form of these proteins (e.g., a form lacking its catalytic domain or a form containing an inactivating mutation). The ability of PARG or ARH3 to modulate RNAi activity in a cell may be measured using the RNAi activity assays described above.

These activity assays will also aid in the identification of which amino acids may be mutated to generate nucleic acids having at least 80% (e.g., at least 85%, 90%, 95%, 99%, or 100% identity) to PARG (SEQ ID NO: 42) or ARH3 (SEQ ID NO: 41). Preferred sites of mutation lie outside the catalytic domains of PARG and/or ARH3.

PARP- and PARG-Specific Antibodies

Antibodies specific to the one or more (e.g., 1, 2, 3, 4, 5, 6, 7, 8, 9, 10, 11, 12, 13, 14, 15, 16, 17, 18, 19, or 20 or more) PARP proteins, PARP fusion proteins, PARG proteins, PARG fusion proteins, ARH3 proteins, and/or ARH3 fusion proteins of the invention can be generated using standard methods, such as those described herein. Antibodies specific for one or more PARP, PARG, or ARH3 fusion proteins; PARP, PARG, or ARH3 proteins; or fragments of PARP, PARG, or ARH3 proteins and/or PARP, PARG, or ARH3 fusion proteins may be used in quantitative assays to measure to amount of one or more (e.g., 1, 2, 3, 4, 5, 6, 7, 8, 9, 10, 11, 12, 13, 14, 15, 16, 17, 18, 19, or 20 or more) PARP, PARG, or ARH3 proteins and/or PARP, PARG, or ARH3 fusion proteins present in a cell, cell lysate, biological sample, or extracellular medium. Antibodies specific to the one or more (e.g., 1, 2, 3, 4, 5, 6, 7, 8, 9, 10, 11, 12, 13, 14, 15, 16, 17, 18, 19, or 20 or more) PARP, PARG, or ARH3 proteins and/or PARP, PARG, or ARH3 fusion proteins of the invention may also be used to identify specific binding partners or potential inhibitors or activators of the one or more PARP, PARG, or ARH3 proteins and/or PARP, PARG, or ARH3 fusion proteins.

For the preparation of polyclonal antibodies reactive with one or more PARP, PARG, or ARH3 proteins; PARP, PARG, or ARH3 fusion proteins; fragments of PARP, PARG, or ARH3 proteins; and/or fragments of PARP, PARG, or ARH3 fusion protein(s) can be purified from natural sources (e.g., cultures of cells expressing one or more PARP proteins) or synthesized in, e.g., mammalian, insect, or bacterial cells by expression of corresponding DNA sequences contained in a suitable cloning vehicle (e.g., the nucleic acids encoding PARP proteins and PARP fusion proteins described herein). Fusion proteins are commonly used as a source of antigen for producing antibodies. The antigenic proteins can be optionally purified, and then coupled to a carrier protein, mixed with Freund's adjuvant to enhance stimulation of the antigenic response in an inoculated animal, and injected into rabbits, mice, or other laboratory animals. Primary immunizations are carried out with Freund's complete adjuvant and subsequent immunizations performed with Freund's incomplete adjuvant. Following booster injections at bi-weekly intervals, the inoculated animals are then bled and the sera isolated. The sera is used directly or is purified prior to use by various methods, including affinity chromatography employing reagents such as Protein A-Sepharose, antigen-Sepharose, and anti-horse-Ig-Sepharose. Antibody titers can be monitored by Western blot and immunoprecipitation analyses using one or more PARP, PARG, or ARH3 proteins; PARP, PARG, or ARH3 fusion proteins; fragments of PARP, PARG, or ARH3 proteins; and/or fragments of PARP, PARG, or ARH3 fusion proteins. Immune sera can be affinity purified using one or more PARP, PARG, or ARH3 proteins; PARP, PARG, or ARH3 fusion proteins; fragments of PARP, PARG, or ARH3 proteins; and/or fragments of PARP, PARG, or ARH3 fusion proteins coupled to beads. Antiserum specificity can be determined using a panel of proteins, such as one or more PARP, PARG, or ARH3 proteins; PARP, PARG, or ARH3 fusion proteins; and/or fragments of PARP, PARG, or ARH3 fusion proteins or proteins.

Alternatively, monoclonal antibodies are produced by removing the spleen from the inoculated animal, homogenizing the spleen tissue, and suspending the spleen cells suspended in phosphate buffered saline (PBS). The spleen cells serve as a source of lymphocytes, some of which produce antibody of the appropriate specificity. These cells are then fused with permanently growing myeloma partner cells, and the products of the fusion plated into a number of tissue culture wells in the presence of selective agents, such as hypoxanthine, aminopterine, and thymidine (Mocikat, *J. Immunol. Methods* 225:185-189, 1999; Jonak et al., *Hum. Antibodies Hybridomas* 3:177-185, 1992; Srikumaran et al., *Science* 220:522, 1983). The wells can then be screened by ELISA to identify those containing cells making antibody capable of binding to one or more PARP, PARG, or ARH3 proteins; PARP, PARG, or ARH3 fusion proteins; and/or fragments of PARP, PARG, or ARH3 proteins or fusion proteins, or mutants thereof. These cells can then be re-plated and, after a period of growth, the wells containing these cells can be screened again to identify antibody-producing cells. Several cloning procedures can be carried out until over 90% of the wells contain single clones that are positive for specific antibody production. From this procedure, a stable cell line of clones that produce the antibody are established. The monoclonal antibody can then be purified by affinity chromatography using Protein A Sepharose and ion-exchange chromatography, as well as variations and combinations of these techniques. Once produced, monoclonal antibodies are also tested for specific PARP, PARG, or ARH3 protein and/or PARP, PARG, or ARH3 fusion protein recognition by ELISA, Western blot, and/or immunoprecipitation analysis (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., In Monoclonal Antibodies and T Cell Hybridomas, Elsevier, New York, N.Y., 1981).

As an alternate or adjunct immunogen to a PARP, PARG, or ARH3 protein and/or PARP, PARG, or ARH3 fusion protein, peptides corresponding to relatively unique regions of a PARP, PARG, or ARH3 protein or PARP, PARG, or ARH3 fusion protein can be generated and coupled to keyhole limpet hemocyanin (KLH) through an introduced C-terminal lysine. Antiserum to each of these peptides can be similarly affinity-purified on peptides conjugated to BSA, and specificity tested by ELISA and Western blotting using peptide conjugates, and by Western blotting and immunoprecipitation using a PARP, PARG, or ARH3 protein; PARP, PARG, or ARH3 fusion protein; and/or fragment of a PARP, PARG, or ARH3 protein or fusion protein.

Antibodies of the invention are desirably produced using PARP, PARG, or ARH3 protein and/or PARP, PARG, or ARH3 fusion protein amino acid sequences that do not reside within highly conserved regions, and that appear likely to be antigenic, as evaluated by criteria such as those provided by the Peptide Structure Program (Genetics Computer Group Sequence Analysis Package, Program Manual for the GCG Package, Version 7, 1991) using the algorithm of Jameson et al., *CABIOS* 4:181, 1988. These fragments can be generated by standard techniques, e.g., by PCR, and cloned into any appropriate expression vector. For example, GST fusion proteins can be expressed in *E. coli* and purified using a glutathione-agarose affinity matrix. To minimize the potential for obtaining antisera that is non-specific or exhibits low-affinity binding to one or more PARP, PARG, or ARH3 proteins; PARP, PARG, or ARH3 fusion proteins; and/or fragments of PARP, PARG, or ARH3 proteins or fusion proteins, two or three PARP, PARG, or ARH3 fusion proteins may be generated for each fragment injected into a separate animal. Antisera are raised by injections in series, preferably including at least three booster injections.

In addition to intact monoclonal and polyclonal anti-PARP, anti-PARG, anti-ARH3, anti-PARP fusion protein, anti-PARG fusion protein, or anti-ARH3 fusion protein antibodies, various genetically engineered antibodies and antibody fragments (e.g., F(ab')2, Fab', Fab, Fv, and sFv fragments) can be produced using standard methods. Truncated versions of monoclonal antibodies, for example, can be produced by recombinant methods in which plasmids are generated that express the desired monoclonal antibody fragment(s) in a suitable host. Ladner (U.S. Pat. Nos. 4,946,778 and 4,704,692) describes methods for preparing single polypeptide chain antibodies. Ward et al., *Nature* 341:544-546, 1989, describes the preparation of heavy chain variable domain which have high antigen-binding affinities. McCafferty et al. (*Nature* 348:552-554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describes various methods for producing immunoglobulins, and immunologically functional fragments thereof, that include at least the variable domains of the heavy and light chains in a single host cell. Cabilly et al. (U.S. Pat. No. 4,816,567) describes methods for preparing chimeric antibodies. In addition, the antibodies can be coupled to compounds, such as toxins or radiolabels.

Methods for Identification of Specific PARP Inhibitors or Activators

The PARP proteins and/or PARP fusion proteins of the invention may be used to identify one or more (e.g., 1, 2, 3, 4, 5, 6, 7, 8, 9, 10, 11, 12, 13, 14, 15, 16, 17, 18, 19, or 20 or more) specific PARP activators or inhibitors. In the provided assays, one or more (e.g., 1, 2, 3, 4, 5, 6, 7, 8, 9, 10, 11, 12, 13, 14, 15, 16, 17, 18, 19, or 20 or more) PARP proteins and/or PARP fusion proteins are contacted with an agent (e.g., a test agent), a labeled $NAD^+$ (e.g., a colorimetrically-labeled, fluorescently-labeled, biotinylated-, or radioisotope-labeled $NAD^+$), and one or more substrates, and measuring the amount of labeled ADP-ribose covalently attached to the one or more substrates. In one example, one or more PARP protein and/or PARP fusion proteins of the invention are incubated with a labeled $NAD^+$ substrate and the amount of label associated with the $NAD^+$ that is covalently attached to the one or more PARP proteins and/or PARP fusion proteins is measured (e.g., auto-modulation activity assay). In this example, an agent that is a specific PARP inhibitor mediates a decrease (e.g., at least a 5%, 10%, 15%, 20%, 25%, 30%, 35%, 40%, 45%, 50%, 55%, 60%, 65%, 70%, 80%, 90%, 95%, or even 100% decrease) in the amount of labeled ADP-ribose covalently attached to one or more (e.g., 1, 2, 3, 4, 5, 6, 7, 8, 9, 10, 11, 12, 13, 14, 15, 16, 17, 18, 19, or 20) PARP proteins and/or fusion proteins, wherein the label on the PARP-fusion proteins is the same as the label of the $NAD^+$. In a method for identifying an agent that is a specific PARP activator, the agent mediates an increase (e.g., at least a 5%, 10%, 15%, 20%, 25%, 30%, 35%, 40%, 45%, 50%, 55%, 60%, 65%, 70%, 80%, 90%, 95%, or even 100% increase) in the amount of labeled ADP-ribose covalently attached to one or more (e.g., 1, 2, 3, 4, 5, 6, 7, 8, 9, 10, 11, 12, 13, 14, 15, 16, 17, 18, 19, or 20) PARP proteins and/or PARP fusion proteins.

The one or more PARP proteins and/or PARP fusion proteins utilized in each assay may be purified, partially purified (e.g., at least 30%, 40%, 50%, 60%, 70%, 80%, 85%, 90%, or 95% pure) or may be present in a cell lysate (e.g., a bacterial cell lysate, a yeast cell lysate, or a mammalian cell lysate), in a biological fluid from a transgenic animal (e.g., milk or serum), or an extracellular medium. The one or more PARP proteins and/or PARP fusion proteins utilized in the assay may be bound to substrate, such as, but not limited to, a solid surface (e.g., a multi-well plate), a resin, or a bead (e.g., a magnetic bead).

In additional examples of the assays, the one or more PARP proteins and/or PARP fusion proteins may be bound to a solid surface, resin, or bead (e.g., a magnetic bead) and subsequently treated with one or more protease(s) (e.g., a TEV protease) prior to contacting the one or more PARP proteins and/or PARP fusion proteins with the labeled $NAD^+$.

In preferred assays, an activator or inhibitor increases or decreases the amount of labeled ADP-ribose covalently attached to a specific PARP protein, PARP fusion protein, and/or subset of PARP proteins or fusion proteins while having no or little (e.g., less than 50%, 40%, 30%, 25%, 20%, 15%, 10%, or 5% change (e.g., increase or decrease)) affect on the amount of labeled ADP-ribose covalently attached to other PARP proteins and/or PARP fusion proteins, is identified as a PARP activator or inhibitor, respectively. For example, the assay desirably identifies an agent that specifically inhibits the amount of labeled ADP-ribose covalently attached to one or more (e.g., 1, 2, 3, 4, 5, 6, 7, 8, 9, or 10) PARP5A proteins or fusion proteins, PARP12 proteins and/or fusion proteins, PARP13.1 proteins and/or fusion proteins, PARP13.2 proteins and/or fusion proteins, and PARP15 proteins and/or fusion proteins. Another assay desirably identifies an agent that specifically increases the amount of labeled ADP-ribose covalently attached to one or more (e.g., 1, 2, 3, 4, 5, 6, 7, 8, 9, or 10) PARP5A proteins and/or fusion proteins, PARP12 proteins and/or fusion proteins, PARP13.1 proteins and/or fusion proteins, PARP13.2 proteins and/or fusion proteins, and PARP15 proteins and/or fusion proteins. Another example of the assay desirable identifies an activator or inhibitor that specifically increases or decreases, respectfully, the amount of labeled ADP-ribose covalently bound to one or more (e.g., 1, 2, 3, 4, 5, or 6) PARP11 proteins and/or fusion proteins. Another example of the assay desirably identifies an agent that specifically decreases the amount of labeled ADP-ribose covalently attached to one or more (e.g., 1, 2, 3, 4, 5, 6, 7, 8, 9, or 10) PARP1 proteins and/or fusion proteins, PARP2 proteins and/or fusion proteins, PARP5A proteins and/or fusion proteins, PARP5B proteins and/or fusion proteins, PARP7 proteins and/or fusion proteins, PARP8 proteins and/or fusion proteins, PARP14 proteins and/or fusion proteins, and PARP16 proteins and/or fusion proteins. Another example of the assay desirably identifies an agent that specifically increases the amount of labeled ADP-ribose covalently attached to one or more (e.g., 1, 2, 3, 4, 5, 6, 7, 8, 9, or 10) PARP1 proteins and/or fusion proteins, PARP2 proteins and/or fusion proteins, PARP5A proteins and/or fusion proteins, PARP5B proteins and/or fusion proteins, PARP7 proteins and/or fusion proteins, PARP8 proteins and/or fusion proteins, PARP14 proteins and/or fusion proteins, and PARP16 proteins and/or fusion proteins. In another desirable embodiment of the assay, the assay identifies an agent that specifically increases or decreases the amount of labeled ADP-ribose covalently attached to one or more (e.g., 1, 2, 3, 4, 5, or 6) different PARP13.1 proteins and/or fusion proteins.

A variety of different agents may be tested in the above-described assays provided by the invention. For example, a tested agent may be a derived from or present in a crude lysate (e.g., a lysate from a mammalian cell or plant extract) or be derived from a commercially available chemical libraries.

Large libraries of natural product or synthetic (or semi-synthetic) extracts or chemical libraries are commercially available and known in the art. The screening methods of the present invention are appropriate and useful for testing agents from a variety of sources for activity as a specific PARP activator or inhibitor. The initial screens may be performed using a diverse library of agents, but the method is suitable for a variety of other compounds and compound libraries. Such compound libraries can also be combinatorial libraries. In addition, compounds from commercial sources can be tested, as well as commercially available analogs of identified inhibitors.

An agent may be a protein, a peptide, a DNA or RNA aptamer (e.g., a RNAi molecule), a lipid, or a small molecule (e.g., a lipid, carbohydrate, a bioinorganic molecule, or an organic molecule).

Agents that may be tested as a specific PARP activator include nucleic acids that contain a sequence encoding one or more (e.g., 1, 2, 3, 4, 5, 6, 7, 8, 9, or 10) domains of a PARP protein (e.g., a domain encoded by part of the nucleic acid sequence having at least 80% sequence identity to any one of SEQ ID NOS: 1-24).

Methods for Identification of an Agent that Specifically Binds One or More PARPs The invention also provides methods for identifying an agent that specifically binds to one or more (e.g., 1, 2, 3, 4, 5, 6, 7, 8, 9, 10, 11, 12, 13, 14, 15, 16, 17, 18, 19, or 20 or more) PARP proteins and/or PARP fusion proteins. These methods require the contacting of one or more of the PARP proteins and/or PARP fusion proteins of the invention with a test agent and determining whether the test agent specifically binds to the one or more PARP proteins and/or PARP fusion proteins. An agent that specifically binds one or more of the described PARP proteins and/or PARP fusion proteins may act as an activator or inhibitor of the expression or activity of the one or more PARP proteins and/or PARP fusion proteins in a cell. For example, an agent that specifically binds to one or more PARP proteins and/or PARP fusion proteins may selectively increase the activity or expression of one or more PARP proteins and/or fusion proteins, while at the same time decreasing the activity or expression of one or more other PARP proteins and/or PARP fusion proteins in the same cell or sample.

The one or more PARP proteins and/or PARP fusion proteins used in this method may be attached to a solid surface or substrate (e.g., a bead) and/or may be present in purified form or present in a crude cell lysate, biological fluid, or extracellular medium. The methods may optionally include one or more (e.g., 1, 2, 3, 4, or 5) washing steps following contacting the one or more PARP proteins and/or PARP fusion proteins with the test agent. The test agent may be a small molecule, a lipid, an RNA molecule, a DNA molecule, a protein, or a peptide fragment. The test agent may be purified in form (e.g., at least 70%, 80%, 85%, 90%, 95%, or 99% pure by weight) or may be present in a crude cell lysate. The test agent may also, optionally be labeled (e.g., a colorimetric label, a radionuclide label, labeled with a biotin molecule, or labeled with a fluorophore).

The binding of the test agent to one of more PARP proteins and/or PARP fusion proteins may detected by any known method including, BIAcore, competitive binding assays (e.g., a competitive binding assay using one or more of the antibodies provided by the invention), and detection of the agent following its release from the one or more PARP proteins and/or PARP fusion proteins (e.g., elution of the bound test agent following exposure to high salt or a high or low pH buffer). The one or more PARP proteins and/or PARP fusion proteins may be any of the example PARP proteins and PARP fusion proteins described herein.

In one example of this method, a bead attached to one or more PARP proteins and/or PARP fusion proteins of the invention (e.g., a ZZ-TEV-PARP fusion protein) may be incubated with a crude cell lysate, and the proteins or peptide fragments bound to the one or more PARP proteins and/or PARP fusion proteins may be eluted from the beads by exposure to a high salt buffer, a high detergent buffer, or a high or low pH buffer. The resulting eluted proteins may be electrophoresed onto an SDS-polyacrylamide gel and the specific protein bands cut out from the gel and analyzed using mass spectrometry to identify the specific agent that binds to the one or more PARP proteins and/or PARP fusion proteins.

In another example of the method, a bead attached to one or more PARP proteins and/or PARP fusion proteins of the invention is incubated with a purified protein or peptide fragment. In this instance, a protein or peptide fragment bound to the one or more PARP proteins and/or PARP fusion proteins may be eluted using a high salt buffer, a high detergent buffer, or a high or low pH buffer. The amount of protein in the eluate may be detected by any method known in the art including UV/vis spectroscopy, mass spectrometry, or any colorimetric protein dye (e.g., a Bradford assay).

In specific screening assays for agents that bind one or more PARP proteins and/or PARP fusion proteins, one or more PARP proteins and/or PARP fusion proteins may be placed in individual wells of a multi-well plate (e.g., one or more PARP proteins and/or PARP fusion proteins covalently linked to the plate surface) and incubated with the test agent. Following a washing step, the amount of test agent remaining in each well may be determined and the ability of the test agent to bind one or more PARP proteins and/or PARP fusion proteins determined.

The methods desirably identify a test agent that specifically binds one or more of a PARP1 protein and/or fusion protein, a PARP2 protein and/or fusion protein, a PARP5A protein and/or fusion protein, a PARP5B protein and/or fusion protein, a PARP7 protein and/or fusion protein, a PARP8 protein and/or fusion protein, a PARP14 protein and/or fusion protein, and a PARP16 protein and/or fusion protein of the invention. The methods also desirably identify a test agent that specifically binds to one or more of a PARP5A protein and/or fusion protein, a PARP12 protein and/or fusion protein, a PARP13.1 protein and/or fusion protein, a PARP13.2 protein and/or fusion protein, and a PARP15 protein and/or fusion protein of the invention. The methods also desirably identify a test agent that specifically binds to a PARP13.1 protein and/or fusion protein or a PARP11 protein and/or fusion protein of the invention.

EXAMPLES

The features and other details of the invention will now be more particularly described and pointed out in the following examples describing preferred techniques and experimental results. These examples are provided for the purpose of illustrating the invention and should not be construed as limiting.

Example 1

Generation of PARP-GFP Fusion Proteins and Assays

Figure 4:
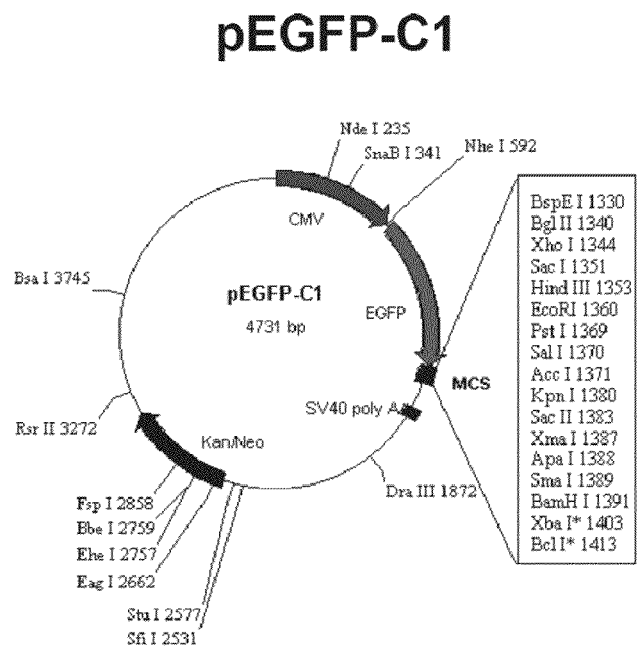
FIG. 4 is a diagram of the pEGFP-C1 vector (Invitrogen) showing the CMV promoter, the EGFP sequence, the multiple cloning site (MCS), and the SV40 poly A sequence. Also shown is the polylinker sequence (SEQ ID NO: 29).

Fusion proteins containing the sequence of each PARP and green fluorescent protein (GFP) were generated using the pEGFP-C1 vector (Invitrogen) (FIG. 4). For these experiments, the DNA sequences encoding each of PARP1 (SEQ ID NOS: 1 and 2), PARP3 (SEQ ID NOS: 4, 5, and 6), PARP4 (SEQ ID NO: 7), PARP5A (SEQ ID NOS: 8 and 9), PARP5B (SEQ ID NO: 10), PARP6 (SEQ ID NO: 11), PARP7 (SEQ ID NO: 12), PARP8 (SEQ ID NO: 13), PARP9 (SEQ ID NO: 14), PARP10 (SEQ ID NOS: 15 and 16), PARP11 (SEQ ID NO: 17), PARP12 (SEQ ID NO: 18), PARP13.1 (SEQ ID NO: 19), PARP13.2 (SEQ ID NO: 20), PARP14 (SEQ ID NO: 21), PARP15 (SEQ ID NOS: 22 and 23), and PARP16 (SEQ ID NO: 24) were cloned into the pEGFP-C1 vector using the restriction sites indicated in Table 2. Each resulting plasmid contained a nucleic acid sequence encoding a PARP-GFP fusion protein, wherein the nucleic acid sequence encoding GFP was located 5' to the nucleic acid sequence encoding the PARP protein.

TABLE 2

Restriction Sites Used for Cloning PARP Sequences into pEGFP-C1

| PARP | Restriction Sites |
| --- | --- |
| 1 | BglII, SalI |
| 3 | BglII, SalI |
| 4 | KpnI, ApaI |
| 5a | HinDIII, BglII |
| 5b | SalI, BamHI |
| 6 | SalI, XmaI |
| 7 | BspEI, EcoRI |
| 8 | BspEI, SalI |
| 9 | BspEI, SalI |
| 10 | BamHI, BglII |
| 11 | SalI, BamHI |
| 12 | SalI, ApaI |
| 13 isoform 1 | BspEI, BamHI |
| 13 isoform 2 | BglII, BamHI |
| 14 | XhoI, SacII |
| 15 | SalI, BamHI |
| 16 | BglII, SalI |

Figure 5:
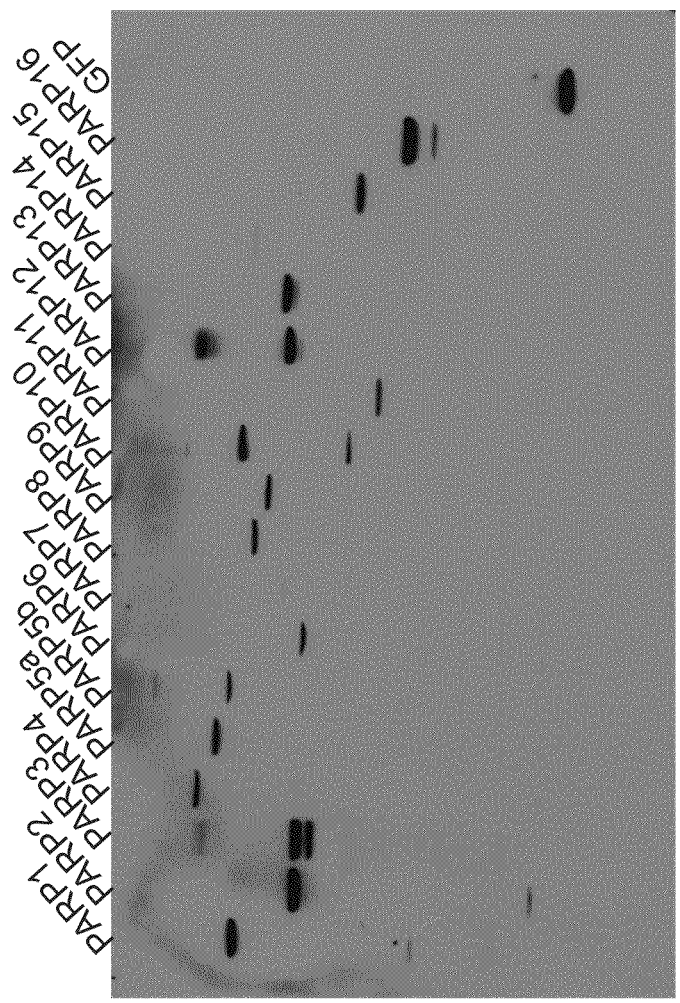
FIG. 5 is an immunoblot showing the expression and relative size of the PARP-GFP fusion proteins of PARP1, PARP2, PARP3, PARP4, PARP5A, PARP5B, PARP6, PARP7, PARP8, PARP9, PARP10, PARP11, PARP12, PARP13, PARP14, PARP15, and PARP16 expressed in HeLa Kyoto cells transfected with pEGFP-C1 plasmids containing a nucleic acid encoding each respective PARP-GFP fusion protein. The immunoblot was developed using a rabbit anti-GFP polyclonal antibody.

Each generated pEGFP-C1 vector was transfected into HeLa Kyoto cells using Lipofectamine 2000, according to the manufacturer's instructions. Cell lysate was prepared from the HeLa cells at 18 hours following transfection. Electrophoresis was performed on the cell lysate using 4-12% SDS-PAGE, and immunoblotting was performed using a rabbit anti-GFP polyclonal antibody (FIG. 5).

Figure 6:
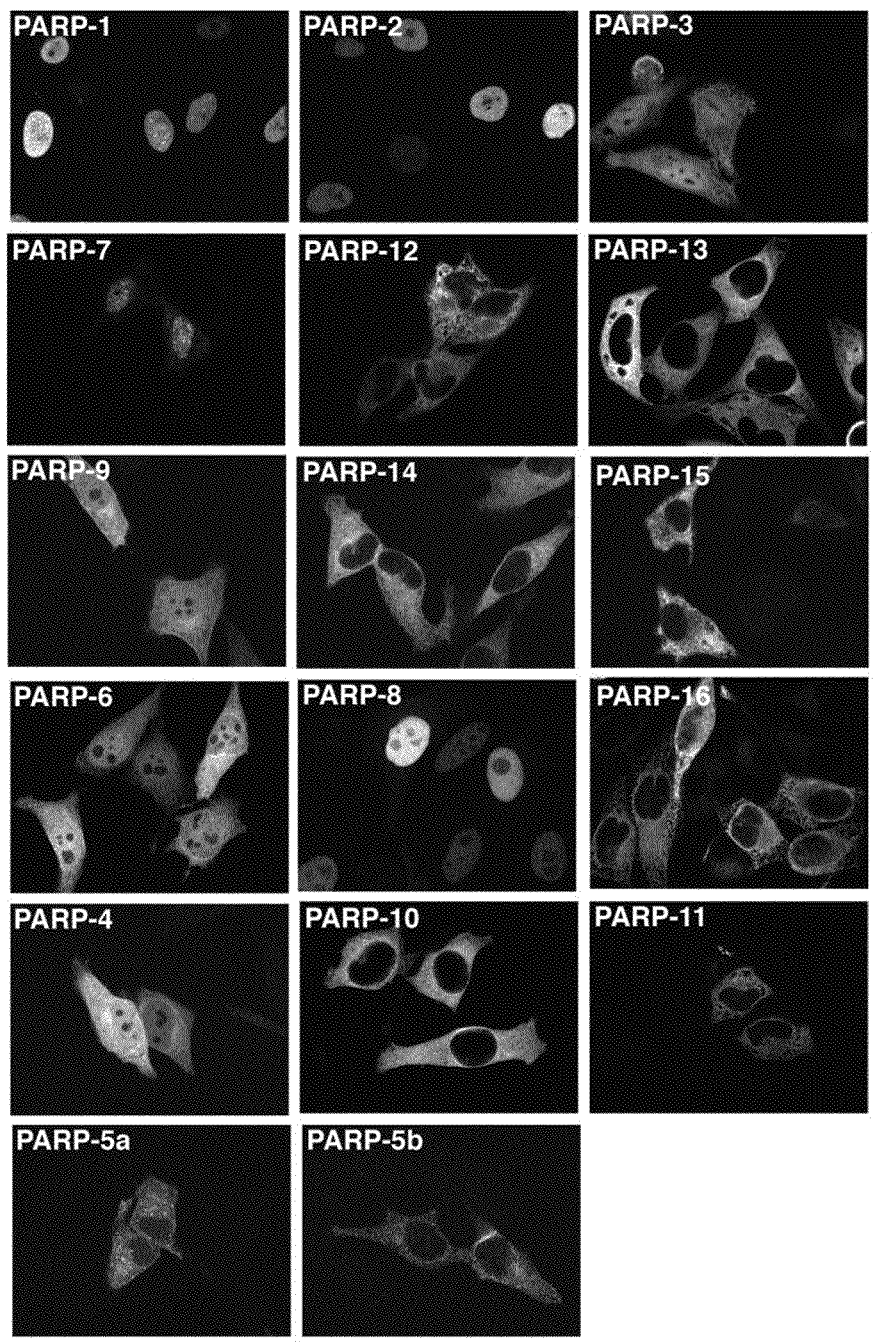
FIG. 6 is a set of micrographs showing the localization of different PARP-GFP fusion proteins in asynchronous HeLa Kyoto cells transfected with a pEGFP-C1 plasmid containing a nucleic acid encoding a PARP-GFP protein. The transfected cells were immunostained with rabbit anti-GFP polyclonal antibody and fluorescently-labeled secondary Alexa Fluor 594 or 488 antibody (Invitrogen), and visualized using fluorescence microscopy. The localization of PARP1-GFP, PARP2-GFP, PARP3-GFP, PARP7-GFP, PARP12-GFP, PARP13-GFP, PARP9-GFP, PARP14-GFP, PARP15-GFP, PARP6-GFP, PARP8-GFP, PARP16-GFP, PARP4-GFP, PARP10-GFP, PARP11-GFP, PARP5A-GFP, and PARP5B-GFP fusion proteins is shown.
Figure 7:
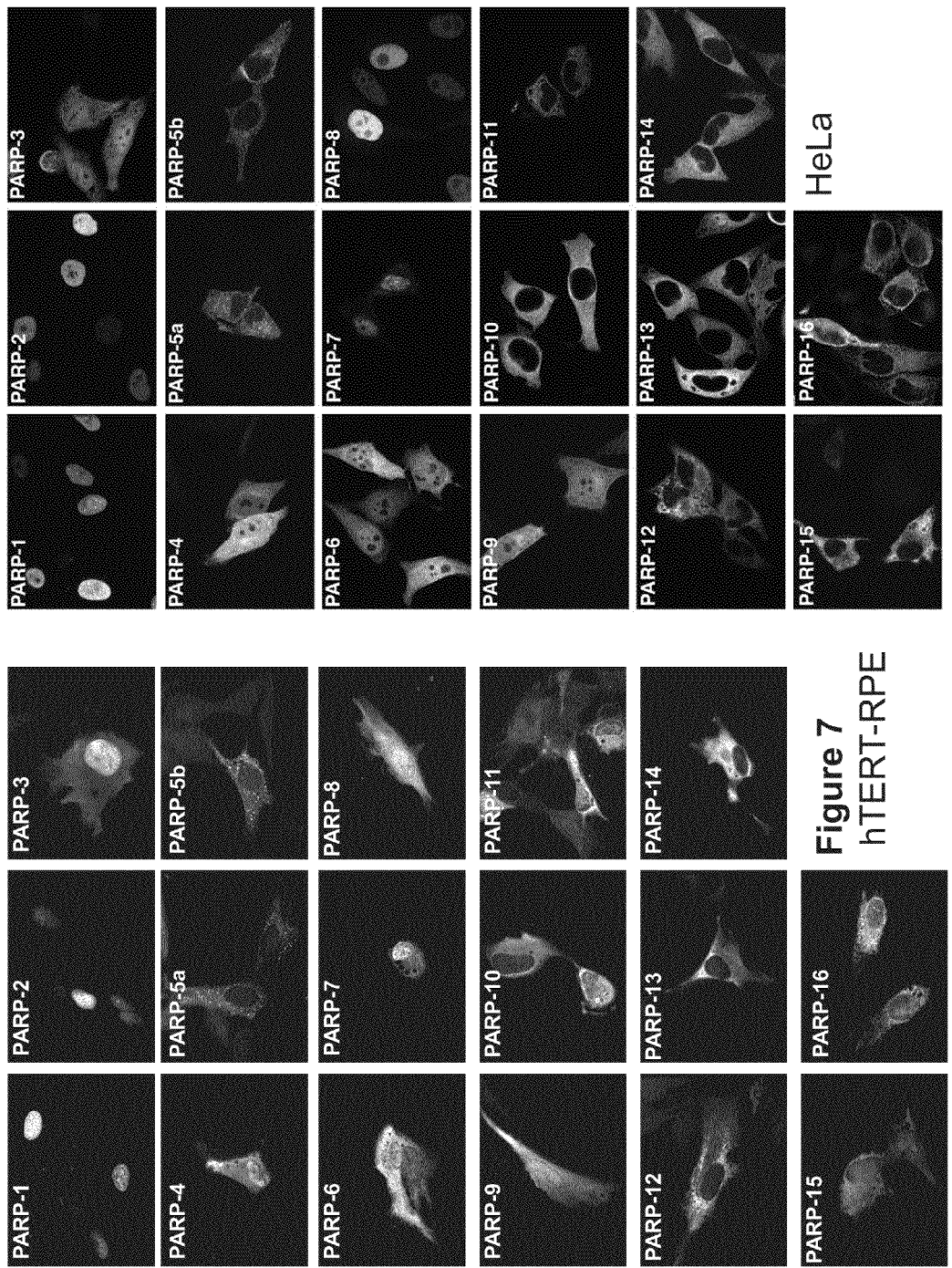
FIG. 7 is two sets of micrographs showing the localization of different PARP-GFP fusion proteins in asynchronous hTERT-RPE and HeLa Kyoto cells transfected with a pEGFP-C1 plasmid containing a nucleic acid encoding a PARP-GFP protein. The transfected cells were immunostained with rabbit anti-GFP polyclonal antibody and fluorescently-labeled Alexa Fluor 594 or 488 antibodies (Invitrogen), and visualized using fluorescence microscopy. The localization of PARP1-GFP, PARP2-GFP, PARP3-GFP, PARP4-GFP, PARP5A-GFP, PARP5B-GFP, PARP6-GFP, PARP7-GFP, PARP8-GFP, PARP9-GFP, PARP10-GFP, PARP11-GFP, PARP12-GFP, PARP13-GFP, PARP14-GFP, PARP15-GFP, and PARP16-GFP fusion proteins is shown for each cell type.

The localization of each PARP-GFP fusion protein in the transfected HeLa Kyoto cells was determined using immunofluorescence microscopy using rabbit anti-GFP polyclonal antibody and a fluorescently-labeled secondary antibody (FIG. 6). The data from this experiment indicate that several PARP-GFP proteins are primarily localized in the nucleus of asynchronous cells, including PARP1-GFP, PARP2-GFP, PARP7-GFP, and PARP8-GFP. The data further indicate that several PARP-GFP fusion proteins are localized in primarily in the cytoplasm of asynchronous cells, including PARP12-GFP, PARP13-GFP, PARP14-GFP, PARP15-GFP, PARP16-GFP, PARP10-GFP, PARP11-GFP, PARP5A-GFP, and PARP5B-GFP. In addition, the data indicate that several PARP-GFP fusion proteins are localized in both the cytoplasm and the nucleus of asynchronous cells, including PARP3-GFP, PARP9-GFP, PARP6-GFP, and PARP4-GFP. The same pattern of cell localization for each PARP-GFP fusion protein was observed in the hTERT-RPE1 cell line (Clontech), a telomerase-immortalized human retinal pigment epithelial (RPE) normal cell line (FIG. 7).

Antibodies specific for each PARP were generated by immunizing rabbits with PARP-specific peptides conjugated to keyhole limpet hemocyanin (KLH) using known methods. The antibodies produced in the rabbit serum were later affinity purified using peptide columns (e.g., columns containing, as substrate, the specific peptide sequence used to inoculate the rabbit).

Figure 8:
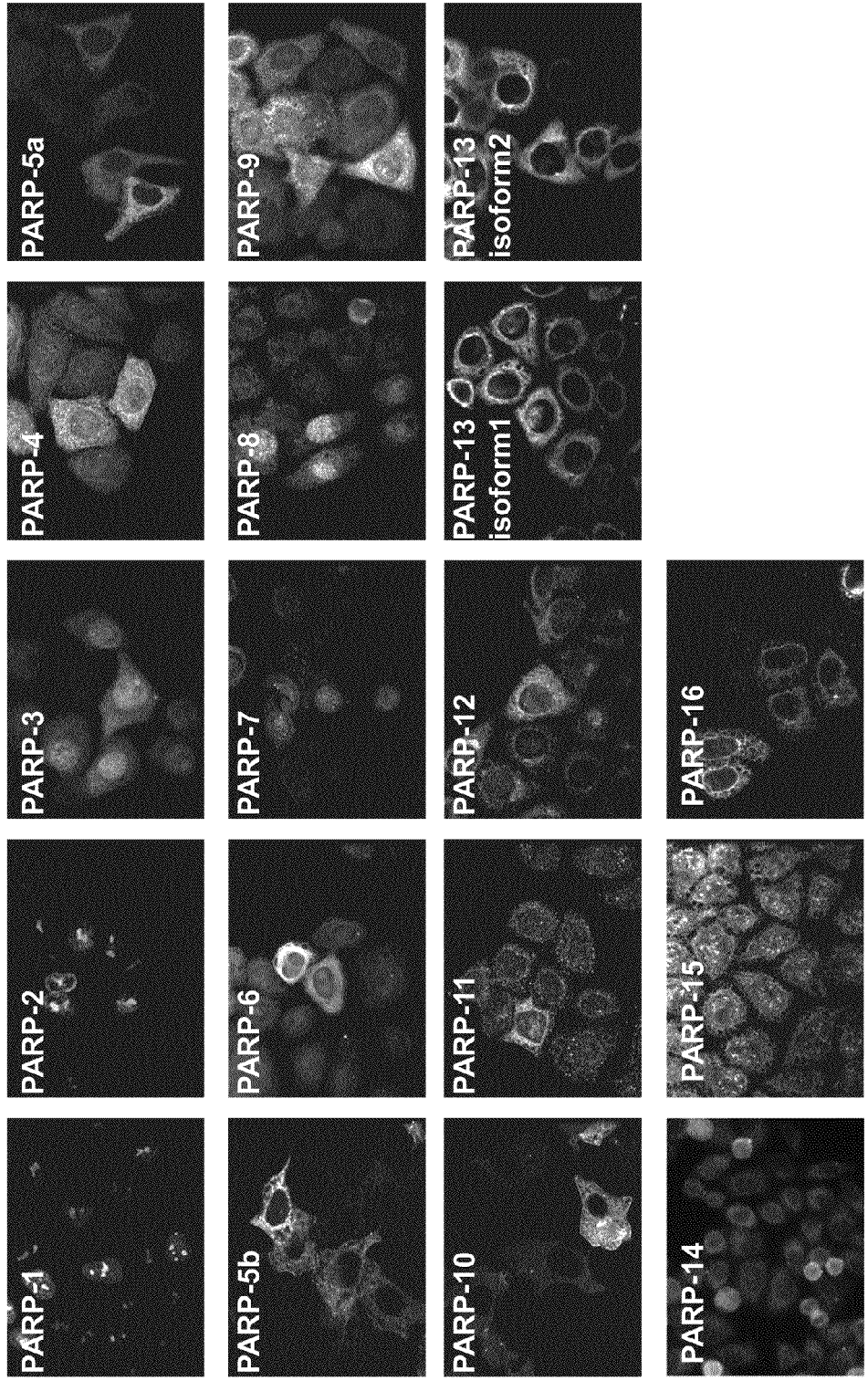
FIG. 8 is a set of micrographs from asynchronous HeLa Kyoto cells transfected with a pEGFP-C1 plasmid containing a nucleic acid encoding a PARP-GFP fusion protein following immunostaining with primary rabbit antibodies raised against each specific PARP and fluorescently-labeled Alexa Fluor 594 or 488 antibodies (Invitrogen). The localization of PARP1, PARP2, PARP3, PARP4, PARP5A, PARP5B, PARP6, PARP7, PARP8, PARP9, PARP10, PARP11, PARP12, PARP13.1, PARP13.2, PARP14, PARP15, and PARP16 is shown.

The antibodies for each PARP and a secondary-fluorescently labeled anti-rabbit polyclonal antibody were used to visualize the location of each PARP in asynchronous HeLa Kyoto cells transfected with a pEGFP-C1 plasmid encoding a PARP-GFP fusion protein (FIG. 8). The data from this experiment confirm that PARP1, PARP2, PARP7, PARP8, and PARP14 are primarily localized in the nucleus of asynchronous cells. The data from this experiment also confirm that PARP3, PARP4, PARP6, PARP9, and PARP15 are localized in the both the nucleus and the cytoplasm of asynchronous cells.

Figure 9:
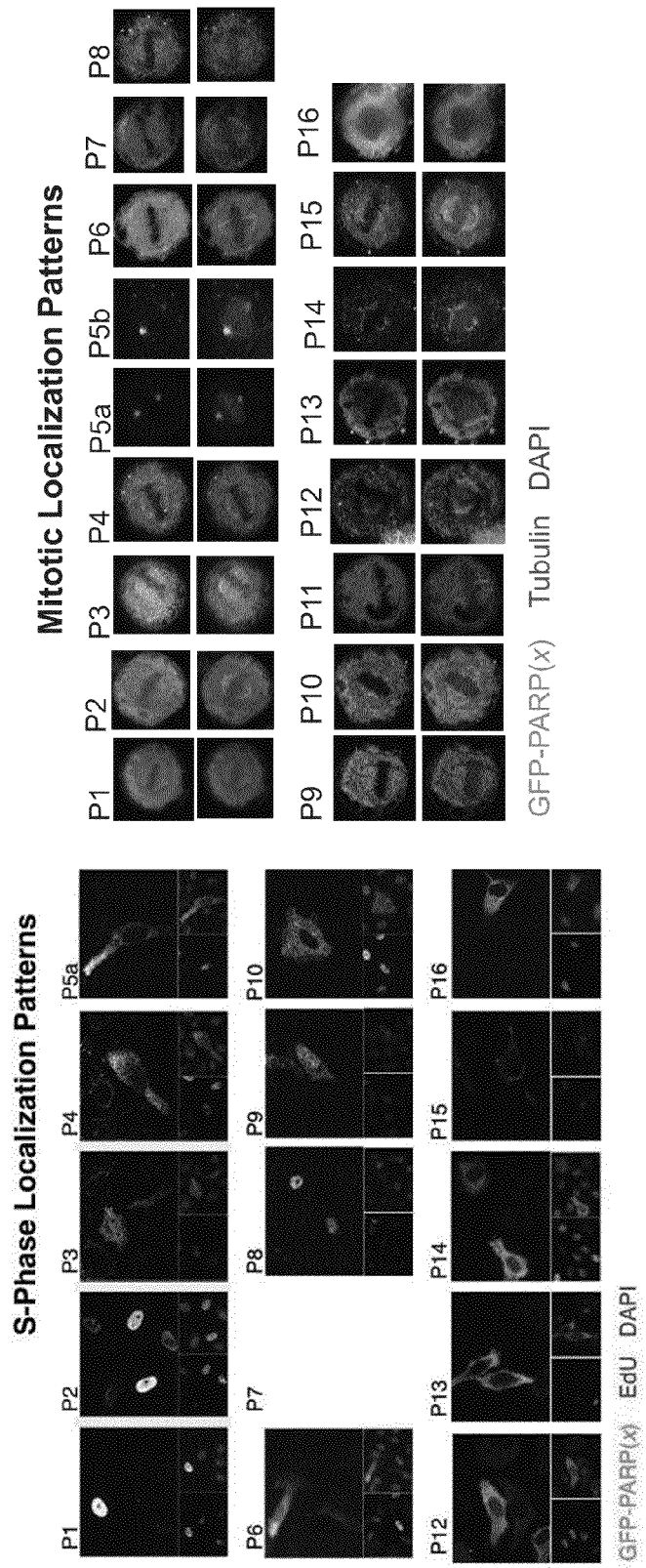
FIG. 9 is a set of micrographs showing the localization of each PARP-GFP fusion protein during S-phase and mitosis in transfected HeLa Kyoto cells. In each experiment, HeLa Kyoto cells were transfected using Lipofectamine 2000 with a specific PARP-GFP expression vector (pEGFP-C1) and were arrested in mitosis or S-phase by treatment with 100 nM nocodazole or 5 μg/mL aphidicolin for 12 hours. The resulting treated cells were immunostained with rabbit anti-GFP polyclonal antibodies and fluorescently-labeled Alexa Fluor 594 or 488 antibodies (Invitrogen), and visualized using fluorescence microscopy. S-phase-arrested cells were also stained with EdU and DAPI, and mitosis-arrested cells were further stained with tubulin and DAPI.

The localization of each PARP-GFP fusion protein (described above) was also determined in HeLa Kyoto cells transfected with a pEGFP-C1 plasmid encoding a PARP-GFP fusion protein following 12-hour treatment with 100 nM nocodazole or 5 µg/mL aphidicolin. Cells treated with nocodazole are arrested in S phase, while cells treated with aphidicolin are arrested in mitosis. FIG. 9 shows the cellular localization for each PARP-GFP fusion protein following cell arrest in S-phase or mitosis. The data show that the PARP1-GFP, PARP2-GFP, and PARP8-GFP fusion proteins localize to the nucleus during S-phase, and that PARP5A-GFP and PARP5B-GFP localize to the mitotic spindle during mitosis. The localization of these PARP-GFP fusion proteins (e.g., PARP1-GFP, PARP2-GFP, PARP5A-GFP, PARP5B-GFP, and PARP8-GFP) to the nucleus during S-phase and mitosis indicate a role for these PARP proteins in cell division and cell proliferation.

Figure 10:
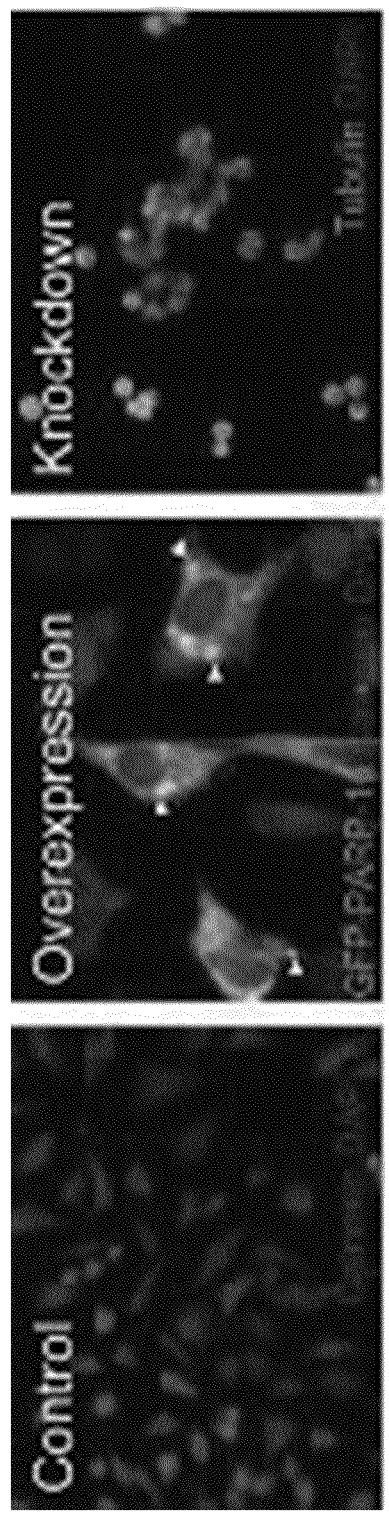
FIG. 10 is a set of micrographs showing the localization of overexpressed PARP16-GFP in the endoplasmic reticulum of HeLa Kyoto cells transfected with a pEGFP-C1 plasmid encoding a PARP16-GFP fusion protein (middle panel) and the phenotype of HeLa Kyoto cells transfected with an RNAi targeting endogenous PARP16 (right panel). The left panel shows untransfected HeLa Kyoto cells stained with anti-calnexin antibodies, secondary fluorescently-labeled antibodies (Alexa Fluor 594 or 488 antibodies (Invitrogen)), and DAPI. The middle panel the localization of PARP16-GFP and calnexin in HeLa Kyoto cells transfected with a pEGFP-C1 plasmid expressing a PARP16-GFP fusion protein following staining with anti-calnexin, anti-GFP, Alexa Fluor 594 or 488 antibodies (Invitrogen), and DAPI. The right panel shows the phenotype of HeLa Kyoto cells following transfection with an RNAi molecule targeting endogenous PARP16 (SEQ ID NO: 43) following staining with an anti-tubulin antibody, Alexa Fluor 594 or 488 antibody (Invitrogen), and DAPI.

In order to study the role of PARP16, additional experiments were performed using RNAi knockdown of endogenous PARP16 or overexpression of PAPR16-GFP fusion proteins to study the effect of PARP16 knockdown and overexpression, respectively on cell morphology. Asynchronous HeLa Kyoto cells overexpressing PARP16-GFP protein had normal cell morphology (FIG. 10; middle panel). In these cells, the PARP16-GFP protein was primarily localized in the endoplasmic reticulum, as demonstrated by its co-localization with calnexin (FIG. 10; middle panel). HeLa Kyoto cells transfected with an RNAi molecule specific for PARP16 demonstrated significant morphological changes, including cell shrinkage and dramatic membrane defects (FIG. 10; right panel).

Figure 11:
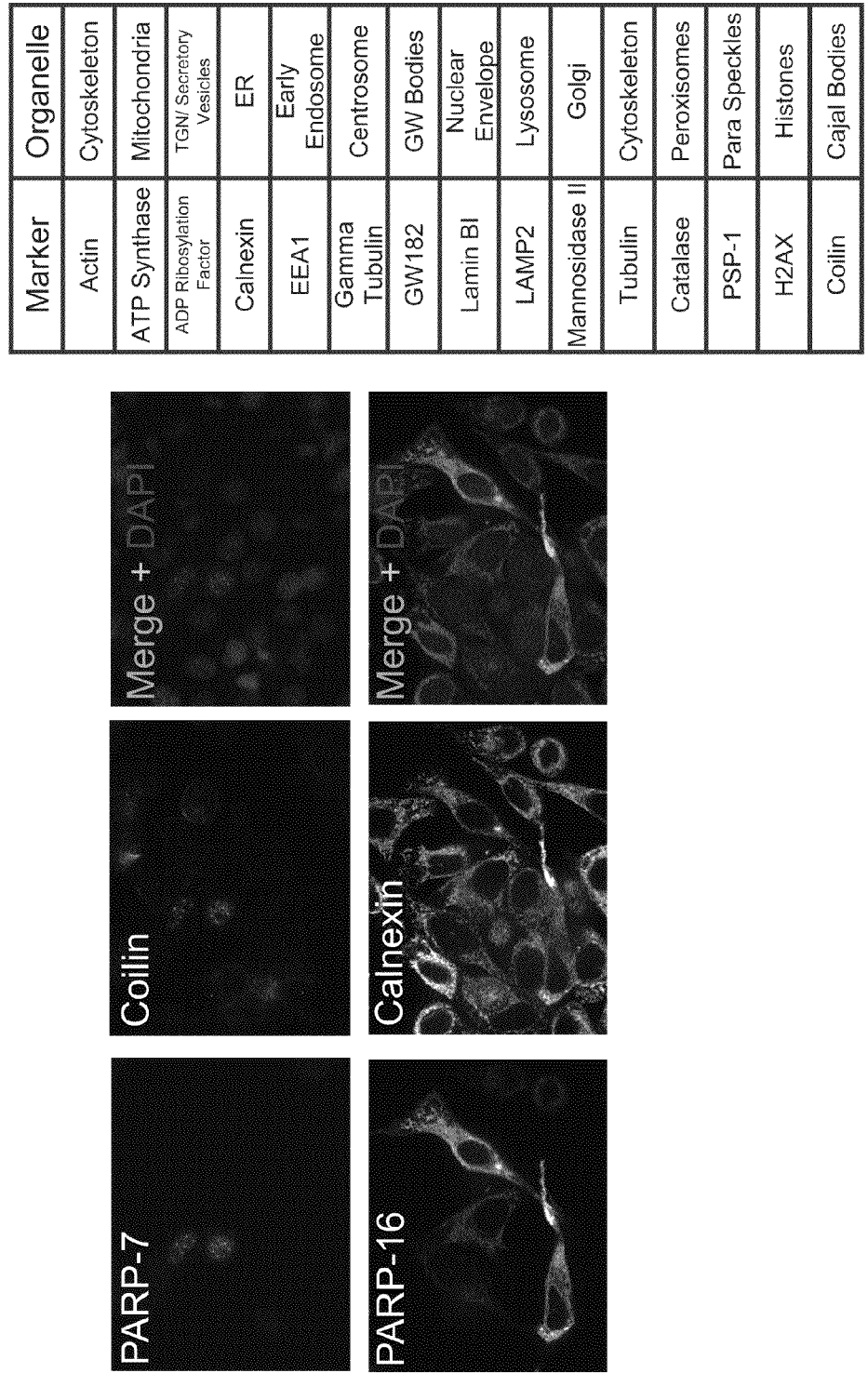
FIG. 11 is a set of micrographs showing the co-localization of PARP7-GFP and coilin, and the co-localization of PARP16-GFP and calnexin. In each experiment, HeLa Kyoto cells transfected with pEGFP-C1 vectors expressing PARP7-GFP or PARP16-GFP were stained with anti-GFP and anti-coilin or anti-calnexin antibodies, and fluorescently labeled secondary antibodies (Alexa Fluor 594 or 488 antibodies). The figure also lists a number of protein markers of specific cellular organelles and structures.

The specific cellular localization of each PARP-GFP fusion protein may be further analyzed by immunofluorescence microscopy using a combination of labeled antibodies specific for the GFP-tag of each PARP-GFP fusion protein and one or more markers of cellular structures or organelles. For example, immunofluorescence staining of asynchronous HeLa Kyoto cells transfected with a pEGFP-C1 vector expressing the PARP7-GFP fusion protein shows co-localization of an anti-GFP antibody and an anti-coilin antibody (a marker of Cajal bodies in the nucleus) (FIG. 11). In another example, asynchronous HeLa Kyoto cells transfected with a pEGFP-C1 vector expressing the PARP16-GFP fusion protein shows co-localization of an anti-GFP antibody and an anti-calnexin antibody (a marker of the endoplasmic reticulum) (FIG. 11). A non-limiting list of marker proteins that may be used to determine the cellular localization of a PARP-GFP fusion protein is also provided in FIG. 11.

Experimental Methods

Kyoto HeLa cells were grown in DMEM supplemented with 10% FCS and penicillin/streptomycin at 37° C. in 5% $CO_2$. Lipofectamine 2000 (Invitrogen) was used to transfect the cells with each pEGFP-C1 vector according to the manufacturer's protocol. Cells were arrested in mitosis and S-phase by treatment with 100 nM nocodazole or 5 µg/mL aphidicolin for 12 hours, respectively. For immunofluorescence imaging, cells on coverslips were fixed in ice-cold methanol for five minutes and rehydrated in phosphate buffered saline (PBS). The cells were blocked in PBS containing 4% bovine serum albumin (BSA) and 0.1% Triton-X 100. All antibodies used for imaging were diluted in blocking buffer. The coverslips were incubated with primary antibodies for 45 minutes and with secondary antibodies for 30 minutes. Images were collected on a Nikon TE2000 confocal microscope equipped with a Yokogawa CSU-X1 spinning disk head, Hamamatsu ORCA ER digital camera, and NIS-Elements imaging software.

In the PARP16-GFP overexpression experiments, HeLa Kyoto cells were transfected using Lipofectamine 2000 with a pEGFP-C1 vector containing a nucleic acid encoding a PARP16-GFP protein as described below. Following transfection with the expression vector, the cells were stained using anti-GFP antibodies and secondary fluorescently-labeled antibodies (Alexa Fluor 594 and 488 antibodies), and visualized using fluorescence microscopy. The stains were further stained with DAPI.

In the PARP16 knockdown experiments, HeLa Kyoto cells were transfected with 20 nM of a PARP16 RNAi molecule (siRNA16; SEQ ID NO: 43). The resulting cells were stained using anti-tubulin antibodies, secondary fluorescently-labeled antibodies (Alexa Fluor 594 and 488 antibodies), and DAPI, and visualized using fluorescence microscopy.

Example 2

Generation of ZZ-TEV-PARP Fusion Proteins

Figure 12:
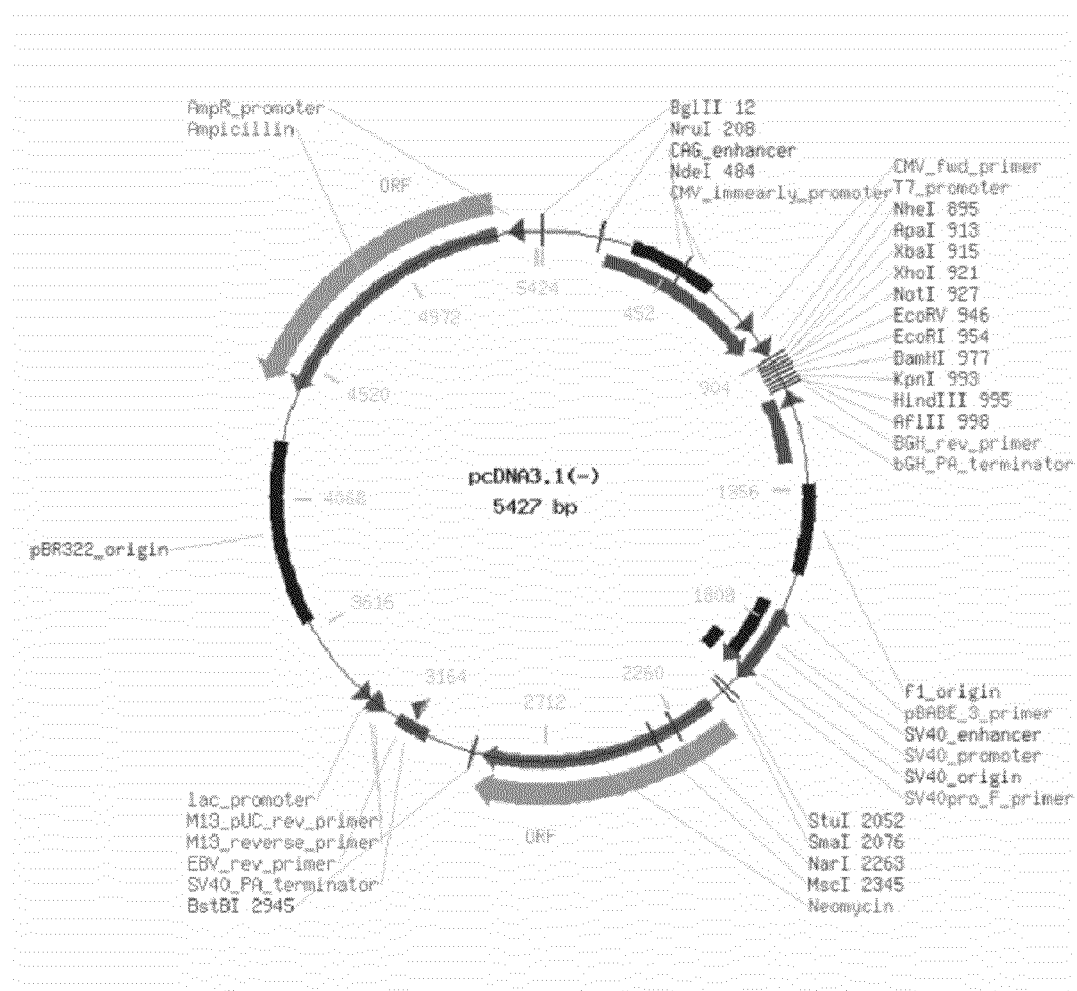
FIG. 12 is a diagram of the pcDNA3.1 vector (Invitrogen) showing the CMV promoter and the restriction sites that may be used for cloning.

Fusion proteins containing the sequence of each PARP, a ZZ-domain of SEQ ID NO: 27, and four TEV protease recognition sequences (SEQ ID NO: 26) were cloned using the pcDNA3.1 vector (Invitrogen) (FIG. 12) to yield a ZZ-4x-TEV-PARP fusion protein for each PARP. For these experiments, the DNA sequences encoding PARP1 (SEQ ID NOS: 1 and 2), PARP2 (SEQ ID NO: 3), PARP3 (SEQ ID NOS: 4, 5, and 6), PARP4 (SEQ ID NO: 7), PARP5A (SEQ ID NOS: 8 and 9), PARP6 (SEQ ID NO: 11), PARP7 (SEQ ID NO: 12), PARP9 (SEQ ID NO: 14), PARP10 (SEQ ID NOS: 15 and 16), PARP11 (SEQ ID NO: 17), PARP13.1 (SEQ ID NO: 19), PARP13.2 (SEQ ID NO: 20), PARP14 (SEQ ID NO: 21), PARP15 (SEQ ID NOS: 22 and 23), and PARP16 (SEQ ID NO: 24) were cloned into the pcDNA3.1 vector using the restriction sites indicated in Table 3. The sequence encoding the ZZ-domain and the sequence encoding the four TEV protease recognition sequences were cloned into the NheI and HinDIII restriction sites in pcDNA3.1.

TABLE 3

Restriction Sites Used for Cloning PARP Sequences into pcDNA3.1

| PARP | Restriction Sites |
| --- | --- |
| 1 | XhoI, PmeI |
| 2 | BamHI, NotI |
| 3 | EcoRV, NotI |
| 4 | KpnI, ApaI |
| 5a | HinDIII, XhoI |
| 6 | EcoRV, NotI |
| 7 | BamHI, NotI |

TABLE 3-continued

Restriction Sites Used for Cloning PARP Sequences into pcDNA3.1

| PARP | Restriction Sites |
| --- | --- |
| 9 | EcoRV, NotI |
| 10 | HinDIII, XbaI |
| 11 | BamHI, XbaI |
| 13 isoform 1 | KpnI, BamHI |
| 13 isoform 2 | BamHI, EcoRV |
| 14 | KpnI, XhoI |
| 15 | KpnI, XhoI |
| 16 | KpnI, XbaI |

Each resulting plasmid contained a nucleic acid sequence encoding a ZZ-TEV-PARP fusion protein, wherein the nucleic acid sequence encoding ZZ domain was located 5' to the nucleic acid sequence encoding the four TEV protease recognition sequences, which in turn, was located 5' to the nucleic acid sequence encoding each PARP.

Nucleic acids encoding each ZZ-TEV-PARP fusion protein may be transfected into target cells (e.g., HeLa Kyoto or HeLa S3 cells) and the resulting ZZ-TEV-PARP fusion proteins purified by binding to magnetic beads coated with a protein containing an Fc domain (e.g., IgG). The resulting ZZ-TEV-PARP fusion proteins may be used in the assays described below for the PARP-GFP fusion proteins and the other assays described herein. Assays utilizing the ZZ-TEV-PARP fusion proteins have the additional advantage of containing an engineered TEV protease recognition sequence, whereby the polypeptide tag on each PARP fusion protein (e.g., the ZZ-domain and the four TEV protease recognition sequences) may optionally be removed from the ZZ-TEV-PARP fusion proteins by treatment with TEV protease. In one example, one or more ZZ-TEV-PARP fusion proteins may be removed from a magnetic bead, resin, or solid surface by treatment with a TEV protease.

Example 3

PARP Activity Assays and Screening Methods

Figure 13:
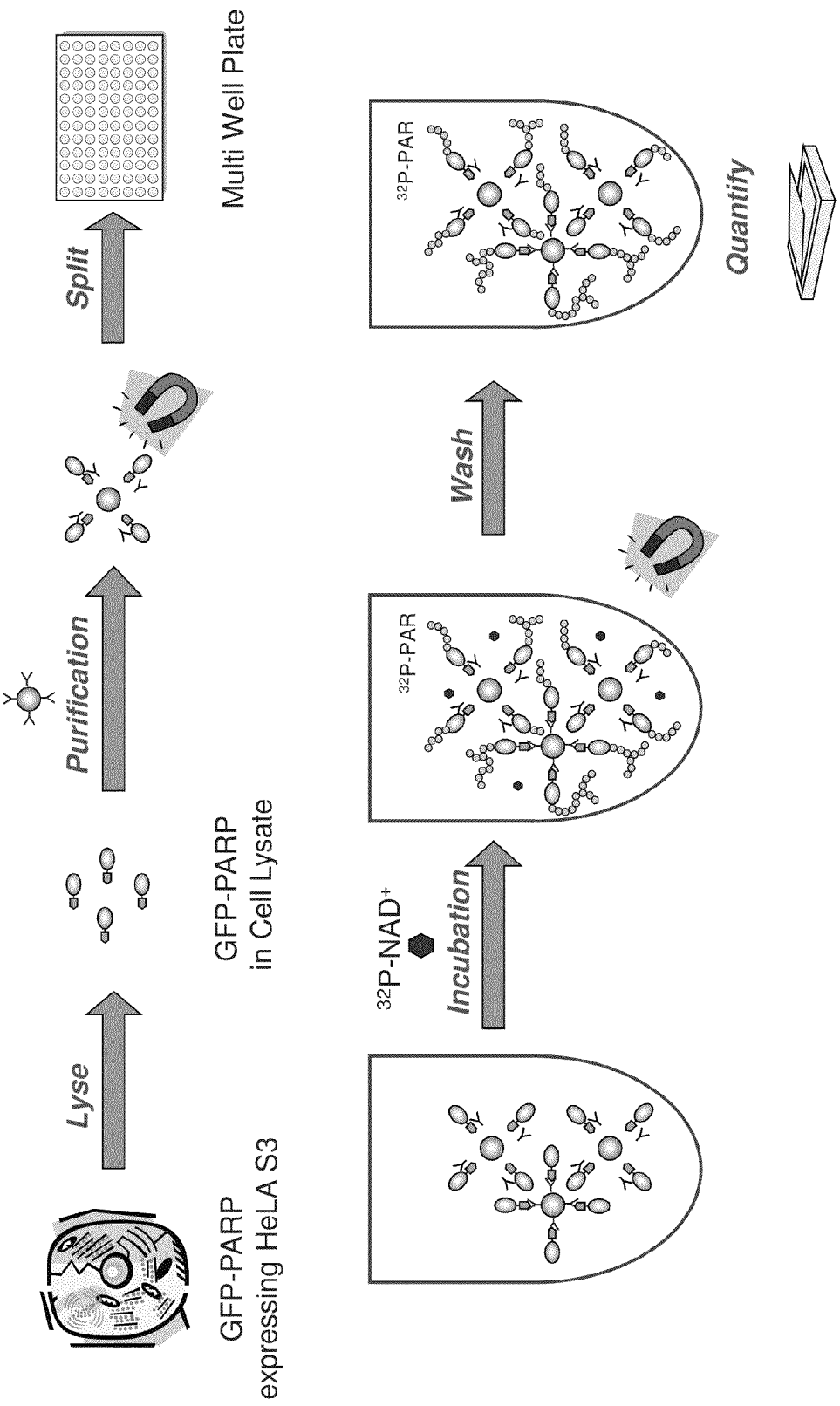
FIG. 13 is a diagram of an example of an activity assay using one or more of the PARP-GFP fusion proteins of the invention.

The above-described PARP fusion proteins may be used in PARP activity assays and in assays to identify an activator or inhibitor for a specific PARP or a specific subset of PARPs. An example of such an activity assay in shown in FIG. 13. In this example, cell lysate is first prepared from a HeLa S3 cell culture expressing one or more PARP-GFP fusion proteins. The cell lysate is then incubated with an anti-GFP polyclonal antibody bound to Dynabead® Protein A beads, and the beads magnetically removed from the cell lysate. The isolated beads bound to one or more PARP-GFP fusion proteins are placed into a multi-well plate and incubated with a labeled NAD$^+$ substrate (e.g., $^{32}$P-NAD$^+$). Following incubation with the labeled NAD$^+$ substrate, the magnetic beads bound with the one or more PARP-GFP proteins are magnetically isolated or washed, and the level of the label (i.e., the label present in the labeled NAD$^+$ substrate) that is covalently attached to the one or more PARP-GFP fusion proteins bound to the magnetic beads is determined (e.g., the amount of $^{32}$P covalently bound to the one or more PARP-GFP proteins attached to the beads). This assay provides a means of measuring the auto-modulation activity of one or more PARP-GFP fusion proteins (e.g., the ability of a PARP to modify its own structure by catalyzing the covalent attachment of one or more ADP-ribose molecules). The assay may also be designed such that lysate or PARP-GFP fusion proteins isolated from several different transfected HeLa S3 cells, each expressing a different PARP-GFP fusion proteins or subset of PARP-GFP fusion proteins, may be placed in different wells of the multi-well plate. The assay may also be designed such that the lysate from several different transfected HeLa S3 cells is combined, wherein the lysate from each transfected HeLa S3 cell culture contains one or more PARP-GFP fusion proteins. In a different version of the assay, the PARP-GFP fusion proteins may contain a protease recognition site. In this version of the assay, the one or more PARP-GFP fusion proteins bound to the magnetic beads may be treated with a specific protease (i.e., a protease that recognizes a protease recognition sequence in the PARP-GFP fusion protein) to mediate release of the PARP-GFP fusion protein from the magnetic bead.

Figure 14:
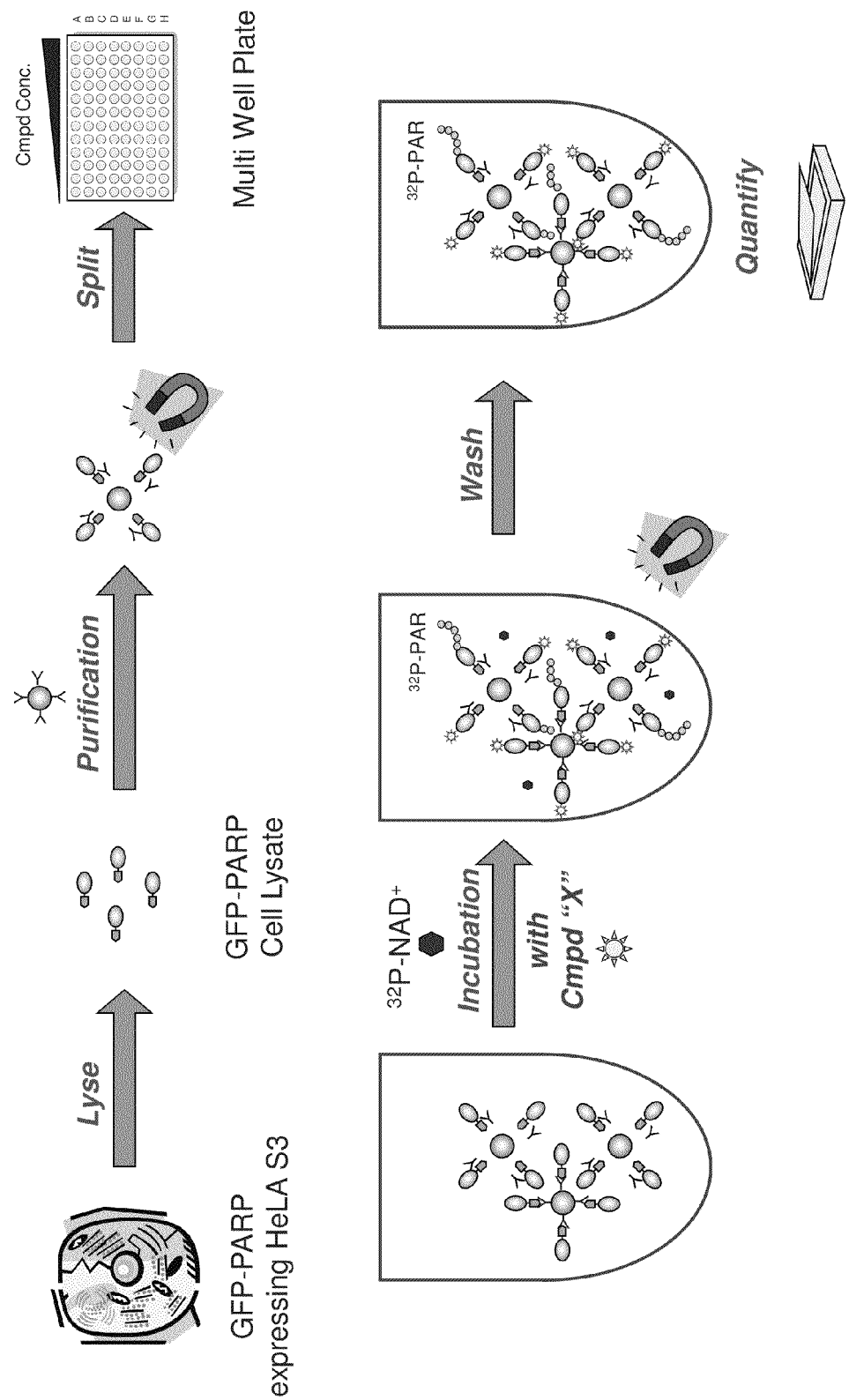
FIG. 14 is a diagram of an example of an assay for identifying an activator of one or more PARP-GFP fusion proteins of the invention.

FIG. 14 provides an example of the use of the PARP-GFP fusion proteins of the invention for the identification of an agent that specifically inhibits the activity of one or more PARPs. This assay is similar to the assay described above, except that the one or more PARP-GFP fusion proteins is incubated with both a test agent and a labeled NAD$^+$ substrate. A specific PARP inhibitor will decrease the amount of the label (i.e., the label present in the labeled NAD$^+$ substrate) covalently attached to the one or more PARP-GFP fusion proteins bound to the magnetic beads relative to the amount of the label attached to the one or more PARP-GFP fusion proteins in the absence of the test agent. In different examples of this assay, lysate or PARP-GFP fusion proteins isolated from two or more different transfected HeLa S3 cells, each expressing a different PARP-GFP fusion protein or subset of PARP-GFP fusion proteins, may be placed in different wells of the multi-well plate. The assay may also be designed such that the lysate from several different transfected HeLa S3 cells is combined, wherein the lysate from each transfected HeLa S3 cells contains one or more PARP-GFP fusion proteins. The assay may also be specifically designed to identify inhibitors of a specific PARP-GFP protein or subset of PARP-GFP proteins including the subsets of: one or more of PARP1-GFP, PARP2-GFP, PARP5A-GFP, PARP5B-GFP, PARP7-GFP, PARP8-GFP, PARP14-GFP, and PARP16-GFP; one or more of PARP5A-GFP, PARP12-GFP, PARP13.1-GFP, PARP13.2-GFP, PARP15-GFP; PARP11-GFP; or PARP13.1-GFP.

Similar to the examples, described above, the PARP-GFP fusion proteins of the invention may be used to identify activators of one or more specific PARPs. In this instance, the assay may be used to identify agents that increase the amount of the label (i.e., the label present in the labeled NAD$^+$ substrate) covalently attached to the one or more PARP-GFP fusion proteins bound to the magnetic beads relative to the amount of the label covalently attached to the one or more PARP-GFP fusion proteins in the absence of the test agent. Preferably, this assay may be designed to identify activators of a specific PARP-GFP fusion protein or subset of PARP-GFP fusion proteins including the subsets of: one or more of PARP1-GFP, PARP2-GFP, PARP5A-GFP, PARP5B-GFP, PARP7-GFP, PARP8-GFP, PARP14-GFP, and PARP16-GFP; one or more of PARP5A-GFP, PARP12-GFP, PARP13.1-GFP, PARP13.2-GFP, and PARP15-GFP; PARP11-GFP; or PARP13.1-GFP.

Example 4

Involvement of PARPs in Stress Granule Formation and Disassembly

Figure 15:
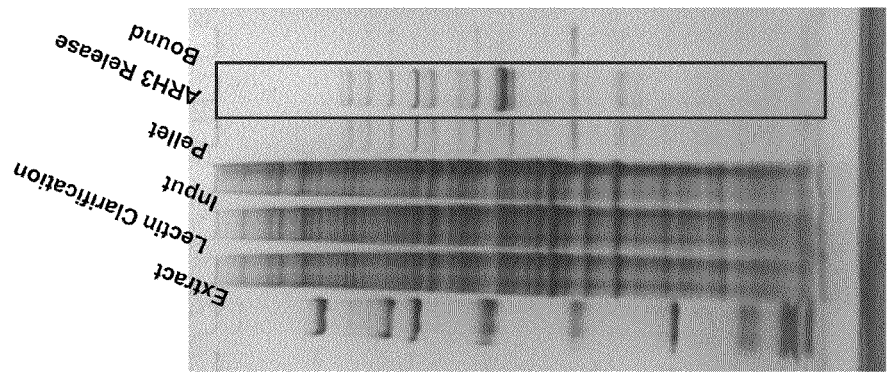
FIG. 15 is a picture of the Bio-Gel P-6 structure and a picture of a Coomassie Blue-stained SDS-PAGE gel showing the use of Bio-Gel P-6 for the purification of proteins from a crude HeLa Kyoto cell extract. The SDS-PAGE gel shows the proteins present in cell extract (Extract), in cell extract following lectin clarification (Lectin Clarification), in the lysate prior to passing over the Bio-Gel P-6 resin (Input), in the pellet following centrifugation of the resin (Pellet), and in the eluate following treatment with poly-ADP-ribose glycohydrolase ARH3 (ARH3 Release).
Figure 15:
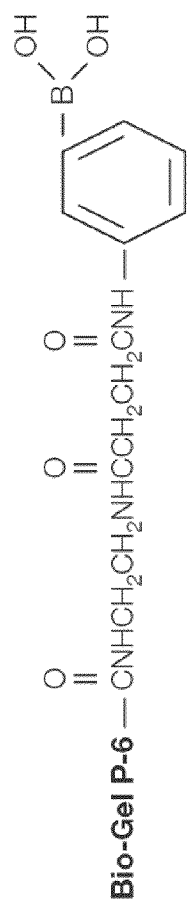

We have discovered through a PARP family-wide RNAi screen that several PARP proteins are involved in the cell cycle and are required for progression through mitosis (e.g., PARP16). The identity of the various substrate proteins of the different PARP proteins remains largely unknown. To further identify PARP substrate proteins and/or proteins that bind to poly-ADP-ribose polymers, the Bio-Gel P-6 resin shown in FIG. 15 was used to purify proteins that bind poly-ADP-ribose polymer and/or act as an acceptor of a ADP-ribose molecule or a poly-ADP-ribose polymer. FIG. 15 also shows a Coomassie Blue-stained SDS-PAGE gel showing the proteins present in the HeLa Kyoto cell extract (Extract), in cell extract following lectin clarification (Lectin Clarification), in the lysate prior to passing over the Bio-Gel P-6 resin (Input), in the pellet following centrifugation of the resin (Pellet), and in the eluate following treatment with poly-ADP-ribose glycohydrolase ARH3 (ARH3 Release). The data in FIG. 15 demonstrates the selective purification of proteins bound to the Bio-Gel P-6 resin.

Figure 16:
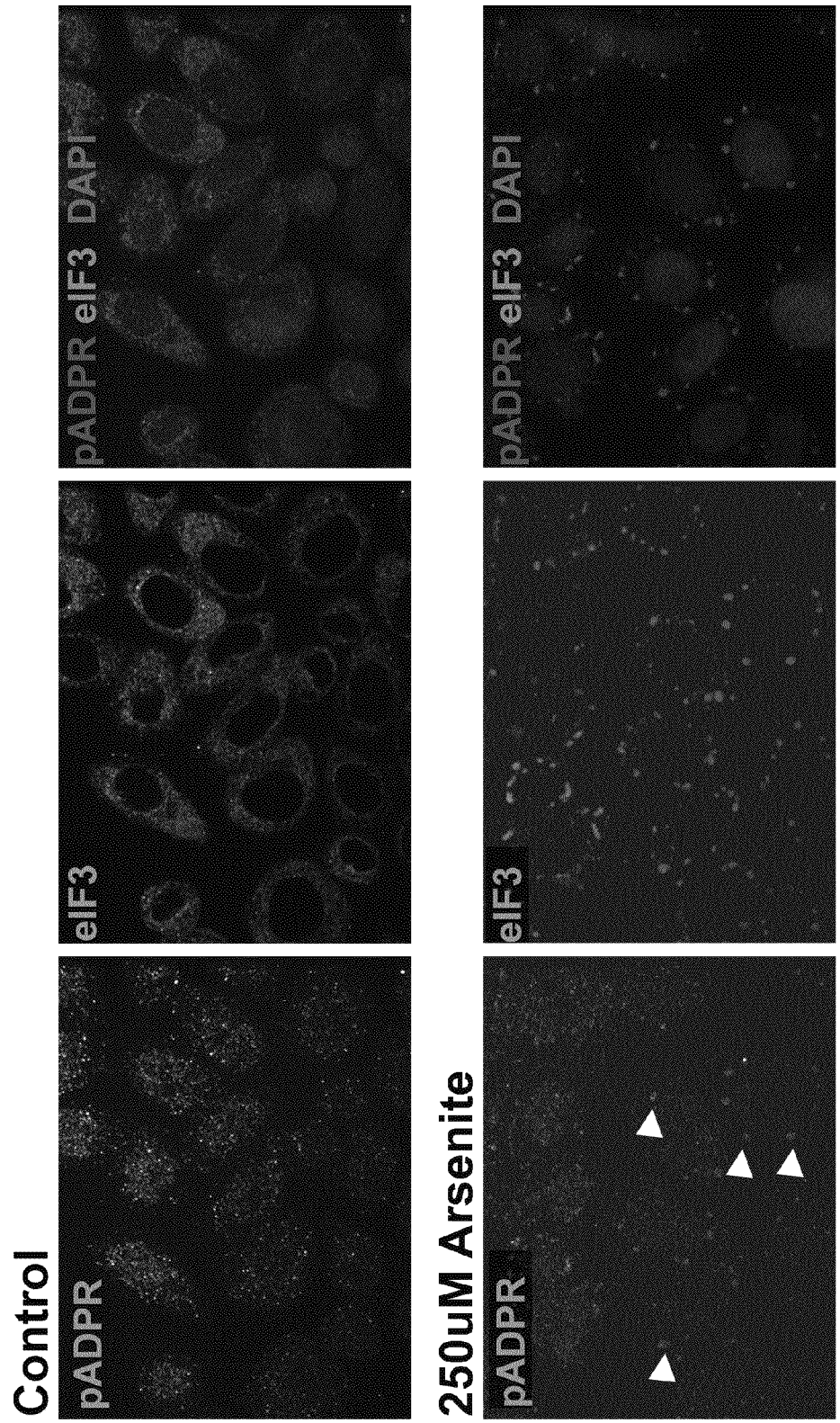
FIG. 16 is a set of micrographs showing the co-localization of poly-ADP ribose polymers (pADPR) and eIF3, a part of the translation initiation complex and a marker of stress granules, in HeLa Kyoto cells following treatment with 0 or 250 µM sodium arsenite for 30 minutes and immunostaining with primary antibodies specific for poly-ADP-ribose polymers and eIF3, and Alexa Fluor 594 or 488 secondary antibodies (Invitrogen).

We have discovered that poly-ADP-ribose polymers are associated with stress granules in cells during exposure to stress conditions. FIG. 16 shows the co-localization of poly-ADP-ribose polymers and eIF3, a marker of stress granules, in HeLa Kyoto cells following treatment with 0 or 250 µM sodium arsenite for 30 minutes and immunostaining with fluorescently-labeled antibodies specific for poly-ADP-ribose polymers and eIF3. The data indicate that stress granules contain proteins modified with poly-ADP-ribose polymers.

Figure 17:
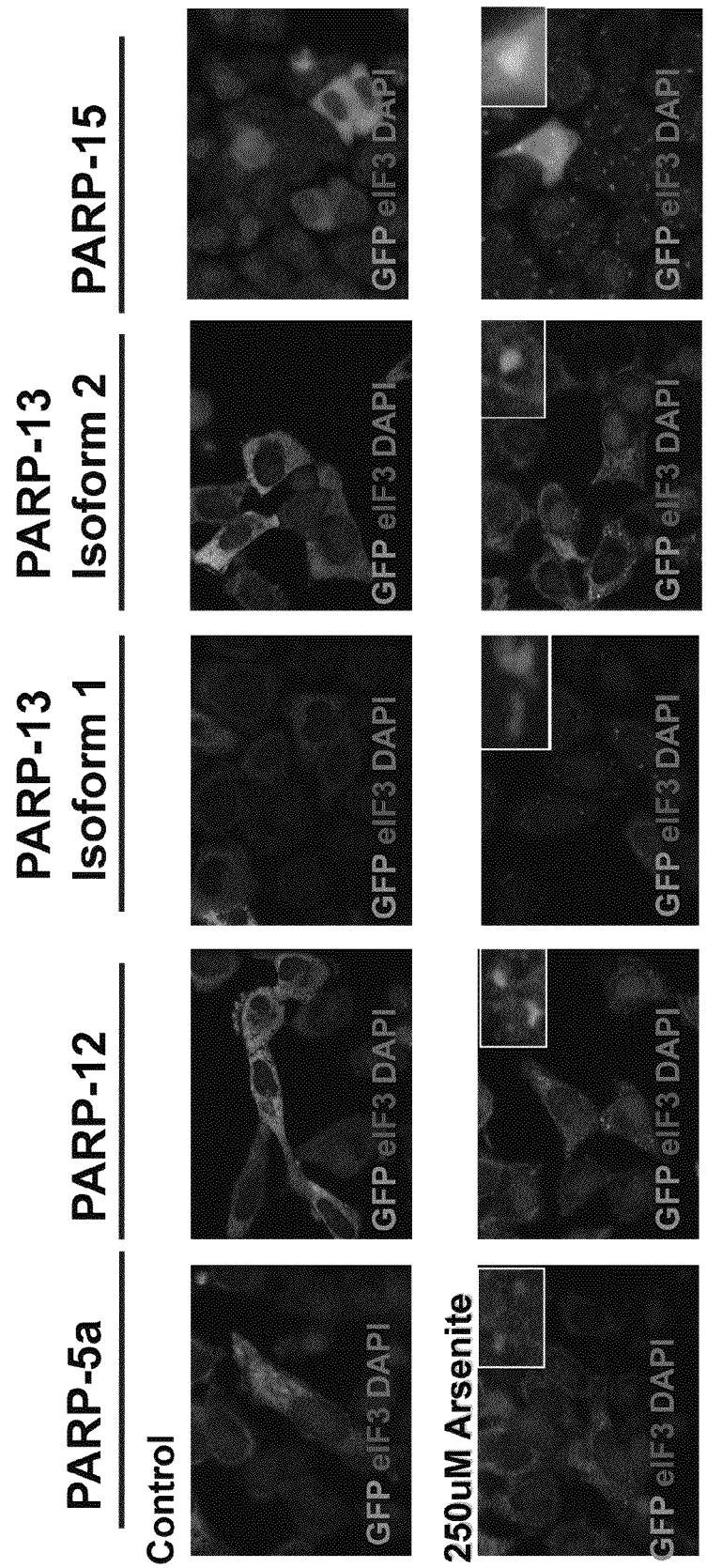
FIG. 17 is a set of micrographs showing the co-localization of PARP-GFP fusion proteins with eIF3 in transfected HeLa Kyoto cells following treatment with 0 or 250 µM sodium arsenite for 30 minutes. In these experiments, HeLa Kyoto cells were transfected with a pEGFP-C1 plasmid expressing PARP5A-GFP, PARP12-GFP, PARP13.1-GFP, PARP13.2-GFP, or PARP15-GFP fusion protein and treated with 0 or 250 µM sodium arsenite. The cells were fixed and stained with anti-GFP and anti-eIF3, and secondary fluorescently-labeled antibodies (Alexa Fluor 594 or 488 antibodies (Invitrogen)) prior to imaging.

In order to identify the specific PARP proteins that mediate the formation of the poly-ADP-ribose polymers present in stress granules, experiments were performed to determine whether the different PARP-GFP fusion proteins localize to stress granules. In these experiments, HeLa Kyoto cells transfected with a pEGFP-C1 plasmid expressing a PARP-GFP fusion protein were visualized using fluorescently-labeled anti-GFP and anti-eIF3 antibodies following treatment with 250 µM sodium arsenite for 30 minutes (FIG. 17). The data indicate that the PARP5A-GFP, PARP12-GFP, PARP13.1-GFP, PARP13.2-GFP, and PARP15-GFP fusion proteins localize to stress granules under stress conditions.

Figure 18:
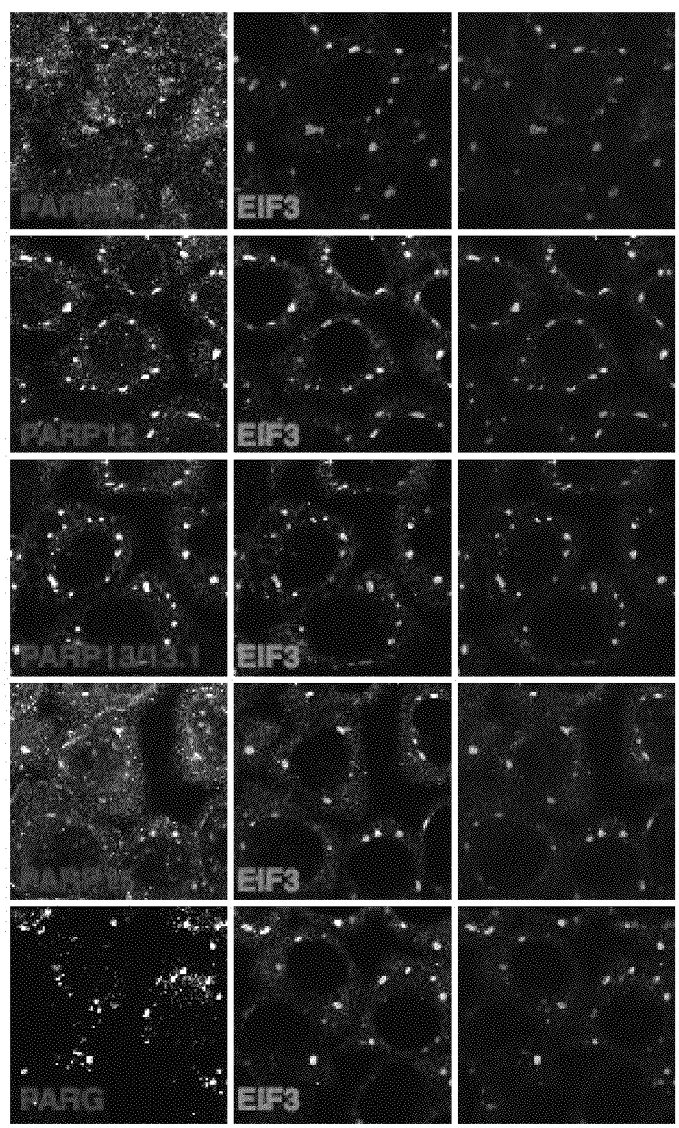
FIG. 18 is a set of micrographs showing the co-localization of endogenous PARP5A, PARP12, PARP13/13.1, PARP15, or poly-ADP-ribose glycohydrolase (PARG), and eIF3 (a stress granule marker) in HeLa Kyoto cells following treatment with 250 µM sodium arsenite for 30 minutes. In these experiments, cells were stained with rabbit antibodies specific for one of PARP5A, PARP12, PARP13/13.1, PARP15, or PARG, and an anti-eIF3 antibody, and fluorescently-labeled secondary antibodies (Alexa Fluor 594 or 488 antibodies (Invitrogen)).
Figure 19:
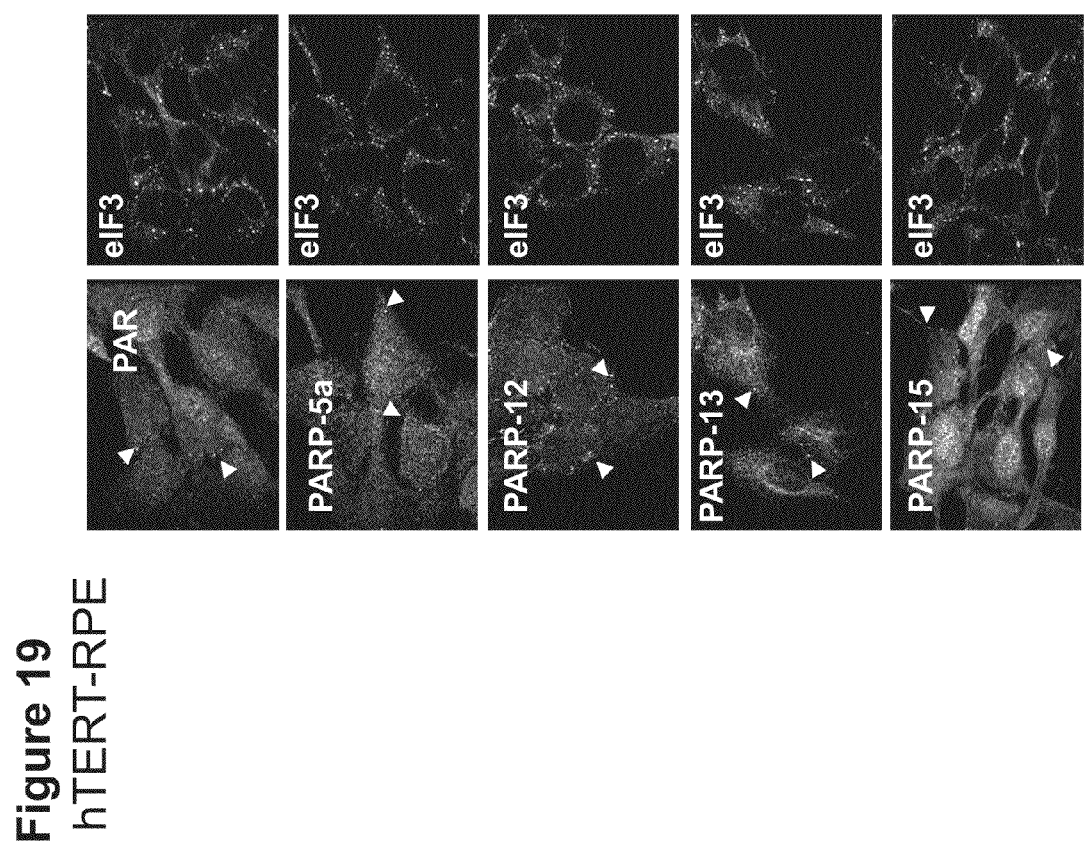
FIG. 19 is a set of micrographs showing the localization of poly-ADP-ribose (PAR), endogenous PARP5A, PARP12, PARP13, and PARP15, and eIF3 (a stress granule marker) in hTERT RPE cells following treatment with 250 µM sodium arsenite for 30 minutes. In these experiments, cells were stained with antibodies specific for one of PAR, PARP5A, PARP12, PARP13, or PARP15, or an anti-eIF3 antibody, and secondary fluorescently-labeled antibodies (Alexa Fluor 594 or 488 antibodies (Invitrogen)).

Endogenous PARP5A, PARP12, PARP13/13.1, PARP15, and poly-ADP-ribose glycohydrolase (PARG) also localize to stress granules in HeLa Kyoto cells following treatment with 250 µM sodium arsenite for 30 minutes (FIG. 18). In these experiments, the fixed cells were visualized using antibodies specific for one of PAR5A, PARP12, PARP13/13.1, PARP15, or PARG, and an anti-eIF3 antibody, and secondary fluorescently-labeled antibodies. The data indicate that PARG, as well as the endogenous- and fusion protein-forms of PARP5A, PARP12, PARP13/13.1, and PARP15, localize to stress granules under stress conditions. In a similar set of experiments using hTERT RPE cells, endogenous PARP5A, PARP12, PARP13, and PARP15 showed a similar cellular localization following exposure to 250 µM sodium arsenite for 30 minutes, as was observed in HeLa Kyoto cells (FIG. 19).

Experiments using time-lapse immunofluorescence microscopy in live HeLa Kyoto cells further indicate that endogenous PARP12, PARP12-GFP, endogenous PARP13, and PARP13-GFP localize to stress granules at an early point in stress granule assembly and therefore, may play a regulatory role in the formation of stress granules (data not shown).

Figure 20:
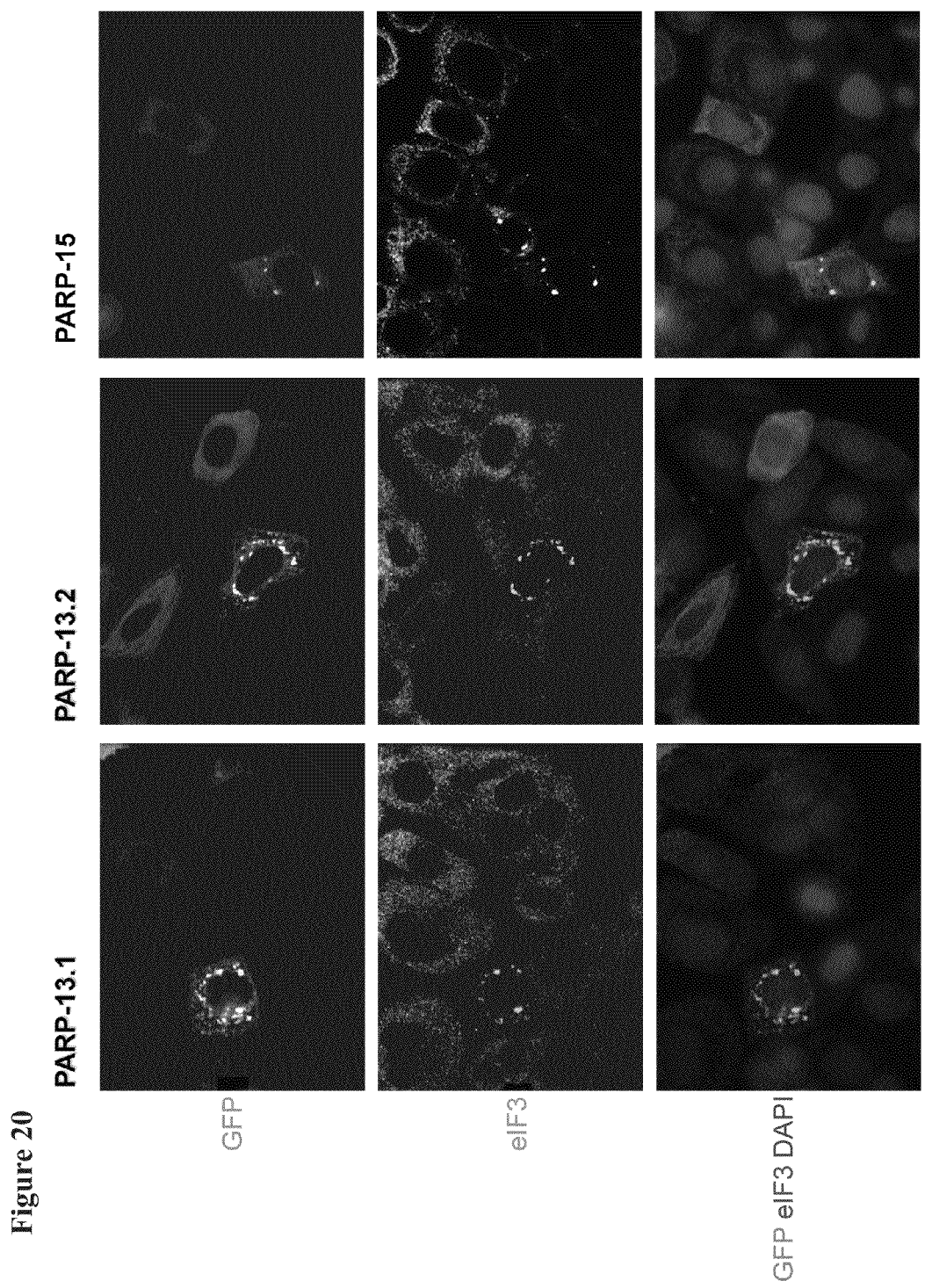
FIG. 20 is a set of micrographs showing the effect of PARP13.1-GFP, PARP13.2-GFP, or PARP15-GFP overexpression on stress granule formation. In these experiments, HeLa Kyoto cells were transfected with a plasmid expressing PARP13.1-GFP, PARP13.2-GFP, or PARP15-GFP. The cells were fixed and stained using rabbit anti-GFP and anti-eIF3 antibodies, and fluorescently-labeled secondary antibodies (Alexa Fluor 594 or 488 antibodies (Invitrogen)). The cells were also co-stained with DAPI.

In an additional set of experiments, the effect of PARP13.1, PARP13.2, and PARP15 on stress granule formation was further studied by measuring the effect of overexpression of PARP13.1-GFP, PARP13.2-GFP, and PARP15-GFP on stress granule formation. In these experiments, HeLa Kyoto cells were transfected with a pEGFP-C1 plasmid encoding PARP13.1-GFP, PARP13.2-GFP, or PARP15-GFP. The transfected cells were stained with anti-GFP antibodies, anti-eIF3 antibodies, and fluorescently-labeled secondary antibodies. These data indicate that overexpression of PARP13.1-GFP, PARP13.2-GFP, or PARP15-GFP fusion protein nucleates stress granule formation (FIG. 20).

Figure 21:
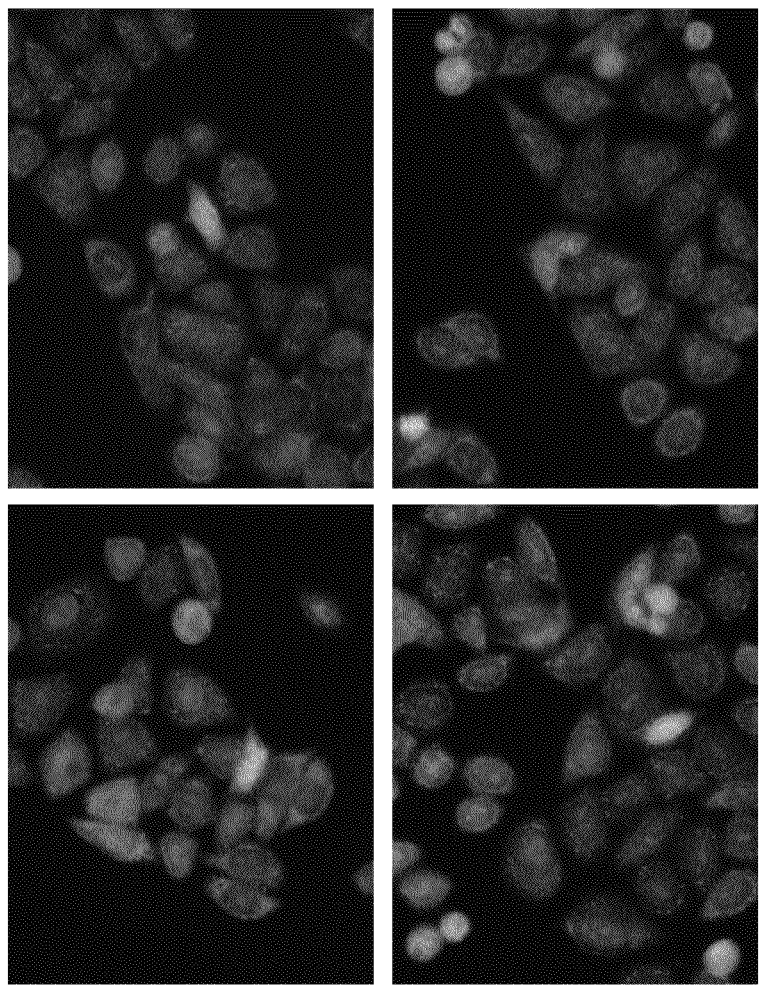
FIG. 21 is a set of micrographs showing the co-localization of PARP11-GFP and eIF3 (a stress granule marker) in HeLa Kyoto cells transfected with a pEGFP-C1 vector expressing PARP11-GFP following treatment with 250 µM arsenite for 30 minutes. Following arsenite treatment, the cells were immediately fixed and stained using rabbit anti-GFP and anti-eIF3 antibodies, and fluorescently-labeled secondary antibodies (Alexa Fluor 594 or 488 antibodies (Invitrogen)). The cells were also stained with DAPI.

In contrast to the effect mediated by overexpression of PARP13.1-GFP, PARP13.2-GFP, or PARP15-GFP fusion protein, overexpression of PARP11-GFP in HeLa Kyoto cells mediates a decrease in stress granule formation following treatment with 250 µM sodium arsenite for 30 minutes (FIG. 21). In this experiment, HeLa Kyoto cells transfected with a pEGFP-C1 vector expressing a PARP11-GFP fusion protein were treated with sodium arsenite, and stained with anti-GFP antibodies, anti-eIF3 antibodies, and fluorescently-labeled secondary antibodies. These data indicate that overexpression of PARP11-GFP suppresses the formation of stress granules in cells exposed to stress conditions.

Experimental Methods

HeLa Kyoto cells were cultured as described above. Lipofectamine 2000 (Invitrogen) was used to transfect the HeLa Kyoto cells with a pEGFP-C1 plasmid encoding a PARP-GFP fusion protein (described above) according to the manufacturer's instructions. For stress granule induction, cells were treated with 250 µM sodium arsenite for 30 minutes. For long-term, real-time imaging of PARP-GFP transfected HeLa cells, the cells were split into 24-well glass bottom plates and imaged every 20 minutes for 48 hours. Images were collected on a Nikon TE2000 confocal microscope equipped with a Yokogawa CSU-X1 spinning disc head, Hamamatsu ORCA ER digital camera, and NIS-Elements imaging software.

Example 5

Involvement of PARG and ARH3 in Stress Granule Disassembly

Figure 22:
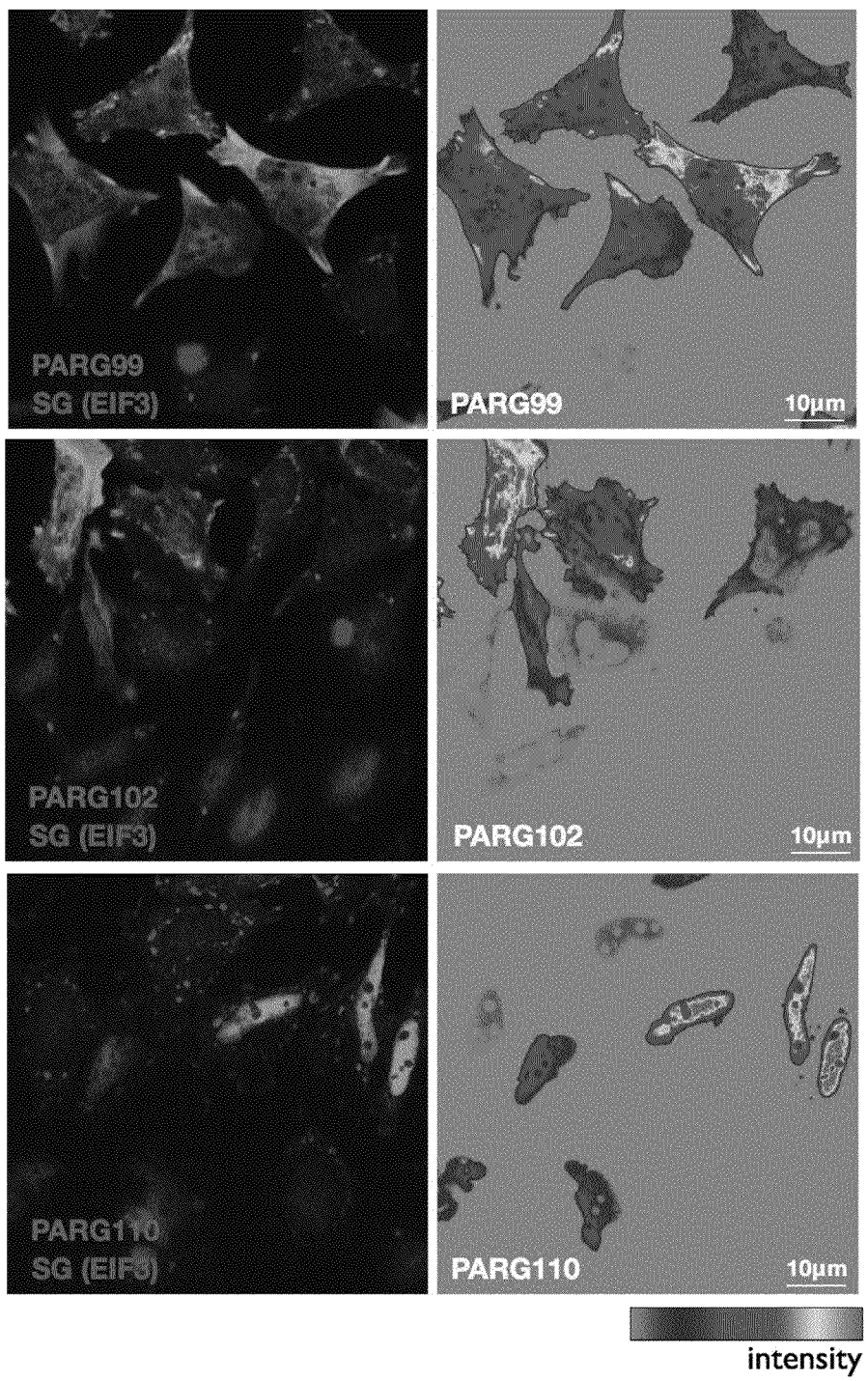
FIG. 22 is a set of micrographs showing the effect of PARG99-GFP, PARG102-GFP, or PARG110-GFP overexpression on stress granule formation in HeLa Kyoto cells transfected with a pEGFP-C1 plasmid containing a nucleic acid sequence encoding each PARG-GFP fusion protein, following treatment with 100 µM sodium arsenite for 30 minutes. Following arsenite treatment, the cells were fixed and stained with rabbit anti-GFP and anti-eIF3 antibodies, and fluorescently-labeled secondary antibodies (Alexa Fluor 594 or 488 antibodies (Invitrogen)). The images shown in the right panels show the same data using a threshold filter.

In order to determine the importance of poly-ADP-ribose polymers on stress granule formation and disassembly, an additional set of experiments were performed to test the effect of PARG and ARH3 activity on stress granule dynamics. In a first set of experiments, HeLa Kyoto cells were transfected with a pEGFP-C1 plasmid encoding PARG99-GFP, PARG102-GFP, or a PARG110-GFP fusion protein. Overexpression of PARG99-GFP, PARG102-GFP, or PARG110-GFP reduces the formation of stress granules in HeLa Kyoto cells following exposure to 100 µM sodium arsenite for 30 minutes (FIG. 22). In these experiments, formation of stress granules was determined by staining the fixed cells with anti-eIF3 antibodies and secondary fluorescently-labeled antibodies. These data indicate that PARG activity (hydrolysis of poly-ADP-ribose) inhibits the formation of stress granules in cells under stress conditions.

Figure 23:
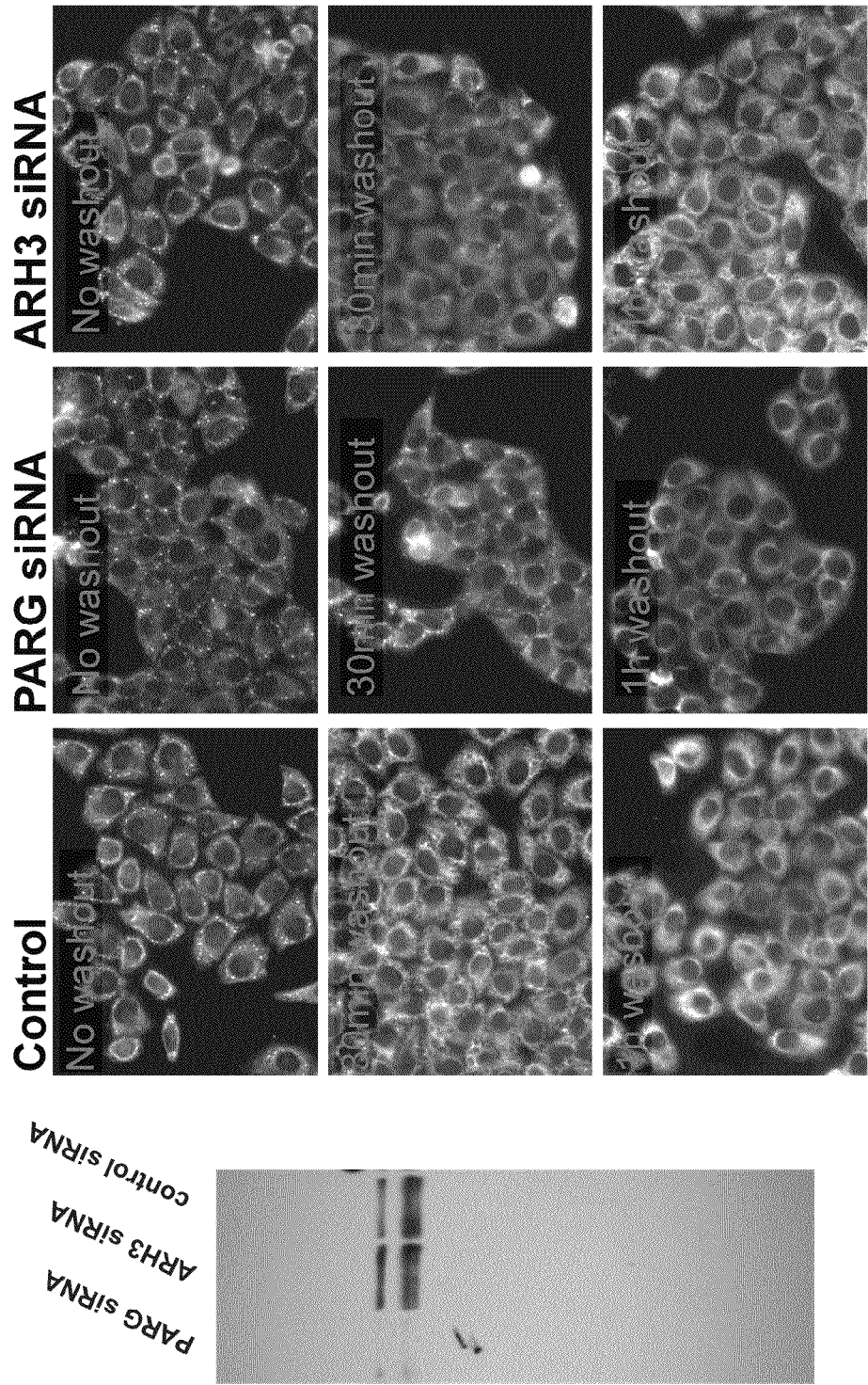
FIG. 23 is a set of micrographs showing the effect of PARG or ARH3 knockdown on stress granule formation in HeLa Kyoto cells transfected with 30 nM PARG siRNA (CCAG-UUGGAUGGACACUAAUU (SEQ ID NO: 34) and UUAC-GAAGGUACCA UAGAAUU (SEQ ID NO: 35)), ARH3 siRNA (GGACAGAAGCCUUGUACUAUU (SEQ ID NO: 36) and CCAUUGCUGGUGCCUACUAUU (SEQ ID NO: 37)), or a control siRNA (All Stars Negative Control siRNA); Qiagen Catalog No. 1027280 following treatment with 100 µM sodium arsenite for 30 minutes, or 30 minutes or 1 hour following sodium arsenite washout. The cells were fixed and stained with an anti-eIF3 antibody and secondary fluorescently-labeled antibodies (Alexa Fluor 594 or 488 antibodies) to visualize stress granule formation. The panel on the left shows an immunoblot of cell lysate from HeLa Kyoto cells treated with 30 nM PARG siRNA, ARH3 siRNA, or control siRNA for 48 hours. The immunoblot was developed using an anti-PARG antibody.
Figure 24:
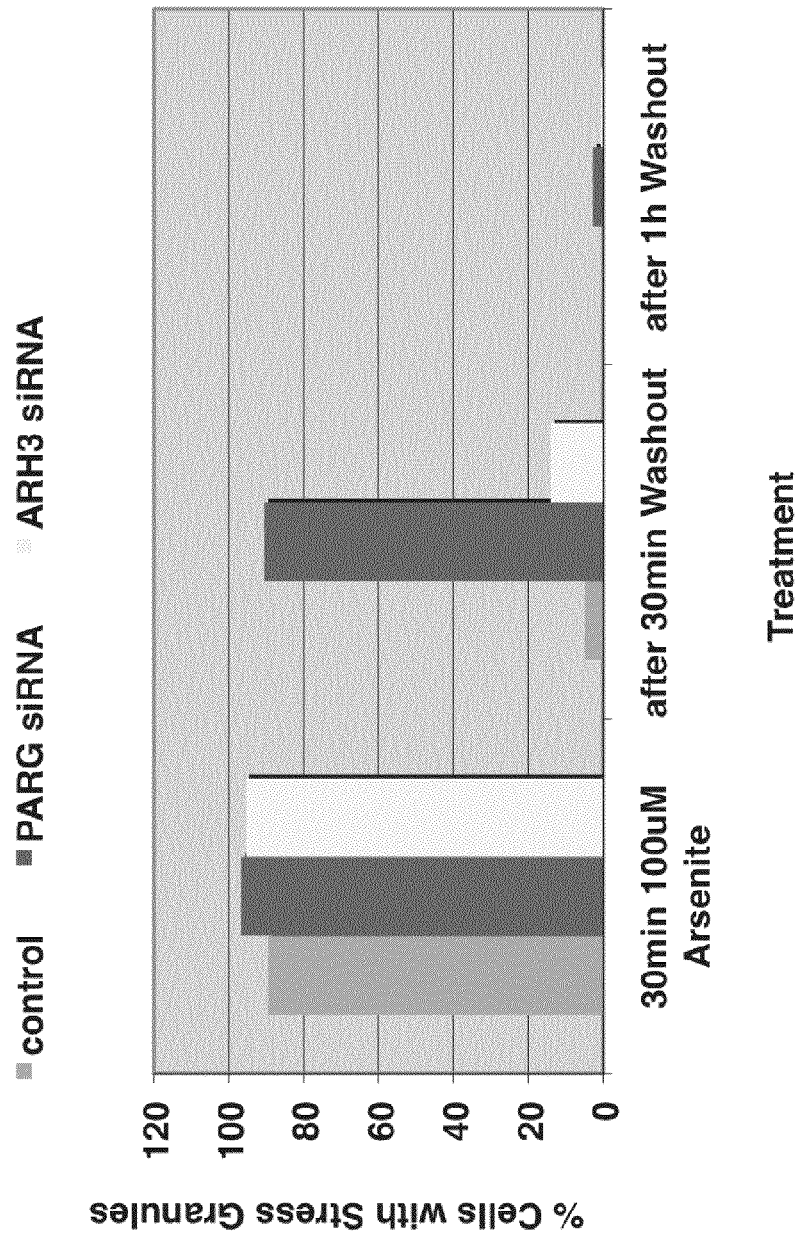
FIG. 24 is a graph showing the percentage of HeLa Kyoto cells transfected with 30 nM PARG siRNA (SEQ ID NOS: 34 and 35), ARH3 siRNA (SEQ ID NOS: 36 and 37), or a control siRNA (All Stars Negative Control siRNA (Qiagen Catalog No. 1027280) containing stress granules following treatment with 100 µM sodium arsenite for 30 minutes, or 30 minutes or 1 hour following sodium arsenite washout. The cells were fixed and stained with a fluorescently-labeled anti-eIF3 antibody to visualize stress granule formation.

Another set of experiments was performed to determine the effect of knockdown of PARG or ARH3 on stress granule formation in cells under stress conditions. In these experiments, HeLa Kyoto cells were treated with 30 nM siRNA specific for PARG (SEQ ID NOS: 34 and 35) or ARH3 (SEQ ID NOS: 36 and 37), or a control siRNA (AllStars Negative Control siRNA; Qiagen Catalog No. 1027280), and treated with 100 µM sodium arsenite for 30 minutes, or 30 minutes or 1 hour following sodium arsenite washout (FIG. 23). Cells treated with a PARG siRNA or ARH3 siRNA show a sustained presence of stress granules following removal of sodium arsenite from the culture medium (via imaging using anti-eIF3 antibodies and fluorescently-labeled secondary antibodies). These data indicate that PARG and ARH3 activity (hydrolysis of poly-ADP-ribose) has a positive effect on stress granule disassembly, and that poly-ADP-ribose turnover kinetics regulate the formation/disassembly of stress granules. The percentage of cells with stress granules following 30-minute washout and 1-hour washout after arsenite treatment was quantitated for cells treated with control siRNA, PARG siRNA, and ARH3 siRNA (FIG. 24). These data indicate that knockdown of PARG and ARH3 reduces the rate of stress granule disassembly following removal of the stress condition (sodium arsenite).

Experimental Methods

HeLa Kyoto cells were cultured in medium as described above. In PARG overexpression experiments, Lipofectamine 2000 (Invitrogen) was used to transfect HeLa Kyoto cells with pEGFP-C1 plasmids containing the nucleic acid sequences for each PARG isoform, i.e., PARG99, PARG102, and PARG110 (sequences described in Meyer-Ficca et al., *Exp. Cell. Res.* 297(2):521-532, 2004) according to the manufacturer's instructions. In PARG knockdown experiments, cells were treated with 30 nM of a siRNA targeting PARG (SEQ ID NOS: 34 and 35), a siRNA targeting ARH3 (SEQ ID NO: 36 and 37), or a control siRNA (SEQ ID NO: 38 and 39) using Lipofectamine 2000 according to the manufacturer's instructions. In these experiments, stress granule formation was induced by treatment with 100 µM sodium arsenite for 30 minutes. For stress granule disassembly experiments, the media was replaced after sodium arsenite treatment, and cells were incubated for 30 minutes and 1 hour prior to fixation and immunostaining. At least 200 cells were counted for each condition (in triplicate) to determine the percentage of cells containing stress granules.

Example 6

Stress Granule Proteins Bind to GFP-PARPs

Experiments were performed to further identify stress granule-related proteins that may bind and be the substrates of one or more of the PARPs localized in stress granules (e.g., PARP5A, PARP12, PARP13, PARP13.1, and PARP15). In these experiments, HeLa S3 cells were transfected with pEGFP-C1 plasmids containing a nucleic acid sequence encoding PARP5A-GFP, PARP12-GFP, PARP13-GFP, PARP13.1-GFP, or PARP15-GFP fusion protein and treated with 0 or 250 µM sodium arsenite for 30 minutes. The resulting cell lysate was immunoprecipitated using anti-GFP antibodies and the resulting immunoprecipitated proteins were electrophoresed using SDS-PAGE. The resulting gel indicates that each PARP-GFP fusion protein binds to several proteins and that treatment with sodium arsenite results in an alteration in the amount and identity of the proteins binding to each PARP-GFP fusion protein (FIG. 25A). In a similar experiment, the immunoprecipitated proteins are transferred to a membrane and immunostained with an anti-poly-ADP-ribose antibody. The data in this experiment show that PARP5A-GFP, PARP12-GFP, PARP13-GFP, and PARP13.1-GFP fusion proteins bind to poly-ADP-ribosylated proteins (FIG. 25B).

Figure 25:
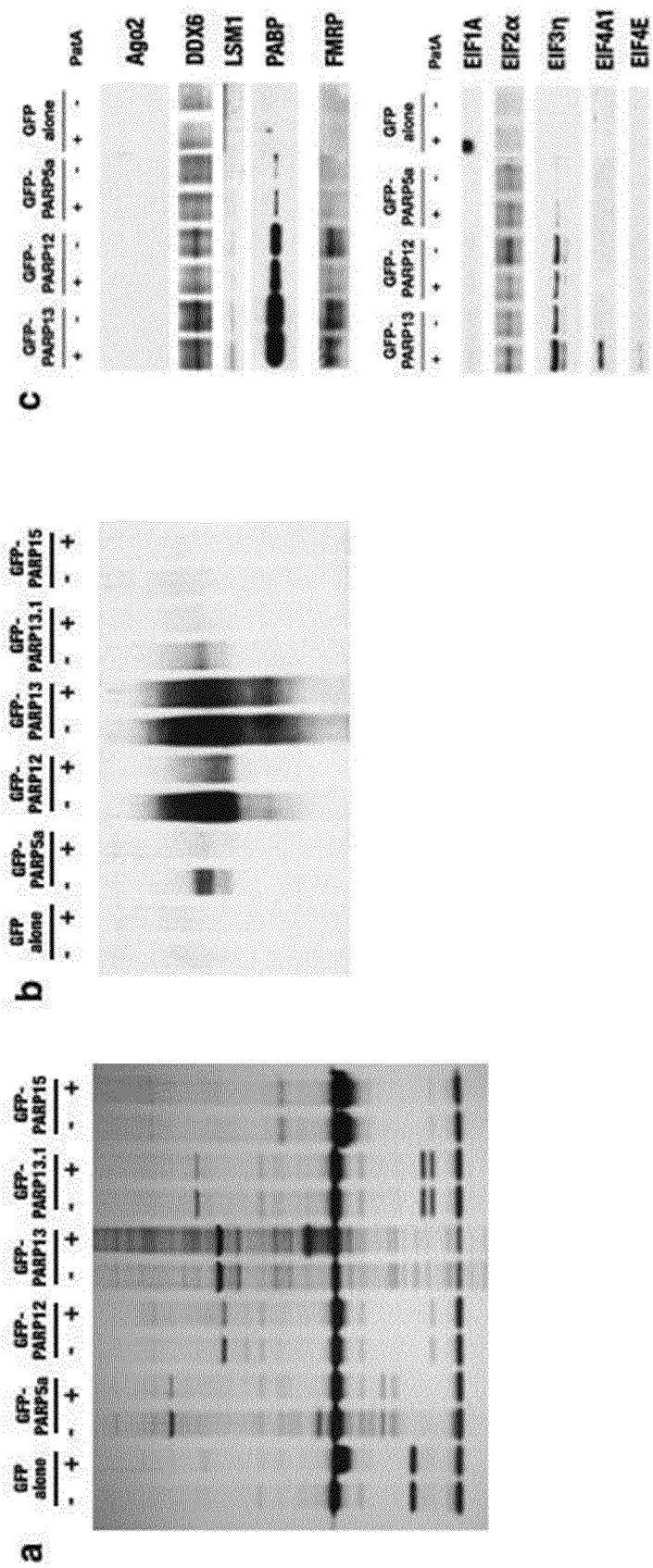
FIG. 25A is a silver-stained 4-12% SDS-PAGE gel showing the proteins immunoprecipitated with an anti-GFP antibody from lysate from HeLa S3 cells transfected with a pEGFP-C1 plasmid expressing GFP alone, PARP5A-GFP, PARP12-GFP, PARP13-GFP, PARP13.1-GFP, or PARP15-GFP following treatment with 0 or 250 µM sodium arsenite for 30 minutes.
FIG. 25B is picture of an immunoblot of a 4-12% SDS-PAGE gel containing proteins immunoprecipitated with an anti-GFP antibody from lysate from HeLa S3 cells transfected with a pEGFP-C1 plasmid expressing GFP, PARP5A-GFP, PARP12-GFP, PARP13-GFP, PARP13.1-GFP, or PARP15-GFP following treatment with 0 or 250 µM sodium arsenite for 30 minutes. The immunoblot was developed using a polyclonal anti-poly-ADP-ribose antibody.
FIG. 25C is a picture of several immunoblots of a 4-12% SDS-PAGE gel containing proteins immunoprecipitated with an anti-GFP antibody from lysate from HeLa S3 cells transfected with a pEGFP-C1 plasmid expressing GFP, PARP5A-GFP, PARP12-GFP, PARP13-GFP, PARP13.1-GFP, or PARP15-GFP following treatment with 0 or 20 nM pateamine A for 30 minutes. The immunoblots were developed using one of the following antibodies: anti-Agog, anti-DDX6, anti-LSM1, anti-PABP, anti-FMRP, anti-eIF1A, anti-eIF2a, anti-eIF3η, anti-eIF4A1, and anti-eIF4E.

Data from a separate set of experiments indicate that several stress granule-associated proteins bind to the PARP13-GFP, PARP12-GFP, and PARP5A-GFP fusion proteins. In these experiments, HeLa S3 cells were transfected with a pEGFP-C1 plasmid encoding a PARP13-GFP, PARP12-GFP, or PARP5A-GFP fusion protein and treated with 0 or 20 nM pateamine A for 30 minutes. Cell lysates from the cells were immunoprecipitated using an anti-GFP antibody and the immunoprecipitated proteins were electrophoresed using 4-12% SDS-PAGE. The resulting proteins were transferred to a membrane and immunoblotted using commercially-available antibodies specific for different stress granule-associated proteins: Ago2, DDX6, LSM1, PABP, FMRP, eIF1A, eIF2α, eIF3η, eIF4A1, and eIF4E. The data indicate that the PARP13-GFP, PARP12-GFP, and PARP5A-GFP fusion proteins have the ability to interact with one or more of these stress granule-associated proteins under both normal (0 nM pateamine A) and stress conditions (30 nM pateamine A) (FIG. 25 C).

Figure 26:
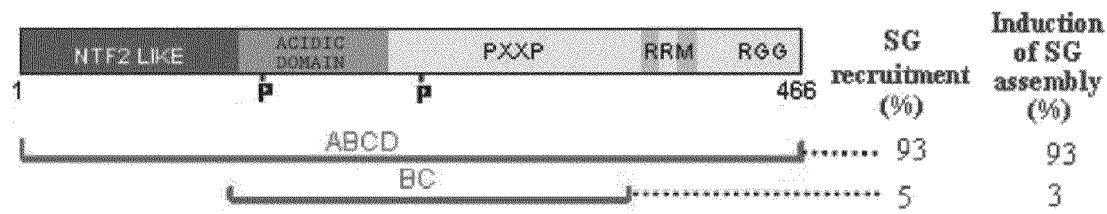
FIG. 26 (right panel) is an immunoblot of a 4-12% SDS-PAGE gel containing proteins immunoprecipitated using an anti-Ago2 antibody from untransfected HeLa cells following treatment with 0 or 250 µM sodium arsenite for 60 minutes. The immunoblot was developed using anti-poly-ADP-ribose antibodies.
Figure 26:
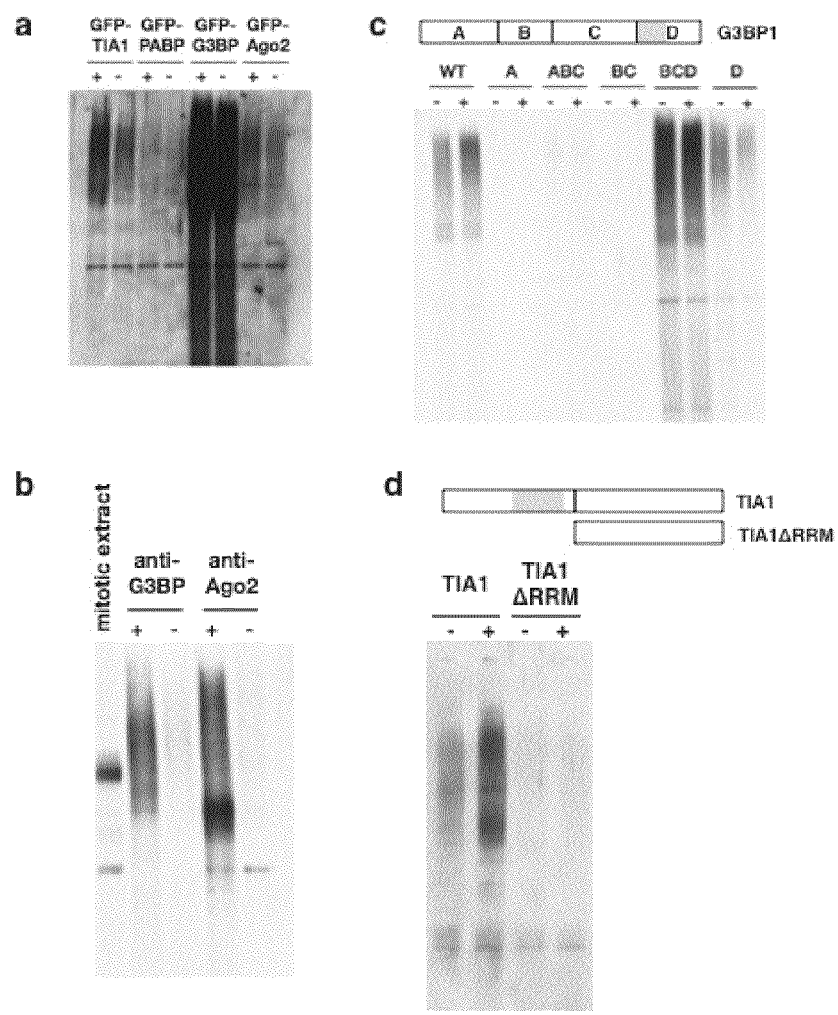

An additional set of experiments was performed to determine whether one or more stress granule-associated proteins are poly-ADP-ribosylated. In these experiments, HeLa S3 cells were transfected with a pEGFP-C1 plasmid encoding a GFP fusion protein of TIA1, PABP, G3BP, or Ago2, and treated with 0 or 20 nM pateamine A for 30 minutes. Lysates from these cells were immunoprecipitated using anti-GFP antibodies and immunoblotted using an anti-poly-ADP ribose antibody. The data show that several proteins bind the TIA1-GFP, PABP-GFP, G3BP-GFP, and Ago2-GFP fusion proteins in untreated (0 nM pateamine A) and treated (20 nM pateamine A) cells (FIG. 26A). In an additional experiment, the proteins that bind to endogenous G3BP and Ago2 proteins in 250 µM sodium arsenite-treated HeLa S3 cells were also shown to be poly-ADP-ribosylated (FIG. 26B). In this experiment, cell lysates from untransfected HeLa S3 cells treated with 0 or 250 µM sodium arsenite for 60 minutes were immunoprecipitated with anti-G3BP or anti-Ago2 antibodies and immunoblotted using an anti-poly-ADP-ribose antibody.

G3BP1, a stress granule-associated protein, was shown to be poly-ADP-ribosylated (FIG. 26C). In order to map the specific domain in G3BP1 that is modified by a poly-ADP-ribose polymer, GFP-fusion proteins of different truncation 250 µM sodium arsenite for 60 minutes. The specific nucleic acid sequences encoding each G3BP1 truncation mutant are described in Tourriere et al. (*J. Cell Biol.* 160:823-831, 2003). The cell lysate from each cell sample was immunoprecipitated using anti-GFP antibodies and immunoblotted using an anti-poly-ADP-ribose antibody. The data demonstrate that poly-ADP-ribosylation of G3BP1 occurs within the RNA-recognition motif (RRM) domain ("D" in FIG. 26C). The RRM domain of G3BP1 is a domain that binds to RNA molecules. The poly-ADP-ribosylation of G3BP1 in the RRM domain is thought to regulate the RNA-binding activity of G3BP1.

TIA1, a stress granule-associated protein, was also shown to be poly-ADP-ribosylated (FIG. 26D). In order to determine whether TIA1 is poly-ADP-ribosylated in its RRM domain, GFP-fusion proteins of full-length TIA1 and a truncation mutant of TIA1 lacking its RRM domain (TIA1ΔRRM) were expressed in HeLa S3 cells treated with 0 or 250 µM sodium arsenite for 60 minutes. The specific nucleic acid sequences encoding the full-length TIA1 and the TIA1ΔRRM truncation mutant are described in Kedersha et al. (*J. Cell Biol.* 151:1257-1268, 2000). The cell lysate from each cell sample was immunoprecipitated using anti-GFP antibodies and immunoblotting was performed using an anti-poly-ADP-ribose antibody. The data demonstrate that poly-ADP-ribosylation of TIA1 also occurs within its RNA-recognition motif (RRM) domain (FIG. 26D). The poly-ADP-ribosylation of TIA1 in its RRM domain is also thought to mediate an alteration in its RNA-binding activity.

Experimental Methods

Immunoprecipitation experiments to identify proteins binding to PARP5A-GFP, PARP12-GFP, PARP13-GFP, PARP13.1-GFP, and PARP15-GFP were performed using HeLa S3 cells transfected with a pEGFP-C1 plasmid containing a nucleic acid sequence encoding each respective PARP-GFP fusion protein following treatment with 0 or 20 nM pateamine A for 30 minutes. In each experiment, the cell lysate is incubated with an anti-GFP antibody to immunoprecipitate proteins bound to each of the PARP-GFP fusion proteins using standard methods. The resulting immunoprepitated proteins were electrophoresed on 4-12% SDS-PAGE gels, and either stained directly with Coomassie Blue or transferred onto a membrane and immunostained with one or more of the following antibodies: anti-poly-ADP-ribose, anti-Ago2, anti-DDX6, anti-LSM1, anti-PABP, anti-FMRP, anti-eIF1A, anti-eIF2α, anti-eIF3η, anti-eIF4A1, and anti-eIF4e antibodies.

Immunoprecipitation experiments using TIA1-GFP, PABP-GFP, G3BP-GFP, and Ago2-GFP fusion proteins were performed using HeLa S3 cells transfected with pEGFP-C1 plasmids containing a sequence encoding a nucleic acid sequence encoding TIA1 (Kedersha et al., *J. Cell Biol.* 151: 1257-1268, 2000), PABP (NCBI Accession No. NM_12154.2), G3BP (Tourriere et al., *J. Cell Biol.* 160:823-831, 2003), Ago2 (NCBI Accession No._002568.3), a truncation mutant of G3BP (i.e., A, ABC, BC, BCD, and D truncation mutants described in Tourriere et al., supra), or the ΔRRM truncation mutation of TIA1 (described in Kedersha et al., supra) following treatment with 0 or 20 nM pateamine A for 30 minutes. In each experiment, the cell lysate is incubated with an anti-GFP antibody to immunoprecipitate proteins bound to each of the GFP fusion proteins using standard methods. The resulting immunoprepitated proteins were electrophoresed on 4-12% SDS-PAGE gels, and either stained directly with Coomassie Blue or transferred onto a membrane and immunostained with anti-poly-ADP-ribose antibody.

Example 7

PARP13 and PARG Regulation of RNAi Activity

Figure 27:
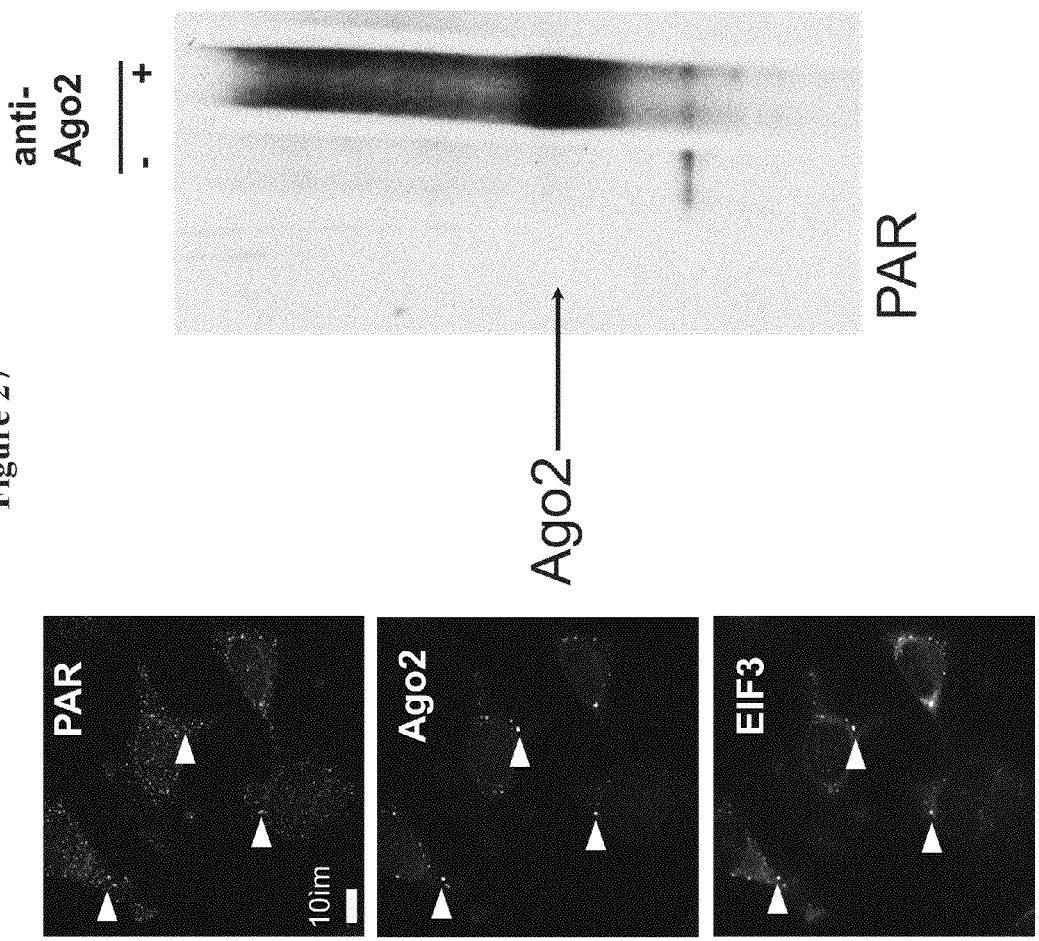
FIG. 27 (left panel) is a set of micrographs showing the localization of poly-ADP-ribose, and endogenous Agog and eIF3 in HeLa cells following treatment with 250 µM sodium arsenite for 30 minutes. The cells were imaged using fluorescently labeled anti-poly-ADP-ribose, anti-Agog, and anti-eIF3 antibodies.

We have further discovered that PARP13 and PARG regulate the activity of RNAi and miRNA molecules in cells. Regulation of RNAi and miRNA activity in cells remains largely uncharacterized. One of the proteins implicated for a role in the regulation of RNAi and miRNA activity is Argonaut 2, a single-stranded RNAse. Using immunofluorescence microscopy we have observed that Argonaut 2 localizes to stress granules in HeLa cells treated with 250 µM sodium arsenite for 30 minutes (FIG. 27, left panel). In these experiments, cells were treated with sodium arsenite and stained using both antibodies against Argonaut 2 and eIF3 (a stress granule marker), and secondary fluorescently-labeled antibodies. The data show that Argonaut 2 is poly-ADP-ribosylated in HeLa cells following exposure to 250 µM sodium arsenite for 30 minutes (FIG. 27, right panel). In these experiments, cell lysate from cells treated with 250 µM sodium arsenite was immunoprecipitated with an anti-Argonaut 2 antibody, and the resulting immunoprecipitated proteins were immunoblotted using an anti-poly-ADP-ribose antibody. The results indicate that Argonaut 2 is localized to stress granules and poly-ADP-ribosylated under cellular stress conditions.

Figure 28:
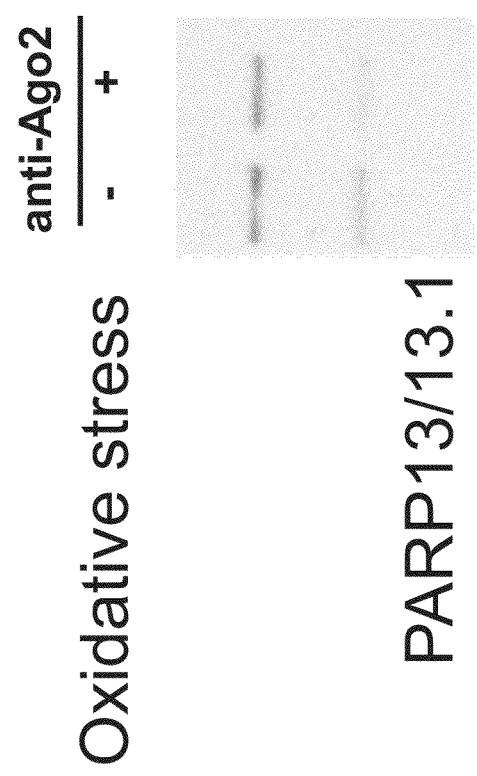
FIG. 28 is a picture of an immunoblot of a 4-12% SDS-PAGE gel containing proteins immunoprecipitated with an anti-Ago2 antibody from lysate from untransfected HeLa cells following treatment with 0 or 250 µM sodium arsenite for 30 minutes. The immunoblot was developed using a polyclonal anti-PARP13/13.1 antibody.

To determine whether one or more of the PARPs identified herein mediate the poly-ADP-riboyslation of Argonaut 2, immunoprecipitation experiments were performed on cell lysate from untransfected HeLa cells treated with 0 or 250 µM sodium arsenite for 30 minutes using an anti-Argonaut 2 antibody. The resulting immunoprecipitated proteins were immunoblotted using an anti-PARP13/13.1 antibody. The data show that PARP13/13.1 binds to Argonaut 2 under both normal (0 µM sodium arsenite) and stress conditions (250 µM sodium arsenite) (FIG. 28).

Figure 29:
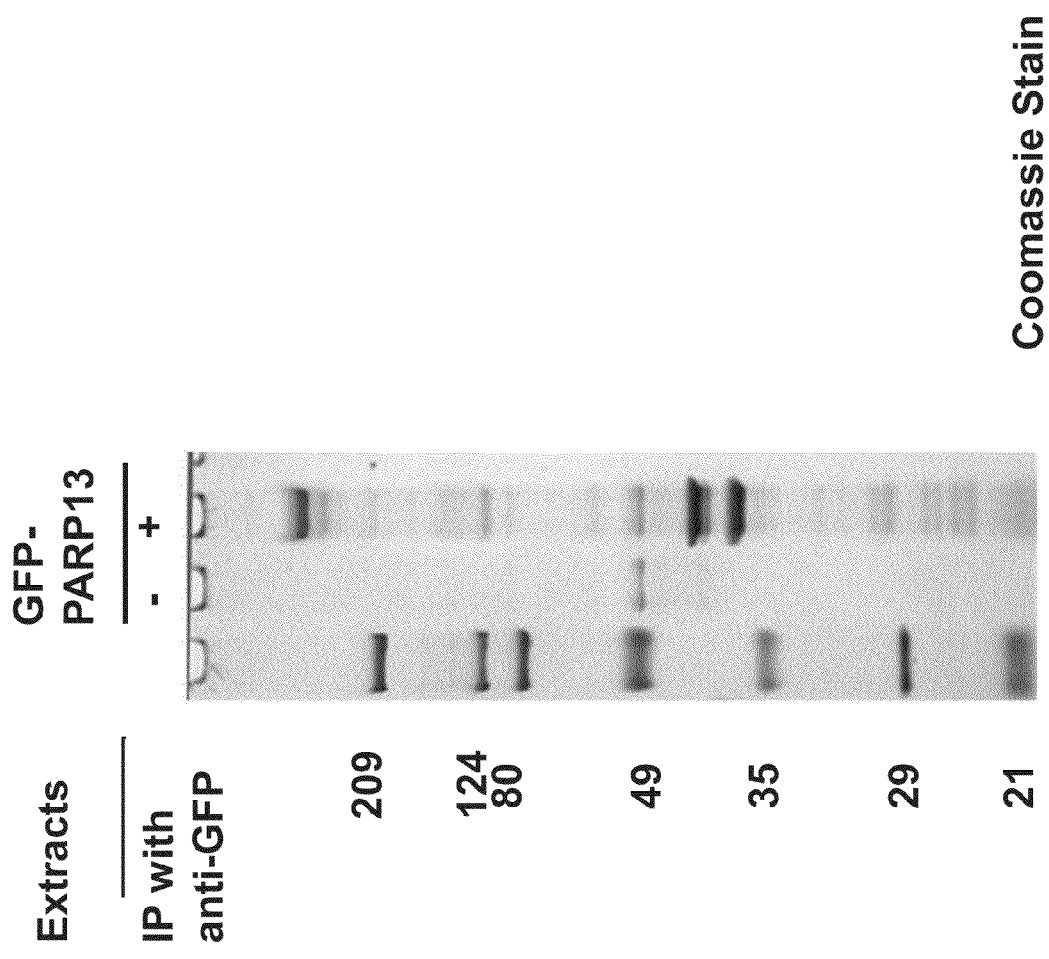
FIG. 29 is a picture of a Coomassie Blue-stained 4-12% SDS-PAGE gel containing proteins immunoprecipitated using an anti-GFP antibody from lysate from HeLa S3 cells transfected with a pEGFP-C1 plasmid expressing PARP13-GFP following treatment with 0 or 250 µM sodium arsenite for 30 minutes.

To identify additional substrate proteins of PAPR13, immunoprecipitation experiments were performed on lysate from HeLa cells transfected with a pEGFP-C1 plasmid containing a sequence encoding a PARP13-GFP fusion protein following treatment with either 0 or 250 µM sodium arsenite for 30 minutes. The cell lysate was treated with an anti-GFP antibody and the resulting immunoprecipitated proteins were electrophoresed using SDS-PAGE. The data show that exposure to 250 µM sodium arsenite increases the number and identity of proteins that bind to the PARP13-GFP fusion protein (FIG. 29). The identification of the specific proteins co-immunoprecipitated with the PARP13-GFP fusion protein will help to further elucidate the role of PARP13 in cellular mechanisms, including its regulation of Argonaut 2 and its role in the regulation of miRNA and RNAi activity.

Figure 30:
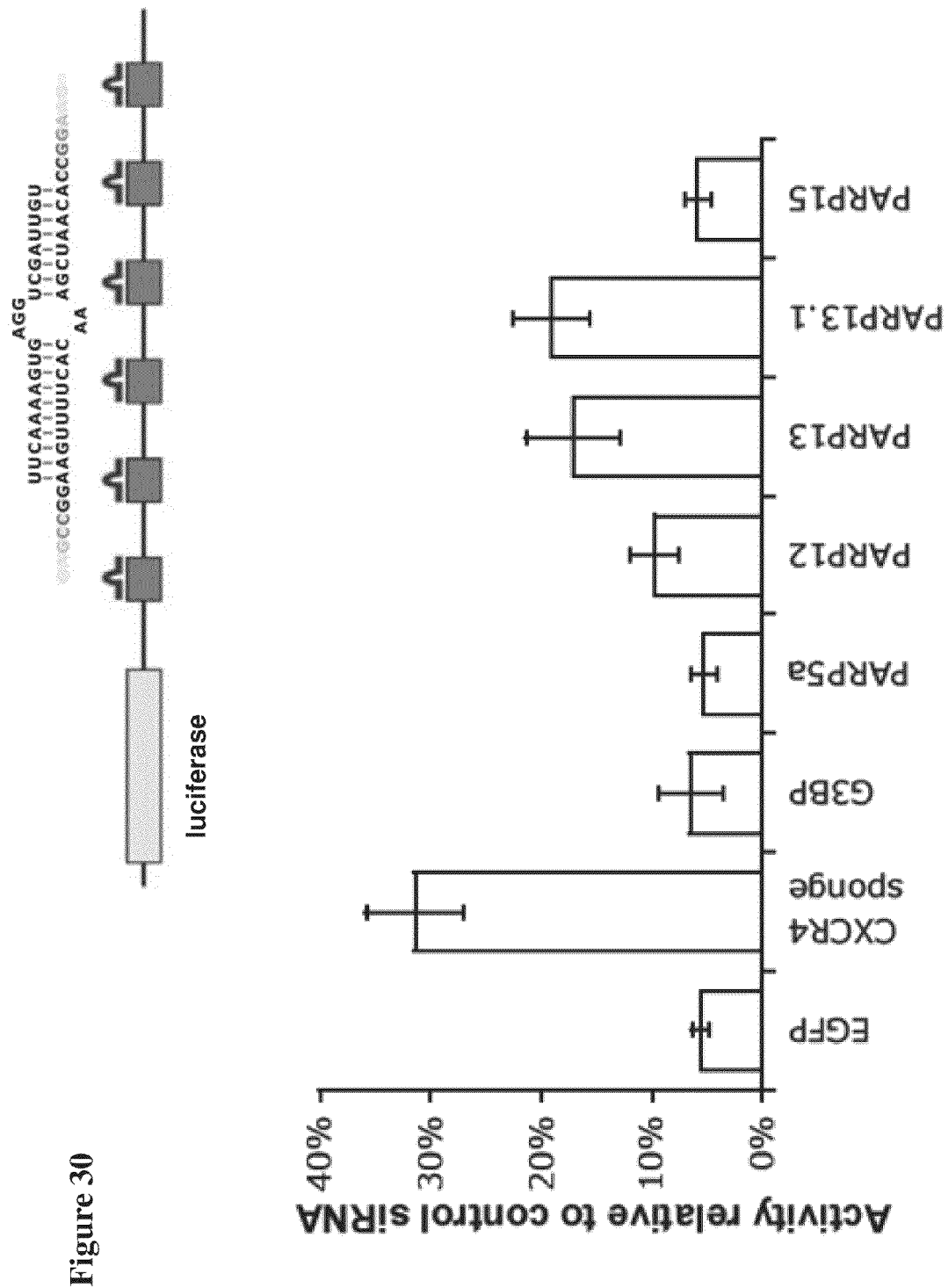
FIG. 30 is a graph showing the relative expression of luciferase in lysates from 293T cells transfected with a modified pGL4.72[hRlucCP]™ vector (Promega); 10 nM of vector-target RNAi (SEQ ID NOS: 38 and 39); and a pEGFP-C1 vector encoding EGFP, G3BP, PAPR5A, PARP12, PARP13, PARP13.1, or PARP15. Luciferase expression was measured in cell lysates at 48 hours post-transfection. The level of luciferase in treated cells is compared to the level of luciferase produced in cells transfected with the modified pGL4.72[hRlucCP]™ vector alone. As another positive control, the level of luciferase produced from cells transfected with the modified pGL4.72[hRlucCP]™ vector and 10 nM vector-target RNAi is shown (CXCR4 sponge).
Figure 31:
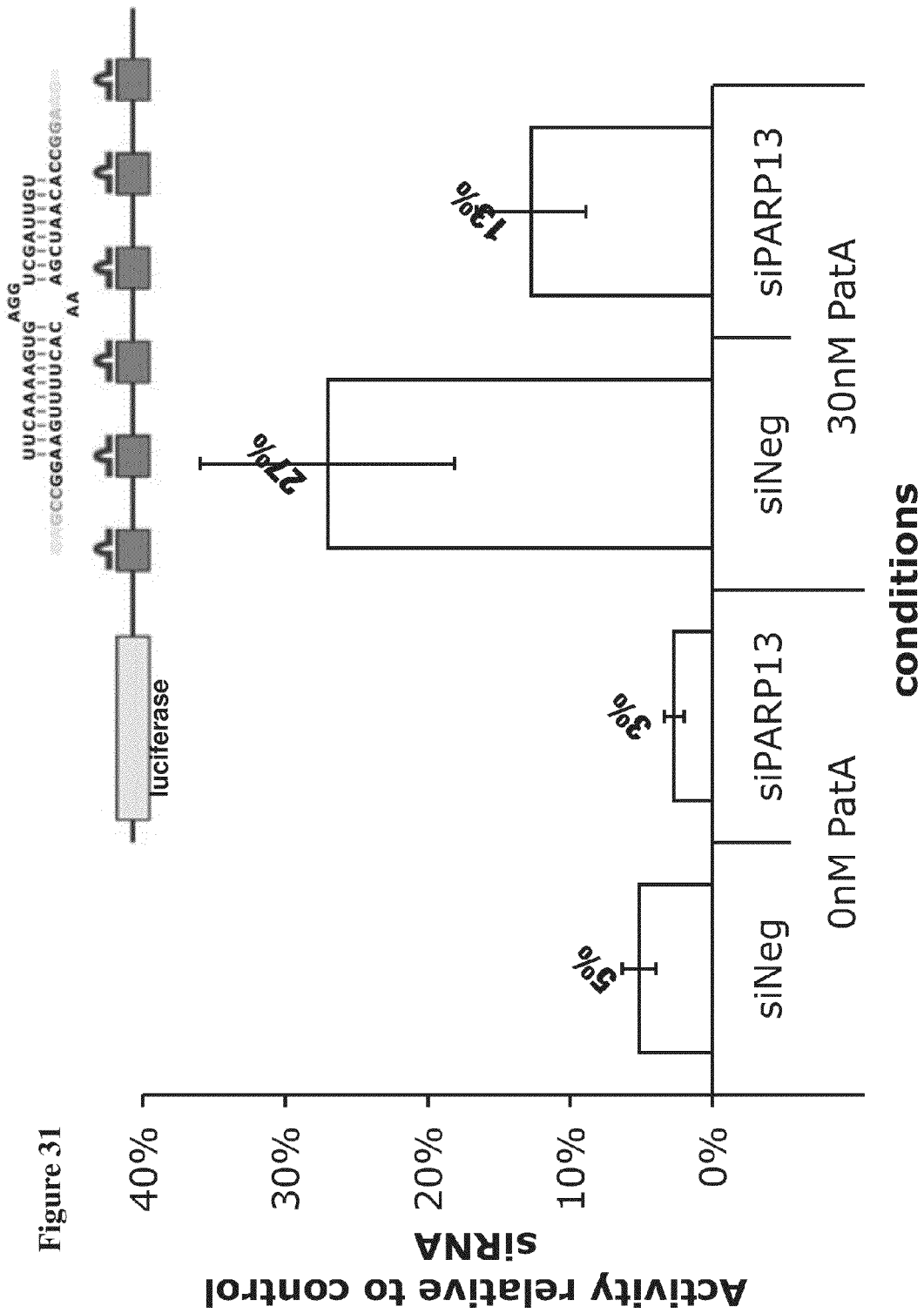
FIG. 31 is a graph showing the relative expression of luciferase in 293T cells transfected with a modified pGL4.72 [hRlucCP]™ vector, 20 nM vector target RNAi (SEQ ID NOS: 38 and 39), and 20 nM of negative RNAi control for PARP13 siRNA (siNeg; All Stars Negative Control siRNA; Qiagen Catalog No. 1027280) or PARP13 siRNA (si-PARP13; GCUCACGGAACUAUGAGCUGAGUUU; SEQ ID NO: 40) following treatment with 0 or 30 nM pateamine A for 30 minutes. Luciferase expression was measured in cell lysates at 48 hours post-transfection. The level of luciferase in treated cells is compared to the level of luciferase produced in cells transfected with the modified pGL4.72[hRlucCP]™ vector alone.

Additional experiments were performed to determine the effect of PARP13 knockdown on miRNA activity. For these experiments, the pGL4.72[hRlucCP]™-vector assay (Promega) was used to measure RNAi activity in 293T cells. The pGL4.72[hRlucCP]™ vector contains a constitutively expressed firefly luciferase gene which is located upstream of several nucleic acid sequences targeted by an RNAi molecule. An increase in the activity of an RNAi molecule targeting the downstream 3' sequences of the vector results in a decrease in the amount of luciferase produced from the vector. In experiments to study the effect of PARP13 on miRNA activity, the pGL4.72[hRlucCP]™ vector was first engineered to contain 6 repeats of a sequence recognized by an RNAi molecule targeting the vector ("vector-target RNAi;" SEQ ID NOS: 38 and 39; GUUUUCACUCCAGCUAA-CACA and TTCAAAAGUGAGGUCGAUUGU, respectively). In a first experiment, cells were transfected with a modified pGL4.72[hRlucCP]™ vector and a pEGFP-C1 plasmid encoding EGFP (negative control), G3BP (negative control), PARP5a, PARP12, PARP13, PARP13.1, or PARP15; and 10 nM of the vector-target RNAi. In a positive control, the cells were transfected with the modified pGL4.72 [hRlucCP]™ vector and vector-target RNAi alone (CXCR4 sponge). Cells overexpressing PARP13 or PARP13.1 showed a 3-fold decrease in the level of miRNA-mediated repression compared to control cells (e.g., EGFP- and G3BP-overexpressing cells) (FIG. 30). In a second set of experiments, the ability of the vector-target RNAi to reduce the expression of luciferase was measured in 293T cells transfected with pGL4.72[hRlucCP]™ vector, 20 nM vector-target RNAi, and 20 nM of negative RNAi control for PARP13 siRNA (siNeg; AllStars Negative Control siRNA; Qiagen Catalog No. 1027280) or PARP13 siRNA (siPARP13; SEQ ID NO: 40) following treatment with 0 or 30 nM pateamine A for 2 hours. The data in FIG. 31 show that knockdown of PARP13 expression by siPARP13 results in an increase in the activity of the vector-target RNAi under stress conditions (i.e., 30 nM pateamine A) (FIG. 31). These data indicate that PARP13 activity in the cell has a negative effect on RNAi activity in the cell. This effect on RNAi activity may occur through the poly-ADP-ribosylation of Argonaut 2 by PARP13 or by the ability of PARP13 to modify or bind other proteins located within stress granules or proteins required for the assembly or disassembly of stress granules.

Figure 32:
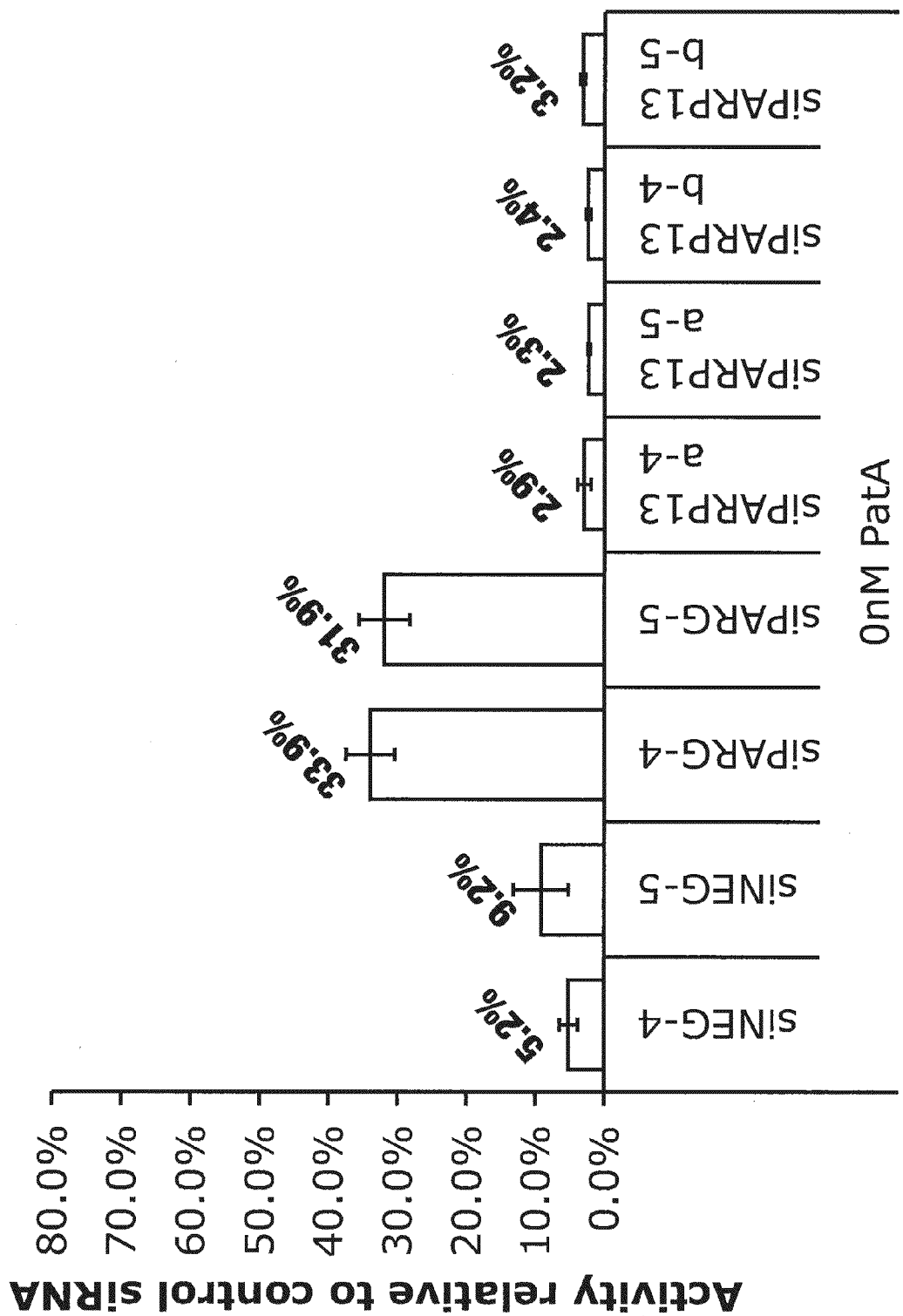
FIG. 32 is a graph showing the relative expression of luciferase in 293T cells transfected with a modified pGL4.72 [hRlucCP]™ vector; 20 nM vector target RNAi (SEQ ID NOS: 38 and 39); and 20 nM of negative RNAi control (siNeg-4 and siNeg-5; All Stars Negative Control siRNA; Qiagen Catalog No. 1027280), siPARG-4 (SEQ ID NO: 34), siPARG-5 (SEQ ID NO: 34), siPARP13a-4 (SEQ ID NO: 40), siPARP13a-5 (SEQ ID NO: 40), siPARP13b-4 (SEQ ID NO: 40), or siPARP13b-5 (SEQ ID NO: 40). Luciferase expression was measured in cell lysates at 48 hours post-transfection. The level of luciferase in treated cells is compared to the level of luciferase produced in cells transfected with the modified pGL4.72[hRlucCP]™ vector alone.

Additional experiments were performed to test the effect of PARG and PARP13 on RNAi activity under non-stressed conditions using the pGL4.72[hRlucCP]™-vector assay. In a first set of experiments, 293T cells were transfected with the pGL4.72[hRlucCP]™ vector; the 20 nM vector target RNAi; and 20 nM of control RNAi (siNEG-4 or siNEG-5; All Stars Negative Control siRNA; Qiagen Catalog No. 1027280), PARG target RNAi (siPARG-4 or siPARG-5; SEQ ID NO: 34), or a PARP13 target RNAi (siPARP13a-4, siPARP13a-5, siPARP13b-4, or siPARP13b-5; SEQ ID NO: 40). The results indicate that the knockdown of PARP13 increases the activity of the target vector RNAi, while knockdown of PARG decreases the activity of the target vector RNAi in unstressed cells (FIG. 32).

Figure 33:
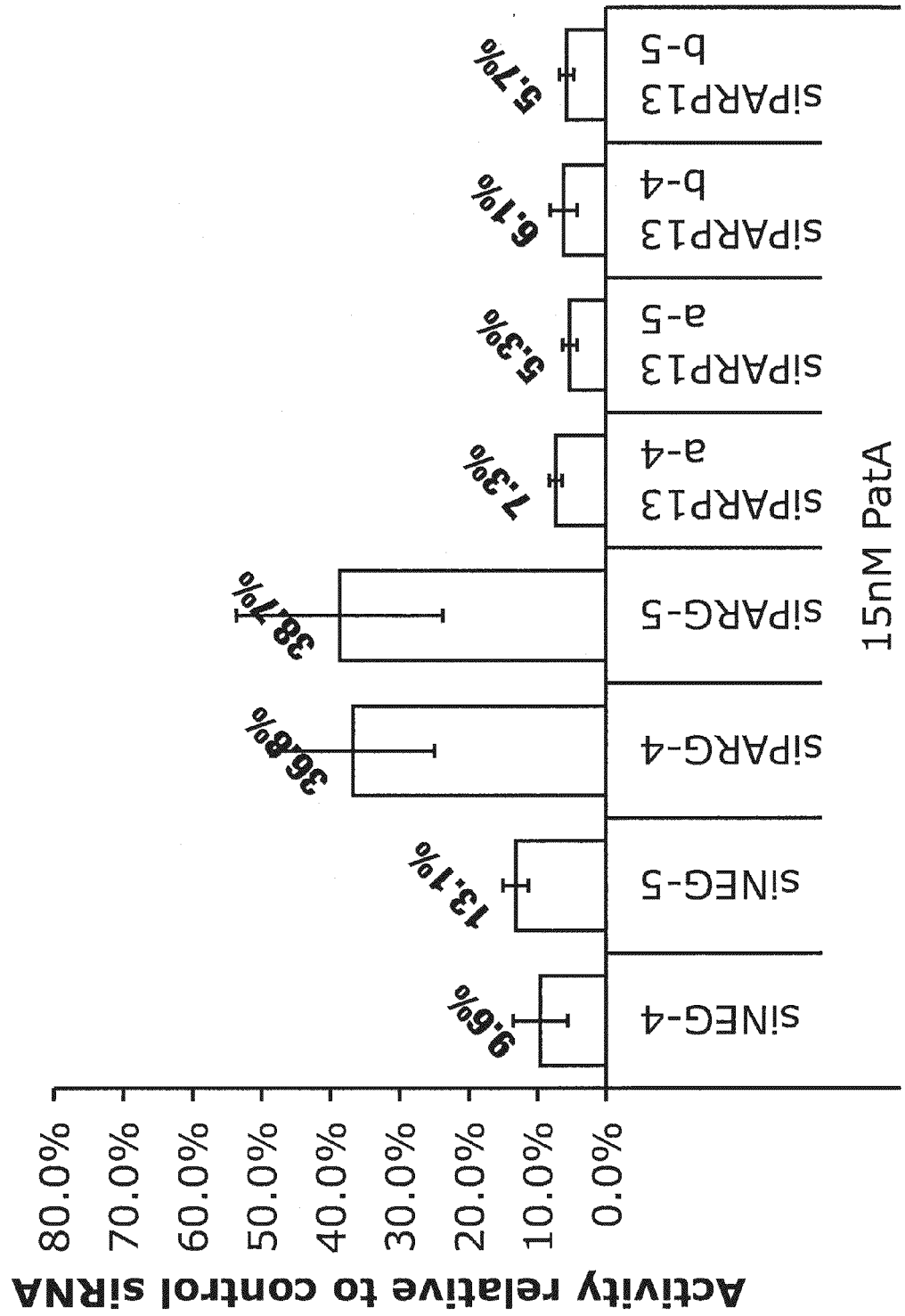
FIG. 33 is a graph showing the relative expression of luciferase in 293T cells transfected with a modified pGL4.72 [hRlucCP]™ vector; 20 nM vector target RNAi (SEQ ID NOS: 38 and 39); and 20 nM of negative RNAi control (siNeg-4 and siNeg-5; All Stars Negative Control siRNA; Qiagen Catalog No. 1027280), siPARG-4 (SEQ ID NO: 34), siPARG-5 (SEQ ID NO: 34), siPARP13a-4 (SEQ ID NO: 40), siPARP13a-5 (SEQ ID NO: 40), siPARP13b-4 (SEQ ID NO: 40), or siPARP13b-5 (SEQ ID NO: 40) following treatment with 15 nM pateamine A for 30 minutes. Luciferase expression was measured in cell lysates at 48 hours post-transfection. The level of luciferase in treated cells is compared to the level of luciferase produced in cells transfected with the modified pGL4.72[hRlucCP]™ vector alone.
Figure 34:
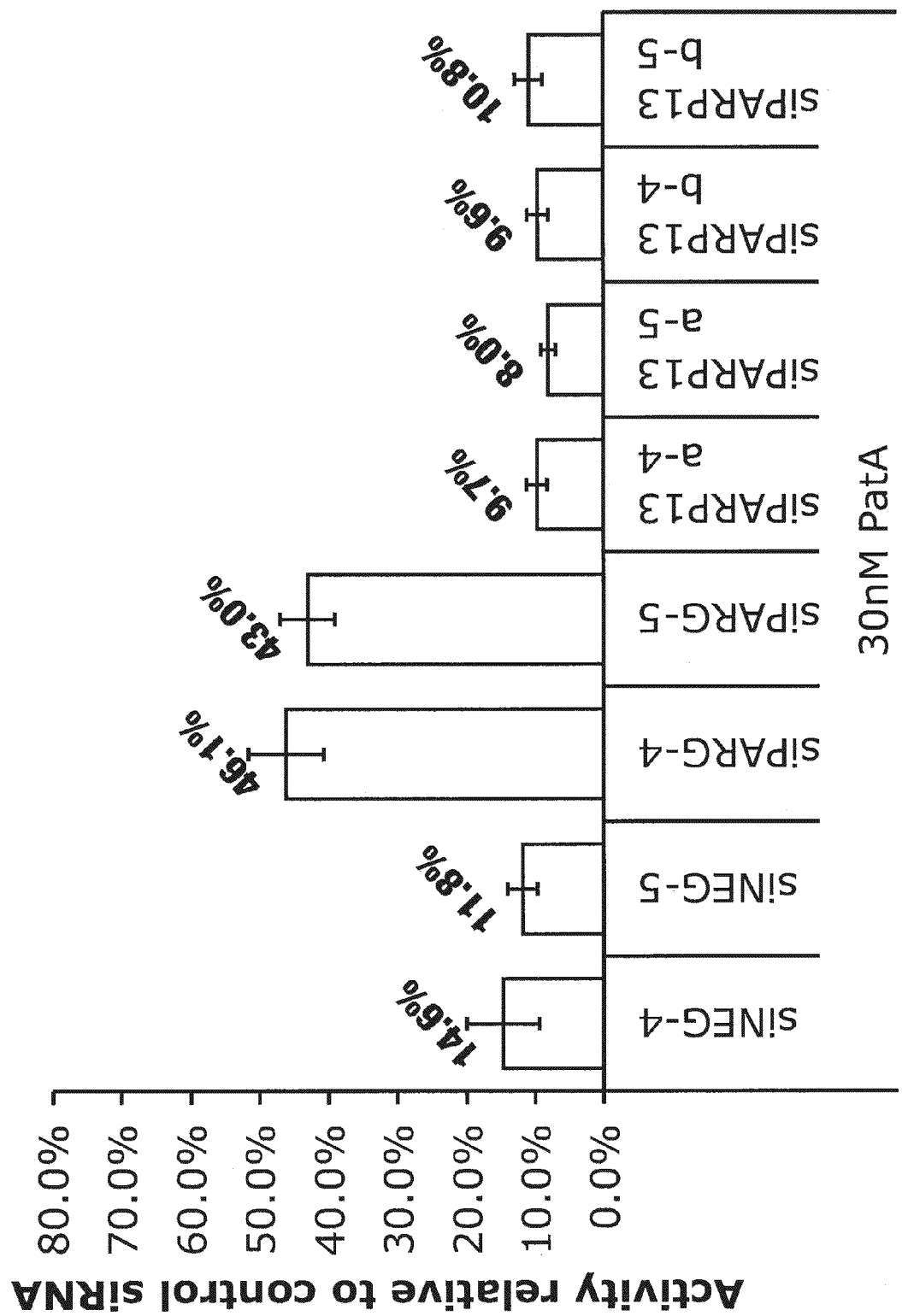
FIG. 34 is a graph showing the relative expression of luciferase in 293T cells transfected with a modified pGL4.72 [hRlucCP]™ vector; 20 nM vector target RNAi (SEQ ID NOS: 38 and 39); and 20 nM of negative RNAi control (siNeg-4 and siNeg-5; All Stars Negative Control siRNA; Qiagen Catalog No. 1027280), siPARG-4 (SEQ ID NO: 34), siPARG-5 (SEQ ID NO: 34), siPARP13a-4 (SEQ ID NO: 40), siPARP13a-5 (SEQ ID NO: 40), siPARP13b-4 (SEQ ID NO: 40), or siPARP13b-5 (SEQ ID NO: 40) following treatment with 30 nM pateamine A for 30 minutes. Luciferase expression was measured in cell lysates at 48 hours post-transfection. The level of luciferase in treated cells is compared to the level of luciferase produced in cells transfected with the modified pGL4.72[hRlucCP]™ vector alone.
Figure 35:
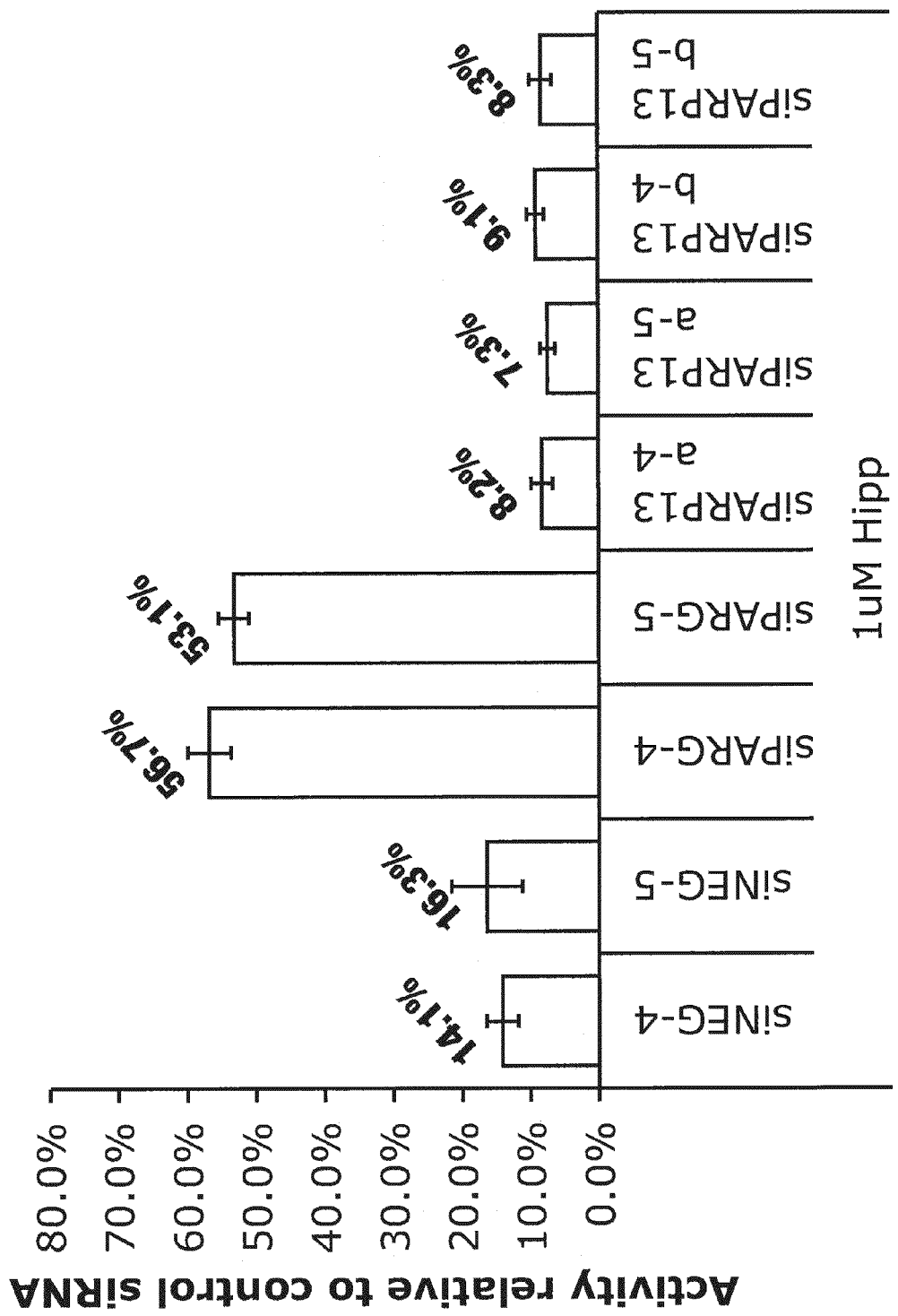
FIG. 35 is a graph showing the relative expression of luciferase in 293T cells transfected with a modified pGL4.72 [hRlucCP]™ vector; 20 nM vector target RNAi (SEQ ID NOS: 38 and 39); and 20 nM of negative RNAi control (siNeg-4 and siNeg-5; All Stars Negative Control siRNA; Qiagen Catalog No. 1027280), siPARG-4 (SEQ ID NO: 34), siPARG-5 (SEQ ID NO: 34), siPARP13a-4 (SEQ ID NO: 40), siPARP13a-5 (SEQ ID NO: 40), siPARP13b-4 (SEQ ID NO: 40), or siPARP13b-5 (SEQ ID NO: 40) following treatment with 1 µM hippuristanol (Hipp) for 30 minutes. Luciferase expression was measured in cell lysates at 48 hours post-transfection. The level of luciferase in treated cells is compared to the level of luciferase produced in cells transfected with the modified pGL4.72[hRlucCP]™ vector alone.
Figure 36:
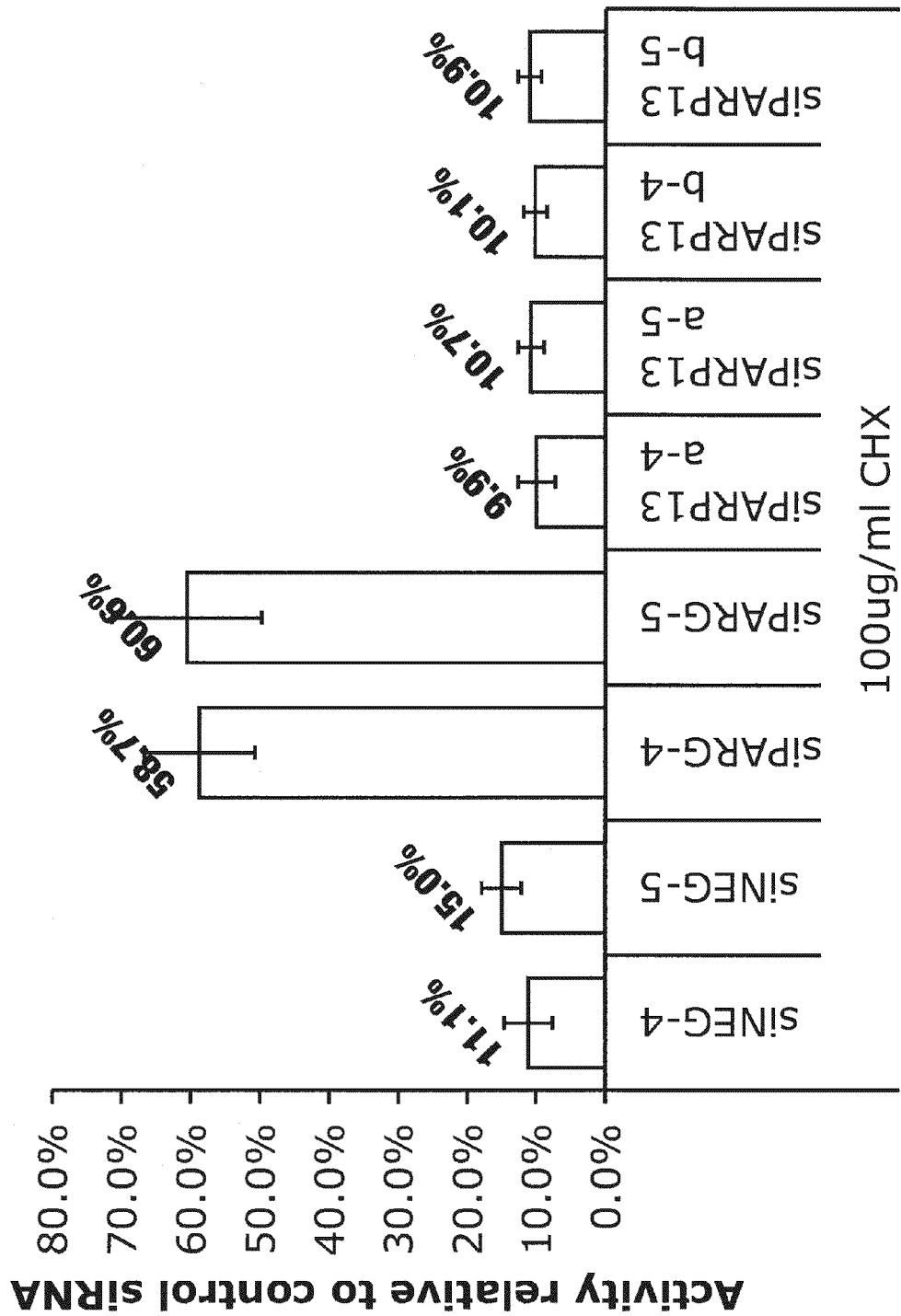
FIG. 36 is a graph showing the relative expression of luciferase in 293T cells transfected with a modified pGL4.72 [hRlucCP]™ vector; 20 nM vector target RNAi (SEQ ID NOS: 38 and 39); and 20 nM of negative RNAi control (siNeg-4 and siNeg-5; All Stars Negative Control siRNA; Qiagen Catalog No. 1027280), siPARG-4 (SEQ ID NO: 34), siPARG-5 (SEQ ID NO: 34), siPARP13a-4 (SEQ ID NO: 40), siPARP13a-5 (SEQ ID NO: 40), siPARP13b-4 (SEQ ID NO: 40), or siPARP13b-5 (SEQ ID NO: 40) in 293T cells treated with 100 µg/mL cycloheximide for 30 minutes. Luciferase expression was measured in cell lysates at 48 hours post-transfection. The level of luciferase in treated cells is compared to the level of luciferase produced in cells transfected with the modified pGL4.72[hRlucCP]™ vector alone.

The same experiment (i.e., transfection of 293 T cells with pGL4.72[hRlucCP]™ vector; the 20 nM vector target RNAi; and 20 nM of control RNAi (siNEG-4 or siNEG-5; All Stars Negative Control siRNA; Qiagen Catalog No. 1027280), PARG target RNAi (siPARG-4 or siPARG-5; SEQ ID NO: 34), or a PARP13 target RNAi (siPARP13a-4, siPARP13a-5, siPARP13b-4, or siPARP13b-5; SEQ ID NO: 40) was also performed under different cellular stress conditions: 15 nM pateamine A (FIG. 33), 30 nM pateamine A (FIG. 34), 1 µM hippuristanol (FIG. 35), or 100 µg/mL cyclohexamide (FIG. 36). These data indicate that knockdown of PARG decreases the activity of the target vector RNAi, while knockdown of PARP13 increases the activity of the vector-target RNAi in cells exposed to a variety of stress conditions.

Experimental Methods

Immunopreciptation experiments were performed using non-transfected HeLa cells following treatment with 0 or 250 µM sodium arsenite for 60 minutes using an anti-Argonaut 2 antibody. The resulting precipitated proteins were electrophoresed using 4-12% SDS-PAGE and immunoblotted using an anti-poly-ADP ribose antibody. Non-transfected HeLa cells treated with 250 µM sodium arsenite for 30 minutes were also stained for immunofluorescence microscopy using antibodies specific for Argonaut 2 and eIF3 (a marker of stress granules), and a secondary fluorescently-labeled antibody (Alexa Fluor 594 and 488 antibodies).

Additional co-immunoprecipitation experiments were performed using methods known in the art. In these experiments, HeLa cell lysate was prepared from cells treated with 0 or 250 µM sodium arsenite for 30 minutes, and the lysate subsequently immunoprecipitated with an anti-Argonaut 2 antibody. The resulting precipitated proteins were immunoblotted using an anti-PARP13/13.1 antibody.

Experiments to identify additional proteins bound to a PARP13-GFP fusion protein were performed by transfecting HeLa S3 cells with a pEGFP-C1 plasmid encoding a PARP13-GFP fusion protein. The transfected cells were treated with 0 or 250 µM sodium arsenite for 30 minutes before lysis. The resulting cell lysate was immunoprecipitated with an anti-GFP antibody and the resulting precipitated proteins were electrophoresed using 4-12% SDS-PAGE and the resulting gel stained with Coomassie Blue.

Experiments to determine the effect of knockdown of PARP13 on miRNA and RNAi activity were performed using a modified pGL4.72[hRlucCP]™-vector assay (Promega). For these experiments, the pGL4.72[hRlucCP]™-vector was modified by placing six copies of a target sequence at a position 3' to the luciferase gene. RNAi molecules targeting the vector were designed to bind the six copies of the target sequence (SEQ ID NOS: 34 and 35). The modified pGL4.72 [hRlucCP]™-vector was introduced into 293T cells using Lipofectamine 2000 (Invitrogen) according to the manufacturer's instructions. In each experiment, the cells were further transfected (Lipofectamine 2000) with 10 or 20 nM of the vector-target RNAi alone or in combination with either 20 nM of a control RNAi molecule for the siRNA targeting PARP13 (siNeg) or an RNAi molecule targeting PARP13 (siPARG13), and the cells treated with 0 or 30 nM pateamine A for 60 minutes. Following 48-hours incubation, the level of luciferase protein production was measured using a luciferase assay kit (Promega). The data are shown as the relative level of luciferase protein produced in cells transfected with the modified vector alone in the absence of any RNAi treatment.

In a similar set of experiments, 293T cells were transfected (Lipofectamine 2000) with pGL4.72[hRlucCP]™ vector; 20 nM vector target RNAi (above); and 20 nM of control RNAi (siNEG-4 or siNEG-5; All Stars Negative Control siRNA; Qiagen Catalog No. 1027280), PARG target RNAi (si-PARG-4 or siPARG-5; SEQ ID NO: 34), or a PARP13 target RNAi (siPARP13a-4, siPARP13a-5, siPARP13b-4, or siPARP13b-5; SEQ ID NO: 40) and the cells exposed to the following stress conditions for 30 minutes: 15 nM pateamine A, 30 nM pateamine A, 1 μM hippuristanol, or 100 μg/mL cyclohexamide. Following 48-hours incubation with the respective RNAi molecules, the level of luciferase protein production was measured using a luciferase assay kit (Promega). The data are shown as the relative level of luciferase protein produced in cells transfected with the modified vector alone in the absence of any RNAi treatment.

Experiments were also performed to determine the effect of overexpression of a PARP-GFP protein on the activity of miRNA using the modified pGL4.72[hRlucCP]™-vector assay described above. In these experiments, 293T cells were transfected with pEGFP-C1 expression vectors encoding EGFP, G3BP, PARP5A, PARP12, PARP13, PARP13.1, or PARP15; the modified pGL4.72[hRlucCP]™ vector; and 10 nM vector-targeting RNAi. As a positive control for RNAi activity, the cells were transfected with the modified pGL4.72 [hRlucCP]™ and the vector-target RNAi alone (CXCR4 sponge).

From the foregoing description, one skilled in the art can easily ascertain the essential characteristics of this invention; can make various changes and modifications of the invention to adapt it to various usages and conditions. Thus, other embodiments are also within the claims.

The invention claimed is:

1. A method for increasing the activity of an inhibitory RNA (RNAi) that has been or is being administered to a subject, said method comprising administering to said subject a therapeutically effective amount of one or more PARP12 inhibitor(s) and/or one or more PARP13 inhibitor(s), wherein said RNAi is not directed against PARP12 or PARP13.

2. The method of claim 1, wherein said one or more PARP13 inhibitors selectively decreases the expression and/or one or more activities of PARP13 isoform 1 (PARP13.1) or PARP13 isoform 2 (PARP13.2).

3. The method of claim 2, wherein said decrease in expression is a decrease in the level of one or more nucleic acid(s) comprising a nucleic acid sequence having at least 95% sequence identity to PARP13.1 (SEQ ID NO: 19), or a decrease in the level of one or more polypeptide(s) encoded by said one or more nucleic acid(s); or said one or more activities of said PARP13.1 is poly-ADP-ribosylation of a target protein that regulates the activity or processing of an RNAi in a cell.

4. The method of claim 1, wherein said activity of an RNAi is the decrease of the level of a target mRNA molecule in the subject.

5. A method for increasing the activity of an inhibitory RNA (RNAi) that has been administered to a subject, said method comprising administering to said subject a therapeutically effective amount of an antibody or antibody fragment that selectively binds to PARP13.1.

6. A method for increasing the activity of an inhibitory RNA (RNAi) in a cell or a population of cells, said method comprising contacting said cell or population of cells with an effective amount of both said RNAi and one or more PARP12 inhibitor(s) and/or one or more PARP13 inhibitor(s), wherein said RNAi is not directed against PARP12 or PARP13.

7. The method of claim 6, wherein said one or more PARP13 inhibitors selectively decreases the expression and/or one or more activities of PARP13 isoform 1 (PARP13.1) or PARP13 isoform 2 (PARP13.2).

8. The method of claim 7, wherein said decrease in expression is a decrease in the level of one or more nucleic acid(s) comprising a nucleic acid sequence having at least 95% sequence identity to PARP13.1 (SEQ ID NO: 19), or a decrease in the level of one or more polypeptide(s) encoded by said one or more nucleic acid(s); or said one or more activities of said PARP13.1 is poly-ADP-ribosylation of a target protein that regulates the activity or processing of RNAi in a cell.

9. The method of claim 6, wherein said activity of an RNAi is the decrease of the level of a target mRNA molecule in the cell or population of cells.

10. A method for increasing the activity of an inhibitory RNA (RNAi) that has been administered to a cell or a population of cells, said method comprising contacting said cell or population of cells with an effective amount of an antibody or antibody fragment that selectively binds to PARP13.1.

11. A method for increasing the activity of an inhibitory RNA (RNAi) that has been administered to a subject, said method comprising administering to said subject a therapeutically effective amount of an RNAi comprising a sequence selected from the group consisting of SEQ ID NOs: 40 and 106-112.

12. A method for increasing the activity of an inhibitory RNA (RNAi) that has been administered to a cell or a population of cells, said method comprising contacting said cell or population of cells with an effective amount of an RNAi comprising a sequence selected from one of SEQ ID NOs: 40 and 106-112.

* * * * *

SEQUENCE LISTING

```
<160> NUMBER OF SEQ ID NOS: 136

<210> SEQ ID NO 1
<211> LENGTH: 3048
<212> TYPE: DNA
<213> ORGANISM: Homo sapiens

<400> SEQUENCE: 1
aggatggcgg agtcttcgga taagctctat cgagtcgagt acgccaagag cgggcgcgcc        60
tcttgcaaga aatgcagcga gagcatcccc aaggactcgc tccggatggc catcatggtg       120
cagtcgccca tgtttgatgg aaaagtccca cactggtacc acttctcctg cttctggaag       180
gtgggccact ccatccggca ccctgacgtt gaggtggatg ggttctctga gcttcggtgg       240
gatgaccagc agaaagtcaa gaagacagcg gaagctggag gagtgacagg caaaggccag       300
gatggaattg gtagcaaggc agagaagact ctgggtgact ttgcagcaga gtatgccaag       360
tccaacagaa gtacgtgcaa ggggtgtatg gagaagatag aaaagggcca ggtgcgcctg       420
tccaagaaga tggtggaccc ggagaagcca cagctaggca tgattgaccg ctggtaccat       480
ccaggctgct ttgtcaagaa cagggaggag ctgggtttcc ggcccgagta cagtgcgagt       540
cagctcaagg gcttcagcct ccttgctaca gaggataaag aagccctgaa gaagcagctc       600
ccaggagtca agagtgaagg aaagagaaaa ggcgatgagg tggatggagt ggatgaagtg       660
gcgaagaaga aatctaaaaa agaaaaagac aaggatagta agcttgaaaa agccctaaag       720
gctcagaacg acctgatctg gaacatcaag gacgagctaa agaaagtgtg ttcaactaat       780
gacctgaagg agctactcat cttcaacaag cagcaagtgc cttctgggga gtcggcgatc       840
ttggaccgag tagctgatgg catggtgttc ggtgccctcc ttccctgcga ggaatgctcg       900
ggtcagctgg tcttcaagag cgatgcctat tactgcactg gggacgtcac tgcctggacc       960
aagtgtatgg tcaagacaca gacacccaac cggaaggagt gggtaacccc aaaggaattc      1020
cgagaaatct cttacctcaa gaaattgaag gttaaaaagc aggaccgtat attcccccca      1080
gaaaccagcg cctccgtggc ggccacgcct ccgcccctcca cagcctcggc tcctgctgct      1140
gtgaactcct ctgcttcagc agataagcca ttatccaaca tgaagatcct gactctcggg      1200
aagctgtccc ggaacaagga tgaagtgaag gccatgattg agaaactcgg ggggaagttg      1260
acggggacgg ccaacaaggc ttccctgtgc atcagcacca aaaaggaggt ggaaaagatg      1320
```

-continued

```
aataagaaga tggaggaagt aaaggaagcc aacatccgag ttgtgtctga ggacttcctc    1380
caggacgtct ccgcctccac caagagcctt caggagttgt tcttagcgca catcttgtcc    1440
ccttggtggg cagaggtgaa ggcagagcct gttgaagttg tggccccaag agggaagtca    1500
ggggctgcgc tctccaaaaa aagcaagggc caggtcaagg aggaaggtat caacaaatct    1560
gaaaagagaa tgaaattaac tcttaaagga ggagcagctg tggatcctga ttctggactg    1620
gaacactctg cgcatgtcct ggagaaaggt gggaaggtct tcagtgccac ccttggcctg    1680
gtggacatcg ttaaaggaac caactcctac tacaagctgc agcttctgga ggacgacaag    1740
gaaaacaggt attggatatt caggtcctgg ggccgtgtgg gtacggtgat cggtagcaac    1800
aaactggaac agatgccgtc caaggaggat gccattgagc agttcatgaa attatatgaa    1860
gaaaaaaccg ggaacgcttg gcactccaaa aatttcacga agtatcccaa aaagttttac    1920
cccctggaga ttgactatgg ccaggatgaa gaggcagtga agaagctcac agtaaatcct    1980
ggcaccaagt ccaagctccc caagccagtt caggacctca tcaagatgat ctttgatgtg    2040
gaaagtatga agaaagccat ggtggagtat gagatcgacc ttcagaagat gcccttgggg    2100
aagctgagca aaaggcagat ccaggccgca tactccatcc tcagtgaggt ccagcaggcg    2160
gtgtctcagg gcagcagcga ctctcagatc ctggatctct caaatcgctt ttacaccctg    2220
atcccccacg actttgggat gaagaagcct ccgctcctga caatgcaga cagtgtgcag    2280 gccaaggtgg aaatgcttga caacctgctg gacatcgagg tggcctacag tctgctcagg    2340
ggagggtctg atgatagcag caaggatccc atcgatgtca actatgagaa gctcaaaact    2400
gacattaagg tggttgacag agattctgaa gaagccgaga tcatcaggaa gtatgttaag    2460
aacactcatg caaccacaca cagtgcgtat gacttggaag tcatcgatat ctttaagata    2520
gagcgtgaag gcgaatgcca gcgttacaag cccttaagc agcttcataa ccgaagattg    2580
ctgtggcacg gtccaggac caccaacttt gctgggatcc tgtcccaggg tcttcggata    2640
gccccgcctg aagcgcccgt gacaggctac atgtttggta aagggatcta tttcgctgac    2700
atggtctcca agagtgccaa ctactaccat acgtctcagg gagacccaat aggcttaatc    2760
ctgttgggag aagttgccct tggaaacatg tatgaactga gcacgcttc acatatcagc    2820 aggttaccca gggcaagca cagtgtcaaa ggtttgggca aaactacccc tgatccttca    2880
gctaacatta gtctgatgg tgtagacgtt cctcttggga ccgggatttc atctggtgtg    2940
atagacacct ctctactata taacgagtac attgtctatg atattgctca ggtaaatctg    3000
aagtatctgc tgaaactgaa attcaatttt aagacctccc tgtggtaa             3048
```

<210> SEQ ID NO 2
<211> LENGTH: 1089
<212> TYPE: DNA
<213> ORGANISM: Homo sapiens

<400> SEQUENCE: 2

```
atgctcacag taaatcctgg caccaagtcc aagctcccca agccagttca ggacctcatc      60
aagatgatct ttgatgtgga agtatgaag aaagccatgg tggagtatga gatcgacctt     120
cagaagatgc ccttggggaa gctgagcaaa aggcagatcc aggccgcata ctccatcctc     180
agtgaggtcc agcaggcggt gtctcagggc agcagcgact ctcagatcct ggatctctca     240
aatcgctttt acaccctgat cccccacgac tttgggatga agaagcctcc gctcctgaac     300
aatgcagaca gtgtgcaggc caaggtggaa atgcttgaca acctgctgga catcgaggtg     360
gcctacagtc tgctcagggg agggtctgat gatagcagca aggatcccat cgatgtcaac     420
```

```
tatgagaagc tcaaaactga cattaaggtg gttgacagag attctgaaga agccgagatc      480
atcaggaagt atgttaagaa cactcatgca accacacaca gtgcgtatga cttggaagtc      540
atcgatatct ttaagataga gcgtgaaggc gaatgccagc gttacaagcc ctttaagcag      600
cttatgcata accgaagatt gctgtggcac gggtccagga ccaccaactt tgctgggatc      660
ctgtcccagg gtcttcggat agccccgcct gaagcgcccg tgacaggcta catgtttggt      720
aaagggatct atttcgctga catggtctcc aagagtgcca actactacca tacgtctcag      780
ggagacccaa taggcttaat cctgttggga gaagttgccc ttggaaacat gtatgaactg      840
aagcacgctt cacatatcag caggttaccc aagggcaagc acagtgtcaa aggtttgggc      900
aaaactaccc ctgatccttc agctaacatt agtctggatg gtgtagacgt tcctcttggg      960
accgggattt catctggtgt gatagacacc tctctactat ataacgagta cattgtctat     1020
gatattgctc aggtaaatct gaagtatctg ctgaaactga aattcaattt taagacctcc     1080
ctgtggtaa                                                              1089

<210> SEQ ID NO 3
<211> LENGTH: 1716
<212> TYPE: DNA
<213> ORGANISM: Homo sapiens

<400> SEQUENCE: 3
gccatggcgg cgcggcggcg acggagcacc ggcggcggca gggcgagagc attaaatgaa       60
agcaaaagag ttaataatgg caacacggct ccagaagact cttcccctgc caagaaaact      120
cgtagatgcc agagacagga gtcgaaaaag atgcctgtgg ctggaggaaa agctaataag      180
gacaggacag aagacaagca agatgaatct gtgaaggcct tgctgttaaa gggcaaagct      240
cctgtggacc cagagtgtac agccaaggtg gggaaggctc atgtgtattg tgaaggaaat      300
gatgtctatg atgtcatgct aaatcagacc aatctccagt tcaacaacaa caagtactat      360
ctgattcagc tattagaaga tgatgcccag aggaacttca gtgtttggat gagatggggc      420
cgagttggga aaatgggaca gcacagcctg gtggcttgtt caggcaatct caacaaggcc      480
aaggaaatct ttcagaagaa attccttgac aaaacgaaaa acaattggga agatcgagaa      540
aagtttgaga aggtgcctgg aaaatatgat atgctacaga tggactatgc caccaatact      600
caggatgaag aggaaacaaa gaaagaggaa tctcttaaat ctcccttgaa gccagagtca      660
cagctagatc ttcgggtaca ggagttaata aagttgatct gtaatgttca ggccatggaa      720
gaaatgatga tggaaatgaa gtataatacc aagaaagccc cacttgggaa gctgacagtg      780
gcacaaatca aggcaggtta ccagtctctt aagaagattg aggattgtat tcgggctggc      840
cagcatggac gagctctcat ggaagcatgc aatgaattct acaccaggat tccgcatgac      900
tttggactcc gtactcctcc actaatccgg acacagaagg aactgtcaga aaaatacaa       960 ttactagagg ctttgggaga cattgaaatt gctattaagc tggtgaaaac agagctacaa     1020
agcccagaac acccattgga ccaacactat agaaacctac attgtgcctt gcgccccctt     1080
gaccatgaaa gttatgagtt caagtgtgatt cccagtacc tacaatctac ccatgctccc     1140
acacacagcg actataccat gaccttgctg gatttgtttg aagtggagaa ggatggtgag     1200
aaagaagcct tcagagagga ccttcataac aggatgcttc tatggcatgg ttccaggatg     1260
agtaactggg tgggaatctt gagccatggg cttcgaattg ccccacctga agctcccatc     1320
acaggttaca tgtttgggaa aggaatctac tttgctgaca tgtcttccaa gagtgccaat     1380
tactgctttg cctctcgcct aaagaataca ggactgctgc tcttatcaga ggtagctcta     1440
```

```
ggtcagtgta atgaactact agaggccaat cctaaggccg aaggattgct tcaaggtaaa    1500
catagcacca aggggctggg caagatggct cccagttctg cccacttcgt caccctgaat    1560
gggagtacag tgccattagg accagcaagt gacacaggaa ttctgaatcc agatggttat    1620
accctcaact acaatgaata tattgtatat aaccccaacc aggtccgtat gcggtacctt    1680
ttaaaggttc agtttaattt ccttcagctg tggtga                              1716

<210> SEQ ID NO 4
<211> LENGTH: 1605
<212> TYPE: DNA
<213> ORGANISM: Homo sapiens

<400> SEQUENCE: 4
gccatggctc caaagccgaa gccctgggta cagactgagg gccctgagaa gaagaagggc      60
cggcaggcag gaagggagga ggacccctt cgctccaccg ctgaggccct caaggccata     120
cccgcagaga agcgcataat ccgcgtggat ccaacatgtc cactcagcag caaccccggg    180
acccaggtgt atgaggacta caactgcacc ctgaaccaga ccaacatcga gaacaacaac    240
aacaagttct acatcatcca gctgctccaa gacagcaacc gcttcttcac ctgctggaac    300
cgctggggcc gtgtgggaga ggtcggccag tcaaagatca ccacttcac aaggctagaa     360 gatgcaaaga aggactttga gaagaaattt cgggaaaaga ccaagaacaa ctgggcagag    420
cgggaccact ttgtgtctca cccgggcaag tacacactta tcgaagtaca ggcagaggat    480
gaggcccagg aagctgtggt gaaggtggac agaggcccag tgaggactgt gactaagcgg    540
gtgcagccct gctccctgga cccagccacg cagaagctca tcactaacat cttcagcaag    600
gagatgttca gaacaccat ggccctcatg gacctggatg tgaagaagat gcccctggga    660
aagctgagca agcaacagat tgcacggggt ttcgaggcct tggaggcgct ggaggaggcc    720
ctgaaaggcc ccacggatgg tggccaaagc ctggaggagc tgtcctcaca cttttacacc    780
gtcatcccgc acaacttcgg ccacagccag ccccgccca tcaattcccc tgagcttctg    840
caggccaaga aggacatgct gctggtgctg gcggacatcg agctggccca ggccctgcag    900
gcagtctctg agcaggagaa gacggtggag gaggtgccac accccctgga ccagactac     960 cagcttctca gtgccagct gcagctgcta gactctggag cacctgagta caaggtgata    1020
cagacctact tagaacagac tggcagcaac cacaggtgcc ctacacttca acacatctgg   1080
aaagtaaacc aagaagggga ggaagacaga ttccaggccc actccaaact gggtaatcgg    1140
aagctgctgt ggcatggcac caacatggcc gtggtggccg ccatcctcac tagtgggctc    1200
cgcatcatgc acattctgg tgggcgtgtt ggcaaggca tctactttgc ctcagagaac     1260
agcaagtcag ctggatatgt tattggcatg aagtgtgggg cccaccatgt cggctacatg    1320
ttcctgggtg aggtggccct gggcagagag caccatatca acacggacaa ccccagcttg    1380
aagagcccac ctcctggctt cgacagtgtc attgcccgag ccacaccgga gcctgatccg    1440
acccaggaca ctgagttgga gctggatggc cagcaagtgg tggtgcccca gggccagcct    1500
gtgccctgcc cagagttcag cagctccaca ttctcccaga gcgagtacct catctaccag    1560
gagagccagt gtcgcctgcg ctacctgctg gaggtccacc tctga                    1605

<210> SEQ ID NO 5
<211> LENGTH: 1602
<212> TYPE: DNA
<213> ORGANISM: Homo sapiens

<400> SEQUENCE: 5
```

-continued

| | |
|---|---|
| gccatggctc caaagccgaa gccctgggta cagactgagg gccctgagaa gaagggccgg | 60 |
| caggcaggaa gggaggagga ccccttccgc tccaccgctg aggccctcaa ggccataccc | 120 |
| gcagagaagc gcataatccg cgtggatcca acatgtccac tcagcagcaa ccccgggacc | 180 |
| caggtgtatg aggactacaa ctgcaccctg aaccagacca catcgagaa caacaacaac | 240 |
| aagttctaca tcatccagct gctccaagac agcaaccgct tcttcacctg ctggaaccgc | 300 |
| tggggccgtg tgggagaggt cggccagtca agatcaacc acttcacaag gctagaagat | 360 |
| gcaaagaagg actttgagaa gaaatttcgg gaaaagacca gaacaactg ggcagagcgg | 420 |
| gaccactttg tgtctcaccc gggcaagtac acacttatcg aagtacaggc agaggatgag | 480 |
| gcccaggaag ctgtggtgaa ggtggacaga ggcccagtga ggactgtgac taagcgggtg | 540 |
| cagccctgct ccctggaccc agccacgcag aagctcatca ctaacatctt cagcaaggag | 600 |
| atgttcaaga acaccatggc cctcatggac ctggatgtga agaagatgcc cctgggaaag | 660 |
| ctgagcaagc aacagattgc acggggtttc gaggccttgg aggcgctgga ggaggccctg | 720 |
| aaaggcccca cggatggtgg ccaaagcctg gaggagctgt cctcacactt ttacaccgtc | 780 |
| atcccgcaca cttcggcca cagccagccc ccgcccatca attcccctga gcttctgcag | 840 |
| gccaagaagg acatgctgct ggtgctggcg gacatcgagc tggcccaggc cctgcaggca | 900 |
| gtctctgagc aggagaagac ggtggaggag gtgccacacc ccctggaccg agactaccag | 960 |
| cttctcaagt gccagctgca gctgctagac tctggagcac ctgagtacaa ggtgatacag | 1020 |
| acctacttag aacagactgg cagcaaccac aggtgcccta cacttcaaca catctggaaa | 1080 |
| gtaaaccaag aaggggagga agacagattc caggcccact ccaaactggg taatcggaag | 1140 |
| ctgctgtggc atggcaccaa catggccgtg gtggccgcca tcctcactag tgggctccgc | 1200 |
| atcatgccac attctggtgg gcgtgttggc aagggcatct actttgcctc agagaacagc | 1260 |
| aagtcagctg gatatgttat tggcatgaag tgtggggccc accatgtcgg ctacatgttc | 1320 |
| ctgggtgagg tggccctggg cagagagcac catatcaaca cggacaaccc cagcttgaag | 1380 |
| agcccacctc ctggcttcga cagtgtcatt gcccgaggcc acaccgagcc tgatccgacc | 1440 |
| caggacactg agttggagct ggatggccag caagtggtgg tgccccaggg ccagcctgtg | 1500 |
| ccctgcccag agttcagcag ctccacattc tcccagagcg agtacctcat ctaccaggag | 1560 |
| agccagtgtc gcctgcgcta cctgctggag gtccacctct ga | 1602 |

<210> SEQ ID NO 6
<211> LENGTH: 1602
<212> TYPE: DNA
<213> ORGANISM: Homo sapiens

<400> SEQUENCE: 6

| | |
|---|---|
| gccatggctc caaagccgaa gccctgggta cagactgagg gccctgagaa gaagggccgg | 60 |
| caggcaggaa gggaggagga ccccttccgc tccaccgctg aggccctcaa ggccataccc | 120 |
| gcagagaagc gcataatccg cgtggatcca acatgtccac tcagcagcaa ccccgggacc | 180 |
| caggtgtatg aggactacaa ctgcaccctg aaccagacca catcgagaa caacaacaac | 240 |
| aagttctaca tcatccagct gctccaagac agcaaccgct tcttcacctg ctggaaccgc | 300 |
| tggggccgtg tgggagaggt cggccagtca agatcaacc acttcacaag gctagaagat | 360 |
| gcaaagaagg actttgagaa gaaatttcgg gaaaagacca gaacaactg ggcagagcgg | 420 |
| gaccactttg tgtctcaccc gggcaagtac acacttatcg aagtacaggc agaggatgag | 480 |
| gcccaggaag ctgtggtgaa ggtggacaga ggcccagtga ggactgtgac taagcgggtg | 540 |

| | |
|---|---|
| cagccctgct ccctggaccc agccacgcag aagctcatca ctaacatctt cagcaaggag | 600 |
| atgttcaaga acaccatggc cctcatggac ctggatgtga agaagatgcc cctgggaaag | 660 |
| ctgagcaagc aacagattgc acggggtttc gaggccttgg aggcgctgga ggaggccctg | 720 |
| aaaggcccca cggatggtgg ccaaagcctg gaggagctgt cctcacactt ttacaccgtc | 780 |
| atcccgcaca acttcggcca cagccagccc ccgcccatca ttcccctga gcttctgcag | 840 |
| gccaagaagg acatgctgct ggtgctggcg gacatcgagc tgcccaggc cctgcaggca | 900 |
| gtctctgagc aggagaagac ggtggaggag gtgccacacc ccctggaccg agactaccag | 960 |
| cttctcaagt gccagctgca gctgctagac tctggagcac tgagtacaa ggtgatacag | 1020 |
| acctacttag aacagactgg cagcaaccac aggtgcccta cacttcaaca catctggaaa | 1080 |
| gtaaaccaag aaggggagga agacagattc caggcccact ccaaactggg taatcggaag | 1140 |
| ctgctgtggc atggcaccaa catggccgtg gtggccgcca tcctcactag tgggctccgc | 1200 |
| atcatgccac attctggtgg gcgtgttggc aagggcatct actttgcctc agagaacagc | 1260 |
| aagtcagctg gatatgttat tggcatgaag tgtggggccc accatgtcgg ctacatgttc | 1320 |
| ctgggtgagt ggcccctggg cagagagcac catatcaaca cggacaaccc cagcttgaag | 1380 |
| agcccacctc ctggcttcga cagtgtcatt gcccgaggcc acaccgagcc tgatccgacc | 1440 |
| caggacactg agttggagct ggatggccag caagtggtgg tgccccaggg ccagcctgtg | 1500 |
| ccctgcccag agttcagcag ctccacattc tcccagagcg agtacctcat ctaccaggag | 1560 |
| agccagtgtc gcctgcgcta cctgctggag gtccacctct ga | 1602 |

<210> SEQ ID NO 7
<211> LENGTH: 5178
<212> TYPE: DNA
<213> ORGANISM: Homo sapiens

<400> SEQUENCE: 7

| | |
|---|---|
| aggatggtga tgggaatctt tgcaaattgt atcttctgtt tgaaagtgaa gtacttacct | 60 |
| cagcagcaga agaaaaagct acaaactgac attaaggaaa atggcggaaa gttttccttt | 120 |
| tcgttaaatc ctcagtgcac acatataatc ttagataatg ctgatgttct gagtcagtac | 180 |
| caactgaatt ctatccaaaa gaaccacgtt catattgcaa acccagattt tatatggaaa | 240 |
| tctatcagag aaaagagact cttggatgta agaattatg atccttataa gcccctggac | 300 |
| atcacaccac ctcctgatca gaaggcgagc agttctgaag tgaaaacaga aggtctatgc | 360 |
| ccggacagtg ccacagagga ggaagacact gtggaactca ctgagtttgg tatgcagaat | 420 |
| gttgaaattc ctcatcttcc tcaagatttt gaagttgcaa aatataacac cttggagaaa | 480 |
| gtgggaatga gggaggcca ggaagctgtg gtggtgagc ttcagtgttc gcgggactcc | 540 |
| agggactgtc ctttcctgat atcctcacac ttcctcctgg atgatggcat ggagactaga | 600 |
| agacagtttg ctataaagaa aacctctgaa gatgcaagtg aatactttga aaattacatt | 660 |
| gaagaactga gaaacaagg atttctacta agagaacatt tcacacctga gcaacccaa | 720 |
| ttagcatctg aacaattgca agcattgctt tggaggaag tcatgaattc aagcactctg | 780 |
| agccaagagg tgagcgattt agtagagatg atttgggcag aggccctggg ccacctggaa | 840 |
| cacatgcttc tcaagccagt gaacaggatt agcctcaacg atgtgagcaa ggcagagggg | 900 |
| attctccttc tagtaaaggc agcactgaaa aatggagaaa cagcagagca attgcaaaag | 960 |
| atgatgacag agttttacag actgatacct cacaaaggca caatgcccaa agaagtgaac | 1020 |
| ctgggactat tggctaagaa agcagacctc tgccagctaa taagagacat ggttaatgtc | 1080 |

-continued

```
tgtgaaacta atttgtccaa acccaaccca ccatccctgg ccaaataccg agctttgagg    1140
tgcaaaattg agcatgttga acagaatact gaagaatttc tcagggttag aaaagaggtt    1200
ttgcagaatc atcacagtaa gagcccagtg gatgtcttgc agatatttag agttggcaga    1260
gtgaatgaaa ccacagagtt tttgagcaaa cttggtaatg tgaggccctt gttgcatggt    1320
tctcctgtac aaaacatcgt gggaatcttg tgtcgagggt tgcttttacc caaagtagtg    1380
gaagatcgtg gtgtgcaaag aacagacgtc ggaaaccttg gaagtgggat ttatttcagt    1440
gattcgctca gtacaagtat caagtactca cacccgggag agacagatgg caccagactc    1500
ctgctcattt gtgacgtagc cctcggaaag tgtatggact acatgagaa ggactttccc    1560 ttaactgaag caccaccagg ctacgacagt gtgcatggag tttcacaaac agcctctgtc    1620
accacagact tgaggatga tgaatttgtt gtctataaaa ccaatcaggt taaaatgaaa    1680
tatattatta aattttccat gcctggagat cagataaagg actttcatcc tagtgatcat    1740
actgaattag aggaatacag acctgagttt tcaaattttt caaaggttga agattaccag    1800
ttaccagatg ccaaaacttc cagcagcacc aaggccggcc tccaggatgc ctctgggaac    1860
ttggttcctc tggaggatgt ccacatcaaa gggagaatca tagacactgt agcccaggtc    1920 attgttttc agacatacac aaataaaagt cacgtgccca ttgaggcaaa atatatcttt    1980
cctttggatg acaaggccgc tgtgtgtggc ttcgaagcct tcatcaatgg gaagcacata    2040
gttggagaga ttaaagagaa ggaagaagcc cagcaagagt acctagaagc cgtgacccag    2100
ggccatggcg cttacctgat gagtcaggat gctccggacg ttttactgt aagtgttgga    2160 aacttacccc ctaaggctaa ggttcttata aaaattacct acatcacaga actcagcatc    2220
ctgggcactg ttggtgtctt tttcatgccc gccaccgtag caccctggca acaggacaag    2280
gctttgaatg aaaaccttca ggatacagta gagaagattt gtataaaaga aataggaaca    2340
aagcaaagct tctcttgac tatgtctatt gagatgccgt atgtgattga attcattttc    2400
agtgatacac atgaactgaa acaaaagcgc acagactgca agctgtcat tagcaccatg    2460 gaaggcagct ccttagacag cagtggattt tctctccaca tcggtttgtc tgctgcctat    2520
ctcccaagaa tgtgggttga aaaacatcca gaaaagaaa gcgaggcttg catgcttgtc    2580
tttcaacccg atctcgatgt cgacctccct gacctagcca gtgagagcga agtgattatt    2640
tgtcttgact gctccagttc catggagggt gtgacattct tgcaagccaa gcaaatcacc    2700
ttgcatgcgc tgtccttggt gggtgagaag cagaaagtaa atattatcca gttcggcaca    2760
ggttacaagg agctattttc gtatcctaag catatcacaa gcaataccac ggcagcagag    2820
ttcatcatgt ctgccacacc taccatgggg aacacagact tctggaaaac actccgatat    2880
cttagcttat tgtaccctgc tcgagggtca cggaacatcc tcctggtgtc tgatgggcac    2940
ctccaggatg agagcctgac attacagctc gtgaagagga ccgcccgca caccaggtta    3000 ttcgcctgcg gtatcggttc tacagcaaat cgtcacgtct taaggatttt gtcccagtgt    3060
ggtgccggag tatttgaata ttttaatgca aaatccaagc atagttggag aaaacagata    3120
gaagaccaaa tgaccaggct atgttctccg agttgccact ctgtctccgt caaatggcag    3180
caactcaatc cagatgcgcc cgaggccctg caggccccag cccaggtgcc atccttgttt    3240
cgcaatgatc gactccttgt ctatggattc attcctcact gcacacaagc aactctgtgt    3300
gcactaattc aagagaaaga attttgtaca atggtgtcga ctactgagct tcagaagaca    3360
actggaacta tgatccacaa gctggcagcc cgagctctaa tcagagatta tgaagatggc    3420
attcttcacg aaaatgaaac cagtcatgag atgaaaaaac aaaccttgaa atctctgatt    3480
```

-continued

| | |
|---|---|
| attaaactca gtaaagaaaa ctctctcata acacaattta caagctttgt ggcagttgag | 3540 |
| aaaagggatg agaatgagtc gccttttcct gatattccaa aagtttctga acttattgcc | 3600 |
| aaagaagatg tagacttcct gccctacatg agctggcagg gggagcccca agaagccgtc | 3660 |
| aggaaccagt ctcttttagc atcctctgag tggccagaat tacgtttatc caaacgaaaa | 3720 |
| cataggaaaa ttccattttc caaaagaaaa atggaattat ctcagccaga agtttctgaa | 3780 |
| gattttgaag aggatggctt aggtgtacta ccagctttca catcaaattt ggaacgtgga | 3840 |
| ggtgtggaaa agctattgga tttaagttgg acagagtcat gtaaaccaac agcaactgaa | 3900 |
| ccactattta agaaagtcag tccatgggaa acatctactt ctagcttttt tcctattttg | 3960 |
| gctccggccg ttggttccta tcttaccccg actacccgcg ctcacagtcc tgcttccttg | 4020 |
| tcttttgcct catatcgtca ggtagctagt ttcggttcag ctgctcctcc cagacagttt | 4080 |
| gatgcatctc aattcagcca aggccctgtg cctggcactt gtgctgactg atcccacag | 4140 |
| tcggcgtctt gtcccacagg acctcccag aacccacctt ctgcaccta ttgtggcatt | 4200 |
| gttttttcag ggagctcatt aagctctgca cagtctgctc cactgcaaca tcctggaggc | 4260 |
| tttactacca ggccttctgc tggcaccttc cctgagctgg attctcccca gcttcatttc | 4320 |
| tctcttccta cagaccctga tcccatcaga ggttttgggt cttatcatcc ctctgcttac | 4380 |
| tctcctttc attttcaacc ttccgcagcc tctttgactg ccaaccttag ctgccaatg | 4440 |
| gcctctgctt tacctgaggc tctttgcagt cagtcccgga ctacccagt agatctctgt | 4500 |
| cttctagaag aatcagtagg cagtctcgaa ggaagtcgat gtcctgtctt tgcttttcaa | 4560 |
| agttctgaca cagaaagtga tgagctatca gaagtacttc aagacagctg cttttacaa | 4620 |
| ataaagtgtg atacaaaga tgacagtatc ccgtgctttc tggaattaaa agaagaggat | 4680 |
| gaaatagtgt gcacacaaca ctggcaggat gctgtgcctt ggacagaact cctcagtcta | 4740 |
| cagacagagg atggcttctg gaaacttaca ccagaactgg gacttatatt aaatcttaat | 4800 |
| acaaatggtt tgcacagctt tcttaaacaa aaaggcattc aatctctagg tgtaaaagga | 4860 |
| agagaatgtc tcctggacct aattgccaca atgctggtac tacagtttat tcgcaccagg | 4920 |
| ttggaaaaag agggaatagt gttcaaatca ctgatgaaaa tggatgaccc ttctatttcc | 4980 |
| aggaatattc cctgggcttt tgaggcaata aagcaagcaa gtgaatgggt aagaagaact | 5040 |
| gaaggacagt acccatctat ctgcccacgg cttgaactgg ggaacgactg ggactctgcc | 5100 |
| accaagcagt tgctgggact ccagcccata agcactgtgt cccctcttca tagagtcctc | 5160 |
| cattacagtc aaggctaa | 5178 |

<210> SEQ ID NO 8
<211> LENGTH: 3987
<212> TYPE: DNA
<213> ORGANISM: Homo sapiens

<400> SEQUENCE: 8

| | |
|---|---|
| aagatggcgg cgtcgcgtcg ctctcagcat catcaccacc atcatcaaca acagctccag | 60 |
| cccgccccag gggcttcagc gccgccgccg ccacctcctc cccactcag ccctggcctg | 120 |
| gccccgggga ccaccccagc ctctcccacg gccagcggcc tggccccctt cgcctccccg | 180 |
| cggcacggcc tagcgctgcc ggaggggat ggcagtcggg atccgcccga caggccccga | 240 |
| tccccggacc cggttgacgg taccagctgt tgcagtacca ccagcacaat ctgtaccgtc | 300 |
| gccgccgctc ccgtggtccc agcggttct acttcatctg ccgctggggt cgctcccaac | 360 |
| ccagccggca gtggcagtaa caattcaccg tcgtcctctt cttcccccgac ttcttcctca | 420 |

| | |
|---|---|
| tcttcctctc catcctcccc tggatcgagc ttggcggaga gccccgaggc ggccggagtt | 480 |
| agcagcacag caccactggg gcctggggca gcaggacctg ggacagsggt cccagcagtg | 540 |
| agcgggcccc tacgggaact gctggaggcc tgtcgcaatg ggacgtgtc ccgggtaaag | 600 |
| aggctggtgg acgcggcaaa cgtaaatgca aggacatgg ccggccggaa gtcttctccc | 660 |
| ctgcacttcg ctgcaggttt tggaaggaag gatgttgtag aacacttact acagatgggt | 720 |
| gctaatgtcc acgctcgtga tgatggaggt ctcatcccgc ttcataatgc ctgttctttt | 780 |
| ggccatgctg aggttgtgag tctgttattg tgccaaggag ctgatccaaa tgccagggat | 840 |
| aactggaact atacacctct gcatgaagct gctattaaag ggaagatcga tgtgtgcatt | 900 |
| gtgctgctgc agcacggagc tgacccaaac attcggaaca ctgatgggaa atcagccctg | 960 |
| gacctggcag atccttcagc aaaagctgtc cttacaggtg aatacaagaa agacgaactc | 1020 |
| ctagaagctg ctaggagtgg taatgaagaa aaactaatgg ctttactgac tcctctaaat | 1080 |
| gtgaattgcc atgcaagtga tgggcgaaag tcgactcctt tacatctagc agcgggctac | 1140 |
| aacagagttc gaatagttca gcttcttctt cagcatggtg ctgatgttca tgcaaaagac | 1200 |
| aaaggtggac ttgtgcctct tcataatgca tgttcatatg gacattatga agtcacagaa | 1260 |
| ctgctactaa agcatggagc ttgtgttaat gccatggatc tctggcagtt tactccactg | 1320 |
| cacgaggctg cttccaagaa ccgtgtagaa gtctgctctt tgttacttag ccatggcgct | 1380 |
| gatcctacgt tagtcaactg ccatggcaaa agtgctgtgg atatggctcc aactccggag | 1440 |
| cttagggaga gattgactta tgaatttaaa ggtcattctt tactacaagc agccagagaa | 1500 |
| gcagacttag ctaaagttaa aaaaacactc gctctggaaa tcattaattt caaacaaccg | 1560 |
| cagtctcatg aaacagcact gcactgtgct gtggcctctc tgcatcccaa acgtaaacaa | 1620 |
| gtgacagaat tgttacttag aaaaggagca aatgttaatg aaaaaaataa agatttcatg | 1680 |
| actcccctgc atgttgcagc cgaaagagcc cataatgatg tcatggaagt tctgcataag | 1740 |
| catggcgcca agatgaatgc actggacacc cttggtcaga ctgctttgca tagagccgcc | 1800 |
| ctagcaggcc acctgcagac ctgccgcctc ctgctgagtt acggctctga cccctccatc | 1860 |
| atctccttac aaggcttcac agcagcacag atgggcaatg aagcagtgca gcagattctg | 1920 |
| agtgagagta cacctatacg tacttctgat gttgattatc gactcttaga ggcatctaaa | 1980 |
| gctggagact tggaaactgt gaagcaactt tgcagctctc aaaatgtgaa ttgtagagac | 2040 |
| ttagagggcc ggcattccac gcccttacac ttcgcagcag gctacaaccg cgtgtctgtt | 2100 |
| gtagagtacc tgctacacca cggtgccgat gtccatgcca aagacaaggg tggcttggtg | 2160 |
| ccccttcata tgcctgttc atatggacac tatgaggtgg ctgagctttt agtaaggcat | 2220 |
| ggggcttctg tcaatgtggc ggacttatgg aaatttaccc ctctccatga agcagcagct | 2280 |
| aaaggaaagt atgaaatctg caagctcctt ttaaaacatg gagcagatcc aactaaaaag | 2340 |
| aacagagatg gaaatacacc tttggatttg gtaaaggaag gagacacaga tattcaggac | 2400 |
| ttactgaaag gggatgctgc tttgttggat gctgccaaga gggctgcct ggcaagagtg | 2460 |
| cagaagctct gtacccagaa gaatatcaac tgcagagaca cccagggcag aaattcaacc | 2520 |
| cctctgcacc tggcagcagg ctataataac ctggaagtag ctgaatatct tctagagcat | 2580 |
| ggagctgatg ttaatgccca ggacaaggt ggtttaattc ctcttcataa tgcggcatct | 2640 |
| tatgggcatg ttgacatagc ggctttattg ataaaataca acacgtgtgt aaatgcaaca | 2700 |
| gataagtggg cgtttactcc cctccatgaa gcagcccaga aaggaaggac gcagctgtgc | 2760 |
| gccctcctcc tagcgcatgg tgcagacccc accatgaaga accaggaagg ccagacgcct | 2820 |

-continued

```
ctggatctgg caacagctga cgatatcaga gctttgctga tagatgccat gcccccagag    2880
gccttaccta cctgtttaa acctcaggct actgtagtga gtgcctctct gatctcacca    2940
gcatccaccc cctcctgcct ctcggctgcc agcagcatag acaacctcac tggcccttta    3000
gcagagttgg ccgtaggagg agcctccaat gcagggatg cgccgcggg aacagaaagg     3060
aaggaaggag aagttgctgg tcttgacatg aatatcagcc aatttctaaa aagccttggc    3120
cttgaacacc ttcgggatat cttgaaaca gaacagatta cactagatgt gttggctgat    3180
atgggtcatg aagagttgaa agaaataggc atcaatgcat atgggcaccg ccacaaatta    3240
atcaaaggag tagaaagact cttaggtgga caacaaggca ccaatcctta tttgactttt    3300
cactgtgtta atcagggaac gattttgctg gatcttgctc cagaagataa agaatatcag    3360
tcagtggaag aagagatgca aagtactatt cgagaacaca gagatggtgg taatgctggc    3420
ggcatcttca acagatacaa tgtcattcga attcaaaag ttgtcaacaa gaagttgagg     3480
gagcggttct gccaccgaca gaaggaagtg tctgaggaga atcacaacca tcacaatgag    3540
cgcatgttgt ttcatggttc tcctttcatt aatgccatta ttcataaagg gtttgatgag    3600
cgacatgcat acataggagg aatgtttggg gccgggattt attttgctga aaactcctca    3660
aaaagcaacc aatatgttta tggaattgga ggaggaacag gctgccctac acacaaggac    3720
aggtcatgct atatatgtca cagacaaatg ctcttctgta gagtgaccct tgggaaatcc    3780
tttctgcagt ttagcaccat gaaaatggcc cacgcgcctc cagggcacca ctcagtcatt    3840
ggtagaccga gcgtcaatgg gctggcatat gctgaatatg tcatctacag aggagaacag    3900
gcatacccag agtatcttat cacttaccag atcatgaagc cagaagcccc ttcccagacc    3960
gcaacagccg cagagcagaa gacctag                                        3987
```

<210> SEQ ID NO 9
<211> LENGTH: 729
<212> TYPE: DNA
<213> ORGANISM: Homo sapiens

<400> SEQUENCE: 9

```
atgttaggtg gacaacaagg caccaatcct tatttgactt ttcactgtgt taatcaggga     60
acgatttgc tggatcttgc tccagaagat aaagaatatc agtcagtgga agaagagatg    120
caaagtacta ttcgagaaca cagagatggt ggtaatgctg gcggcatctt caacagatac    180
aatgtcattc gaattcaaaa agttgtcaac aagaagttga gggagcggtt ctgccaccga    240
cagaaggaag tgtctgagga gaatcacaac catcacaatg agcgcatgtt gttcatggt    300
tctcctttca ttaatgccat tattcataaa gggtttgatg agcgacatgc atacatagga    360
ggaatgtttg gggccgggat ttattttgct gaaaactcct caaaaagcaa ccaatatgtt    420
tatggaattg gaggaggaac aggctgccct acacacaagg acaggtcatg ctatatatgt    480
cacagacaaa tgctcttctg tagagtgacc cttgggaaat cctttctgca gtttagcacc    540
atgaaaatgg cccacgcgcc tccagggcac cactcagtca ttggtagacc gagcgtcaat    600
gggctggcat atgctgaata tgtcatctac agaggagaac aggcataccc agagtatctt    660
atcacttacc agatcatgaa gccagaagcc ccttcccaga ccgcaacagc cgcagagcag    720
aagacctag                                                            729
```

<210> SEQ ID NO 10
<211> LENGTH: 3504
<212> TYPE: DNA
<213> ORGANISM: Homo sapiens

<400> SEQUENCE: 10

```
atcatgtcgg gtcgccgctg cgccggcggg ggagcggcct gcgcgagcgc cgcggccgag      60
gccgtggagc cggccgcccg agagctgttc gaggcgtgcc gcaacgggga cgtggaacga     120
gtcaagaggc tggtgacgcc tgagaaggtg aacagccgcg cacggcgggg caggaaatcc     180
accccgctgc acttcgccgc aggttttggg cggaaagacg tagttgaata tttgcttcag     240
aatggtgcaa atgtccaagc acgtgatgat gggggcctta ttcctcttca taatgcatgc     300
tcttttggtc atgctgaagt agtcaatctc cttttgcgac atggtgcaga ccccaatgct     360
cgagataatt ggaattatac tcctctccat gaagctgcaa ttaaaggaaa gattgatgtt     420
tgcattgtgc tgttacagca tggagctgag ccaaccatcc gaaatacaga tggaaggaca     480
gcattggatt tagcagatcc atctgccaaa gcagtgctta ctggtgaata taagaaagat     540
gaactcttag aaagtgccag gagtggcaat gaagaaaaaa tgatggctct actcacacca     600
ttaaatgtca actgccacgc aagtgatggc agaaagtcaa ctccattaca tttggcagca     660
ggatataaca gagtaaagat tgtacagctg ttactgcaac atggagctga tgtccatgct     720
aaagataaag gtgatctggt accattacac aatgcctgtt cttatggtca ttatgaagta     780
actgaacttt tggtcaagca tggtgcctgt gtaaatgcaa tggacttgtg gcaattcact     840
cctcttcatg aggcagcttc taagaacagg gttgaagtat gttctcttct cttaagttat     900
ggtgcagacc caacactgct caattgtcac aataaaagtg ctatagactt ggctcccaca     960
ccacagttaa agaaagatt agcatatgaa tttaaaggcc actcgttgct gcaagctgca    1020
cgagaagctg atgttactcg aatcaaaaaa catctctctc tggaaatggt gaatttcaag    1080
catcctcaaa cacatgaaac agcattgcat tgtgctgctg catctccata tcccaaaaga    1140
aagcaaatat gtgaactgtt gctaagaaaa ggagcaaaca tcaatgaaaa gactaaagaa    1200
ttcttgactc ctctgcacgt ggcatctgag aaagctcata atgatgttgt tgaagtagtg    1260
gtgaaacatg aagcaaaggt taatgctctg ataatcttg gtcagacttc tctacacaga    1320
gctgcatatt gtggtcatct acaaacctgc cgcctactcc tgagctatgg gtgtgatcct    1380
aacattatat cccttcaggg ctttactgct ttacagatgg gaaatgaaaa tgtacagcaa    1440
ctcctccaag agggtatctc attaggtaat tcagaggcag acagacaatt gctggaagct    1500
gcaaaggctg gagatgtcga aactgtaaaa aaactgtgta ctgttcagag tgtcaactgc    1560
agagacattg aagggcgtca gtctacacca cttcattttg cagctgggta taacagagtg    1620
tccgtggtga aatatctgct acagcatgga gctgatgtgc atgctaaaga taaggaggc    1680
cttgtacctt tgcacaatgc atgttcttat ggacattatg aagttgcaga acttcttgtt    1740
aaacatggag cagtagttaa tgtagctgat ttatggaaat ttacaccttt acatgaagca    1800
gcagcaaaag gaaaatatga aatttgcaaa cttctgctcc agcatggtgc agaccctaca    1860
aaaaaaaaca gggatggaaa tactcctttg gatcttgtta aagatggaga tacagatatt    1920
caagatctgc ttaggggaga tgcagctttg ctagatgctg ccaagaaggg ttgtttagcc    1980
agagtgaaga agttgtcttc tcctgataat gtaaattgcc gcgataccca aggcagacat    2040
tcaacacctt tacatttagc agctggttat aataatttag aagttgcaga gtatttgtta    2100
caacacggag ctgatgtgaa tgcccaagac aaaggaggac ttattccttt acataatgca    2160
gcatcttacg ggcatgtaga tgtagcagct ctactaataa agtataatgc atgtgtcaat    2220
gccacgggaca aatgggcttt cacacctttg cacgaagcag cccaaaaggg acgaacacag    2280
cttttgtgctt tgttgctagc ccatggagct gacccgactc ttaaaaatca ggaaggacaa    2340
```

-continued

| | | |
|---|---|---|
| acacctttag atttagtttc agcagatgat gtcagcgctc ttctgacagc agccatgccc | 2400 | |
| ccatctgctc tgcccctcttg ttacaagcct caagtgctca atggtgtgag aagcccagga | 2460 | |
| gccactgcag atgctctctc ttcaggtcca tctagcccat caagccttc tgcagccagc | 2520 | |
| agtcttgaca acttatctgg gagttttca gaactgtctt cagtagttag ttcaagtgga | 2580 | |
| acagagggtg cttccagttt ggagaaaaag gaggttccag gagtagattt tagcataact | 2640 | |
| caattcgtaa ggaatcttgg acttgagcac ctaatggata tatttgagag agaacagatc | 2700 | |
| actttggatg tattagttga gatggggcac aaggagctga aggagattgg aatcaatgct | 2760 | |
| tatggacata ggcacaaact aattaaagga gtcgagagac ttatctccgg acaacaaggt | 2820 | |
| cttaacccat atttaacttt gaacacctct ggtagtggaa caattcttat agatctgtct | 2880 | |
| cctgatgata aagagtttca gtctgtggag gaagagatgc aaagtacagt tcgagagcac | 2940 | |
| agagatggag gtcatgcagg tggaatcttc aacagataca atattctcaa gattcagaag | 3000 | |
| gtttgtaaca agaaactatg ggaaagatac actcaccgga gaaagagt ttctgaagaa | 3060 | |
| aaccacaacc atgccaatga acgaatgcta tttcatgggt ctccttttgt gaatgcaatt | 3120 | |
| atccacaaag gctttgatga aaggcatgcg tacataggtg gtatgtttgg agctggcatt | 3180 | |
| tattttgctg aaaactcttc caaaagcaat caatatgtat atggaattgg aggaggtact | 3240 | |
| gggtgtccag ttcacaaaga cagatcttgt tacatttgcc acaggcagct gctctttgc | 3300 | |
| cgggtaacct tgggaaagtc tttcctgcag ttcagtgcaa tgaaaatggc acattctcct | 3360 | |
| ccaggtcatc actcagtcac tggtaggccc agtgtaaatg cctagcatt agctgaatat | 3420 | |
| gttatttaca gaggagaaca ggcttatcct gagtatttaa ttacttacca gattatgagg | 3480 | |
| cctgaaggta tggtcgatgg ataa | 3504 | |

<210> SEQ ID NO 11
<211> LENGTH: 1563
<212> TYPE: DNA
<213> ORGANISM: Homo sapiens

<400> SEQUENCE: 11

| | | |
|---|---|---|
| ccaatggaca tcaaaggcca gttctggaat gatgacgact cggagggaga taatgaatca | 60 | |
| gaggaatttc tctatggcgt tcaggggaac tgtgcagccg acctgtatcg acacccacag | 120 | |
| cttgatgcag acattgaagc cgtgaaggag atctacagtg agaactctgt atccatcaga | 180 | |
| gaatatggaa ctatcgatga cgtggacatt gacctccaca tcaacatcag cttcctcgat | 240 | |
| gaggaagtct ctacagcctg gaaggtcctc cggacagaac ctattgtgtt gaggctgcga | 300 | |
| tttctctct cccagtacct agatggacca gaaccatcca ttgaggtttt ccagccatca | 360 | |
| aataaggaag gatttgggct gggtcttcag ttgaaaaaga tcctgggtat gtttacatcc | 420 | |
| caacaatgga acatctgag caatgatttc ttgaagaccc agcaggagaa gaggcacagt | 480 | |
| tggttcaagg caagtggtac catcaagaag ttccgagctg gcctcagcat cttttcaccc | 540 | |
| atccccaagt ctcccagttt ccctatcata caggactcca tgctgaaagg caaactaggt | 600 | |
| gtaccagagc ttcgggttgg gcgcctcatg aaccgttcca tctcctgtac catgaagaac | 660 | |
| cccaaagtgg aagtgtttgg ctaccctccc agccccagg caggtctcct gtgccctcag | 720 | |
| cacgtgggcc tccctccccc agcacggacc tctcctttgg tcagtggtca ctgcaagaac | 780 | |
| attcccactc tggagtatgg attcctcgtt cagatcatga agtatgcaga acagaggatt | 840 | |
| ccaacattga atgagtactg tgtggtgtgt gatgagcagc atgtcttcca aaatggatct | 900 | |
| atgctgaagc cagctgtctg tactcgtgaa ctatgcgttt tctcccttcta cacactgggc | 960 | |

| | | | | |
|---|---|---|---|---|
| gtcatgtctg | gagctgcaga | ggaggtggcc | actggagcag | aggtggtgga | tctgctggtg | 1020 |
| gccatgtgta | gggcagcttt | agagtcccct | agaaagagca | tcatctttga | gccttatccc | 1080 |
| tctgtggtgg | accccactga | tcccaagact | ctggccttta | accctaagaa | gaagaattat | 1140 |
| gagcggcttc | agaaagctct | ggatagtgtg | atgtctattc | gggagatgac | ccagggctca | 1200 |
| tatttggaaa | tcaagaaaca | gatggacaag | ttggatcccc | tggcccatcc | tctcctgcag | 1260 |
| tggatcatct | ctagcaacag | gtcacacatt | gtcaaactac | ctctcagcag | gcagctgaag | 1320 |
| ttcatgcaca | cctcacacca | gttcctcctg | ctgagcagcc | ctcctgccaa | ggaggctcgg | 1380 |
| ttccggaccg | ccaagaagct | ctatggcagc | acctttgcct | tccatgggtc | ccacattgag | 1440 |
| aactggcatt | cgatcctgcg | caatgggctg | gtcaatgcat | cctacaccaa | actgcaggaa | 1500 |
| tgggaaaagg | acagcacagg | atgccctcca | aggatgagct | ggtccagaga | tacaacagga | 1560 |
| tga | | | | | | 1563 |

<210> SEQ ID NO 12
<211> LENGTH: 1977
<212> TYPE: DNA
<213> ORGANISM: Homo sapiens

<400> SEQUENCE: 12

| | | | | | | |
|---|---|---|---|---|---|---|
| attatggaaa | tggaaaccac | cgaacctgag | ccagactgtg | tagtgcagcc | tccctctcct | 60 |
| cctgatgact | tttcatgcca | aatgagactc | tctgagaaga | tcactccatt | gaagacttgt | 120 |
| tttaagaaaa | aggatcagaa | aagattggga | actggaaccc | tgaggtcttt | gaggccaata | 180 |
| ttaaacactc | ttctagaatc | tggctcactt | gatggggttt | ttagatctag | gaaccagagt | 240 |
| acagatgaga | acagcttaca | tgaacctatg | atgaagaaag | ccatggaaat | caattcatca | 300 |
| tgcccaccag | cagaaaataa | tatgtctgtt | ctgattcctg | ataggacaaa | tgttggggac | 360 |
| cagataccgg | aagcccatcc | ttccactgaa | gctccagaac | gagtggttcc | aatccaagat | 420 |
| cacagctttc | catcagaaac | cctcagtggg | acggtggcag | attccacacc | agctcacttc | 480 |
| cagactgatc | ttttgcaccc | agtttcaagt | gatgttccta | ctagtcctga | ctgcttagac | 540 |
| aaagtcatag | attatgttcc | aggcattttc | caagaaaaca | gttttacaat | ccaatacatt | 600 |
| ctggacacca | gtgataagct | gagtactgag | ctctttcagg | acaaaagtga | agaggcttcc | 660 |
| cttgacctcg | tgtttgagct | ggtgaaccag | ttgcagtacc | acactcacca | agagaacgga | 720 |
| attgaaattt | gcatggactt | tctgcaaggc | acttgtattt | atggcaggga | ttgtttgaag | 780 |
| caccacactg | tcttgccata | tcattggcag | atcaaaagga | caactactca | aaagtggcag | 840 |
| agtgtattca | atgattctca | ggagcacttg | gaaagatttt | actgtaaccc | agaaaatgat | 900 |
| agaatgagaa | tgaagtatgg | aggacaagaa | ttttgggcag | atttgaatgc | catgaacgtg | 960 |
| tatgaaacaa | ctgaatttga | ccaactacga | aggctgtcca | caccaccctc | tagcaatgtc | 1020 |
| aactctattt | accacacagt | ctggaaattc | ttctgtaggg | accactttgg | atggagagag | 1080 |
| tatcccgagt | ctgtcattcg | attgattgaa | gaagccaact | ctcgggtctc | tgaaagaggtt | 1140 |
| cgatttatga | tgtggaataa | ccactacatc | ctccacaatt | cattcttcag | gagagagata | 1200 |
| aaaaggagac | ccctcttccg | ctcctgtttt | atactgcttc | catatttaca | gacacttggt | 1260 |
| ggggttccca | cacaagctcc | tccacctctt | gaagcaactt | catcatcaca | aattatctgc | 1320 |
| ccagatgggg | tcacttcagc | aaactttttac | cctgaaactt | gggtttatat | gcatccatct | 1380 |
| caggacttca | tccaagtccc | tgtttctgca | gaggataaaa | gttatcggat | catttacaat | 1440 |
| cttttttcata | agactgtgcc | tgagtttaaa | tacagaattt | tgcagatatt | gagagtccaa | 1500 |

-continued

| | | |
|---|---|---|
| aaccagtttc tttgggagaa atataaaagg aaaaaggaat atatgaacag gaaaatgttt | 1560 | |
| ggccgtgaca ggataataaa tgagagacat ttatttcatg gaacatccca ggatgtggta | 1620 | |
| gatggaatct gcaaacacaa cttttgaccct cgagtctgtg gaaagcatgc tacaatgttt | 1680 | |
| ggacaaggca gttattttgc aaagaaggca agctactctc ataacttttc taagaagtcc | 1740 | |
| tccaaaggag tccacttcat gtttctggcc aaagtgctga cgggcagata cacaatgggc | 1800 | |
| agtcatggca tgagaaggcc cccgccagtc aatcctggca gtgtcaccag tgacctttat | 1860 | |
| gactcttgtg tggataattt ctttgagcct cagattttg tcattttaa tgatgaccag | 1920 | |
| agttacccctt attttgttat ccaatatgaa gaagtcagta acactgtttc catttga | 1977 | |

<210> SEQ ID NO 13
<211> LENGTH: 2568
<212> TYPE: DNA
<213> ORGANISM: Homo sapiens

<400> SEQUENCE: 13

| | | |
|---|---|---|
| ttaatgggga tgtgttcaag gcaagagcga attcagaagg atatcgacgt cgtgatccag | 60 | |
| aagtccagag ctgagaagga ctgcctgttt gcagatttca gatactctga ctccaccttt | 120 | |
| acttttacct acgttggcgg ccccagaagt gtatcctact cagtacatgt atctgaagat | 180 | |
| tacccagata atacatatgt gtcaagttca gagaatgatg aagatgtgct agttactaca | 240 | |
| gagccaatac cagtaatttt tcatagaata gcaacagaat taagaaaaac aaatgacatt | 300 | |
| aactgttgct tatccataaa atccaaatta caaaaggaaa atggggagga atcaagacag | 360 | |
| aatagtacag tggaggaaga ttctgaaggt gacaatgatt ccgaagaatt ttattacgga | 420 | |
| ggacaggtga actatgatgg ggaactgcac aagcacccac aactggaagc tgatttgtca | 480 | |
| gcagttagag agatatatgg gccacatgca gtttctctca gggaatatgg agccattgat | 540 | |
| gatgtagata ttgatctgca tatcgatgtt agctttcttg atgaggagat tgctgtggct | 600 | |
| tgggaagtaa ttcgaacaga acctataatt gttcgactac actgttcact tacacagtat | 660 | |
| ttaaatggcc cagtgcccac tgttgatgtc tttcagattt ccacaaaaga gcgatttgga | 720 | |
| ttgggacatc agctgaaaaa aatcatgcag acatttgtta cacagcagtg gaaacagagc | 780 | |
| aaagaaaaat ccaattgcct gcacaataaa aagttgtcag agaagaaagt gaagtctccc | 840 | |
| ctgcatttat tttctacttt gcgcaggtcg ccaagttatc ctcccccctgg ttgtggcaaa | 900 | |
| agcaaatcca aactgaaatc tgagcaggac ggaatctcca aaacgcataa gctgctgcgg | 960 | |
| aggacttgtt ccagcacagt caagactgat gatgtgtgtg tcacaaagtc acacaggacc | 1020 | |
| tttggccgct ccttgtccag cgatcccagg gcggagcagg ctatgacagc aattaaatcg | 1080 | |
| cacaaacttt tgaaccgtcc ttgccctgca gctgttaagt cagaggaatg cctaactcta | 1140 | |
| aagtcgcata gactattgac tcgatcttgt tctggagatc cacgatgtga gcacaacaca | 1200 | |
| aacttgaagc cccataaact gttaagcagg tcttactcta gtaatctcag aatggaagaa | 1260 | |
| ttatatggac tgaaaaatca caaattgctc agcaagtcct actccagtgc ccccaagtca | 1320 | |
| tccaaaactg agcttttcaa ggaacctaac gcagagggca ggaggctctc tcttacctca | 1380 | |
| gggcttattg gtatcctaac accatcttca tcttcatctt ctcagcttgc tccaaatggt | 1440 | |
| gcaaaatgca ttccagtacg agaccgtggc ttcctggtgc agacaattga gtttgctgaa | 1500 | |
| cagcggatcc ctgtattaaa tgaatattgt gtggtttgtg atgagccaca tgtgtttcaa | 1560 | |
| aatggcccta tgcttaggcc taccgtatgt gaacgggagc tgtgtgtgtt tgcttttcaa | 1620 | |
| accctgggag taatgaatga agctgctgat gaaatagcaa ctggagctca ggtggtagat | 1680 | |

| | |
|---|---|
| ctactagtat ccatgtgtag gtctgcgttg aatctccta gaaaagttgt gattttcgag | 1740 |
| ccatatcctt ctgtggtaga tcctaatgat cctcagatgt tggccttcaa ccccaggaaa | 1800 |
| aagaactatg atcgagtaat gaaagcactg gatagcataa cttctatcag agaaatgaca | 1860 |
| caagcaccat atctggaaat caagaagcaa atggataaac aggacccct tgctcatccc | 1920 |
| ttactgcaat gggttatatc aagtaataga tcacatattg tgaaactgcc agttaacagg | 1980 |
| caattgaagt ttatgcatac tccacatcag ttccttcttc tcagcagtcc accagccaaa | 2040 |
| gaatccaatt ttagagctgc taaaaaactc tttggaagca cctttgcatt tcatggctca | 2100 |
| cacattgaaa actggcactc catcctgagg aatggtctgg ttgttgcttc taatacacga | 2160 |
| ttgcagctcc atggtgcaat gtatggaagt ggaatctatc ttagtccaat gtcaagcata | 2220 |
| tcatttggtt actcagggat gaacaagaaa cagaaggtgt cagccaagga cgagccagct | 2280 |
| tcaagcagta aaagcagcaa tacatcacag tcacagaaaa aaggacagca atcccaattc | 2340 |
| ctgcaaagcc gtaacttaaa atgcatagcc ttatgtgaag tgatcacctc atctgacctg | 2400 |
| cacaaacatg gagagatatg ggttgtcccc aatactgacc atgtctgcac acgattcttt | 2460 |
| ttcgtctatg aagacggcca agtgggagat gcaaatatta atacacaaga aggaggcatt | 2520 |
| cacaaagaga tcctccgagt aattggtaat caaactgcta ctggttaa | 2568 |

<210> SEQ ID NO 14
<211> LENGTH: 2568
<212> TYPE: DNA
<213> ORGANISM: Homo sapiens

<400> SEQUENCE: 14

| | |
|---|---|
| aggatggact tttccatggt ggccggagca gcagcttaca atgaaaaatc aggtaggatt | 60 |
| acctcgctct cactcttgtt tcagaaagtc tttgctcaga tctttcctca gtggagaaag | 120 |
| gggaatacag aagaatgtct cccctacaag tgctcagaga ctggtgctct tggagaaaac | 180 |
| tatagttggc aaattcccat taaccacaat gacttcaaaa ttttaaaaaa taatgagcgt | 240 |
| cagctgtgtg aagtcctcca gaataagttt ggctgtatct ctaccctggt ctctccagtt | 300 |
| caggaaggca acagcaaatc tctgcaagtg ttcagaaaaa tgctgactcc taggatagag | 360 |
| ttatcagtct ggaaagatga cctcaccaca catgctgttg atgctgtggt gaatgcagcc | 420 |
| aatgaagatc ttctgcatgg gggaggcctg gccctggccc tggtaaaagc tggtggattt | 480 |
| gaaatccaag aagagagcaa acagtttgtt gccagatatg gtaaagtgtc agctggtgag | 540 |
| atagctgtca cgggagcagg gaggcttccc tgcaaacaga tcatccatgc tgttgggcct | 600 |
| cggtggatgg aatgggataa acagggatgt actggaaagc tgcagagggc cattgtaagt | 660 |
| attctgaatt atgtcatcta taaaatact cacattaaga cagtagcaat tccagccttg | 720 |
| agctctggga ttttcagtt ccctctgaat ttgtgtacaa agactattgt agagactatc | 780 |
| cgggttagtt tgcaagggaa gccaatgatg agtaatttga agaaattca cctggtgagc | 840 |
| aatgaggacc ctactgttgc tgcctttaaa gctgcttcag aattcatcct agggaagagt | 900 |
| gagctgggac aagaaaccac cccttctttc aatgcaatgg tcgtgaacaa cctgacctc | 960 |
| cagattgtcc agggccacat tgaatggcag acggcagatg taattgttaa ttctgtaaac | 1020 |
| ccacatgata ttcagttgg acctgtggca aagtcaattc tacaacaagc aggagttgaa | 1080 |
| atgaaatcgg aatttcttgc cacaaaggct aaacagtttc aacggtccca gttggtactg | 1140 |
| gtcacaaaag gatttaactt gttctgtaaa tatatatacc atgtactgtg gcattcagaa | 1200 |
| tttcctaaac ctcagatatt aaaacatgca atgaaggagt gtttggaaaa atgcattgag | 1260 |

```
caaaatataa cttccatttc ctttcctgcc cttgggactg gaaacatgga aataaagaag    1320
gaaacagcag cagagatttt gtttgatgaa gttttaacat ttgccaaaga ccatgtaaaa    1380
caccagttaa ctgtaaaatt tgtgatcttt ccaacagatt tggagatata aaggctttc     1440 agttctgaaa tggcaaagag gtccaagatg ctgagtttga acaattacag tgtccccag     1500 tcaaccagag aggagaaaag agaaaatggg cttgaagcta gatctcctgc catcaatctg    1560
atgggattca acgtgaaga gatgtgtgag gcccacgcat ggatccaaag aatcctgagt     1620
ctccagaacc accacatcat tgagaataat catattctgt accttgggag aaaggaacat    1680
gacattttgt ctcagcttca gaaaacttca agtgtctcca tcacagaaat tatcagccca    1740
ggaaggacag agttagagat tgaaggagcc cgggctgacc tcattgaggt ggttatgaac    1800
attgaagata tgctttgtaa agtacaggag gaaatggcaa ggaaaaagga gcgaggcctt    1860
tggcgctcgt taggacagtg gactattcag caacaaaaaa cccaagacga aatgaaagaa    1920
aatatcatat ttctgaaatg tcctgtgcct ccaactcaag agcttctaga tcaaaagaaa    1980
cagtttgaaa aatgtggttt gcaggttcta aaggtggaga agatagacaa tgaggtcctt    2040
atggctgcct ttcaaagaaa gaagaaaatg atggaagaaa aactgcacag gcaacctgtg    2100
agccataggc tgtttcagca agtcccatac cagttctgca atgtggtatg cagagttggc    2160
tttcaaagaa tgtactcgac accttgcgat ccaaaatacg gagctggcat atacttcacc    2220
aagaacctca aaaacctggc agagaaggcc aagaaaatct ctgctgcaga taagctgatc    2280
tatgtgtttg aggctgaagt actcacaggc ttcttctgcc agggacatcc gttaaatatt    2340
gttcccccac cactgagtcc tggagctata gatggtcatg acagtgtggt tgacaatgtc    2400
tccagccctg aaacctttgt tattttttagt ggcatgcagg ctatacctca gtatttgtgg    2460
acatgcaccc aggaatatgt acagtcacaa gattactcat caggaccaat gagacccttt    2520
gcacagcatc cttggagggg attcgcaagt ggcagccctg ttgattaa                 2568

<210> SEQ ID NO 15
<211> LENGTH: 3081
<212> TYPE: DNA
<213> ORGANISM: Homo sapiens

<400> SEQUENCE: 15
ggaatggttg caatggcgga ggcagaggca ggggtggcag tggaggtccg tggactgccc      60
cctgccgtgc ccgacgagct gctcactctc tactttgaaa accgccgacg ctctggaggg     120
ggacctgtgt tgagctggca gagactgggc tgtgggggcg tcctcacctt cagagagcct     180
gcagacgccg agagggtctt ggcccaggca gatcatgaac tacatggtgc ccagctgagc     240
ctgcggccag ctccaccacg agcccctgca cgcctgctgc tccaaggact gccccctggc     300
accacgcccc agcgcttgga gcagcatgtc caggccttgc tgcgggcctc ggggctccca     360
gtacagcctt gctgtgcctt ggccagcccc cggccagacc gggctctggt ccagttgccc     420
aagccccttt ctgaggcaga tgtccgtgtc ctggaggagc aggcccagaa tctgggcctg     480
gagggaccct tggtgtccct ggcccgggtt cccaggcccc gagcggtgcg tgtggtgggg     540
gatggtgcct ctgtggacct gctgttgctg gagttgtacc tggagaatga cgccgcagt     600 ggtgggggc ccctggagga cctgcaacgc ctacccgggc ccctgggcac tgttgcctcc     660
ttccagcagt ggcaagtggc agaacgagtg ttgcagcagg agcaccggtt gcagggctca     720
gagctgagcc ttgtccccca ctacgacgtc ctggagcccg aggagctggc tgagaacacc     780
agtggagggg accacccgtc cacccagggg cctagggcta ccaagcatgc tctcctgagg     840
```

```
accggagggt tggtgacggc tctgcagggt gcagggactg tgacaatggg ctctggcgag      900
gaaccagggc agtcagggc ctctctgagg acaggtccca tagtgcaggg tagagggatt      960
atgacaacag gctctggcca ggaaccaggg cagtcaggga cctctctgag acaggtccc     1020 atggggtctc tgggacaggc agagcaagtc agctcgatgc ccatgggtc tctggaacat     1080 gaggggctgg taagcctgag gcctgtgggg ttgcaggaac aggaggggcc catgagcctg     1140
gggcctgtgg ggtctgcagg cccagtggag acctctaagg ggttgccggg gcaggagggc     1200
ctggtggaaa ttgccatgga ctcaccagag caagagggc tggtgggtcc catggagatc      1260
accatggggt ctctggagaa ggcagggcct gtgagcccag gatgtgtgaa gctggcaggg     1320
caggagggcc tggtggagat ggtgctattg atggagccag gggcgatgcg cttcctgcag     1380
ctctaccatg aggaccttct tgcgggcctg ggagacgtcg ctctcttgcc acttgaagga     1440
ccggatatga ctggctttcg gctctgtgga gcccaggctt cctgccaggc ggctgaggag     1500
tttctgcgga gcctgctggg cagcattagc tgccatgtgt tgtgcctgga gcactcgggc     1560
agcgccaggt ttctcctggg cccagaaggg cagcaccttc tccagggggct ggaggctcag    1620 ttccagtgtg tctttgggac agagcgcctg gccacagcca cgttggacac aggccttgaa     1680
gaggtggacc ctaccgaggc cctcccagtg ctccctggca acgccacac cctgtggacc      1740 ccagacagta caggtggtga ccaggaggac gtgagcctgg aggaggtccg agaactgctg     1800
gccaccctgg agggcctaga cctagacggg gaggactggc tgcctcggga gctggaggag     1860
gaagggcctc aggagcagcc agaggaggag gcgaccccag ggcatgagga ggaggagcct     1920
gtggccccca gcactgtggc acccaggtgg ctggaggagg aggccgctct gcagctggcc     1980
ctccaccggt cactggagcc tcaaggtcag gtggctgagc aggaggaggc tgctgccctg     2040
cggcaagccc taaccctctc cctgctggag cagcccccgt tggaggcaga agagccccca    2100
gatgggggga ctgatggcaa ggcccagctg gtggtgcact cggcctttga gcaggatgtg     2160
gaggagctgg accgggcgct caggcctgcc ttggaggtcc acgtccagga ggagacggtg     2220
gggccctggc gccgcacact gcctgcagag ctgcgtgctc gcctggagcg gtgccatggt     2280
gtgagtgttg ccctgcgtgg tgactgcacc atcctccgtg gcttcgggc ccaccctgcc      2340 cgtgctgccc gccacttggt ggcacttctg gctggcccct gggatcagag tttggccttt     2400
cccttggcag cttcaggccc taccttggcg gggcagacgc tgaagggcc ctggaacaac      2460 ctggagcgtc tggcagagaa caccggggag ttccaggagg tggtgcgggc cttctacgac     2520
accctggacg ctgcccgcag cagcatccgc gtcgttcgtg tggagcgcgt gtcgcacccg     2580
ctgctgcagc agcagtatga gctgtaccgg gagcgcctgc tgcagcgatg cgagcggcgc     2640
ccggtggagc aggtgctgta ccacggcacg acggcaccgg cagtgcctga catctgcgcc     2700
cacggcttca accgcagctt ctgcggccgc aacgccacgg tctacgggaa gggcgtgtat     2760
ttcgccaagc gcgcctccct gtcggtgcag accgctact cgccccccaa cgccgatggc      2820
cataaggcgg tgttcgtggc acgggtgctg actggcgact acgggcaggg ccgccgcggt    2880
ctgcgggcgc ccctctgcg gggtcctggc cacgtgctcc tgcgctacga cagcgccgtg     2940
gactgcatct gccagcccag catcttcgtc atcttccacg acacccaggc gctgcccacc    3000
cacctcatca cctgcgagca cgtgcccgc gcttcccccg acgaccctc tgggctcccg      3060 ggccgctccc cagacactta a                                              3081
```

<210> SEQ ID NO 16
<211> LENGTH: 3081
<212> TYPE: DNA

<213> ORGANISM: Homo Sapiens

<400> SEQUENCE: 16

| | | | | | |
|---|---|---|---|---|---|
| ggaatggttg | caatggcgga | ggcagaggca | ggggtggcag | tggaggtccg | tggactgccc | 60 |
| cctgccgtgc | ccgacgagct | gctcactctc | tactttgaaa | accgccgacg | ctctggaggg | 120 |
| ggacctgtgt | tgagctggca | gagactgggc | tgtggggggcg | tcctcacctt | cagagagcct | 180 |
| gcagacgccg | agagggtctt | ggcccaggca | gatcatgaac | tacatggtgc | ccagctgagc | 240 |
| ctgcggccag | ctccaccacg | agccctgca | cgcctgctgc | tccaaggact | gccccctggc | 300 |
| accacgcccc | agcgcttgga | gcagcatgtc | caggccttgc | tgcgggcctc | ggggctccca | 360 |
| gtacagcctt | gctgtgcctt | ggccagcccc | cggccagacc | gggctctggt | ccagttgccc | 420 |
| aagccccttt | ctgaggcaga | tgtccgtgtc | ctggaggagc | aggcccagaa | tctgggcctg | 480 |
| gaggggacct | tggtgtccct | ggcccgggtt | ccccaggccc | gagcggtgcg | tgtggtgggg | 540 |
| gatggtgcct | ctgtggacct | gctgttgctg | gagttgtacc | tggagaatga | gcgccgcagt | 600 |
| ggtgggggggc | ccctggagga | cctgcaacgc | ctacccgggc | ccctgggcac | tgttgcctcc | 660 |
| ttccagcagt | ggcaagtggc | agaacgagtg | ttgcagcagg | agcaccggtt | gcagggctca | 720 |
| gagctgagcc | ttgtccccca | ctacgacgtc | ctggagcccg | aggagctggc | tgagaacacc | 780 |
| agtggagggg | accaccgtc | cacccagggg | cctagggcta | ccaagcatgc | tctcctgagg | 840 |
| accggagggt | tggtgacggc | tctgcagggt | gcagggactg | tgacaatggg | ctctggcgag | 900 |
| gaaccagggc | agtcagggc | ctctctgagg | acaggtccca | tagtgcaggg | tagagggatt | 960 |
| atgacaacag | gctctggcca | ggaaccaggg | cagtcaggga | cctctctgag | gacaggtccc | 1020 |
| atggggtctc | tgggacaggc | agagcaagtc | agctcgatgc | ccatgggtc | tctggaacat | 1080 |
| gaggggctgg | taagcctgag | gcctgtgggg | ttgcaggaac | aggaggggcc | catgagcctg | 1140 |
| gggcctgtgg | ggtctgcagg | cccagtggag | acctctaagg | ggttgccggg | gcaggagggc | 1200 |
| ctggtggaaa | ttgccatgga | ctcaccagag | caagaggggc | tggtgggtcc | catggagatc | 1260 |
| accatggggt | ctctggagaa | ggcagggcct | gtgagcccag | gatgtgtgaa | gctggcaggg | 1320 |
| caggagggcc | tggtggagat | ggtgctattg | atggagccag | gggcgatgcg | cttcctgcag | 1380 |
| ctctaccatg | aggaccttct | tgcgggcctg | ggagacgtcg | ctctcttgcc | acttgaagga | 1440 |
| ccggatatga | ctgctttcg | gctctgtgga | gcccaggctt | cctgccaggc | ggctgaggag | 1500 |
| tttctgcgga | gcctgctggg | cagcattagc | tgccatgtgt | tgtgcctgga | gcactcgggc | 1560 |
| agcgccaggt | ttctcctggg | cccagaaggg | cagcaccttc | tccaggggct | ggaggctcag | 1620 |
| ttccagtgtg | tctttgggac | agagcgcctg | gccacagcca | cgttggacac | aggccttgaa | 1680 |
| gaggtggacc | ctaccgaggc | cctcccagtg | ctccctggca | acgcccacac | cctgtggacc | 1740 |
| ccagacagta | caggtggtga | ccaggaggac | gtgagcctgg | aggaggtccg | agaactgctg | 1800 |
| gccacccctgg | agggcctaga | cctagacggg | gaggactggc | tgcctcggga | gctgaggag | 1860 |
| gaagggcctc | aggagcagcc | agaggaggag | gcgaccccag | gcatgaggag | ggaggagcct | 1920 |
| gtggccccca | gcactgtggc | acccaggtgg | ctggaggagg | aggccgctct | gcagctggcc | 1980 |
| ctccaccggt | cactggagcc | tcaaggtcag | gtggctgagc | aggaggaggc | tgctgccctg | 2040 |
| cggcaagccc | taaccctctc | cctgctggag | cagccccgt | tggaggcaga | agagccccca | 2100 |
| gatgggggga | ctgatggcaa | ggcccagctg | gtggtgcact | cggcctttga | gcaggatgtg | 2160 |
| gaggagctggg | accgggcgct | cagggctgcc | ttggaggtcc | acgtccagga | ggagacggtg | 2220 |
| gggccctggc | gccgcacact | gcctgcagag | ctgcgtgctc | gcctggagcg | gtgccatggt | 2280 |

-continued

```
gtgagtgttg ccctgcgtgg tgactgcacc atcctccgtg gcttcggggc ccaccctgcc    2340
cgtgctgccc gccacttggt ggcacttctg gctggcccct gggatcagag tttggccttt    2400
cccttggcag cttcaggccc taccttggcg gggcagacgc tgaaggggcc ctggaacaac    2460
ctggagcgtc tggcagagaa caccggggag ttccaggagg tggtgcgggc cttctacgac    2520
accctggacg ctgcccgcag cagcatccgc gtcgttcgtg tggagcgcgt gtcgcacccg    2580
ctgctgcaga gcagtatga gctgtaccgg gagcgcctgc tgcagcgatg cgagcggcgc    2640
ccggtggagc aggtgctgta ccacggcacg acggcaccgg cagtgcctga catctgcgcc    2700
cacggcttca accgcagctt ctgcggccgc aacgccacgg tctacgggaa gggcgtgtat    2760
ttcgccaagc gcgcctccct gtcggtgcag gaccgctact cgcccccaa cgccgatggc    2820 cataaggcgg tgttcgtggc acgggtgctg actggcgact acgggcaggg ccgccgcggt    2880
ctgcgggcgc ccctctgcg gggtcctggc cacgtgctcc tgcgctacga cagcgccgtg    2940
gactgcatct gccagcccag catcttcgtc atcttccacg acaccaggc gctgcccacc    3000 cacctcatca cctgcgagca cgtgccccgc gcttccccg acgaccctc tgggctcccg    3060 ggccgctccc cagacactta a                                             3081
```

<210> SEQ ID NO 17
<211> LENGTH: 999
<212> TYPE: DNA
<213> ORGANISM: Homo sapiens

<400> SEQUENCE: 17

```
gagatgtttc acaaagcaga agaattattt tctaaaacaa caaacaatga agtggatgac      60
atggacacgt cagatacccca gtggggctgg ttttacttgg cagaatgtgg gaagtggcac    120
atgtttcagc cggataccaa cagtcagtgt tcagttagca gtgaagatat cgaaaaaagc    180
ttcaaaacaa accttgtgg ctccatttct tttactactt ccaaattcag ctacaagata     240
gactttgcag aaatgaagca aatgaatctc accactggaa agcagcgctt aataaaaaga    300
gccccctttt ctatcagtgc tttcagttac atctgtgaaa acgaggccat ccctatgcca    360
ccacactggg agaatgtgaa tactcaagta ccatatcagc ttattcctct gcacaatcaa    420
acacatgaat ataatgaagt tgctaatctc tttgggaaga cgatggatcg caaccgaatt    480
aaaagaattc agagaattca aaacctagat tgtgggagt tcttttgcag gaaaaaggct    540
cagctcaaga aaaagagg tgtgcctcag attaatgaac aaatgctgtt tcatggtacc    600
agcagtgaat ttgtggaagc aatctgcatt cataactttg attggagaat aaatggtata    660
catggtgctg tctttgggaaa aggaaacctat tttgctagag atgctgctta ttccagtcgt    720
ttctgcaaag atgacataaa gcatgggaac acattccaaa ttcatggtgt cagcttgcaa    780
cagcggcatc tgtttagaac atataatct atgtttcttg ctcgagtgct aattggagat    840
tacataaacg gagactccaa atacatgcga cctccttcca aagacgggag ctatgtgaat    900
ttatatgaca gctgtgtgga tgatacctgg aacccaaaga tctttgtggt ttttgatgcc    960
aaccaaatct atcctgagta cttgatagac tttcattga                           999
```

<210> SEQ ID NO 18
<211> LENGTH: 2109
<212> TYPE: DNA
<213> ORGANISM: Homo sapiens

<400> SEQUENCE: 18

```
gccatggccc aggccggcgt cgtcggtgag gtcacccagg tgctgtgcgc ggccgggggc      60
```

-continued

```
gccctggagt tgcccgagct gcggcgccgc ttgcggatgg gcttgagcgc cgacgcgctg      120
gagcggctgc tgcggcagcg tgggcgcttc gtggtggcgg tgcgggcggg cggcgcagcc      180
gcggccccgg agcgcgtggt gctggccgcc tcgccgctgc gcctgtgtcg cgcgcaccag      240
ggctccaagc cgggctgcgt ggggctctgc gcgcagctcc acctctgcag gttcatggtc      300
tacggcgcct gcaagttcct gagagccggg aagaactgta ggaatagtca cagcttgaca      360
accgaacaca acctgagtgt gctgagaact catggcgttg accacctgag ctataatgag      420
ctatgccaac tcttgtttca gaacgacccc tggcttttgc cagaaatttg ccaacattac      480
aacaaaggag atggacccca cggctcttgt gcctttcaaa agcagtgcat caagctccat      540
atctgccagt attttttaca ggggaatgc aagtttggca ctagctgtaa gagatcccat      600
gatttctcta attctgagaa tctggaaaaa ttggagaagt tgggtatgag ctcagacctg      660
gtgagcaggc tgcctaccat ttatagaaat gcacatgaca tcaagaataa gagctctgcc      720
cccagcagag tgcctcctct ttttgtccca caggggactt ctgaaagaaa agacagttca      780
ggttctgtgt ccccaaacac tcttagccag gaggagggtg atcagatctg tttgtaccat      840
atccggaaaa gttgtagctt tcaagataag tgccatagag ttcatttcca tttgccgtat      900
cgatggcaat tcttggatag aggcaaatgg gaggatttgg acaacatgga acttattgaa      960
gaggcatatt gcaatcccaa aatagaaagg atcctgtgct ctgagtcagc cagtaccttt     1020
cactctcatt gtctgaactt taacgccatg acttacggtg ctacccaggc tcgccgcctc     1080 tccacgcct cctctgtcac caaacctcca cacttcatcc tcaccactga ctggatttgg     1140
tactggagtg atgagtttgg ttcttggcag gaatatggaa gacagggcac ggtgcaccct     1200
gtgaccactg tcagcagtag cgacgtggag aaggcctacc tggcctactg tacaccgggg     1260
tctgacggcc aggcagccac cttgaagttc caggccggaa agcacaacta cgagttagat     1320
ttcaaagcct tcgttcagaa aaacctggtc tatggcacaa ctaaaaaggt ttgccgcaga     1380
cccaaatacg tgtctcccca ggatgtgacg accatgcaaa cctgcaatac caagtttcca     1440
ggcccgaaga gcatcccaga ctattgggac tcctctgccc tgccagaccc aggctttcag     1500
aagatcaccc ttagttcttc ctcggaagag tatcagaagg tctggaacct ctttaaccgc     1560
acgctgcctt tctactttgt tcagaagatt gagcgagtac agaacctggc cctctgggaa     1620
gtctaccagt ggcaaaaagg acagatgcag aagcagaatg gagggaaggc cgtggacgag     1680
cggcagctgt tccacggcac cagcgccatt tttgtggacg ccatctgcca gcagaacttt     1740
gactggcggg tctgtggtgt tcatggcact tcctacggca aggggagcta ctttgcccga     1800
gatgctgcat attcccacca ctacagcaaa tccgacacgc agacccacac gatgttcctg     1860
gcccgggtgc tggtgggcga gttcgtcagg ggcaatgcgt cctttgtccg tccgccggcc     1920
aaggagggct ggagcaacgc cttctatgat agctgcgtga acagtgtgtc cgaccccctcc     1980 atctttgtga tctttgagaa acaccaggtc tacccagagt atgtcatcca gtacaccacc     2040
tcctccaagc cctcggtcac accctccatc ctgctggcct tgggctccct gttcagcagc     2100
cgacagtga                                                             2109
```

<210> SEQ ID NO 19
<211> LENGTH: 2712
<212> TYPE: DNA
<213> ORGANISM: Homo sapiens

<400> SEQUENCE: 19

```
gccatggcgg acccggaggt gtgctgcttc atcaccaaaa tcctgtgcgc ccacgggggc       60
```

-continued

```
cgcatggccc tggacgcgct gctccaggag atcgcgctgt ctgagccgca gctctgtgag    120
gtgctgcagg tggccgggcc cgaccgcttt gtggtgttgg agaccggcgg cgaggccggg    180
atcacccgat cggtggtggc caccactcga gcccgggtct gccgtcgcaa gtactgccag    240
agaccctgcg ataacctgca tctctgcaaa ctcaacttgc tgggccggtg caactattcg    300
cagtccgagc ggaatttatg caaatattct catgaggttc tctcagaaga gaacttcaaa    360
gtcctgaaaa atcacgaact ctctggactg aacaaagagg aattagcagt gctcctcctc    420
caaagtgatc cttttttat gcccgagata tgcaaaagtt ataagggaga gggtcggcag      480
cagatttgta accagcagcc accgtgttca agactccaca tctgtgacca cttcacccga    540
gggaactgtc gttttcccaa ctgcctccgg tcccataacc tgatggacag aaaggtgctg    600
gccatcatga gggagcacgg gctgaaccc gacgtggtcc agaacatcca ggacatctgc      660
aacagcaagc acatgcagaa gaatccccca gggcccagag ctccttcttc acatcgtaga    720
aacatggcat atagggctag aagcaagagt agagatcggt tctttcaggg cagccaagaa    780
tttcttgcgt ctgcttcagc gtctgctgag aggtcctgca cacctagtcc agatcagatc    840
agccacaggg cttccctgga ggacgcgcct gtggacgatc tcacccgcaa gttcacgtat    900
ctggggagtc aggatcgcgc tcggcctccc tcaggctcgt ccaaggctac tgatcttgga    960
ggaacaagtc aggccgggac aagccagagg ttttagaga acggcagtca agaggacctc     1020
ttgcatggaa atccaggcag cacttacctt gcttccaatt caacatcagc ccccaactgg    1080
aagagcctca catcctggac gaatgaccaa ggcgccagga aaagactgt gttttctccc      1140 acgctacctg ccgcccgctc ttctcttggc tctctgcaaa cacctgaagc tgtgaccacc    1200
agaaagggca caggcttgct ttcctcagac tacaggatca tcaatggcaa aagtggaact    1260
caggacatcc agcctggccc tcttttaat aataatgctg atggagtggc cacagatata     1320
acttctacca gatccttaaa ttacaaaagc actagcagcg gtcacagaga aatatcatca    1380
cctaggattc aggatgctgg acctgcttcc gagatgtcc aggccactgg cagaatcgca      1440
gatgatgctg acccaagagt agcacttgtt aacgattctt tatctgatgt cacaagtacc    1500
acatcttcta gggtggatga tcatgactca gaggaaattt gtcttgacca tctgtgtaag    1560
ggttgtccgc ttaatggtag ctgcagcaaa gtccacttcc atctgcctta ccggtggcag    1620
atgcttattg gtaaaacctg gacggacttt gagcacatgg agacgatcga aaaggctac     1680 tgtaaccccg gaatccacct ctgttctgta ggaagttata caatcaattt tcgggtaatg    1740
agttgtgatt cctttcccat ccgacgcctc tccactcctt cttctgtcac aagccagcc    1800 aattctgtct tcaccaccaa atggatttgg tattggaaga atgaatctgg cacatggatt    1860
cagtatggag aagagaaaga caaacggaaa aattcaaacg tcgactcttc atacctggag    1920
tctctctatc aatcctgtcc gagggagtt gtgccatttc aggcgggctc acggaactat      1980
gagctgagtt ccaagggat gattcagaca aacatagctt ccaaaactca aaaggatgtc     2040
atcagaagac caacatttgt gcctcagtgg tatgtgcagc agatgaagag agggccagac    2100
catcagccag caaagacctc gtcagtgtct ttaactgcga cctttcgtcc tcaggaggac    2160
ttttgcttcc tatcctcaaa gaaatataag ttgtcagaga tccatcacct acatccagaa    2220
tatgtcagag taagtgagca ttttaaagct tccatgaaaa atttcaagat tgaaaagata    2280
aagaagatcg agaactcaga gctcctggat aaatttacat ggaagaaatc gcagatgaag    2340
gaagaaggaa aactcctatt ttatgcgaca agccgtgcct atgtggaatc tatctgttcg    2400
aataattttg acagtttcct acatgaaact catgaaaaca aatacggaaa aggaatttac    2460
```

```
tttgcaaaag atgccatcta ttcccacaaa aattgcccgt atgatgccaa aaacgtcgtt    2520
atgtttgtag cccaagttct ggttggaaag tttactgaag gaaatataac gtacacgagc    2580
cctcctccac agttcgacag ctgtgtggat accagatcga atccctccgt ttttgtcatc    2640
tttcagaaag atcaggttta cccacaatat gtgattgaat atactgaaga caaagcctgc    2700
gtgattagtt ag                                                        2712

<210> SEQ ID NO 20
<211> LENGTH: 2103
<212> TYPE: DNA
<213> ORGANISM: Homo sapiens

<400> SEQUENCE: 20
gccatggcgg acccggaggt gtgctgcttc atcaccaaaa tcctgtgcgc ccacgggggc      60
cgcatggccc tggacgcgct gctccaggag atcgcgctgt ctgagccgca gctctgtgag     120
gtgctgcagg tggccgggcc cgaccgcttt gtggtgttgg agaccggcgg cgaggccggg     180
atcacccgat cggtggtggc caccactcga gcccgggtct gccgtcgcaa gtactgccag     240
agaccctgcg ataacctgca tctctgcaaa ctcaacttgc tgggccggtg caactattcg     300
cagtccgagc ggaatttatg caaatattct catgaggttc tctcagaaga gaacttcaaa     360
gtcctgaaaa atcacgaact ctctggactg aacaaagagg aattagcagt gctcctcctc     420
caaagtgatc ctttttttat gcccgagata tgcaaaagtt ataagggaga gggtcggcag     480
cagatttgta accagcagcc accgtgttca agactccaca tctgtgacca cttcacccga     540
gggaactgtc gttttcccaa ctgcctccgg tcccataacc tgatggacag aaaggtgctg     600
gccatcatga gggagcacgg gctgaacccc gacgtggtcc agaacatcca ggacatctgc     660
aacagcaagc acatgcagaa gaatccccca gggcccagag ctccttcttc acatcgtaga     720
aacatggcat atagggctag aagcaagagt agagatcggt tctttcaggg cagccaagaa     780
tttcttgcgt ctgcttcagc gtctgctgag aggtcctgca cacctagtcc agatcagatc     840
agccacaggg cttccctgga ggacgcgcct gtggacgatc tcacccgcaa gttcacgtat     900
ctggggagtc aggatcgcgc tcggcctccc tcaggctcgt ccaaggctac tgatcttgga     960
ggaacaagtc aggccgggac aagccagagg tttttagaga acggcagtca agaggacctc    1020
ttgcatggaa atccaggcag cacttacctt gcttccaatt caacatcagc ccccaactgg    1080
aagagcctca catcctggac gaatgaccaa ggcgccagga gaaagactgt gttttctccc    1140
acgctacctg ccgcccgctc ttctcttggc tctctgcaaa cacctgaagc tgtgaccacc    1200
agaaagggca caggcttgct ttcctcagac tacaggatca tcaatggcaa agtggaact     1260 caggacatcc agcctggccc tcttttaat aataatgctg atggagtggc cacagatata    1320
acttctacca gatccttaaa ttacaaaagc actagcagcg gtcacagaga atatcatca    1380 cctaggattc aggatgctgg acctgcttcc cgagatgtcc aggccactgg cagaatcgca    1440
gatgatgctg acccaagagt agcacttgtt aacgattctt tatctgatgt cacaagtacc    1500
acatcttcta gggtggatga tcatgactca gaggaaattt gtcttgacca tctgtgtaag    1560
ggttgtccgc ttaatggtag ctgcagcaaa gtccacttcc atctgcctta ccggtggcag    1620
atgcttattg gtaaaacctg gacggacttt gagcacatgg agacgatcga gaaaggctac    1680
tgtaaccccg gaatccacct ctgttctgta ggaagttata caatcaattt tcgggtaatg    1740
agttgtgatt ccttttccat ccgacgcctc tccactcctt cttctgtcac caagccagcc    1800
aattctgtct tcaccaccaa atggatttgg tattggaaga atgaatctgg cacatggatt    1860
```

```
cagtatggag aagagaaaga caaacggaaa aattcaaacg tcgactcttc atacctggag    1920
tctctctatc aatcctgtcc gaggggagtt gtgccatttc aggcgggctc acggaactat    1980
gagctgagtt tccaagggat gattcagaca aacatagctt ccaaaactca aaaggatgtc    2040
atcagaagac caacatttgt gcctcagtgg tatgtgcagc agatgaagag agggccagag    2100
taa                                                                  2103

<210> SEQ ID NO 21
<211> LENGTH: 4560
<212> TYPE: DNA
<213> ORGANISM: Homo sapiens

<400> SEQUENCE: 21
atcatggcca caaaactcga cttcaataaa atgccacttt ctgtgttccc atactatgcc      60
tcattgggca cagccttgta tggaaaggag aagcctctga tcaagcttcc agcaccattt     120
gaagagtcac tagatcttcc cttatggaag ttcttacaga aaaagaatca cctcattgag     180
gagataaacg atgaaatgag gcgttgtcac tgtgagctca cgtggtccca actcagtggt     240
aaagttacca tcagaccagc agccaccttA gtcaatgaag aagaccgag  aatcaagacc     300 tggcaggcag atacttccac aacactctct agcatcaggt ctaaatataa agtcaaccca     360
attaaagtgg atccaacaat gtgggacacc ataaaaaatg atgtgaaaga tgacaggatt     420
ttgattgagt ttgatacact taaggagatg gtaatcttag cagggaaatc agaggatgtc     480
caaagcattg aggtacaagt cagggagtta atagaaagca ctactcaaaa aattaaaagg     540
gaagagcaaa gtttgaagga aaaaatgatc atttctccag gcaggtattt tcttttgtgt     600
cacagcagtc tactggacca tttactcacg gagtgcccag atagagat  t tgttacgat     660 agagtcactc aacacttgtg cttgaaagga cctagtgcag atgtgtataa agcaaagtgt     720
gaaatccagg aaaaggtgta caccatggct cagaaaaaca ttcaggtttc tcctgagatt     780
tttcagtttt tgcaacaggt aaactggaaa gaattctcta gtgtctttt  catagcacag     840 aagattcttg cacttatga gctagagggt acaactgttc tcttaaccag ctgttcttct     900
gaagccctgt tagaagcaga aaagcaaatg ctcagtgcct taaattataa gcgcattgaa     960
gttgagaaca agaagttct tcatggcaag aaatggaaag ggctcactca caatttgctt    1020
aagaaacaaa attcctcccc aaacactgta atcatcaatg agttaacttc agaaaccaca    1080
gctgaagtca tcattacagg ctgtgtaaaa gaagtaaatg aaacctataa attgcttttt    1140
aacttcgttg aacaaaacat gaaaatagag agactggttg aagtaaagcc ttccttagtt    1200
attgactatt taaagacaga aaagaagcta ttctggccaa agataaagaa ggtaaatgtg    1260
caggtaagtt tcaatcctga gaacaaacaa aaaggcatt  tactaactgg ctcaaagacc    1320
gaagtactga aggcagtgga cattgtcaag caagtctggg attcagtctg tgttaaaagt    1380
gtccatactg ataagccagg agccaagcag ttcttccagg ataaagcacg gttttatcaa    1440
agtgagatca acggttgtt  tggttgttac attgaactac aggagaatga agtaatgaag    1500
gagggaggca gccccgctgg gcagaagtgc ttctctcgga cagtcttggc ccctggcgtt    1560
gtgctgattg tgcagcaggg tgacttggca cggcttcctg tcgatgtggt ggtgaatgca    1620
tctaatgagg accttaagca ttatggtggc ctggccgctg cgctctcaaa agcagctggc    1680
cctgagctcc aggccgactg tgaccagata gtgaagagag agggcagact cctaccgggc    1740
aatgccacca tctccaaggc aggaaagctg cctaccacc  acgtgatcca tgcagtgggg    1800
ccccgctgga gcgatatga ggccccgagg tgtgtgtacc tattaaggag agctgtgcaa    1860
```

```
ctcagtctct gtctagccga aaaatacaag taccgatcca tagccatccc agctattagt    1920
tctggagtct ttggctttcc cttaggccga tgcgtggaga ccattgtttc tgccatcaag    1980
gaaaacttcc aattcaagaa ggatggacac tgcttgaaag aaatctacct tgtggatgta    2040
tctgagaaga ctgttgaggc cttttgcagaa gctgtgaaaa ctgtatttaa agccaccctg   2100
ccagatacag ctgccccgcc aggtttacca ccagcagcag cggggcctgg gaaaacatca    2160
tgggaaaaag gaagcctggt gtccccggga ggctgcagaa tgctgttggt gaagagggt     2220
gtgcagaatg ctaagaccga tgttgttgtc aactccgttc ccttggatct cgtgcttagt    2280
agagggcctc tttctaagtc cctcttggaa aaagctggac cagagctcca ggaggaattg    2340
gacacagttg gacaagggggt ggctgtcagc atgggcacag tgctcaaaac cagcagctgg   2400
aatctggact gtcgctatgt gcttcacgtg gtagctccgg agtggagaaa tggtagcaca    2460
tcttcactca agataatgga agacataatc agagaatgta tggagatcac tgagagcttg    2520
tccttaaaat caattgcatt tccagcaata ggaacaggaa acttgggatt tcctaaaaac    2580
atattcgctg aattaatcat ttcagaggtg ttcaaattta gtagcaagaa tcagctgaaa    2640
actttacaag aggttcactt tctgctgcac ccgagtgatc atgaaaatat tcaggcattt    2700
tcagatgaat ttgccagaag ggctaatgga aatctcgtca gtgacaaaat tccgaaggct    2760
aaagatacac aaggttttta tgggactgtt tctagccctg attcaggtgt gtatgaaatg    2820
aagattggct ccatcatctt ccaggtggct tctggagata tcacgaaaga agaggcagat    2880
gtgattgtaa attcaacatc aaactcattc aatctcaaag cagggtctc caaagcaatt    2940
ttagaatgtg ctggacaaaa tgtagaaagg gaatgttctc agcaagctca gcagcgcaaa    3000
aatgattata taatcaccgg aggtggattt ttgaggtgca agaatatcat tcatgtaatt    3060
ggtggaaatg atgtcaagag ttcagtttcc tctgttttgc aggagtgtga aaaaaaaat    3120
tactcatcca tttgcctccc agccattggg acaggaaatg ccaaacaaca cccagataag   3180
gttgctgaag ccataattga tgccattgaa actttgtcc agaaaggatc agcccagtct     3240
gtgaaaaaag ttaaagttgt tatctttctg cctcaagtac tggatgtgtt ttatgccaac    3300
atgaagaaaa gagaagggac tcagctttct tcccaacagt ctgtgatgtc taaacttgca    3360
tcattttttgg gcttttcaaa gcaatctccc caaaaaaga atcatttggt tttggaaaag    3420
aaaacagaat cagcaacttt tcgggtgtgt ggtgaaaatg tcacgtgtgt ggaatatgct    3480
atctcctggc tacaagacct gattgaaaaa gaacagtgtc cttacaccag tgaagatgag    3540
tgcatcaaag acttttgatga aaaggagtat caggagttga tgagctgca gaagaagtta     3600
aatattaaca tttccctgga ccataagaga cctttgatta aggttttggc aattagcaga    3660
gatgtgatgc aggctagaga tgaaattgag gcgatgatca agagagttcg attgggcaaa    3720
gaacaggaat cccgggcaga ttgtatcagt gagtttatag aatggcagta taatgacaat    3780
aacacttctc attgttttaa caaaatgacc aatctgaaat tagaggatgc aaggagagaa    3840
aagaaaaaaa cagttgatgt caaaattaat catcggcact acacagtgaa cttgaacaca    3900
tacactgcca cagacacaaa gggccacagt ttatctgttc agcgcctcac gaaatccaaa    3960
gttgacatcc ctgcacactg gagtgatatg aagcagcaga atttctgtgt ggtggagctg    4020
ctgcctagtg atcctgagta caacacggtg gcaagcaagt taatcagac ctgctcacac     4080
ttcagaatag agaagattga gaggatccag aatccagatc tctggaatag ctaccaggca    4140
aagaaaaaaa ctatggatgc caagaatggc cagacaatga atgagaagca actcttccat    4200
gggacagatg ccggctccgt gccacacgtc aatcgaaatg gctttaaccg cagctatgcc    4260
```

| | |
|---|---:|
| ggaaagaatg ctgtggcata tggaaaggga acctatttg ctgtcaatgc caattattct | 4320 |
| gccaatgata cgtactccag accagatgca aatgggagaa agcatgtgta ttatgtgcga | 4380 |
| gtacttactg gaatctatac acatggaaat cattcattaa ttgtgcctcc ttcaaagaac | 4440 |
| cctcaaaatc ctactgacct gtatgacact gtcacagata atgtgcacca tccaagttta | 4500 |
| tttgtggcat tttatgacta ccaagcatac ccagagtacc ttattacgtt tagaaaataa | 4560 |

<210> SEQ ID NO 22
<211> LENGTH: 2040
<212> TYPE: DNA
<213> ORGANISM: Homo sapiens

<400> SEQUENCE: 22

| | |
|---|---:|
| aggatggctg cgccaggccc ccttcctgcc gctgctctga gtccaggggc tccgaccccc | 60 |
| agagaactta tgcacggagt tgcaggtgtt acttccagag ccggacgaga tcgggaggcg | 120 |
| gggagcgtgc tgccggccgg gaaccgtggg gcgcggaagg cctcccggcg ctcttcctcc | 180 |
| cggagtatgt ccagagacaa caagttcagc aagaaagatt gtctttcaat caggaatgtt | 240 |
| gtagcttcaa tccaaaccaa agaaggtctg aatctcaagt tgataagtgg agatgttctg | 300 |
| tacatctggg ccgatgtcat tgtcaacagc gttcccatga atcttcagct tggaggagga | 360 |
| ccactatctc gggcattttt gcagaaagct ggtcccatgc tccagaaaga gttagatgac | 420 |
| agaaggcggg aaacagagga aaagtaggt aacatattca tgacaagcgg ctgcaatctg | 480 |
| gactgcaaag ctgtgctcca tgctgtggct ccatactgga ataatggagc agagacttct | 540 |
| tggcagatca tggcaaatat aatcaagaaa tgtttgacaa ctgtagaagt gctatctttc | 600 |
| tcatcaatca catttcccat gattggaaca ggaagtttgc agtttcccaa agctgttttt | 660 |
| gctaaactaa tcctttcaga agtgttcgaa tacagtagca gcacaaggcc gataactagc | 720 |
| cctttacaag aagtccactt tctggtatat acaaatgacg atgaaggctg tcaggcattt | 780 |
| ttagatgaat tcactaactg gtcaagaata aatcccaaca aggccaggat tcccatggca | 840 |
| ggagataccc aaggtgtggt cgggactgtc tctaagcctt gtttcacagc atatgaaatg | 900 |
| aaaatcggtg caattacttt tcaggttgct actggagata tagccactga acaggtagat | 960 |
| gttattgtaa actcaacagc aaggacattt aatcggaaat caggtgtgtc aagagctatt | 1020 |
| ttagaaggtg ctggacaagc tgtggaaagt gaatgtgctg tactagctgc acagcctcac | 1080 |
| agagatttta taattacacc aggtggatgc ttaaagtgca aaataataat tcatgttcct | 1140 |
| gggggaaaag atgtcaggaa aacggtcacc agtgttctag aagagtgtga acagaggaag | 1200 |
| tacacatcgg tttcccttcc agccattgga acaggaaatg ccggaaaaaa ccctatcaca | 1260 |
| gttgctgata acataatcga tgctattgta gacttctcat cacaacattc caccccatca | 1320 |
| ttaaaaacag ttaaagttgt catttttcaa cctgagctgc taaatatatt ctacgacagc | 1380 |
| atgaaaaaaa gagacctctc tgcatcactg aactttcagt ccacattctc catgactaca | 1440 |
| tgtaatcttc ctgaacactg gactgacatg aatcatcagc tgttttgcat ggtccagcta | 1500 |
| gagccaggac aatcagaata taataccata aaggacaagt tcacccgaac ttgttcttcc | 1560 |
| tacgcaatag agaagattga gaggatacag aatgcatttc tctggcagag ctaccaggta | 1620 |
| aagaaaaggc aaatggatat caagaatgac cataagaata atgagagact cctcttccat | 1680 |
| gggacagatg cagactcagt gccatatgtc aatcagcacg gctttaatag aagttgtgct | 1740 |
| gggaaaaatg ctgtatccta tggaaaagga acctatttg ctgtggatgc cagttattct | 1800 |
| gccaaggaca cctactccaa gccagacagc aatgggagaa agcacatgta cgttgtgcga | 1860 |

```
gtacttactg gagtcttcac aaagggacgt gcaggattag tcaccccctcc acccaagaat    1920 cctcacaatc ccacagatct ctttgactca gtgacaaaca atacacgatc tccaaagcta    1980
tttgtggtat tctttgataa tcaggcttac ccagaatatc tcataacttt cacggcttaa    2040
```

<210> SEQ ID NO 23
<211> LENGTH: 1338
<212> TYPE: DNA
<213> ORGANISM: Homo sapiens

<400> SEQUENCE: 23

```
tcaatgctcc aaagaattgg attaatattt ttacacaata ttgttgtagt cagtaactgt      60
ttctatttcc aggcattttt agatgaattc actaactggt caagaataaa tcccaacaag     120
gccaggattc ccatggcagg agatacccaa ggtgtggtcg ggactgtctc taagccttgt     180
ttcacagcat atgaaatgaa atcggtgca attacttttc aggttgctac tggagatata     240
gccactgaac aggtagatgt tattgtaaac tcaacagcaa ggacatttaa tcggaaatca     300
ggtgtgtcaa gagctatttt agaaggtgct ggacaagctg tggaaagtga atgtgctgta     360
ctagctgcac agcctcacag agattttata attacaccag gtggatgctt aaagtgcaaa     420
ataataattc atgttcctgg gggaaaagat gtcaggaaaa cggtcaccag tgttctagaa     480
gagtgtgaac agaggaagta cacatcggtt tcccttccag ccattggaac aggaaatgcc     540
ggaaaaaacc ctatcacagt tgctgataac ataatcgatg ctattgtaga cttctcatca     600
caacattcca ccccatcatt aaaaacagtt aaagttgtca ttttttcaacc tgagctgcta     660 aatatattct acgacagcat gaaaaaaaga gacctctctg catcactgaa ctttcagtcc     720
acattctcca tgactacatg taatcttcct gaacactgga ctgacatgaa tcatcagctg     780
ttttgcatgg tccagctaga gccaggacaa tcagaatata ataccataaa ggacaagttc     840
acccgaactt gttcttccta cgcaatagag aagattgaga ggatacagaa tgcatttctc     900
tggcagagct accaggtaaa gaaaaggcaa atggatatca agaatgacca taagaataat     960
gagagactcc tcttccatgg gacagatgca gactcagtgc catatgtcaa tcagcacggc    1020
tttaatagaa gttgtgctgg gaaaaatgct gtatcctatg gaaaaggaac ctattttgct    1080
gtggatgcca gttattctgc caaggacacc tactccaagc cagacagcaa tgggagaaag    1140
cacatgtacg ttgtgcgagt acttactgga gtcttcacaa agggacgtgc aggattagtc    1200
acccctccac ccaagaatcc tcacaatccc acagatctct tgactcagt gacaaacaat    1260 acacgatctc caaagctatt tgtggtattc tttgataatc aggcttaccc agaatatctc    1320
ataactttca cggcttaa                                                  1338
```

<210> SEQ ID NO 24
<211> LENGTH: 975
<212> TYPE: DNA
<213> ORGANISM: Homo sapiens

<400> SEQUENCE: 24

```
gggatgcagc cctcaggctg gcggccgcc agggaggcgg cgggccgcga catgctggcc       60
gccgacctcc ggtgcagcct cttcgcctcg gccctgcaga gctacaagcg cgactcggtg     120
ctgcggccct tccccgcgtc ctacgcccgc ggcgactgta aggactttga agccctgctt     180
gcagatgcca gcaagttacc taacctgaaa gaacttctcc agtcctccgg agacaaccac     240
aaacgggcct gggacctggt gagctggatt ttatcctcaa aggtcctgac aatccacagt     300
gcagggaagg cagagtttga aaagatccaa aagctgactg gggctcctca cacgcctgtt     360
```

```
cctgcaccgg acttcctgtt tgaaattgag tactttgacc cagccaacgc caaatttat    420 gagaccaaag gagaacgaga cctaatctat gcatttcatg gtagccgcct agaaaacttc    480
cattccatta tccacaatgg cctgcactgc catctgaaca agacatcctt gttcggagag    540
gggacctacc tcaccagtga cttgagcctg gccctcatat acagccccca tggccatggg    600
tggcagcaca gcctcctcgg ccccatcctt agctgtgtgg ccgtgtgtga ggtcattgac    660
catccggacg tcaagtgcca aaccaagaag aaggattcca aggagataga tcgcagacga    720
gcgagaatca acatagtga aggggagac atccctccca agtacttcgt ggtcaccaat    780
aaccagctgc tgcgagtgaa gtacctcctg gtgtattcac agaagccacc caagagcagg    840
gcttcgagcc agctctcctg gttttccagc cattggttta ccgtcatgat atccctgtat    900
ctgctgctgc tgctcatagt gagtgtcatc aactcctctg ctttccaaca cttttggaat    960
cgtgcgaaaa gataa                                                    975
```

<210> SEQ ID NO 25
<211> LENGTH: 238
<212> TYPE: PRT
<213> ORGANISM: Aequorea coerulescens

<400> SEQUENCE: 25

```
Met Ser Lys Gly Ala Glu Leu Phe Thr Gly Val Val Pro Ile Leu Ile
1               5                   10                  15

Glu Leu Asn Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Lys Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Tyr Lys
225                 230                 235
```

<210> SEQ ID NO 26
<211> LENGTH: 7
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid

<400> SEQUENCE: 26

Glu Xaa Xaa Tyr Xaa Gln Ser
1               5

<210> SEQ ID NO 27
<211> LENGTH: 126
<212> TYPE: PRT
<213> ORGANISM: Staphylococcus aureus

<400> SEQUENCE: 27

Gly Pro Ser Ala Val Asp Asn Lys Phe Asn Lys Glu Gln Gln Asn Ala
1               5                   10                  15

Phe Tyr Glu Ile Leu His Leu Pro Asn Leu Asn Glu Glu Gln Arg Asn
            20                  25                  30

Ala Phe Ile Gln Ser Leu Lys Asp Asp Pro Ser Gln Ser Ala Asn Leu
        35                  40                  45

Leu Ala Glu Ala Lys Lys Leu Asn Asp Ala Gln Ala Pro Lys Val Asp
    50                  55                  60

Asn Lys Phe Asn Lys Glu Gln Gln Asn Ala Phe Tyr Glu Ile Leu His
65                  70                  75                  80

Leu Pro Asn Leu Asn Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Val Asp Ala Asn His Gln
        115                 120                 125

<210> SEQ ID NO 28
<211> LENGTH: 4731
<212> TYPE: DNA
<213> ORGANISM: Artificial Sequence
<220> FEATURE:
<223> OTHER INFORMATION: Synthetic Construct

<400> SEQUENCE: 28
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
```

```
acggtgggag gtctatataa gcagagctgg tttagtgaac cgtcagatcc gctagcgcta    600
ccggtcgcca ccatggtgag caagggcgag gagctgttca ccggggtggt gcccatcctg    660
gtcgagctgg acggcgacgt aaacggccac aagttcagcg tgtccggcga gggcgagggc    720
gatgccacct acggcaagct gaccctgaag ttcatctgca ccaccggcaa gctgcccgtg    780
ccctggccca ccctcgtgac cacccctgacc tacggcgtgc agtgcttcag ccgctacccc    840
gaccacatga agcagcacga cttcttcaag tccgccatgc ccgaaggcta cgtccaggag    900
cgcaccatct tcttcaagga cgacggcaac tacaagaccc gcgccgaggt gaagttcgag    960
ggcgacaccc tggtgaaccg catcgagctg aagggcatcg acttcaagga ggacggcaac   1020
atcctggggc acaagctgga gtacaactac aacagccaca cgtctatat catggccgac   1080
aagcagaaga cggcatcaa ggtgaacttc aagatccgcc acaacatcga ggacggcagc   1140
gtgcagctcg ccgaccacta ccagcagaac accccatcg gcgacggccc cgtgctgctg   1200
cccgacaacc actacctgag cacccagtcc gccctgagca agacccccaa cgagaagcgc   1260
gatcacatgg tcctgctgga gttcgtgacc gccgccggga tcactctcgg catggacgag   1320
ctgtacaagt ccggactcag atctcgagct caagcttcga attctgcagt cgacggtacc   1380
gcgggcccgg gatccaccgg atctagataa ctgatcataa tcagccatac cacatttgta   1440
gaggttttac ttgctttaaa aaacctccca cacctccccc tgaacctgaa acataaaatg   1500
aatgcaattg ttgttgttaa cttgtttatt gcagcttata atggttacaa ataaagcaat   1560
agcatcacaa atttcacaaa taaagcattt ttttcactgc attctagttg tggtttgtcc   1620
aaactcatca atgtatctta cgcgtaaat tgtaagcgtt aatattttgt taaaattcgc   1680
gttaaatttt tgttaaatca gctcattttt taaccaatag gccgaaatcg gcaaaatccc   1740
ttataaatca aagaataga ccgagatagg gttgagtgtt gttccagttt ggaacaagag   1800
tccactatta agaacgtgg actccaacgt caaagggcga aaaccgtct atcagggcga   1860
tggcccacta cgtgaaccat caccctaatc aagttttttg gggtcgaggt gccgtaaagc   1920
actaaatcgg aaccctaaag ggagcccccg atttagagct tgacggggaa agccggcgaa   1980
cgtggcgaga aggaaggga agaaagcgaa aggagcgggc gctagggcgc tggcaagtgt   2040
agcggtcacg ctgcgcgtaa ccaccacacc cgccgcgctt aatgcgccgc tacagggcgc   2100
gtcaggtggc acttttcggg gaaatgtgcg cggaaccccct atttgtttat ttttctaaat   2160
acattcaaat atgtatccgc tcatgagaca ataaccctga taaatgcttc aataatattg   2220
aaaaaggaag agtcctgagg cggaaagaac cagctgtgga atgtgtgtca gttagggtgt   2280
ggaaagtccc caggctcccc agcaggcaga agtatgcaaa gcatgcatct caattagtca   2340
gcaaccaggt gtggaaagtc cccaggctcc ccagcaggca gaagtatgca aagcatgcat   2400
ctcaattagt cagcaaccat agtcccgccc ctaactccgc ccatcccgcc cctaactccg   2460
cccagttccg cccattctcc gccccatggc tgactaattt ttttatttta tgcagaggcc   2520
gaggccgcct cggcctctga gctattccag aagtagtgag gaggcttttt tggaggccta   2580
ggcttttgca aagatcgatc aagagacagg atgaggatcg tttcgcatga ttgaacaaga   2640
tggattgcac gcaggttctc cggccgcttg ggtggagagg ctattcggct atgactgggc   2700
acaacagaca atcggctgct ctgatgccgc cgtgttccgg ctgtcagcgc aggggcgccc   2760
ggttcttttt gtcaagaccg acctgtccgg tgccctgaat gaactgcaag acgaggcagc   2820
gcggctatcg tggctggcca cgacgggcgt tccttgcgca gctgtgctcg acgttgtcac   2880
tgaagcggga agggactggc tgctattggg cgaagtgccg gggcaggatc tcctgtcatc   2940
```

-continued

| | |
|---|---|
| tcaccttgct cctgccgaga aagtatccat catggctgat gcaatgcggc ggctgcatac | 3000 |
| gcttgatccg gctacctgcc cattcgacca ccaagcgaaa catcgcatcg agcgagcacg | 3060 |
| tactcggatg gaagccggtc ttgtcgatca ggatgatctg gacgaagagc atcaggggct | 3120 |
| cgcgccagcc gaactgttcg ccaggctcaa ggcgagcatg cccgacggcg aggatctcgt | 3180 |
| cgtgacccat ggcgatgcct gcttgccgaa tatcatggtg gaaaatggcc gcttttctgg | 3240 |
| attcatcgac tgtggccggc tgggtgtggc ggaccgctat caggacatag cgttggctac | 3300 |
| ccgtgatatt gctgaagagc ttggcggcga atgggctgac cgcttcctcg tgctttacgg | 3360 |
| tatcgccgct cccgattcgc agcgcatcgc cttctatcgc cttcttgacg agttcttctg | 3420 |
| agcgggactc tggggttcga atgaccgac caagcgacgc ccaacctgcc atcacgagat | 3480 |
| ttcgattcca ccgccgcctt ctatgaaagg ttgggcttcg aatcgttttt ccggacgcc | 3540 |
| ggctggatga tcctccagcg cggggatctc atgctggagt tcttcgccca ccctaggggg | 3600 |
| aggctaactg aaacacggaa ggagacaata ccggaaggaa cccgcgctat gacggcaata | 3660 |
| aaaagacaga ataaaacgca cggtgttggg tcgtttgttc ataaacgcgg ggttcggtcc | 3720 |
| cagggctggc actctgtcga tacccaccg agaccccatt ggggccaata cgcccgcgtt | 3780 |
| tcttcctttt ccccacccca cccccaagt tcgggtgaag gcccagggct cgcagccaac | 3840 |
| gtcgggggcgg caggccctgc catagcctca ggttactcat atatacttta gattgattta | 3900 |
| aaacttcatt tttaatttaa aaggatctag gtgaagatcc ttttttgataa tctcatgacc | 3960 |
| aaaatccctt aacgtgagtt ttcgttccac tgagcgtcag accccgtaga aaagatcaaa | 4020 |
| ggatcttctt gagatccttt ttttctgcgc gtaatctgct gcttgcaaac aaaaaaacca | 4080 |
| ccgctaccag cggtggtttg tttgccggat caagagctac caactctttt tccgaaggta | 4140 |
| actggcttca gcagagcgca gataccaaat actgtccttc tagtgtagcc gtagttaggc | 4200 |
| caccacttca agaactctgt agcaccgcct acatacctcg ctctgctaat cctgttacca | 4260 |
| gtggctgctg ccagtggcga taagtcgtgt cttaccgggt tggactcaag acgatagtta | 4320 |
| ccggataagg cgcagcggtc gggctgaacg gggggttcgt gcacacagcc cagcttggag | 4380 |
| cgaacgacct acaccgaact gagatacta cagcgtgagc tatgagaaag cgccacgctt | 4440 |
| cccgaaggga gaaaggcgga caggtatccg gtaagcggca gggtcggaac aggagagcgc | 4500 |
| acgagggagc ttccaggggg aaacgcctgg tatctttata gtcctgtcgg gtttcgccac | 4560 |
| ctctgacttg agcgtcgatt tttgtgatgc tcgtcagggg ggcggagcct atggaaaaac | 4620 |
| gccagcaacg cggccttttt acggttcctg gccttttgct ggccttttgc tcacatgttc | 4680 |
| tttcctgcgt tatcccctga ttctgtggat aaccgtatta ccgccatgca t | 4731 |

<210> SEQ ID NO 29
<211> LENGTH: 108
<212> TYPE: DNA
<213> ORGANISM: Artificial Sequenec
<220> FEATURE:
<223> OTHER INFORMATION: Synthetic Construct

<400> SEQUENCE: 29

| | |
|---|---|
| ctgtacaagt ccggactcag atctcgagct caagcttcga attctgcagt cgacggtacc | 60 |
| gcgggcccgg gatccaccgg atctagataa ctgatcataa tcagccat | 108 |

<210> SEQ ID NO 30
<211> LENGTH: 8
<212> TYPE: PRT
<213> ORGANISM: Artificial
<220> FEATURE:

<223> OTHER INFORMATION: Synthetic Construct

<400> SEQUENCE: 30

Asp Tyr Lys Asp Asp Asp Asp Lys
1               5

<210> SEQ ID NO 31
<211> LENGTH: 11
<212> TYPE: PRT
<213> ORGANISM: Artificial sequence
<220> FEATURE:
<223> OTHER INFORMATION: Synthetic Construct

<400> SEQUENCE: 31

Lys Pro Pro Thr Pro Pro Pro Glu Pro Glu Thr
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Tyr Pro Tyr Asp Val Pro Asp Tyr Ala
1               5

<210> SEQ ID NO 33
<211> LENGTH: 5427
<212> TYPE: DNA
<213> ORGANISM: Artificial Sequence
<220> FEATURE:
<223> OTHER INFORMATION: Synthetic Construct

<400> SEQUENCE: 33

| | | | | | |
|---|---|---|---|---|---|
| gacggatcgg | gagatctccc | gatccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaacgg | gccctctaga | ctcgagcggc | cgccactgtg | ctggatatct | gcagaattcc | 960 |
| accacactgg | actagtggat | ccgagctcgg | taccaagctt | aagtttaaac | cgctgatcag | 1020 |
| cctcgactgt | gccttctagt | tgccagccat | ctgttgtttg | cccctccccc | gtgccttcct | 1080 |
| tgaccctgga | aggtgccact | cccactgtcc | tttcctaata | aaatgaggaa | attgcatcgc | 1140 |

```
attgtctgag taggtgtcat tctattctgg ggggtggggt ggggcaggac agcaaggggg   1200
aggattggga agacaatagc aggcatgctg gggatgcggt gggctctatg gcttctgagg   1260
cggaaagaac cagctggggc tctagggggt atccccacgc gccctgtagc ggcgcattaa   1320
gcgcggcggg tgtggtggtt acgcgcagcg tgaccgctac acttgccagc gccctagcgc   1380
ccgctccttt cgctttcttc ccttcctttc tcgccacgtt cgccggcttt ccccgtcaag   1440
ctctaaatcg gggctccct  ttagggttcc gatttagtgc tttacggcac ctcgacccca   1500
aaaaacttga ttagggtgat ggttcacgta gtgggccatc gccctgatag acggtttttc   1560
gccctttgac gttggagtcc acgttcttta atagtggact cttgttccaa actgaacaa   1620 cactcaaccc tatctcggtc tattcttttg atttataagg gattttgccg atttcggcct   1680
attggttaaa aaatgagctg atttaacaaa aatttaacgc gaattaattc tgtggaatgt   1740
gtgtcagtta gggtgtggaa agtccccagg ctccccagca ggcagaagta tgcaaagcat   1800
gcatctcaat tagtcagcaa ccaggtgtgg aaagtcccca ggctcccag  caggcagaag   1860 tatgcaaagc atgcatctca attagtcagc aaccatagtc cgcccctaa  ctccgcccat   1920 cccgccccta actccgccca gttccgccca ttctccgccc catggctgac taatttttt   1980 tatttatgca gaggccgagg ccgcctctgc ctctgagcta ttccagaagt agtgaggagg   2040 ctttttttgga ggcctaggct tttgcaaaaa gctcccggga gcttgtatat ccattttcgg   2100
atctgatcaa gagacaggat gaggatcgtt tcgcatgatt gaacaagatg gattgcacgc   2160
aggttctccg gccgcttggg tggagaggct attcggctat gactgggcac aacagacaat   2220
cggctgctct gatgccgccg tgttccggct gtcagcgcag gggcgcccgg ttcttttgt   2280 caagaccgac ctgtccggtg ccctgaatga actgcaggac gaggcagcgc ggctatcgtg   2340
gctggccacg acgggcgttc cttgcgcagc tgtgctcgac gttgtcactg aagcgggaag   2400
ggactggctg ctattgggcg aagtgccggg gcaggatctc ctgtcatctc accttgctcc   2460
tgccgagaaa gtatccatca tggctgatgc aatgcggcgg ctgcatacgc ttgatccggc   2520
tacctgccca ttcgaccacc aagcgaaaca tcgcatcgag cgagcacgta ctcggatgga   2580
agccggtctt gtcgatcagg atgatctgga cgaagagcat caggggctcg cgccagccga   2640
actgttcgcc aggctcaagg cgcgcatgcc cgacggcgag gatctcgtcg tgacccatgg   2700
cgatgcctgc ttgccgaata tcatggtgga aaatggccgc ttttctggat tcatcgactg   2760
tggccggctg ggtgtggcgg accgctatca ggacatagcg ttggctaccc gtgatattgc   2820
tgaagagctt ggcggcgaat gggctgaccg cttcctcgtg ctttacggta tcgccgctcc   2880
cgattcgcag cgcatcgcct tctatcgcct tcttgacgag ttcttctgag cgggactctg   2940
gggttcgaaa tgaccgacca agcgacgccc aacctgccat cacgagattt cgattccacc   3000
gccgccttct atgaaaggtt gggcttcgga atcgttttcc gggacgccgg ctggatgatc   3060
ctccagcgcg gggatctcat gctggagttc ttcgcccacc ccaacttgtt tattgcagct   3120
tataatggtt acaaataaag caatagcatc acaaatttca caaataaagc atttttttca   3180
ctgcattcta gttgtggttt gtccaaactc atcaatgtat cttatcatgt ctgtataccg   3240
tcgacctcta gctagagctt ggcgtaatca tggtcatagc tgtttcctgt gtgaaattgt   3300
tatccgctca caattccaca acatacgag  ccggaagca  taaagtgtaa agcctggggt   3360
gcctaatgag tgagctaact cacattaatt gcgttgcgct cactgcccgc tttccagtcg   3420
ggaaacctgt cgtgccagct gcattaatga atcggccaac gcgcggggag aggcggtttg   3480
cgtattgggc gctcttccgc ttcctcgctc actgactcgc tgcgctcggt cgttcggctg   3540
```

-continued

| | |
|---|---|
| cggcgagcgg tatcagctca ctcaaaggcg gtaatacggt tatccacaga atcagggat | 3600 |
| aacgcaggaa agaacatgtg agcaaaaggc cagcaaaagg ccaggaaccg taaaaaggcc | 3660 |
| gcgttgctgg cgttttttcca taggctccgc cccctgacg agcatcacaa aaatcgacgc | 3720 |
| tcaagtcaga ggtggcgaaa cccgacagga ctataaagat accaggcgtt tccccctgga | 3780 |
| agctccctcg tgcgctctcc tgttccgacc ctgccgctta ccggatacct gtccgccttt | 3840 |
| ctcccttcgg gaagcgtggc gctttctcat agctcacgct gtaggtatct cagttcggtg | 3900 |
| taggtcgttc gctccaagct gggctgtgtg cacgaacccc ccgttcagcc cgaccgctgc | 3960 |
| gccttatccg gtaactatcg tcttgagtcc aacccggtaa gacacgactt atcgccactg | 4020 |
| gcagcagcca ctggtaacag gattagcaga gcgaggtatg taggcggtgc tacagagttc | 4080 |
| ttgaagtggt ggcctaacta cggctacact agaagaacag tatttggtat ctgcgctctg | 4140 |
| ctgaagccag ttaccttcgg aaaaagagtt ggtagctctt gatccggcaa acaaaccacc | 4200 |
| gctggtagcg gtttttttgt ttgcaagcag cagattacgc gcagaaaaaa aggatctcaa | 4260 |
| gaagatcctt tgatctttc tacggggtct gacgctcagt ggaacgaaaa ctcacgttaa | 4320 |
| gggattttgg tcatgagatt atcaaaaagg atcttcacct agatcctttt aaattaaaaa | 4380 |
| tgaagtttta aatcaatcta agtatatat gagtaaactt ggtctgacag ttaccaatgc | 4440 |
| ttaatcagtg aggcacctat ctcagcgatc tgtctatttc gttcatccat agttgcctga | 4500 |
| ctccccgtcg tgtagataac tacgatacgg gagggcttac catctggccc cagtgctgca | 4560 |
| atgataccgc gagacccacg ctcaccggct ccagatttat cagcaataaa ccagccagcc | 4620 |
| ggaagggccg agcgcagaag tggtcctgca actttatccg cctccatcca gtctattaat | 4680 |
| tgttgccggg aagctagagt aagtagttcg ccagttaata gtttgcgcaa cgttgttgcc | 4740 |
| attgctacag gcatcgtggt gtcacgctcg tcgtttggta tggcttcatt cagctccggt | 4800 |
| tcccaacgat caaggcgagt tacatgatcc cccatgttgt gcaaaaaagc ggttagctcc | 4860 |
| ttcggtcctc cgatcgttgt cagaagtaag ttggccgcag tgttatcact catggttatg | 4920 |
| gcagcactgc ataattctct tactgtcatg ccatccgtaa gatgcttttc tgtgactggt | 4980 |
| gagtactcaa ccaagtcatt ctgagaatag tgtatgcggc gaccgagttg ctcttgcccg | 5040 |
| gcgtcaatac gggataatac cgcgccacat agcagaactt taaaagtgct catcattgga | 5100 |
| aaacgttctt cggggcgaaa actctcaagg atcttaccgc tgttgagatc cagttcgatg | 5160 |
| taacccactc gtgcacccaa ctgatcttca gcatctttta ctttcaccag cgtttctggg | 5220 |
| tgagcaaaaa caggaaggca aaatgccgca aaaagggaa taagggcgac acggaaatgt | 5280 |
| tgaatactca tactcttcct ttttcaatat tattgaagca tttatcaggg ttattgtctc | 5340 |
| atgagcggat acatatttga atgtatttag aaaaataaac aaatagggt tccgcgcaca | 5400 |
| tttccccgaa aagtgccacc tgacgtc | 5427 |

<210> SEQ ID NO 34
<211> LENGTH: 21
<212> TYPE: RNA
<213> ORGANISM: Artificial Sequence
<220> FEATURE:
<223> OTHER INFORMATION: PARG RNAi

<400> SEQUENCE: 34
ccaguuggau ggacacuaau u                                              21

<210> SEQ ID NO 35
<211> LENGTH: 21

-continued

<212> TYPE: RNA
<213> ORGANISM: Artificial Sequence
<220> FEATURE:
<223> OTHER INFORMATION: PARG RNAi

<400> SEQUENCE: 35
uuacgaaggu accauagaau u                                              21

<210> SEQ ID NO 36
<211> LENGTH: 21
<212> TYPE: RNA
<213> ORGANISM: Artificial Sequence
<220> FEATURE:
<223> OTHER INFORMATION: ARH3 RNAi

<400> SEQUENCE: 36
ggacagaagc cuuguacuau u                                              21

<210> SEQ ID NO 37
<211> LENGTH: 21
<212> TYPE: RNA
<213> ORGANISM: Artificial Sequence
<220> FEATURE:
<223> OTHER INFORMATION: ARH3 RNAi

<400> SEQUENCE: 37
ccauugcugg ugccuacuau u                                              21

<210> SEQ ID NO 38
<211> LENGTH: 21
<212> TYPE: RNA
<213> ORGANISM: Artificial Sequence
<220> FEATURE:
<223> OTHER INFORMATION: Vector-target RNAi

<400> SEQUENCE: 38 guuucacuc cagcuaacac a                                               21

<210> SEQ ID NO 39
<211> LENGTH: 21
<212> TYPE: RNA
<213> ORGANISM: Artificial Sequence
<220> FEATURE:
<223> OTHER INFORMATION: Vector-target RNAi

<400> SEQUENCE: 39
uucaaaagug aggucgauug u                                              21

<210> SEQ ID NO 40
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 40
gcucacggaa cuaugagcug aguuu                                          25

<210> SEQ ID NO 41
<211> LENGTH: 1671
<212> TYPE: DNA
<213> ORGANISM: Homo sapiens

<400> SEQUENCE: 41
gcagtctgcg cgcggatggc cgcagcggcg atggcggcag cggcaggtgg aggggctggc    60
gcggcccgct ccctctcgcg cttccgaggc tgcctggctg gcgcgctgct cggggactgc   120

| | |
|---|---|
| gtgggctcct tctacgaggc ccacgacacc gtcgacctga cgtcagtcct gcgtcatgtc | 180 |
| cagagtctgg agccggaccc cggcacgccc gggagtgagc ggacagaagc cttgtactac | 240 |
| acagatgaca cagccatggc cagggccctg gtgcagtccc tgctagccaa ggaggccttt | 300 |
| gacgaggtgg acatggctca cagatttgct caggagtaca agaaagaccc tgacaggggc | 360 |
| tatggtgctg gagtagtcac tgtcttcaag aagctcctga accccaaatg tcgcgatgtc | 420 |
| tttgagcctg cccgggccca gtttaacggg aaaggctcct atggcaatgg aggtgccatg | 480 |
| cgggtggctg gcatctccct ggcctatagc agtgtccagg atgtgcagaa gtttgcccgg | 540 |
| ctctcggccc agctgacaca cgcctcctcc ctgggttaca atggcgccat cctgcaggcc | 600 |
| ctggctgtgc acctggcctt gcagggcgag tcttccagcg agcactttct caagcaactc | 660 |
| ctgggccaca tggaggatct ggaggtgat gcccagtccg tcttggatgc cagggagttg | 720 |
| ggcatggagg agcgtccata ctccagccgc ctgaagaaga ttggagagct tctagaccag | 780 |
| gcatcggtga ccagggagga agtggtgtct gagctaggga atggcattgc tgcctttgag | 840 |
| tcggtaccca ccgccatcta ctgcttccta cgctgcatgg agccagaccc tgagatccct | 900 |
| tctgccttca atagcctcca aaggactctc atttattcca tctcacttgg tgggacaca | 960 |
| gacaccattg ccaccatggc tggggccatt gctggtgcct actatgggat ggatcaggtg | 1020 |
| ccagagagct ggcagcaaag ctgtgaaggc tacgaggaga cagacatcct ggcccaaagc | 1080 |
| ctgcaccgtg tcttccagaa gagttgatga gggctacagc tgttggggct gccaggtc | 1140 |
| ccctgggacc aactacagct ccaatcagaa accctgcgct tccttgagtg tggcttccca | 1200 |
| cttttcctgc attgtggagc tgactgagta caccggtgag gctggggtct ctgcaggga | 1260 |
| ggtcactgga acagcgagca agggactggt gcctcgctgg tgctgggtct ctggtttgct | 1320 |
| gcagagccgt aggacactcc tggctcctca gtaggacaga cagacgcagg cgggtttatt | 1380 |
| ttggaggggt acttgtggca ttttcctgta ttgtcttgga catgggatgt ggggaggtgg | 1440 |
| aaatgatgag cagtagcatc atttctccct gttgggtttt agccagtttg ccagcaagcg | 1500 |
| catcctagca gggtccccga gcagcaggtt gtgtggatga agggacaggc acttgcatcc | 1560 |
| agctgatcta ggtcacacct ggctcttggc tgccatgtgg cttattaaca gcttccagtg | 1620 |
| gaagtcgcaa taaacagttt ttggtaaatc tcaaaaaaaa aaaaaaaaa a | 1671 |

<210> SEQ ID NO 42
<211> LENGTH: 4276
<212> TYPE: DNA
<213> ORGANISM: Homo sapiens

<400> SEQUENCE: 42

| | |
|---|---|
| cggtggtggg aaagtgaacg aatcccgaat caaagcggcg cattgaggca ggtggggtgc | 60 |
| cagtggaaga gagaaagcag gcgagtgttt acggcctgac ttgggaggcc ggcggatcag | 120 |
| caattgcaga agcaggcagc ggcagagagg gaatggtgca ggcaggcgct gagaaggacg | 180 |
| cgcagtccat ctctctcagg ttagtgaaat gaggctctcc gcccgggcc ggcccgggga | 240 |
| cagtgcgctg ctggtcccag catgaatgcg ggccccggct gtgaaccctg caccaagcga | 300 |
| ccccgctggg gcgccgctac aacttcgccg gctgcttcgg acgcccgag ctttcccagc | 360 |
| aggcagaggc gcgtcctcga ccccaaggac gctcacgtgc agttcagggt cccaccgtcc | 420 |
| tcgccagcct gcgtcccagg gcgggcggga cagcacagag gcagcgccac ctcgcttgtt | 480 |
| ttcaaacaaa agactattac cagttggatg gacactaaag gaatcaagac agcggaatca | 540 |
| gaaagtttgg atagtaaaga aaacaacaat acaagaatag aatccatgat gagttctgta | 600 |

```
caaaaagata actttttacca acataatgta gaaaaattag aaaatgtttc tcagctaagt    660
cttgataagt cacccactga aaaaagtaca cagtatttga accagcatca gactgcagca    720
atgtgtaagt ggcaaaatga agggaaacac acggagcagc ttttggaaag tgaacctcaa    780
acagtaaccc tggtaccaga gcagtttagt aatgctaaca ttgatcggtc acctcaaaat    840
gatgatcaca gtgacacaga tagtgaagag aatagagaca atcaacagtt tctcacaact    900
gtaaagcttg caaatgcaaa gcagactacg gaagatgaac aggccagaga agccaaaagc    960
caccagaagt gcagcaagtc ttgcgatcct ggggaagact gtgcaagttg tcagcaagat   1020
gagatagatg tggtgccaga gagtccattg tcagatgttg gctctgagga tgttggtact   1080
gggccaaaaa atgacaacaa attgactaga caagaaagtt gcctaggaaa ttctcctcca   1140
tttgagaagg aaagtgaacc cgagtcaccg atggatgtgg ataattctaa aaatagttgt   1200
caagactcag aagcagatga ggagacaagt ccaggtttgt atgaacaaga agatggtagt   1260
tcctcccaaa cagcaaataa accttcaagg ttccaagcaa gagacgctga cattgaattt   1320
aggaaacggt actctactaa gggcggtgaa gttagattac atttccaatt tgaaggagga   1380
gagagtcgca ctggaatgaa tgatttaaat gctaaactac ctggaaatat ttctagcctg   1440
aatgtagaat gcagaaattc taagcaacat ggaaaaaagg attctaaaat cacagatcat   1500
ttcatgagac tgcccaaagc agaggacaga agaaaagaac agtgggaaac caaacatcaa   1560
agaacagaaa ggaagatccc taaatacgtt ccacctcacc tttctccaga taagaagtgg   1620
cttggaactc ccattgagga gatgagaaga atgcctcggt gtgggatccg gctgcctctc   1680
ttgagaccat ctgccaatca cacagtaact attcgggtag atcttttgcg agcaggagaa   1740
gttcctaaac cttttccaac acattataaa gatttgtggg ataacaagca tgttaaaatg   1800
ccttgttcag aacaaaattt gtacccagtg gaagatgaga atggtgagcg aactgcgggg   1860
agccggtggg agctcattca gactgcactt ctcaacaaat ttacacgacc caaaacttg   1920
aaggatgcta ttctgaaata caatgtggca tattctaaga atgggacttt acagctttg    1980
atcgatttct gggataaggt acttgaagaa gcagaagctc aacatttata tcagtccatc   2040
ttgcctgata tggtgaaaat tgcactctgt ctgccaaata tttgcaccca gccaatacca   2100
ctcctgaaac agaagatgaa tcattccatc acaatgtcgc aggaacagat tgccagtctt   2160
ttagctaatg ctttcttctg cacatttcca cgacgaaatg ctaagatgaa atcggagtat   2220
tctagttacc cagacattaa cttcaatcga ttgtttgagg acgttcatc aaggaaaccg   2280
gagaaactta aaacgctctt ctgctacttt agaagagtca cagagaaaaa acctactggg   2340
ttggtgacat ttacaagaca gagtcttgaa gattttccag aatgggaaag atgtgaaaaa   2400
cccttgacac gattgcatgt cacttacgaa ggtaccatag aagaaatgg ccaaggcatg   2460
ctacaggtgg attttgcaaa tcgttttgtt ggaggtggtg taaccagtgc aggacttgtg   2520
caagaagaaa tccgcttttt aatcaatcct gagttgatta tttcacggct cttcactgag   2580
gtgctggatc acaatgaatg tctaattatc acaggtactg agcagtacag tgaatacaca   2640
ggctatgctg agacatatcg ttggtcccgg agccacgaag atgggagtga aagggacgac   2700
tggcagcggc gctgcactga gatcgttgcc atcgatgctc ttcacttcag acgctacctc   2760
gatcagtttg tgcctgagaa aatgagacgc gagctgaaca aggcttactg tggatttctc   2820
cgtcctggag tttcttcaga gaatctttct gcagtggcca caggaaactg gggctgtggt   2880
gccctttggg gtgatgccag gttaaaagcc ttaatacaga tattggcagc tgctgcagct   2940
gagcgagatg tggtttattt cacctttggg gactcagaat tgatgagaga catttacagc   3000
```

| | |
|---|---|
| atgcacattt tccttactga aaggaaactc actgttggag atgtgtataa gctgttgcta | 3060 |
| cgatactaca atgaagaatg cagaaactgt tccacccctg gaccagacat caagctttat | 3120 |
| ccattcatat accatgctgt cgagtcctgt gcagagaccg ctgaccattc agggcaaagg | 3180 |
| acagggacct gaggagccga gcgaatagca tctcctccca cctcccacca gagacgtcct | 3240 |
| gtttgagctg tcaggtgtaa tatatgaatt gacttaagtt aatataaatg tgtacataat | 3300 |
| ccacatttgt agtcaaggac gcaatctctt ccacacatgt gcagttgtca gttggtacat | 3360 |
| ctaaactccc tccatcctga ctcacgtgga cttagatatg ttttgtttct attttcttct | 3420 |
| atttcagttt ttcattcttt gatgtttatt tcttttgtcc atcagatctc ttgtgaaatc | 3480 |
| ccatggaagg ttgtgctcag cctgtcgggt ctctttcttc ctgcccatat attataccag | 3540 |
| ttgcttctgc agcccgcaga tgccagcgat gccaggaaac aagttgaaat ccaggaatct | 3600 |
| ctttaactga ttttgctaaa aatctccctg tgagccttcc actcaactct taatatgctt | 3660 |
| gcattgttta agttttttaaa ttctgaaaat taataattag ggttttttttc atatgtgttg | 3720 |
| cataatgcaa acctcctagg ttaaaatagt ttctttattt aagatagaat aatttccaga | 3780 |
| aattgtactt tgaggtatc attttttatct gtaatggttt gtctgtcttt tttcctctga | 3840 |
| tcagtatttt tttataccag ttttggagac tggctgagat gaaaggaaat gtggaataaa | 3900 |
| aggaggtttt cctgatgtgg tgtaaagaaa acagattcaa gagaattgaa gatttttttt | 3960 |
| gtttcttggt acttttttct ttttaaatta ggactaatgt ttcttttgtg gtgcttgagg | 4020 |
| catattcata taaccaaagt ttgagaactg ggaacttcat gctgatttgt acatattgaa | 4080 |
| gtttctctgg tattcaaagg ttatatagtg aatgaatttt cattaataaa tcactttgtc | 4140 |
| agaaactccc atatcatcta tattttatat atgtatatat aaacgtatgc tctttaagtg | 4200 |
| tgtctatatg tgagcacata aaatctaaat aaaattggac tggtgggaaa caaaaaaaaa | 4260 |
| aaaaaaaaaa aaaaaa | 4276 |

<210> SEQ ID NO 43
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 43
cccaaguacu ucguggucac caaua                         25

<210> SEQ ID NO 44
<211> LENGTH: 21
<212> TYPE: RNA
<213> ORGANISM: Artificial Sequence
<220> FEATURE:
<223> OTHER INFORMATION: PARP1 RNAi

<400> SEQUENCE: 44
aagccuccgc uccugaacaa u                             21

<210> SEQ ID NO 45
<211> LENGTH: 21
<212> TYPE: RNA
<213> ORGANISM: Artificial Sequence
<220> FEATURE:
<223> OTHER INFORMATION: PARP2A RNAi

<400> SEQUENCE: 45
aaucagugua augaacuacu a                             21

```
<210> SEQ ID NO 46
<211> LENGTH: 21
<212> TYPE: RNA
<213> ORGANISM: Artificial Sequence
<220> FEATURE:
<223> OTHER INFORMATION: PARP2B RNAi

<400> SEQUENCE: 46
aaugauucag cuauuagaag a                                              21

<210> SEQ ID NO 47
<211> LENGTH: 25
<212> TYPE: RNA
<213> ORGANISM: Artificial Sequence
<220> FEATURE:
<223> OTHER INFORMATION: PARP3 RNAi

<400> SEQUENCE: 47
ggacccaggu guaugaggac uacaa                                          25

<210> SEQ ID NO 48
<211> LENGTH: 21
<212> TYPE: RNA
<213> ORGANISM: Artificial Sequence
<220> FEATURE:
<223> OTHER INFORMATION: PARP4 RNAi

<400> SEQUENCE: 48
aaacaaggau uucuacuaag a                                              21

<210> SEQ ID NO 49
<211> LENGTH: 21
<212> TYPE: RNA
<213> ORGANISM: Artificial Sequence
<220> FEATURE:
<223> OTHER INFORMATION: PARP5A RNAi

<400> SEQUENCE: 49
aacaauucac cgucguccuc u                                              21

<210> SEQ ID NO 50
<211> LENGTH: 21
<212> TYPE: RNA
<213> ORGANISM: Artificial Sequence
<220> FEATURE:
<223> OTHER INFORMATION: PARP5B RNAi

<400> SEQUENCE: 50
aagcuucaga auggugcaaa u                                              21

<210> SEQ ID NO 51
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 51
cccaacaaug gaaacaucug agcaa                                          25

<210> SEQ ID NO 52
<211> LENGTH: 25
<212> TYPE: RNA
<213> ORGANISM: Artificial Sequence
<220> FEATURE:
<223> OTHER INFORMATION: PARP6 RNAi
```

-continued

<400> SEQUENCE: 52
uugcucagau guuccauug uuggg                                          25

<210> SEQ ID NO 53
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 53
gguucaaggc aagugguacc aucaa                                         25

<210> SEQ ID NO 54
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 54
uugaugguac cacuugccuu gaacc                                         25

<210> SEQ ID NO 55
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 55
caaaguggaa guguuggcu acccu                                          25

<210> SEQ ID NO 56
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 56
aggguagcca aacacuucca cuuug                                         25

<210> SEQ ID NO 57
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 57
cagaacagag gauuccaaca uugaa                                         25

<210> SEQ ID NO 58
<211> LENGTH: 25
<212> TYPE: RNA
<213> ORGANISM: Artificial Sequence
<220> FEATURE:
<223> OTHER INFORMATION: PARP6 RNAi

<400> SEQUENCE: 58
uucaauguug gaauccucug uucug                                         25

<210> SEQ ID NO 59
<211> LENGTH: 25

```
<212> TYPE: RNA
<213> ORGANISM: Artificial Sequence
<220> FEATURE:
<223> OTHER INFORMATION: PARP7 RNAi

<400> SEQUENCE: 59
ugaggucuuu gaggccaaua uuaaa                                          25

<210> SEQ ID NO 60
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 60
uuuaauauug gccucaaaga ccuca                                          25

<210> SEQ ID NO 61
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 61
gacuuucugc aaggcacuug uauuu                                          25

<210> SEQ ID NO 62
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 62
aaauacaagu gccuugcaga aaguc                                          25

<210> SEQ ID NO 63
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 63
uccuccaccu cuugaagcaa cuuca                                          25

<210> SEQ ID NO 64
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 64
ugaaguugcu ucaagaggug gagga                                          25

<210> SEQ ID NO 65
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 65
aaugaugacc agaguuaccc uuauu                                          25
```

<210> SEQ ID NO 66
<211> LENGTH: 25
<212> TYPE: RNA
<213> ORGANISM: Artificial Sequence
<220> FEATURE:
<223> OTHER INFORMATION: PARP7 RNAi

<400> SEQUENCE: 66
aauaagggua acucugguca ucauu                                  25

<210> SEQ ID NO 67
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 67
ggaagauucu gaaggugaca augau                                  25

<210> SEQ ID NO 68
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 68
aucauuguca ccuucagaau cuucc                                  25

<210> SEQ ID NO 69
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 69
cccacaacug gaagcugauu uguca                                  25

<210> SEQ ID NO 70
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 70
ugacaaauca gcuuccaguu guggg                                  25

<210> SEQ ID NO 71
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 71
gaaguggaau cuaucuuagu ccaau                                  25

<210> SEQ ID NO 72
<211> LENGTH: 25
<212> TYPE: RNA
<213> ORGANISM: Artificial Sequence
<220> FEATURE:
<223> OTHER INFORMATION: PARP8 RNAi

```
<400> SEQUENCE: 72
auuggacuaa gauagauucc acuuc                                             25

<210> SEQ ID NO 73
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 73
gccuuaugug aagugaucac cucau                                             25

<210> SEQ ID NO 74
<211> LENGTH: 25
<212> TYPE: RNA
<213> ORGANISM: Artificial Sequence
<220> FEATURE:
<223> OTHER INFORMATION: PARP8 RNAi

<400> SEQUENCE: 74
augaggugau cacuucacau aaggc                                             25

<210> SEQ ID NO 75
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 75
gccggagcag cagcuuacaa ugaaa                                             25

<210> SEQ ID NO 76
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 76
uuucauugua agcugcugcu ccggc                                             25

<210> SEQ ID NO 77
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 77
cccucugaau uuguacaa agacu                                               25

<210> SEQ ID NO 78
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 78
agucuuugua cacaaauuca gaggg                                             25

<210> SEQ ID NO 79
<211> LENGTH: 25
```

```
<212> TYPE: RNA
<213> ORGANISM: Artificial Sequence
<220> FEATURE:
<223> OTHER INFORMATION: PARP9 RNAi

<400> SEQUENCE: 79
ggacccuacu guugcugccu uuaaa                                              25

<210> SEQ ID NO 80
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 80
uuuaaaggca gcaacaguag ggucc                                              25

<210> SEQ ID NO 81
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 81
uggcagacgg cagauguaau uguua                                              25

<210> SEQ ID NO 82
<211> LENGTH: 25
<212> TYPE: RNA
<213> ORGANISM: Artificial Sequence
<220> FEATURE:
<223> OTHER INFORMATION: PARP9 RNAi

<400> SEQUENCE: 82
uaacaauuac aucugccguc ugcca                                              25

<210> SEQ ID NO 83
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 83
cauggugcag gguagaggga uuaug                                              25

<210> SEQ ID NO 84
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 84
cauaaucccu cuacccugca ccaug                                              25

<210> SEQ ID NO 85
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 85
gccuggugga gauggugcua uugau                                              25
```

<210> SEQ ID NO 86
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 86
aucaauagca ccaucuccac caggc                                          25

<210> SEQ ID NO 87
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 87
agacgucgcu cucuugccac uugaa                                          25

<210> SEQ ID NO 88
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 88
uucaaguggc aagagagcga cgucu                                          25

<210> SEQ ID NO 89
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 89
ugggcagcau uagcugccau uguu                                           25

<210> SEQ ID NO 90
<211> LENGTH: 25
<212> TYPE: RNA
<213> ORGANISM: Artificial Sequence
<220> FEATURE:
<223> OTHER INFORMATION: PARP10 RNAi

<400> SEQUENCE: 90
aacacauggc agcuaaugcu gccca                                          25

<210> SEQ ID NO 91
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 91
caacaaacaa ugaaguggau gacau                                          25

<210> SEQ ID NO 92
<211> LENGTH: 25
<212> TYPE: RNA
<213> ORGANISM: Artificial Sequence
<220> FEATURE:
<223> OTHER INFORMATION: PARP11 RNAi

```
<400> SEQUENCE: 92
augucaucca cuucauuguu uguug                                              25

<210> SEQ ID NO 93
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 93
cagccggaua ccaacaguca guguu                                              25

<210> SEQ ID NO 94
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 94
aacacugacu guugguaucc ggcug                                              25

<210> SEQ ID NO 95
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 95
caaacccuug uggcuccauu ucuuu                                              25

<210> SEQ ID NO 96
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 96
aaagaaaugg agccacaagg guuug                                              25

<210> SEQ ID NO 97
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 97
ugccaccaca cugggagaau gugaa                                              25

<210> SEQ ID NO 98
<211> LENGTH: 25
<212> TYPE: RNA
<213> ORGANISM: Artificial Sequence
<220> FEATURE:
<223> OTHER INFORMATION: PARP11 RNAi

<400> SEQUENCE: 98
uucacauucu cccagugugg uggca                                              25

<210> SEQ ID NO 99
<211> LENGTH: 25
```

```
<212> TYPE: RNA
<213> ORGANISM: Artificial Sequence
<220> FEATURE:
<223> OTHER INFORMATION: PARP12 RNAi

<400> SEQUENCE: 99
uccaccucug cagguucaug gucua                                            25

<210> SEQ ID NO 100
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 100
uagaccauga accugcagag gugga                                            25

<210> SEQ ID NO 101
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 101
ugccagaaau uugccaacau uacaa                                            25

<210> SEQ ID NO 102
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 102
uuguaauguu ggcaaauuuc uggca                                            25

<210> SEQ ID NO 103
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 103
ggugagcagg cugccuacca uuuau                                            25

<210> SEQ ID NO 104
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 104
auaaauggua ggcagccugc ucacc                                            25

<210> SEQ ID NO 105
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 105
aggauuugga caacauggaa cuuau                                            25
```

<210> SEQ ID NO 106
<211> LENGTH: 25
<212> TYPE: RNA
<213> ORGANISM: Artificial Sequence
<220> FEATURE:
<223> OTHER INFORMATION: PARP12 RNAi

<400> SEQUENCE: 106
auaaguucca uguguccaa auccu                                    25

<210> SEQ ID NO 107
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 107
gcugacccaa gaguagcacu uguua                                   25

<210> SEQ ID NO 108
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 108
uaacaagugc uacucuuggg ucagc                                   25

<210> SEQ ID NO 109
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 109
ccgguggcag augcuuauug guaaa                                   25

<210> SEQ ID NO 110
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 110
uuuaccaaua agcaucugcc accgg                                   25

<210> SEQ ID NO 111
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 111
aaacucagcu cauaguuccg ugagc                                   25

<210> SEQ ID NO 112
<211> LENGTH: 25
<212> TYPE: RNA
<213> ORGANISM: Artificial Sequence
<220> FEATURE:
<223> OTHER INFORMATION: PARP13 RNAi

```
<400> SEQUENCE: 112
ugccucagug guaugugcag cagau                                          25

<210> SEQ ID NO 113
<211> LENGTH: 25
<212> TYPE: RNA
<213> ORGANISM: Artificial Sequence
<220> FEATURE:
<223> OTHER INFORMATION: PARP13 RNAi

<400> SEQUENCE: 113
aucugcugca cauaccacug aggca                                          25

<210> SEQ ID NO 114
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 114
uggccugucu aaugaugacu uucaa                                          25

<210> SEQ ID NO 115
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 115
uugaaaguca ucauuagaca ggcca                                          25

<210> SEQ ID NO 116
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 116
ccuggugcug augacuacag uuuaa                                          25

<210> SEQ ID NO 117
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 117
uuaaacugua gucaucagca ccagg                                          25

<210> SEQ ID NO 118
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 118
gccacuuucu guguucccau acuau                                          25

<210> SEQ ID NO 119
<211> LENGTH: 25
```

```
<212> TYPE: RNA
<213> ORGANISM: Artificial Sequence
<220> FEATURE:
<223> OTHER INFORMATION: PARP14 RNAi

<400> SEQUENCE: 119
auaguauggg aacacagaaa guggc                                        25

<210> SEQ ID NO 120
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 120
gaagagucac uagaucuucc cuuau                                        25

<210> SEQ ID NO 121
<211> LENGTH: 25
<212> TYPE: RNA
<213> ORGANISM: Artificial Sequence
<220> FEATURE:
<223> OTHER INFORMATION: PARP14 RNAi

<400> SEQUENCE: 121
auaagggaag aucuagugac ucuuc                                        25

<210> SEQ ID NO 122
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 122
gaugaauuca cuaacugguc aagaa                                        25

<210> SEQ ID NO 123
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 123
uucuugacca guuagugaau ucauc                                        25

<210> SEQ ID NO 124
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 124 ccaucacag uugcugauaa cauaa                                         25

<210> SEQ ID NO 125
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 125
uuauguuauc agcaacugug auagg                                        25
```

<210> SEQ ID NO 126
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 126
ggacugacau gaaucaucag cuguu                                          25

<210> SEQ ID NO 127
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 127
aacagcugau gauucauguc agucc                                          25

<210> SEQ ID NO 128
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 128
cgaguacuua cuggagucuu cacaa                                          25

<210> SEQ ID NO 129
<211> LENGTH: 25
<212> TYPE: RNA
<213> ORGANISM: Artificial Sequence
<220> FEATURE:
<223> OTHER INFORMATION: PARP15 RNAi

<400> SEQUENCE: 129
uugugaagac uccaguaagu acucg                                          25

<210> SEQ ID NO 130
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 130
cagugcaggg aaggcagagu uugaa                                          25

<210> SEQ ID NO 131
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 131
uucaaacucu gccuucccug cacug                                          25

<210> SEQ ID NO 132
<211> LENGTH: 25
<212> TYPE: RNA
<213> ORGANISM: Artificial Sequence
<220> FEATURE:
<223> OTHER INFORMATION: PARP16 RNAi

```
<400> SEQUENCE: 132
gagaccaaag gagaacgaga ccuaa                                            25

<210> SEQ ID NO 133
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 133
uuaggucucg uucuccuuug gucuc                                            25

<210> SEQ ID NO 134
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 134
gacuugagcc uggcccucau auaca                                            25

<210> SEQ ID NO 135
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 135
uguauaugag ggccaggcuc aaguc                                            25

<210> SEQ ID NO 136
<211> LENGTH: 25
<212> TYPE: RNA
<213> ORGANISM: Artificial Sequence
<220> FEATURE:
<223> OTHER INFORMATION: PARP16 RNAi

<400> SEQUENCE: 136
uauuggugac cacgaaguac uuggg                                            25
```